(12) United States Patent
Jang et al.

(10) Patent No.: US 10,381,572 B2
(45) Date of Patent: Aug. 13, 2019

(54) HETEROCYCLIC COMPOUND AND ORGANIC LIGHT-EMITTING ELEMENT COMPRISING SAME

(71) Applicant: LG CHEM, LTD., Seoul (KR)

(72) Inventors: Boonjae Jang, Daejeon (KR); Dong Hoon Lee, Daejeon (KR); Dong Uk Heo, Daejeon (KR); Miyeon Han, Daejeon (KR); Minyoung Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 91 days.

(21) Appl. No.: 15/125,924

(22) PCT Filed: Apr. 2, 2015

(86) PCT No.: PCT/KR2015/003292
§ 371 (c)(1),
(2) Date: Sep. 13, 2016

(87) PCT Pub. No.: WO2015/152651
PCT Pub. Date: Oct. 8, 2015

(65) Prior Publication Data
US 2017/0018718 A1    Jan. 19, 2017

(30) Foreign Application Priority Data

Apr. 4, 2014 (KR) .......... 10-2014-0040818
Feb. 5, 2015 (KR) .......... 10-2015-0017929
Mar. 31, 2015 (KR) .......... 10-2015-0045578

(51) Int. Cl.
*H01L 51/00* (2006.01)
*C07D 251/24* (2006.01)
*C09K 11/02* (2006.01)
*C09K 11/06* (2006.01)
*H01L 51/50* (2006.01)

(52) U.S. Cl.
CPC ........ *H01L 51/0067* (2013.01); *C07D 251/24* (2013.01); *C09K 11/025* (2013.01); *C09K 11/06* (2013.01); *H01L 51/0052* (2013.01); *H01L 51/0054* (2013.01); *H01L 51/0055* (2013.01); *H01L 51/0058* (2013.01);
(Continued)

(58) Field of Classification Search
None
See application file for complete search history.

(56) References Cited

U.S. PATENT DOCUMENTS 6,821,643 B1    11/2004  Hu et al.
9,502,669 B2    11/2016  Huh et al.
(Continued)

FOREIGN PATENT DOCUMENTS

CN    1702065 A    11/2005
CN    1867646 A    11/2006
(Continued)

OTHER PUBLICATIONS

Ren et al. (J. Phys. Chem. 2010, 114, p. 10374).*
(Continued)

*Primary Examiner* — Jay Yang
(74) *Attorney, Agent, or Firm* — Dentons US LLP

(57) ABSTRACT

The present specification provides a hetero-cyclic compound and an organic light emitting device comprising the same.

14 Claims, 2 Drawing Sheets

(52) U.S. Cl.
CPC ...... *H01L 51/0077* (2013.01); *H01L 51/5076* (2013.01); *H01L 51/5092* (2013.01)

(56) References Cited

U.S. PATENT DOCUMENTS

| | | | |
|---|---|---|---|
| 9,960,363 | B2 | 5/2018 | Eum et al. |
| 10,032,990 | B2 | 7/2018 | Lee et al. |
| 2003/0165715 | A1 | 9/2003 | Yoon et al. |
| 2003/0170490 | A1 | 9/2003 | Hu et al. |
| 2006/0135766 | A1 | 6/2006 | Hayoz et al. |
| 2007/0190355 | A1 | 8/2007 | Ikeda et al. |
| 2009/0162612 | A1 | 6/2009 | Hatwar et al. |
| 2010/0039026 | A1 | 2/2010 | Yang et al. |
| 2011/0037062 | A1 | 2/2011 | Fukumatsu et al. |
| 2011/0095282 | A1 | 4/2011 | Pflumm et al. |
| 2011/0121274 | A1 | 5/2011 | Parham et al. |
| 2011/0215308 | A1 | 9/2011 | Im et al. |
| 2011/0284831 | A1 | 11/2011 | Kaiser et al. |
| 2012/0286249 | A1* | 11/2012 | Lee ............... C07D 401/14 257/40 |
| 2013/0248830 | A1 | 9/2013 | Welsh et al. |
| 2014/0014927 | A1 | 1/2014 | Kim et al. |
| 2014/0061629 | A1 | 3/2014 | Murase et al. |
| 2014/0110694 | A1 | 4/2014 | Shin et al. |
| 2015/0123089 | A1 | 5/2015 | Lee et al. |
| 2015/0144897 | A1 | 5/2015 | Kang et al. |
| 2015/0243897 | A1 | 8/2015 | Montenegro et al. |
| 2015/0349270 | A1 | 12/2015 | Lee et al. |
| 2016/0072073 | A1 | 3/2016 | Lee et al. |
| 2016/0093808 | A1 | 3/2016 | Adamovich et al. |
| 2016/0248020 | A1 | 8/2016 | Ondari et al. |
| 2017/0005273 | A1 | 1/2017 | Hwang et al. |
| 2018/0053900 | A1 | 2/2018 | Eum et al. |

FOREIGN PATENT DOCUMENTS

| | | |
|---|---|---|
| CN | 1934213 A | 3/2007 |
| CN | 101656301 A | 2/2010 |
| CN | 101960637 A | 1/2011 |
| CN | 102077379 A | 5/2011 |
| CN | 102077384 A | 5/2011 |
| CN | 102201432 A | 9/2011 |
| CN | 102292841 A | 12/2011 |
| CN | 105392789 A | 3/2016 |
| EP | 2 463 351 A2 | 6/2012 |
| EP | 2749560 A1 | 7/2014 |
| EP | 2752902 A1 | 7/2014 |
| JP | 2012513668 A | 6/2012 |
| KR | 10-2000-0051826 A | 8/2000 |
| KR | 10-2011-0085174 A | 7/2011 |
| KR | 10-2011-0111093 A | 10/2011 |
| KR | 10-2011-0113469 A | 10/2011 |
| KR | 1020120138673 A | 12/2012 |
| KR | 10-2013-0115160 A | 10/2013 |
| KR | 1020130116041 A | 10/2013 |
| KR | 10-2014-0008126 A | 1/2014 |
| KR | 10-2015-0002072 A | 1/2015 |
| KR | 10-2011-0111093 A | 10/2017 |
| KR | 10-2011-0113469 A | 10/2017 |
| TW | 201522317 A | 6/2015 |
| WO | 2004/077885 A2 | 9/2004 |
| WO | 2007/029798 A1 | 3/2007 |
| WO | 2009/072587 A1 | 6/2009 |
| WO | 2010/072300 A1 | 7/2010 |
| WO | 2010/102706 A1 | 9/2010 |
| WO | 2010/126270 A1 | 11/2010 |
| WO | 2011/021520 A1 | 2/2011 |
| WO | 2012-150826 A1 | 11/2012 |
| WO | 2012/150826 A1 | 11/2012 |
| WO | 2012/173369 A2 | 12/2012 |
| WO | 2013077352 A1 | 5/2013 |
| WO | 2013-085243 A1 | 6/2013 |
| WO | 2013/085243 A1 | 6/2013 |
| WO | 2013/154378 A1 | 10/2013 |
| WO | 2013/180503 A1 | 12/2013 |
| WO | 2014023388 A1 | 2/2014 |
| WO | 2014185694 A1 | 11/2014 |
| WO | WO-2014/185694 A1 * | 11/2014 |
| WO | 2014200148 A1 | 12/2014 |
| WO | 2015005559 A1 | 1/2015 |
| WO | 2016/024728 A1 | 2/2016 |
| WO | 2016024728 A1 | 2/2016 |
| WO | 2016105141 A2 | 3/2016 |
| WO | 2016/105141 A2 | 6/2016 |

OTHER PUBLICATIONS

Reghu, Renji R., et al., "Glass forming donor-substituted s-triazines: Photophysical and electrochemical properties," Dyes and Pigments, 2013, 97, pp. 412-422.

Zhong, H., et al., "New Conjugated Triazine Based Molecular Materials for Application in Optoelectronic Devices: Design, Synthesis, and Properties," J. Phys. Chem., 2011, 115, pp. 2423-2427.

Hongliang Zhong et al., "New Conjugated Triazine Based Molecular Materials for Application in Optoelectronic Devices: Design, Synthesis, and Properties", The Journal of Physical Chemistry, C 2011,115, pp. 2423-2427.

Shijie Ren et al, "Star-Shaped Donor-Acceptor Conjugated Oligomers with 1,3,5-Triazine Cores: Convergent Synthesis and Multifunctional Properties," J. Phys. Chem, B 2010, 114, pp. 10374-10383.

International Search Report from PCT/KR2015/003292, dated Jun. 29, 2015.

International Search Report from PCT/KR2015/003291, dated Jun. 29, 2015.

International Search Report from PCT/KR2015/003255, dated Jun. 29, 2015.

International Search Report from PCT/KR2015/003256, dated Jul. 16, 2015.

International Search Report from PCT/KR2015/003273, dated Jul. 21, 2015.

Written Opinion of the ISA from PCT/KR2015/003292, dated Jun. 29, 2015.

Written Opinion of the ISA from PCT/KR2015/003291, dated Jun. 29, 2015.

Written Opinion of the ISA from PCT/KR2015/003255, dated Jun. 29, 2015.

Written Opinion of the ISA from PCT/KR2015/003256, dated Jul. 16, 2015.

Written Opinion of the ISA from PCT/KR2015/003273, dated Jul. 21, 2015.

Office Action issued by the Korean Patent Office in Appl'n No. 10-2015-0045586, dated Feb. 1, 2016.

Office Action issued by the Korean Patent Office in Appl'n No. 10-2015-0045586, dated Aug. 4, 2016.

Office Action issues by the Taiwanese Patent Office in Appl'n No. 104110794, dated Oct. 15, 2015.

* cited by examiner

[Figure 1]
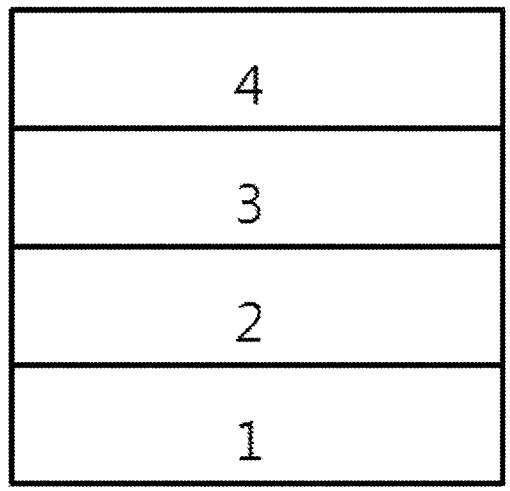
[Figure 2]
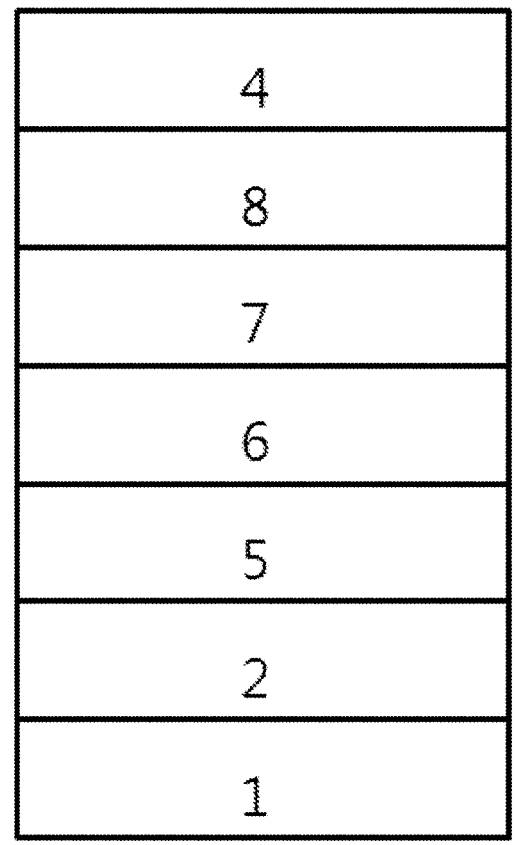

[Figure 3]
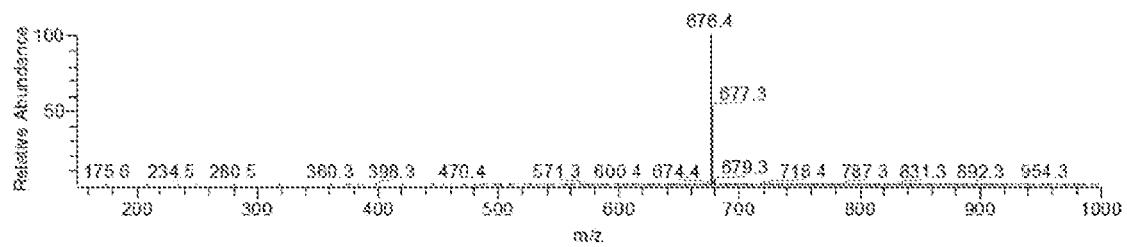

HETEROCYCLIC COMPOUND AND ORGANIC LIGHT-EMITTING ELEMENT COMPRISING SAME

TECHNICAL FIELD

This application is a National Stage Application of International Application No. PCT/KR2015/003292 filed on Apr. 2, 2015, which claims the benefit of Korean Patent Application No. 10-2014-0040818 filed on Apr. 4, 2014, Korean Patent Application No. 10-2015-0017929 filed on Feb. 5, 2015 and Korean Patent Application No. 10-2015-0045578 filed on Mar. 31, 2015, all of which are hereby incorporated by reference in their entirety for all purposes as if fully set forth herein.

The present specification relates to a hetero-cyclic compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DISCLOSURE

Technical Problem

The present specification describes a hetero-cyclic compound and an organic light emitting device comprising the same.

Technical Solution

An exemplary embodiment of the present specification provides a compound represented by the following Formula 1:

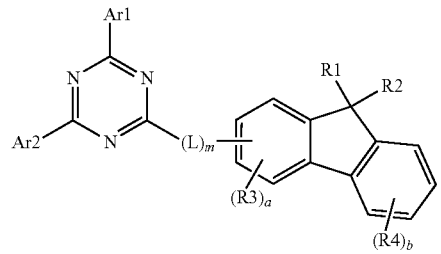

[Formula 1]

in Formula 1,

Ar1 and Ar2 are the same as each other, and a substituted or unsubstituted aryl group, L is a substituted or unsubstituted naphthylene; a substituted or unsubstituted phenanthrylene; or a substituted or unsubstituted fluorenylene, R1 and R2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted hetero-cyclic group, or may combine with an adjacent group to form a substituted or unsubstituted ring, R3 and R4 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted hetero-cyclic group, or may combine with an adjacent group to form a substituted or unsubstituted ring, m is an integer of 1 to 5, a is an integer of 0 to 3, and b is an integer of 0 to 4, and when m, a, and b are each 2 or more, the structures in the parenthesis are the same as or different from each other.

Further, an exemplary embodiment of the present specification provides: an organic light emitting device including: a first electrode; a second electrode provided to face the first electrode; and one or more organic material layers provided between the first electrode and the second electrode, in which one or more of the organic material layers includes the compound of Formula 1.

Advantageous Effects

The compound described in the present specification may be used as a material for the organic material layer of the organic light emitting device. The compound according to at least one exemplary embodiment may improve the efficiency and improve low driving voltage and/or service life characteristics in the organic light emitting device. In particular, the compound described in the present specification may be used as a material for hole injection, hole transport, hole injection and hole transport, light emission, electron transport, or electron injection. In addition, the compound described in the present specification may be used preferably as a material for a light emitting layer, electron transport, or electron injection, and more preferably as a material for electron transport or electron injection.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.

FIG. 3 illustrates an MS data result of Compound 1 prepared in the Examples.

MODE FOR INVENTION

Hereinafter, the present specification will be described in more detail.

An exemplary embodiment of the present specification provides the compound represented by Formula 1.

Examples of the substituents will be described below, but are not limited thereto.

In the present specification, the term "substituted or unsubstituted" means that a group is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group, or a substituent to which two or more substituents among the substituents exemplified above are linked is substituted or unsubstituted. For example, "the substituent to which two or more substituents are linked" may be a biphenyl group. That is, the biphenyl group may also be an aryl group, and may be interpreted as a substituent to which two phenyl groups are linked.

According to an exemplary embodiment of the present specification, the term "substituted or unsubstituted" may preferably mean that a group is unsubstituted or substituted with one or more substituents selected from the group consisting of deuterium; an alkyl group; an alkoxy group; and an aryl group.

According to an exemplary embodiment of the present specification, the compound represented by Formula 1 may be unsubstituted or substituted with at least one deuterium. Further, according to an exemplary embodiment of the present specification, a substituent of the compound represented by Formula 1 may be unsubstituted or substituted with at least one deuterium.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the number of carbon atoms of the carbonyl group is not particularly limited, but is preferably 1 to 40. Specifically, the carbonyl group may be a compound having the following structure, but is not limited thereto.

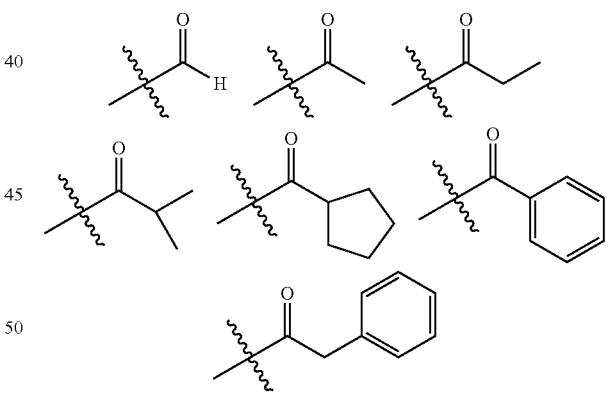

In the present specification, in the ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structure, but is not limited thereto.

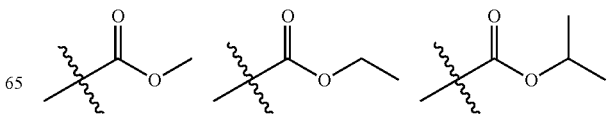

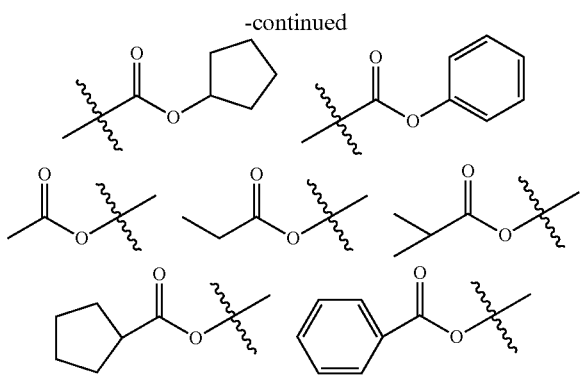

In the present specification, the number of carbon atoms of the imide group is not particularly limited, but is preferably 1 to 25. Specifically, the imide group may be a compound having the following structure, but is not limited thereto.

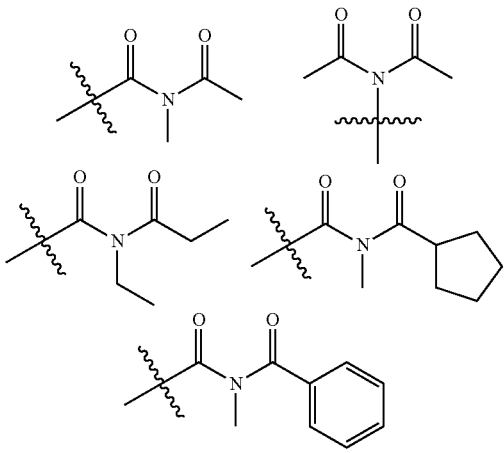

In the present specification, the silyl group may be represented by a formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be represented by a formula of —BRR'R", and R, R', and R" may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of the halogen group include fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but has preferably 3 to 60 carbon atoms, and according to an exemplary embodiment, the number of carbon atoms of the cycloalkyl group is 3 to 30. According to yet another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including the two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic hetero-cyclic group or a polycyclic hetero-cyclic group. The heteroarylamine group including the two or more hetero-cyclic groups may include a monocyclic hetero-cyclic group, a polycyclic hetero-cyclic group, or both a monocyclic hetero-cyclic group and a polycyclic hetero-cyclic group. In the present specification, the arylheteroarylamine group means an amine group substituted with an aryl group and a hetero-cyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a polycyclic aryl group. The arylphosphine group including the two or more aryl groups may include a monocyclic aryl group, a polycyclic aryl group, or both a monocyclic aryl group and a polycyclic aryl group.

In the present specification, examples of the arylamine group mean a substituted or unsubstituted monocyclic diarylamine group, a substituted or unsubstituted polycyclic diarylamine group, or a substituted or unsubstituted monocyclic and polycyclic diarylamine group.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, the fluorenyl group may be substituted, and two substituents may combine with each other to form a spiro structure.

When the fluorenyl group is substituted, the fluorenyl group may be

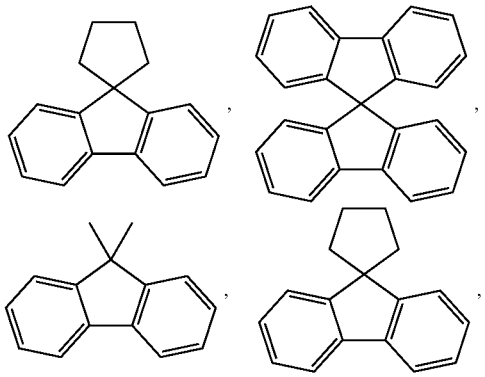

and the like. However, the fluorenyl group is not limited thereto.

In the present specification, the hetero-cyclic group is a hetero-cyclic group including one or more of N, O, P, S, Si, and Se as a hetero atom, and the number of carbon atoms thereof is not particularly limited, but is preferably 2 to 60. Examples of the hetero-cyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described hetero-cyclic group may be applied to a heteroaryl group except for an aromatic group.

In the present specification, the description on the above-described aryl group may be applied to an aryl group of an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the description on the above-described alkyl group may be applied to an alkyl group of an alkylthioxy group, an alkylsulfoxy group, an aralkyl group, an aralkylamine group, an alkylaryl group, and an alkylamine group.

In the present specification, the description on the above-described hetero-cyclic group may be applied to a heteroaryl group of a heteroaryl group, a heteroarylamine group, and an arylheteroarylamine group.

In the present specification, the description on the above-described alkenyl group may be applied to an alkenyl group of an aralkenyl group.

In the present specification, the description on the above-described aryl group may be applied to an arylene except for a divalent arylene group.

In the present specification, the description on the above-described hetero-cyclic group may be applied to a heteroarylene except for a divalent heteroarylene group.

In the present specification, the meaning of combining with an adjacent group to form a ring means of combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

In the present specification, the aliphatic hydrocarbon ring means a ring composed only of carbon and hydrogen atoms as a ring which is not an aromatic group.

In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Formula 1 may be represented by any one of the following Formulae 2 to 4.

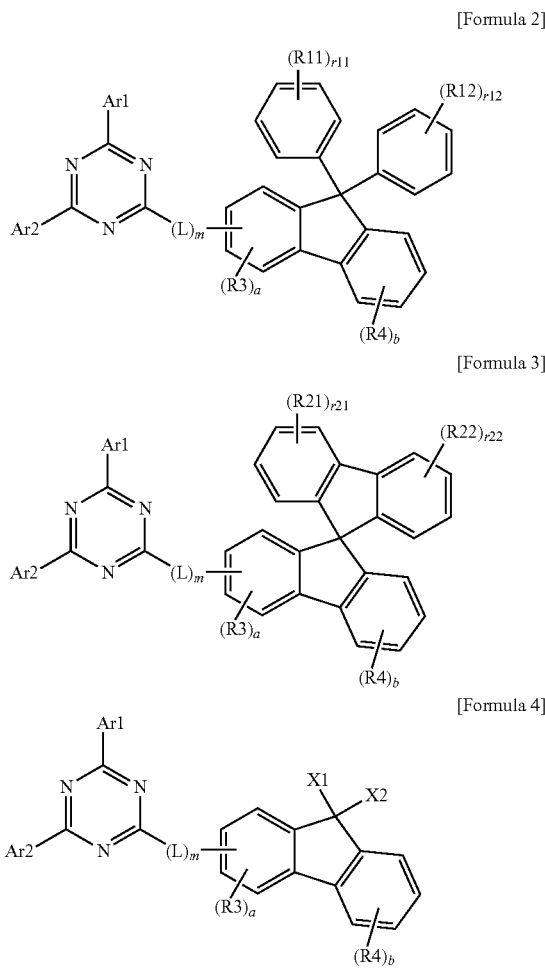

[Formula 2]

[Formula 3]

[Formula 4]

In Formulae 2 to 4, the definition of Ar1, Ar2, L, R3, R4, a, b, and m is the same as defined in Formula 1, the definition of R11, R12, R21, and R22 is the same as the definition of R3 and R4, X1 and X2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted phosphineoxide group; or may combine with an adjacent group to form a substituted or unsubstituted ring, r11 and r12 are the same as or different from each other, and each independently an integer of 0 to 5, r21 and r22 are the same as or different from each other, and each independently an integer of 0 to 4, and when r11, r12, r21, and r22 are each 2 or more, the structures in the parenthesis are the same as or different from each other.

According to an exemplary embodiment of the present specification, Formula 1 may be represented by any one of the following Formulae 5 to 8.

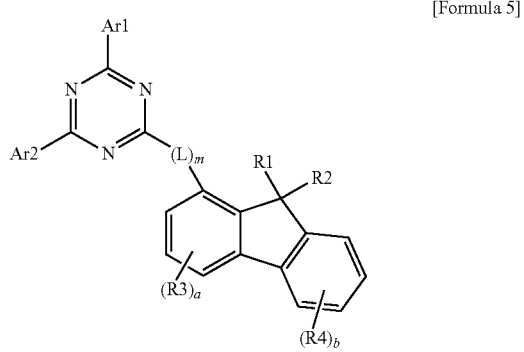

[Formula 5]

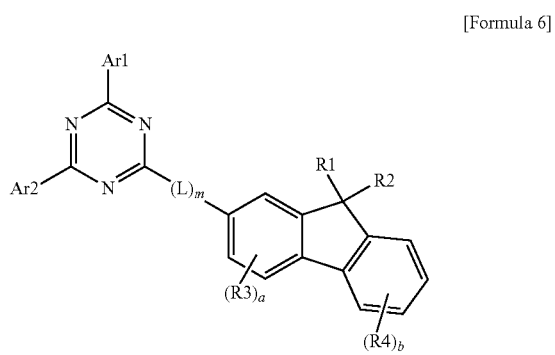

[Formula 6]

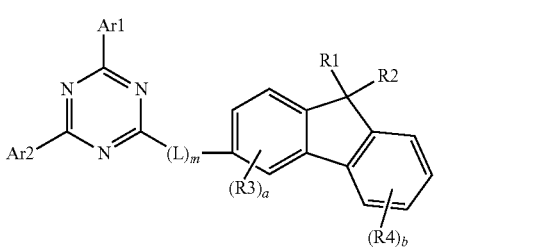

[Formula 7]

-continued

[Formula 8]

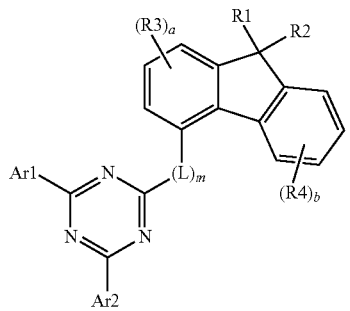

In Formulae 5 to 8, the definition of Ar1, Ar2, L, R1 to R4, m, a, and b is the same as defined in Formula 1.

According to an exemplary embodiment of the present specification, Formula 2 may be represented by any one of the following Formulae 2-1 to 2-4.

[Formula 2-1]

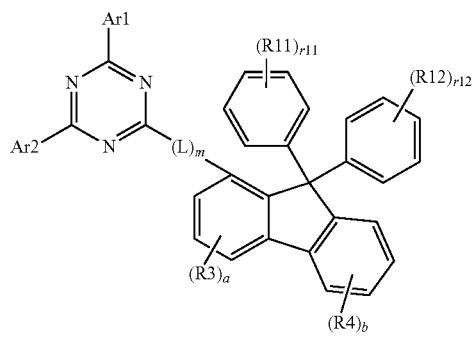

[Formula 2-2]

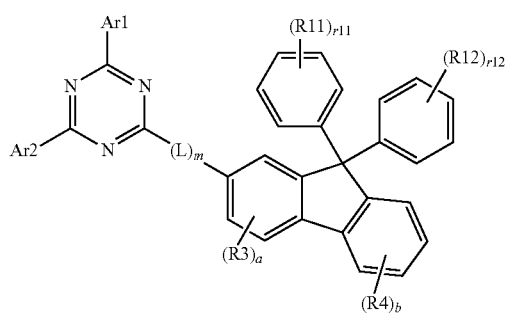

[Formula 2-3]

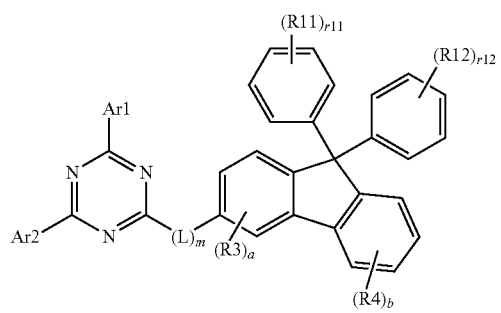

[Formula 2-4]

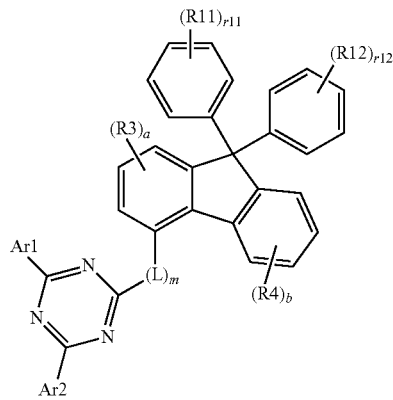

In Formulae 2-1 to 2-4, the definition of Ar1, Ar2, L, R3, R4, a, and b is the same as defined in Formula 1, the definition of R11, R12, r11, and r12 is the same as defined in Formula 2.

According to an exemplary embodiment of the present specification, Formula 3 may be represented by any one of the following Formulae 3-1 to 3-4.

[Formula 3-1]

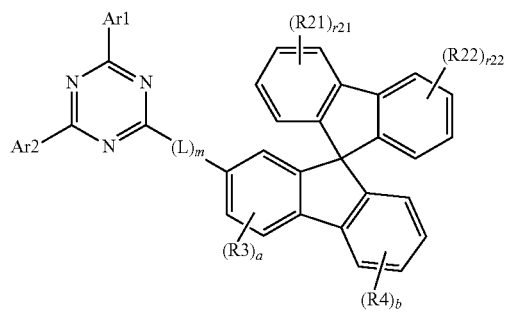

[Formula 3-2]

-continued

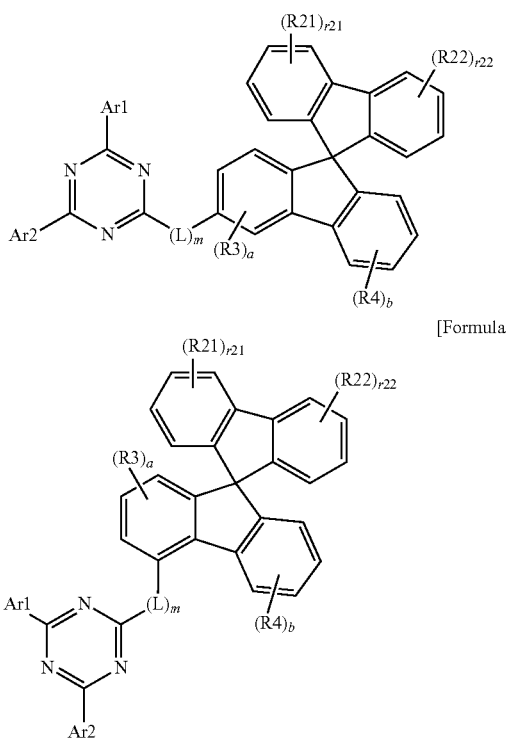

[Formula 3-3]

[Formula 3-4]

In Formulae 3-1 to 3-4, the definition of Ar1, Ar2, L, R3, R4, a, and b is the same as defined in Formula 1, and the definition of R21, R22, r21, and r22 is the same as defined in Formula 3.

According to an exemplary embodiment of the present specification, X1 and X2 are the same as or different from each other, and each independently a substituted or unsubstituted alkyl group.

According to an exemplary embodiment of the present specification, X1 and X2 are the same as or different from each other, and each independently an alkyl group.

According to an exemplary embodiment of the present specification, X1 and X2 are a methyl group.

According to an exemplary embodiment of the present specification, Ar1 and Ar2 are the same as each other, and a substituted or unsubstituted aryl group.

According to an exemplary embodiment of the present specification, Ar1 and Ar2 are the same as each other, and a substituted or unsubstituted monocyclic to tricyclic aryl group.

According to an exemplary embodiment of the present specification, Ar1 and Ar2 are the same as each other, and a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar1 and Ar2 are the same as each other, and a phenyl group; a biphenyl group; a naphthyl group; or a phenanthryl group.

According to an exemplary embodiment of the present specification, R1 and R2 are the same as or different from each other, and each independently hydrogen; deuterium; a halogen group; a nitrile group; a nitro group; a hydroxy group; a carbonyl group; an ester group; an imide group; an amino group; a silyl group; a boron group; an alkyl group; a cycloalkyl group; an alkoxy group; an aryloxy group; an alkylthioxy group; an arylthioxy group; an alkylsulfoxy group; an arylsulfoxy group; an alkenyl group; an aralkyl group; an aralkenyl group; an alkylaryl group; an alkylamine group; an aralkylamine group; a heteroarylamine group; an arylamine group; an arylheteroarylamine group; an arylphosphine group; a phosphineoxide group; an aryl group; or a hetero-cyclic group, or may combine with an adjacent group to form a ring.

According to an exemplary embodiment of the present specification, R1 and R2 are the same as or different from each other, and each independently a substituted or unsubstituted alkyl group; or a substituted or unsubstituted monocyclic to tricyclic aryl group, or combine with each other to form a substituted or unsubstituted ring.

According to an exemplary embodiment of the present specification, R1 and R2 are the same as or different from each other, and each independently a substituted or unsubstituted alkyl group; or a substituted or unsubstituted phenyl group, or combine with each other to form a substituted or unsubstituted ring.

According to an exemplary embodiment of the present specification, R1 and R2 are the same as or different from each other, and each independently hydrogen; deuterium; halogen; an alkyl group; or an aryl group, which is unsubstituted or substituted with one or more substituents selected from the group consisting of deuterium, an alkyl group, and an alkoxy group, or combine with each other to form a ring.

According to an exemplary embodiment of the present specification, R1 and R2 are the same as or different from each other, and each independently an alkyl group; and an aryl group, or combine with each other to form a ring.

According to an exemplary embodiment of the present specification, R1 and R2 are the same as or different from each other, and each independently an alkyl group; or a phenyl group, or combine with each other to form a ring.

According to an exemplary embodiment of the present specification, R1 and R2 are the same as or different from each other, and each independently a methyl group; or a phenyl group, or combine with each other to form a ring.

According to an exemplary embodiment of the present specification, R3 and R4 are the same as or different from each other, and each independently hydrogen; deuterium; a halogen group; a nitrile group; a nitro group; a hydroxy group; a carbonyl group; an ester group; an imide group; an amino group; a silyl group; a boron group; an alkyl group; a cycloalkyl group; an alkoxy group; an aryloxy group; an alkylthioxy group; an arylthioxy group; an alkylsulfoxy group; an arylsulfoxy group; an alkenyl group; an aralkyl group; an aralkenyl group; an alkylaryl group; an alkylamine group; an aralkylamine group; an arylphosphine group; a phosphineoxide group; an aryl group; or a hetero-cyclic group.

According to an exemplary embodiment of the present specification, R3 and R4 are the same as or different from each other, and each independently hydrogen; deuterium; a substituted or unsubstituted alkyl group; a substituted or unsubstituted alkoxy group; or a substituted or unsubstituted aryl group.

According to an exemplary embodiment of the present specification, R3 and R4 are the same as or different from each other, and each independently hydrogen; deuterium; a halogen group; an alkyl group, which is unsubstituted or substituted with one or more substituents selected from the group consisting of deuterium, a halogen group, an alkyl group, and an aryl group; an alkoxy group, which is unsubstituted or substituted with one or more substituents selected from the group consisting of deuterium, a halogen group, an alkyl group, and an aryl group; or an aryl group, which is unsubstituted or substituted with one or more substituents selected from the group consisting of deuterium, a halogen group, an alkyl group, and an aryl group.

According to an exemplary embodiment of the present specification, R3 and R4 are the same as or different from each other, and each independently hydrogen; deuterium; an alkyl group; an alkoxy group; or an aryl group.

According to an exemplary embodiment of the present specification, R3 is hydrogen, and R4 is hydrogen; deuterium; a substituted or unsubstituted alkyl group; a substituted or unsubstituted alkoxy group; or a substituted or unsubstituted aryl group.

According to an exemplary embodiment of the present specification, R3 is hydrogen, and R4 is hydrogen; deuterium; an alkyl group; an alkoxy group; or an aryl group.

According to an exemplary embodiment of the present specification, R3 and R4 are the same as or different from each other, and each independently hydrogen; deuterium; a halogen group; or an alkyl group.

According to an exemplary embodiment of the present specification, R3 and R4 are hydrogen.

According to an exemplary embodiment of the present specification, R4 is hydrogen; or a substituted or unsubstituted fluorenyl group.

According to an exemplary embodiment of the present specification, R4 is hydrogen; or a fluorenyl group, which is unsubstituted or substituted with an alkyl group or an aryl group.

According to an exemplary embodiment of the present specification, R4 is hydrogen; or a fluorenyl group, which is unsubstituted or substituted with an alkyl group or a phenyl group.

According to an exemplary embodiment of the present specification, R4 is hydrogen; or a fluorenyl group, which is unsubstituted or substituted with an alkyl group.

According to an exemplary embodiment of the present specification, R4 is hydrogen.

According to an exemplary embodiment of the present specification, R3 is hydrogen.

According to an exemplary embodiment of the present specification, L is a naphthylene, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; a phenanthrylene, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group; or a fluorenylene, which is unsubstituted or substituted with one or more substituents selected from the group consisting of deuterium, a halogen group, a nitrile group, a nitro group, a hydroxy group, a carbonyl group, an ester group, an imide group, an amino group, a phosphineoxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group.

According to an exemplary embodiment of the present specification, L is naphthylene; phenanthrylene; or fluorenylene substituted with an alkyl group.

According to an exemplary embodiment of the present specification, L may be any one selected from the following structures.

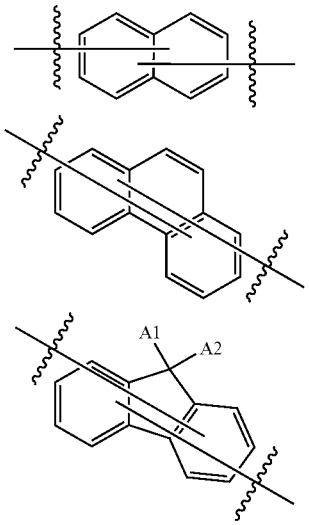

In the structural formulae,

A1 and A2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted hetero-cyclic group, or may combine with an adjacent group to form a substituted or unsubstituted ring, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, L may be any one selected from the following structures.

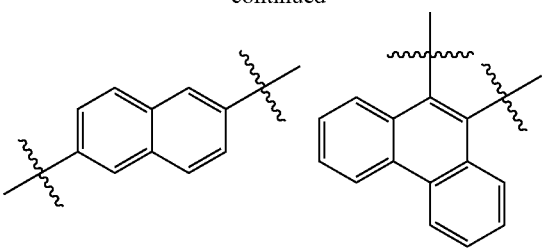
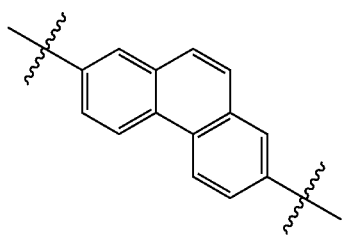
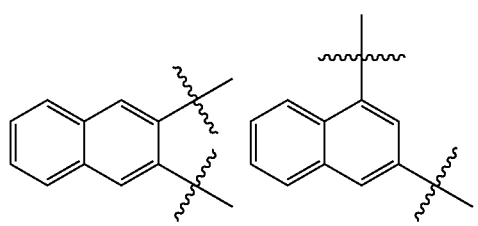
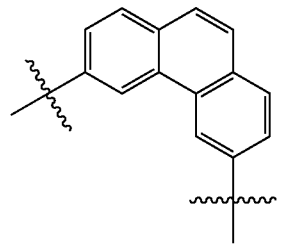
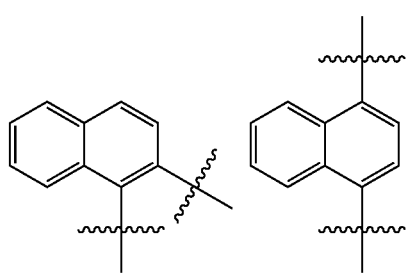
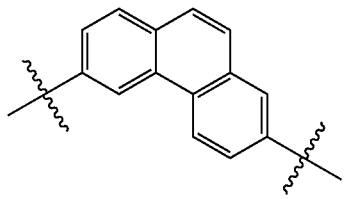
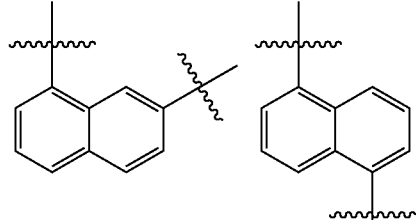
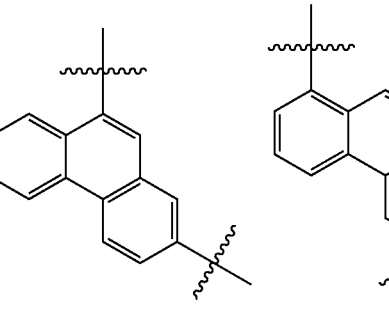
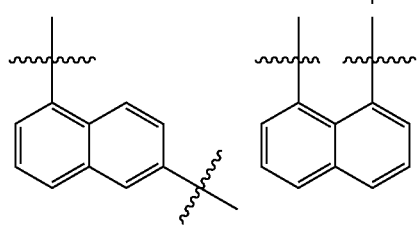
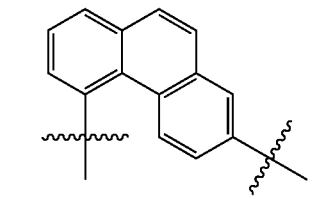
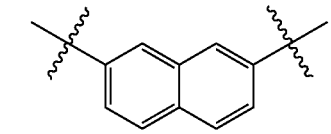
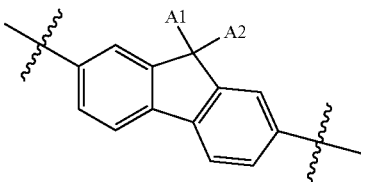

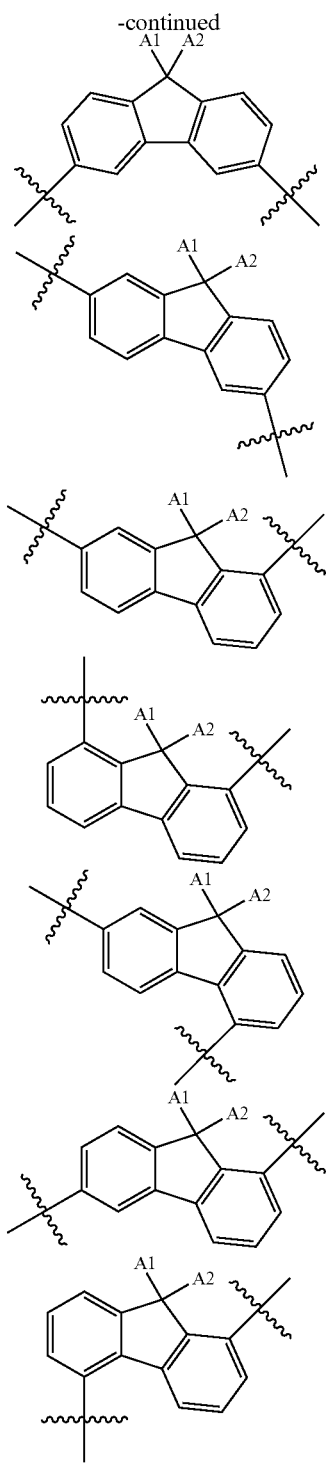

In the structural formulae,

A1 and A2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted hetero-cyclic group, or may combine with an adjacent group to form a substituted or unsubstituted ring, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, the

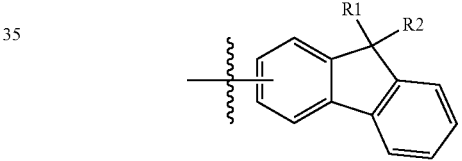

moiety may be any one selected from the following structures.

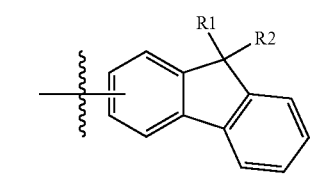

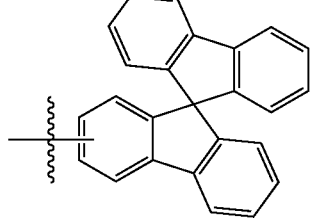

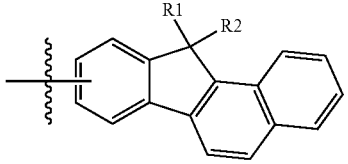

-continued

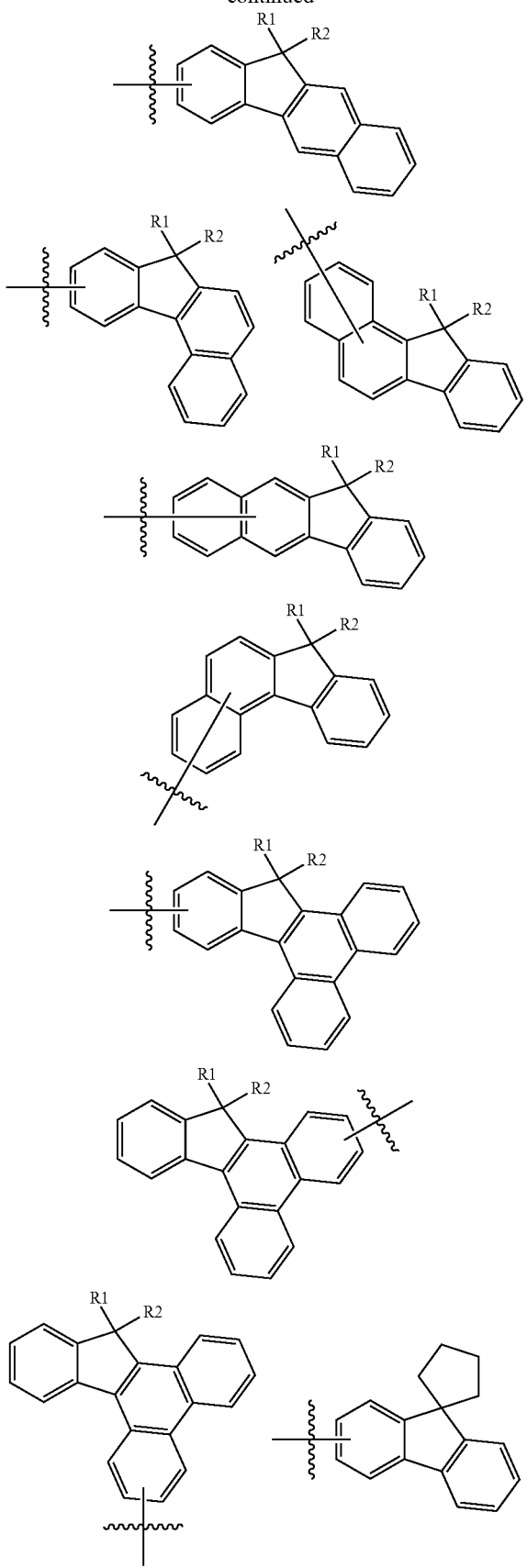

In the structures, the definition of R1 and R2 is the same as defined in Formula 1, and the structures may be unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

According to an exemplary embodiment of the present specification, m is 1.

According to an exemplary embodiment of the present specification, the compound of Formula 1 may be any one selected from the following compounds.

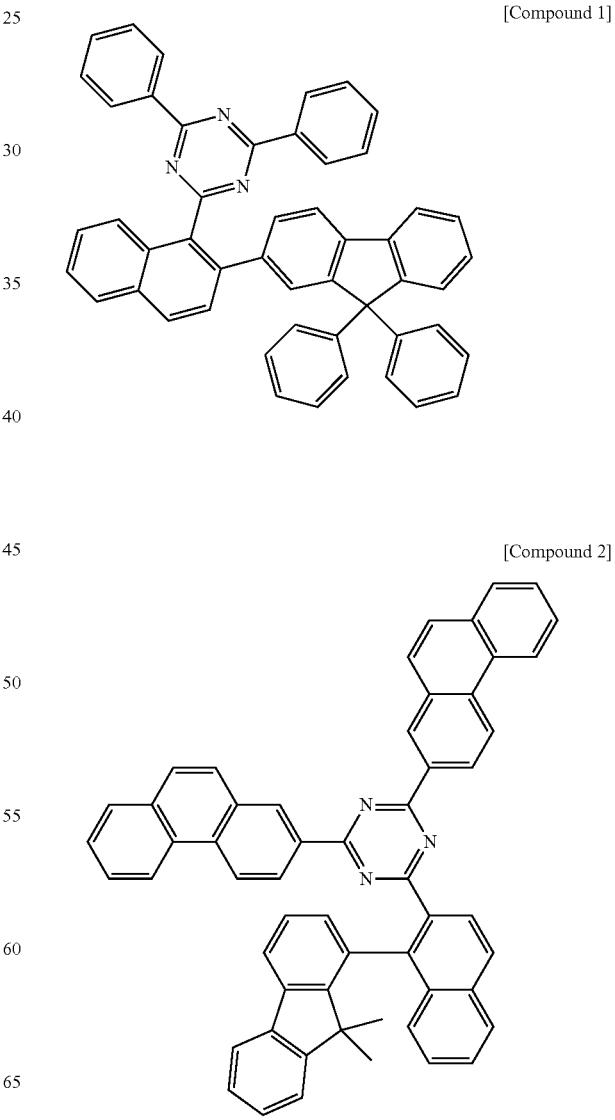

[Compound 3]
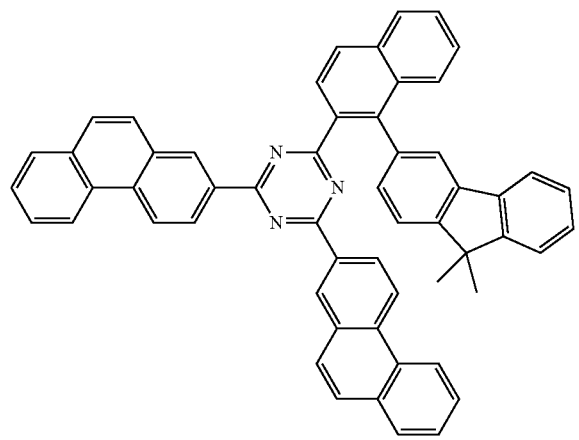
[Compound 4]
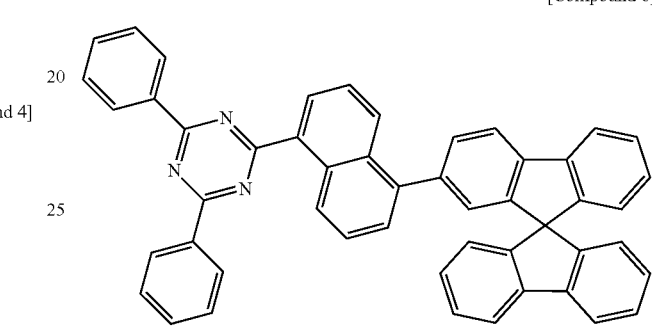
[Compound 5]
[Compound 6]
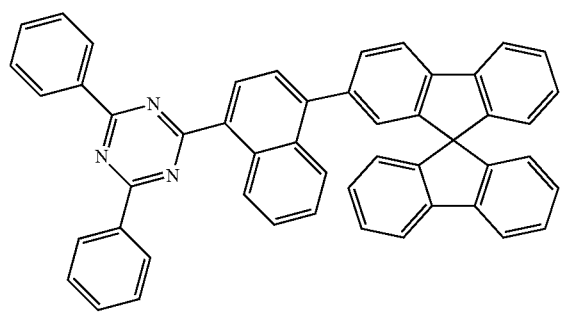
[Compound 7]
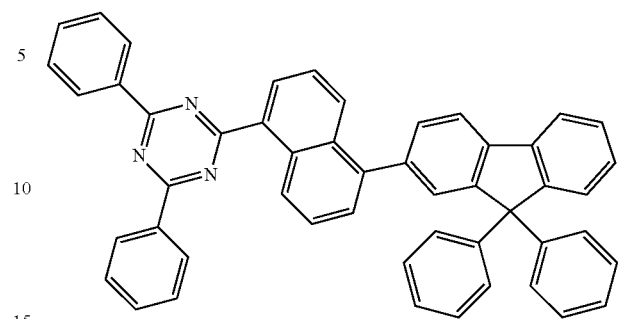
[Compound 8]
[Compound 9]
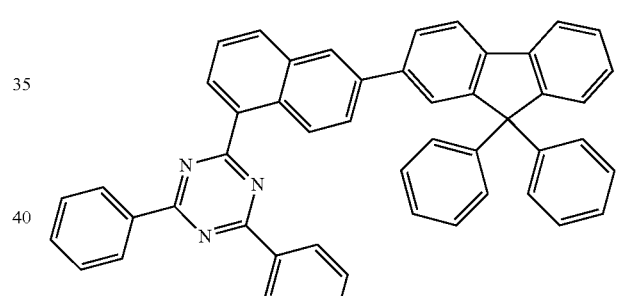
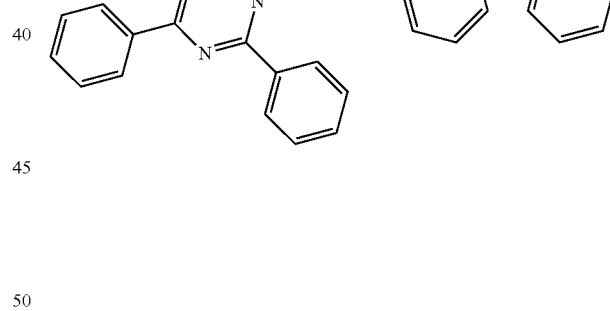
[Compound 10]
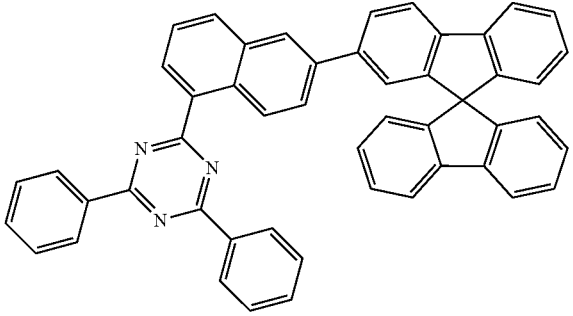

[Compound 11]
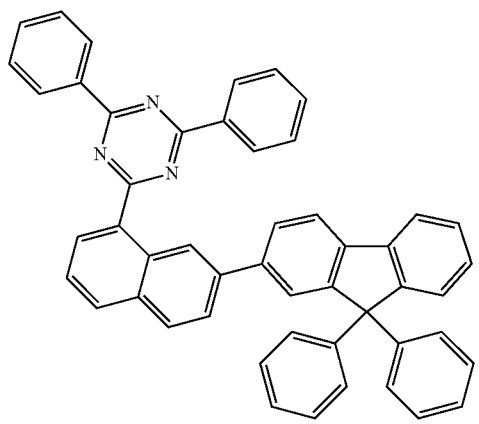
[Compound 12]
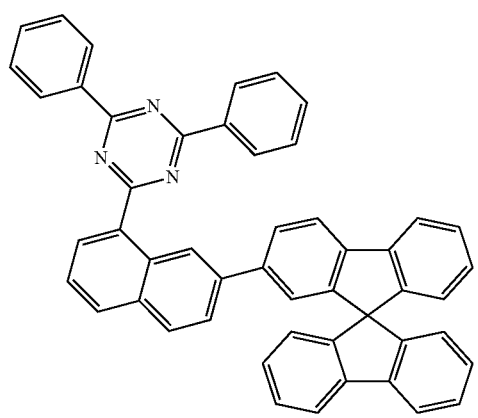
[Compound 13]
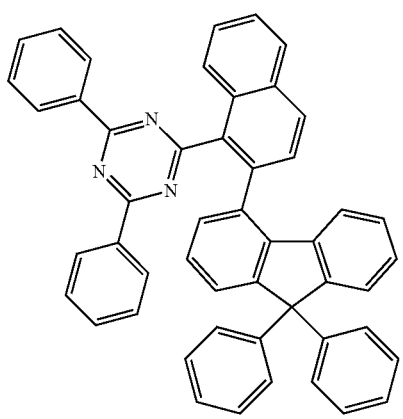
[Compound 14]
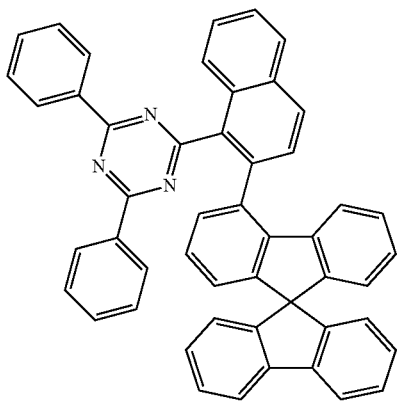
[Compound 15]
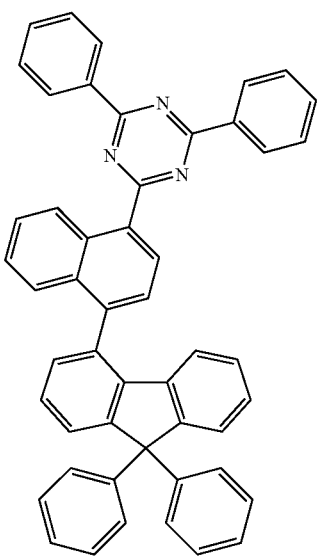
[Compound 16]
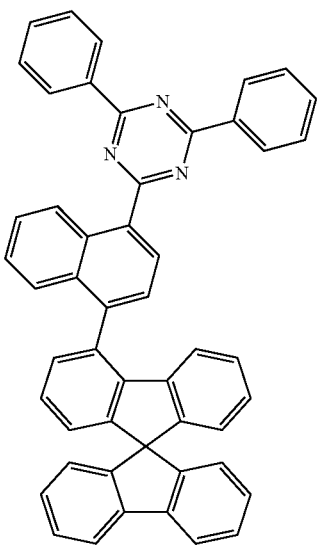

[Compound 17]
[Compound 18]
[Compound 19]
[Compound 20]
[Compound 21]
[Compound 22]
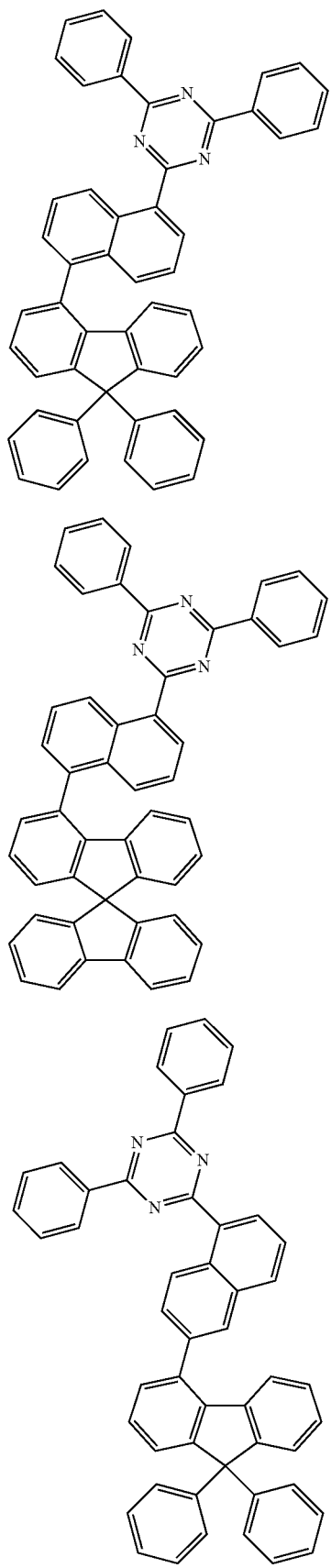
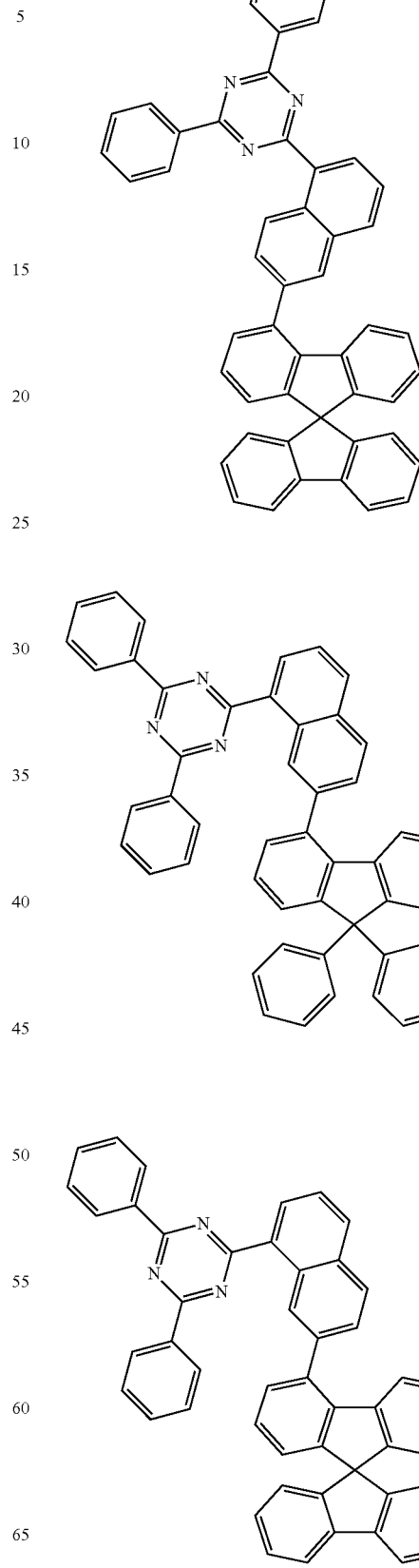

[Compound 23]
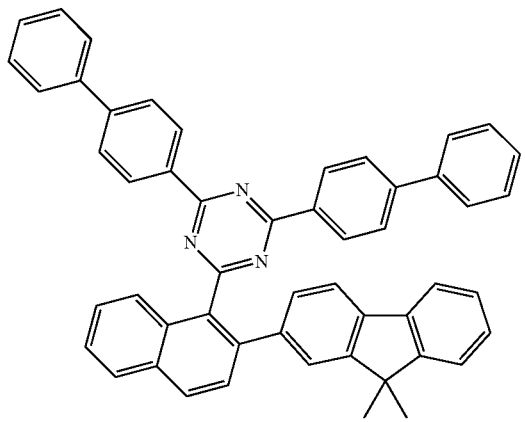
[Compound 24]
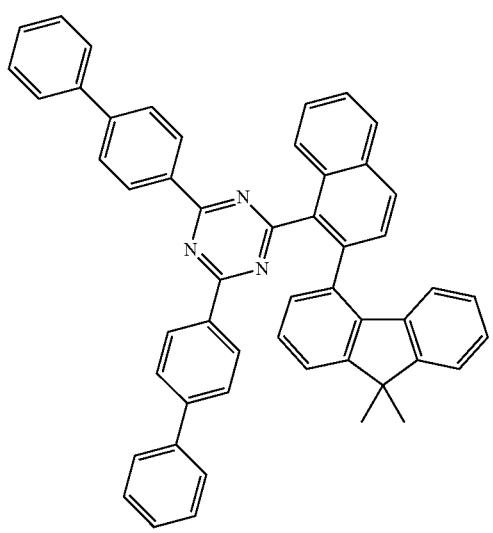
[Compound 25]
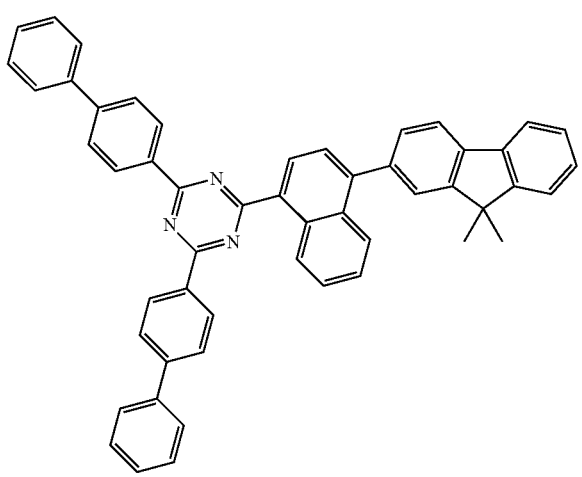
[Compound 26]
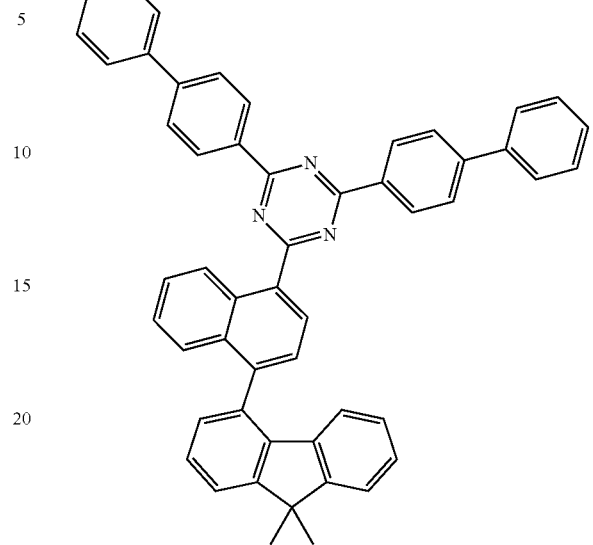
[Compound 27]
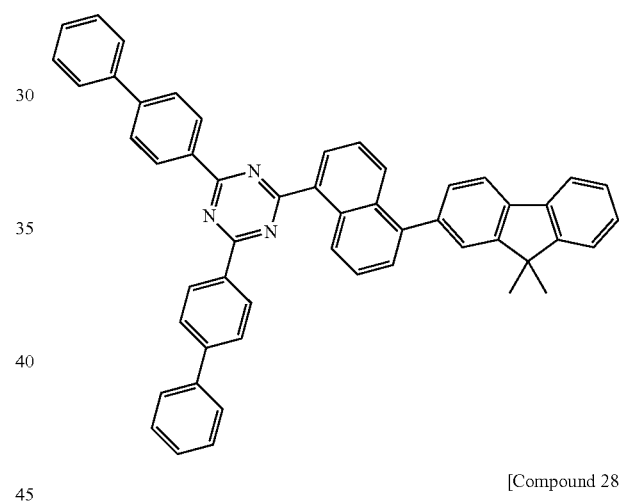
[Compound 28]
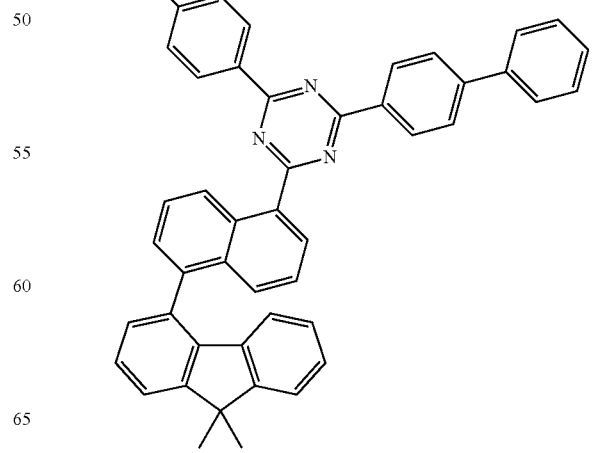

[Compound 29]
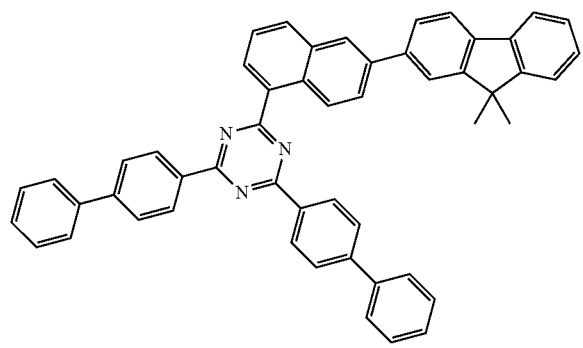
[Compound 30]
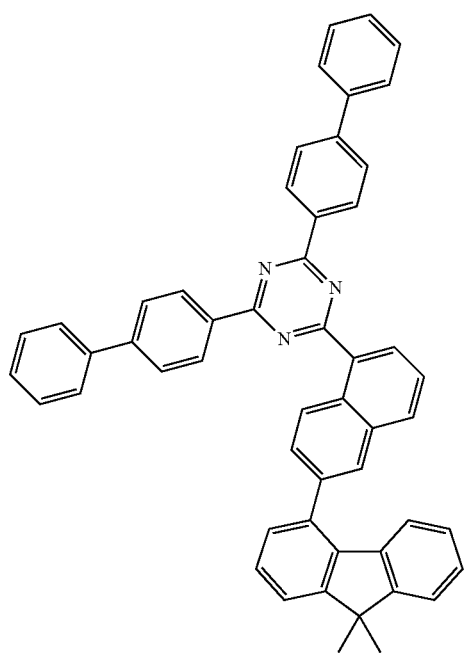
[Compound 31]
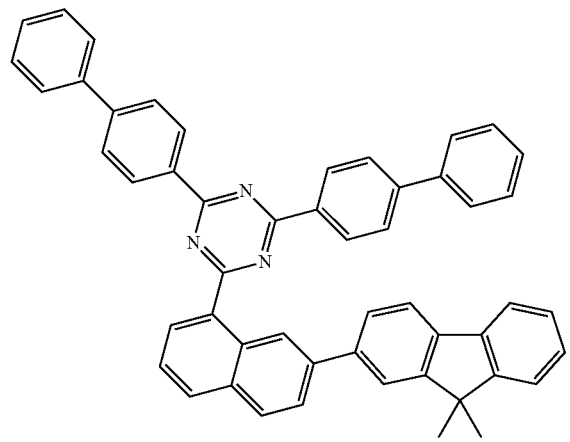
[Compound 32]
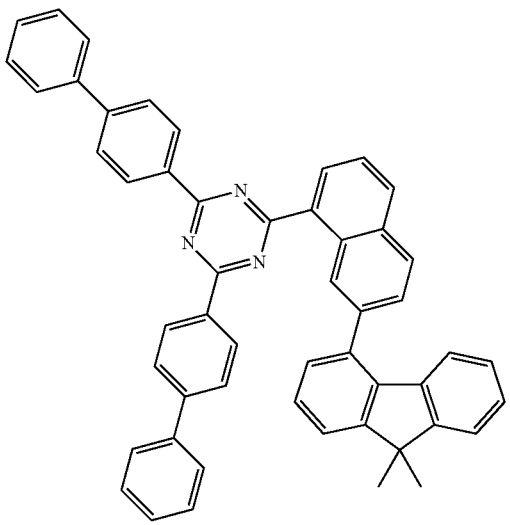
[Compound 33]
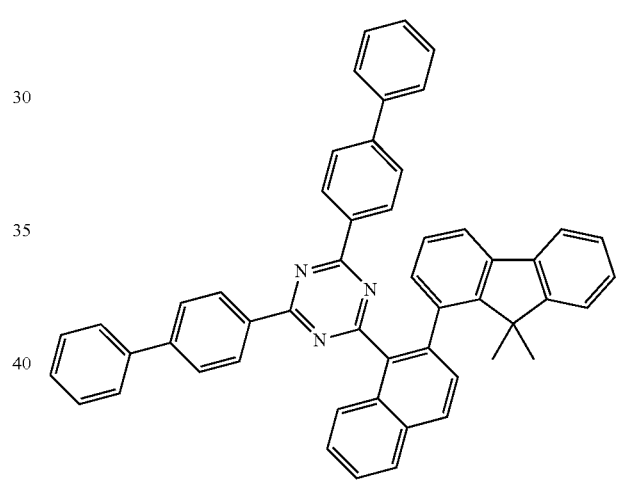
[Compound 34]
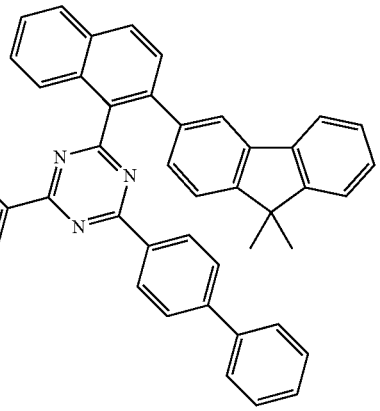

[Compound 35]
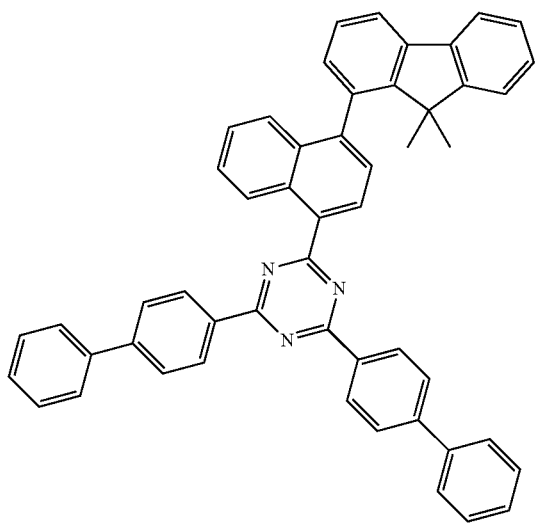
[Compound 36]
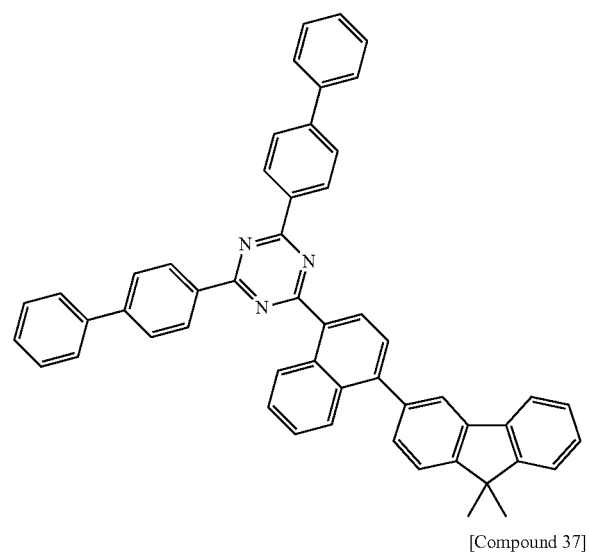
[Compound 37]
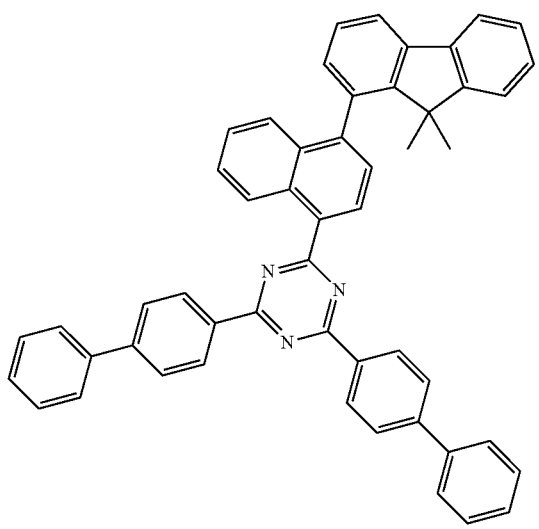
[Compound 38]
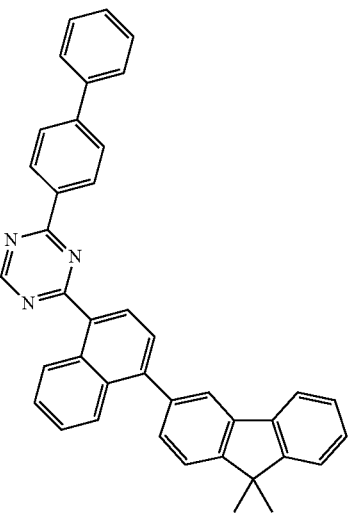
[Compound 39]
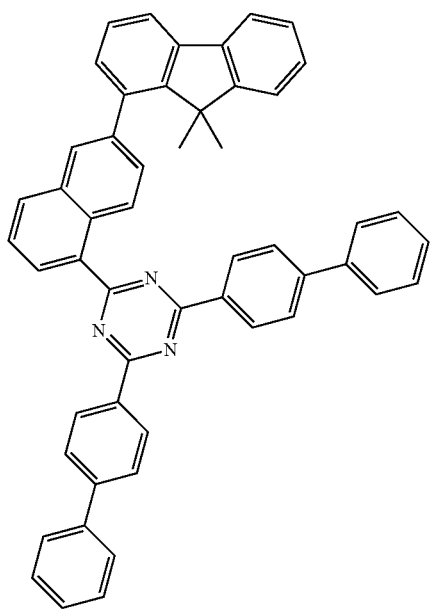
[Compound 40]

[Compound 41]
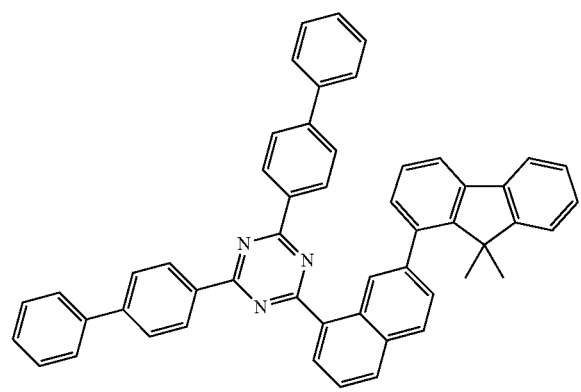
[Compound 44]
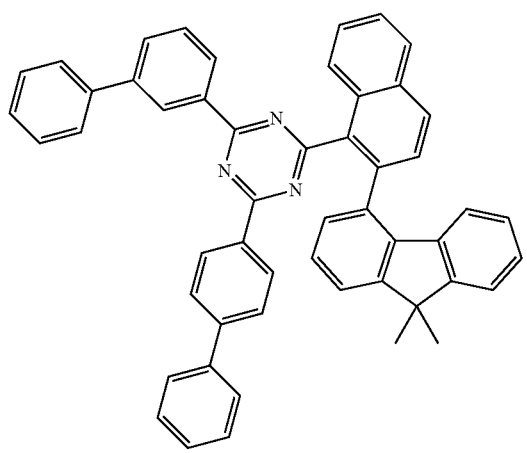
[Compound 42]
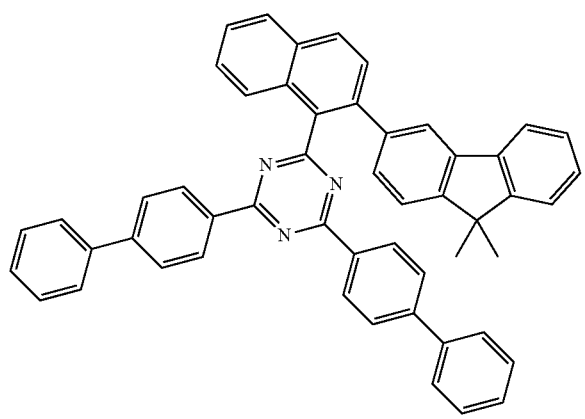
[Compound 45]
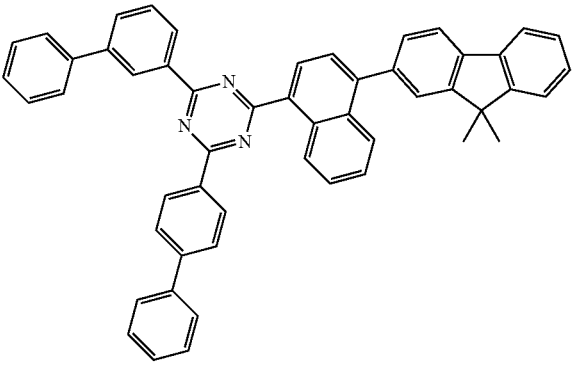
[Compound 43]
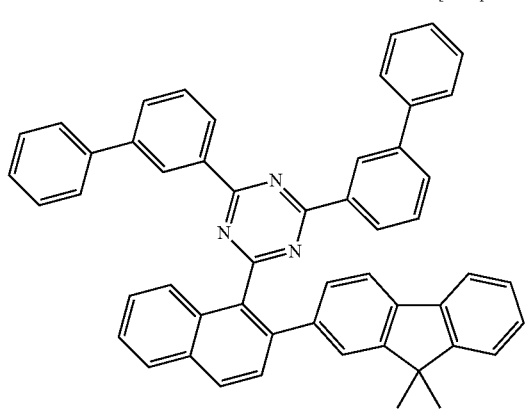
[Compound 46]
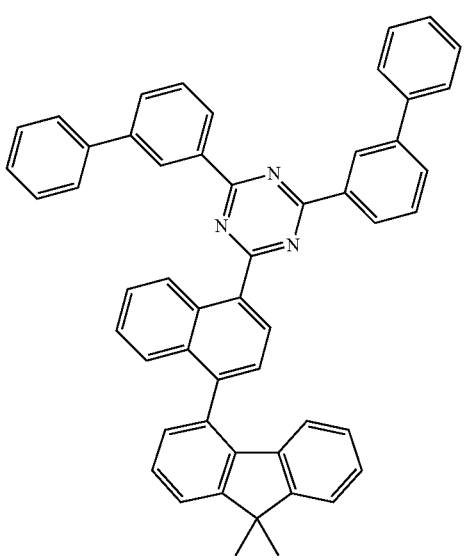

[Compound 47]
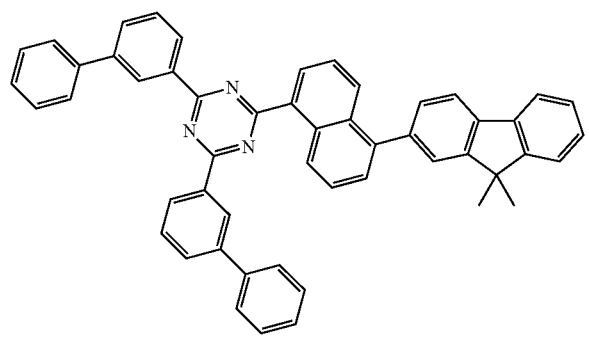
[Compound 48]
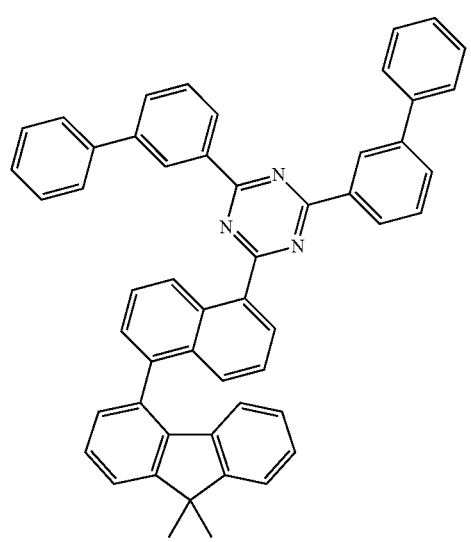
[Compound 49]
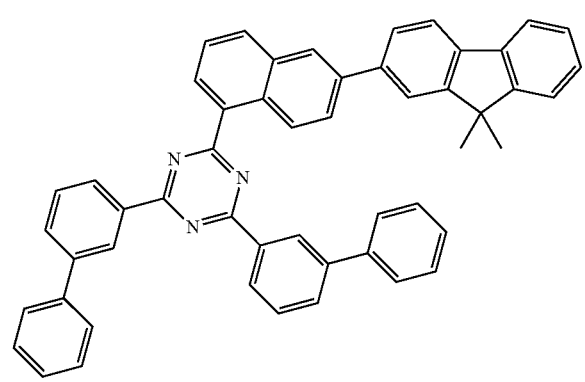
[Compound 50]
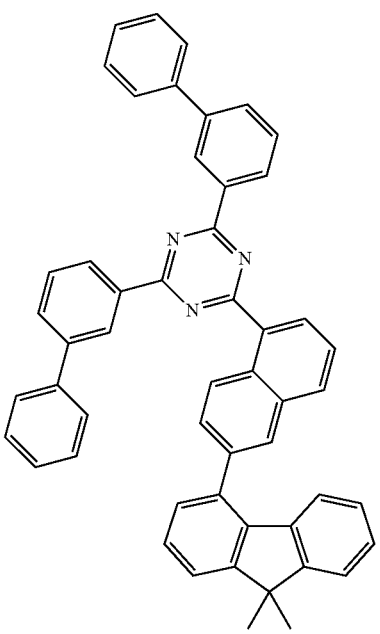
[Compound 51]
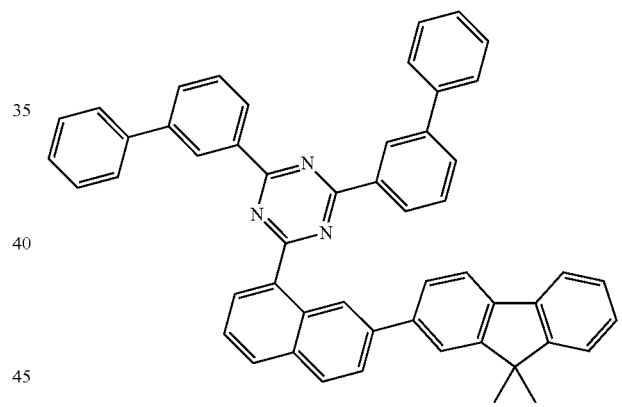
[Compound 52]
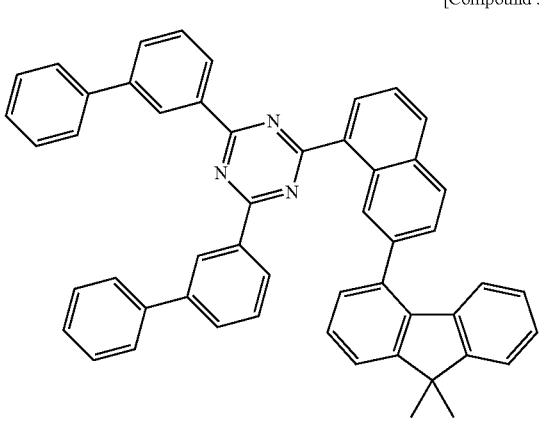

[Compound 53]
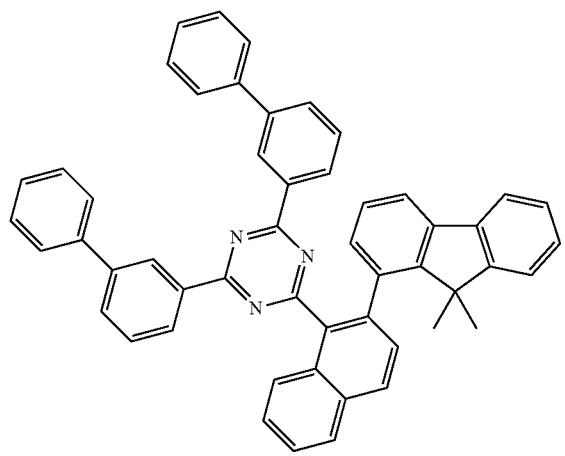
[Compound 54]
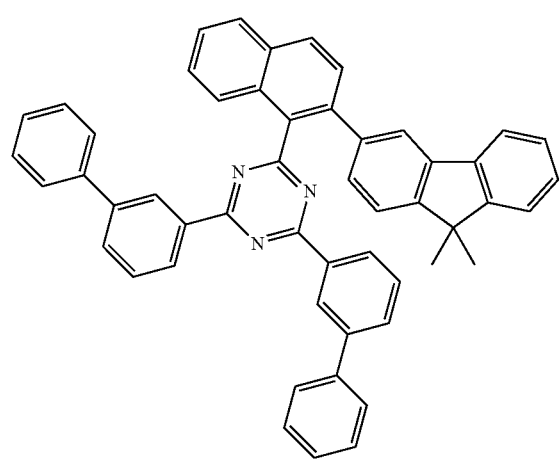
[Compound 55]
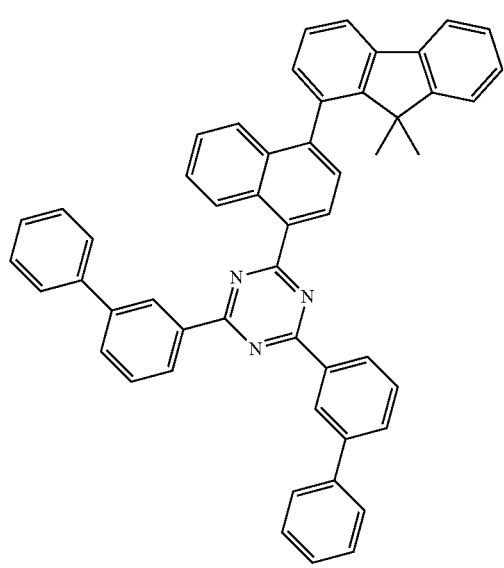
[Compound 56]
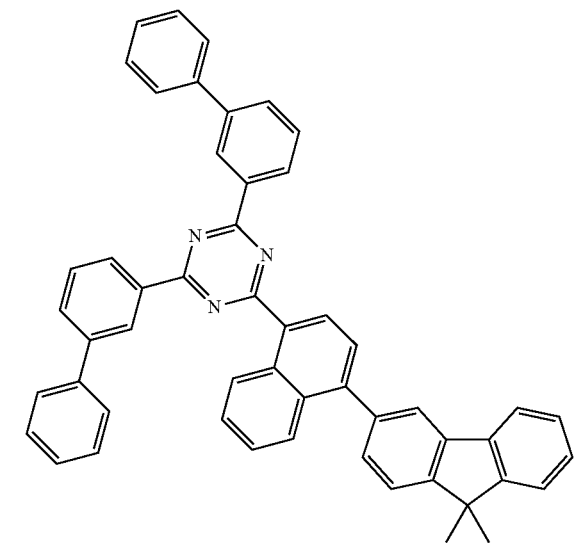
[Compound 57]
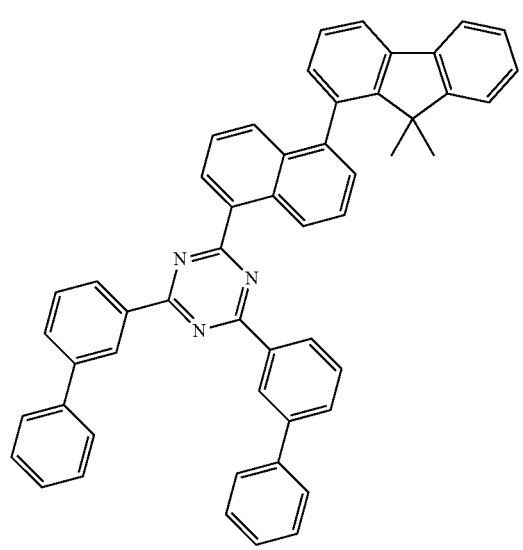

[Compound 58]
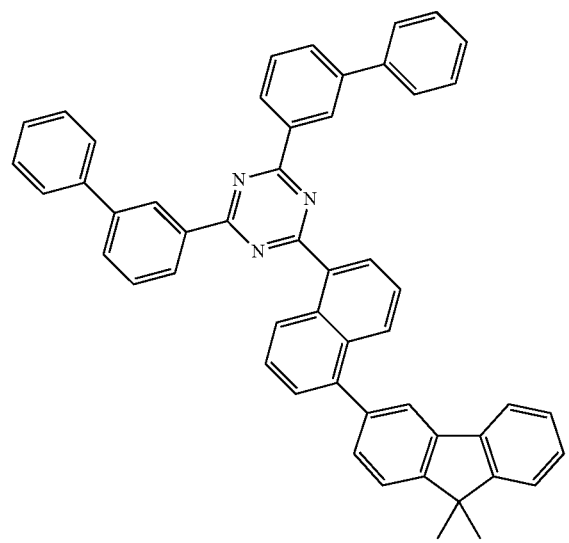
[Compound 59]
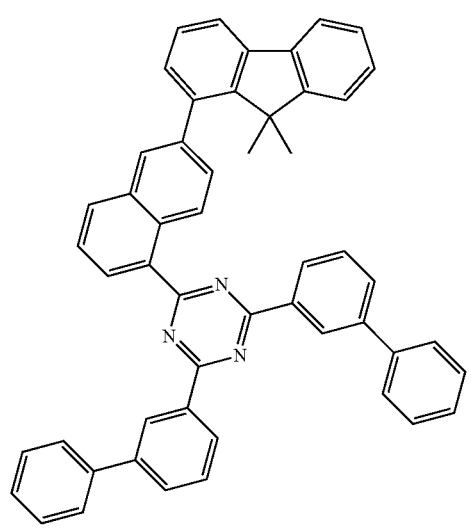
[Compound 60]
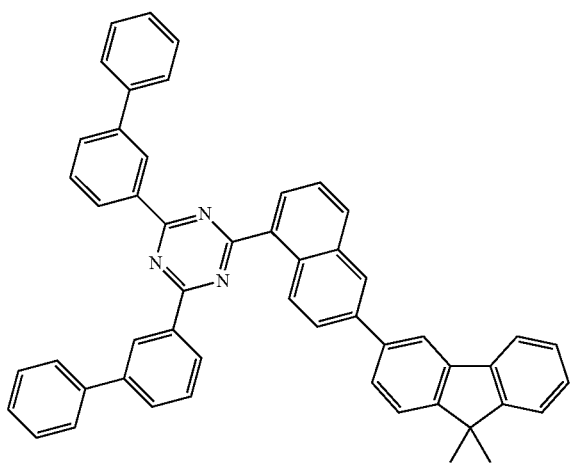
[Compound 61]
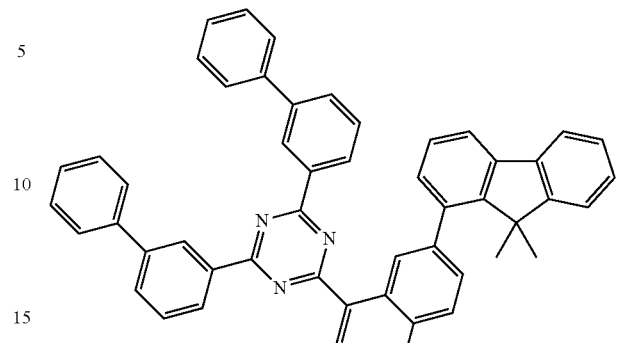
[Compound 62]
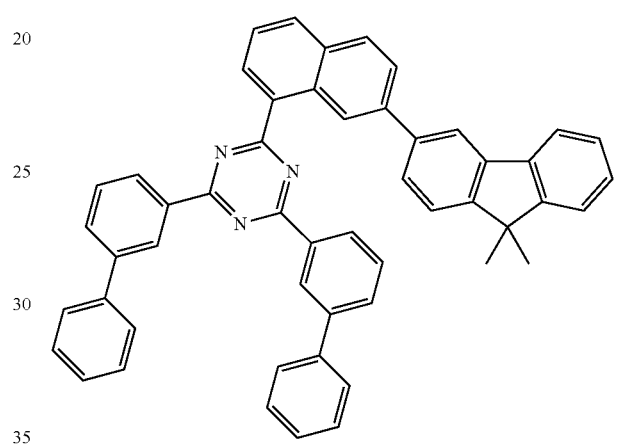
[Compound 63]
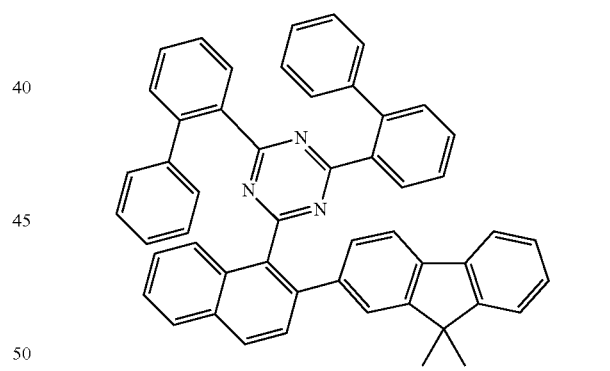
[Compound 64]
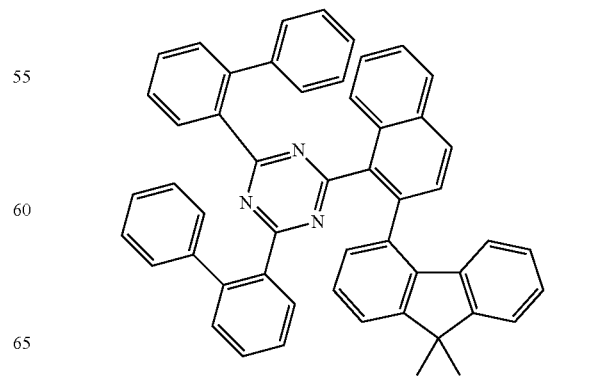

[Compound 65]
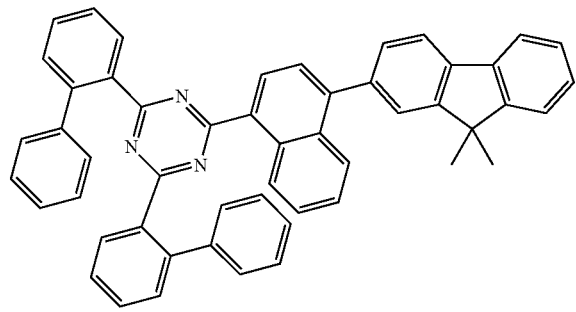
[Compound 68]
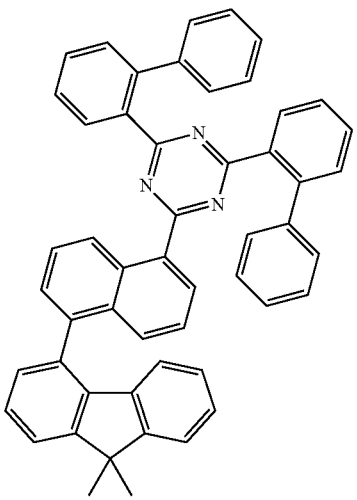
[Compound 66]
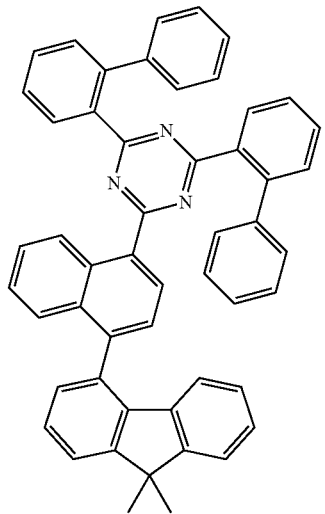
[Compound 69]
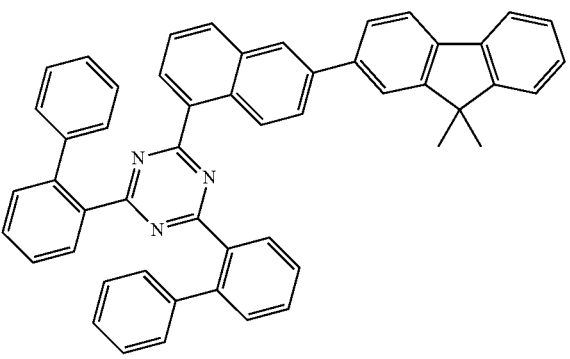
[Compound 67]
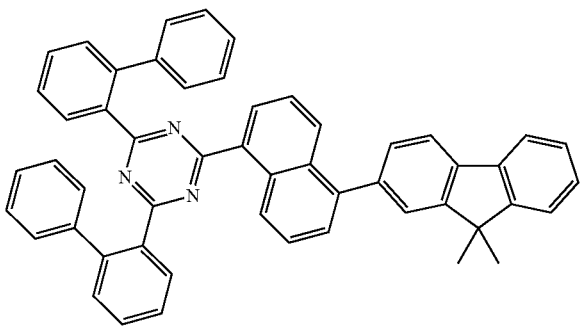
[Compound 70]
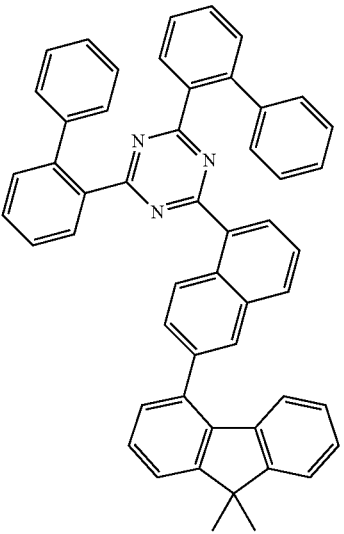

[Compound 71]
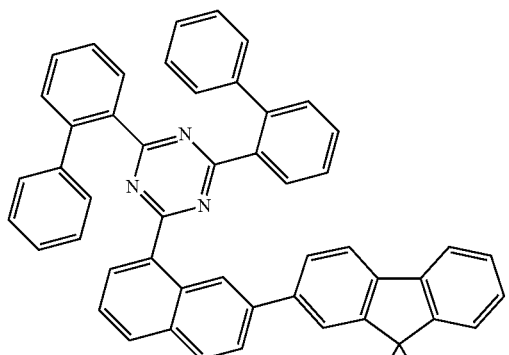
[Compound 72]
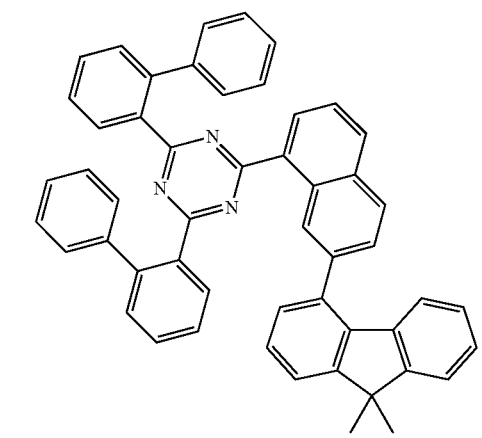
[Compound 73]
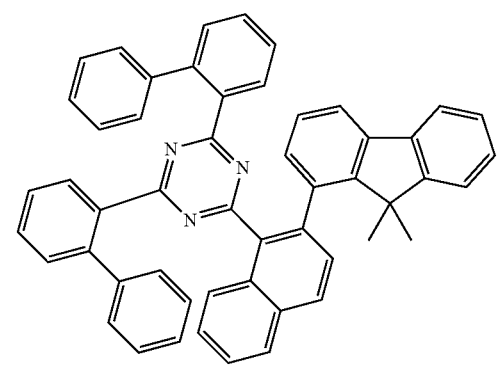
[Compound 74]
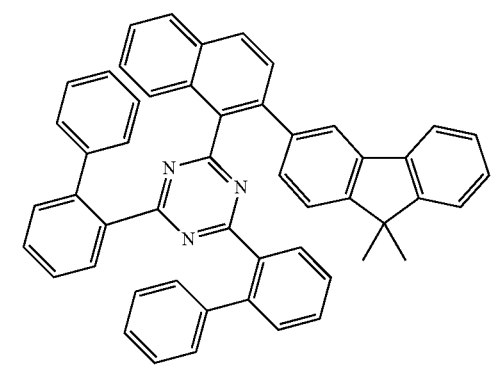
[Compound 75]
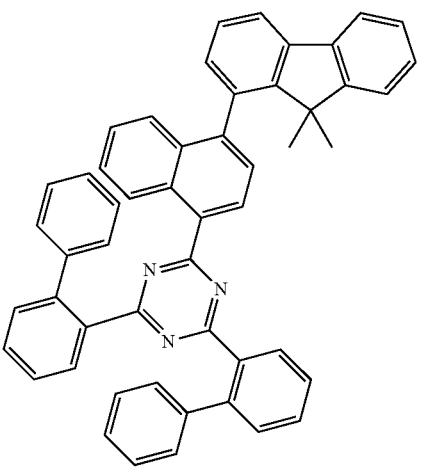
[Compound 76]
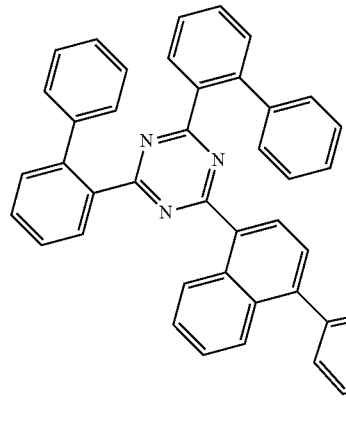
[Compound 77]
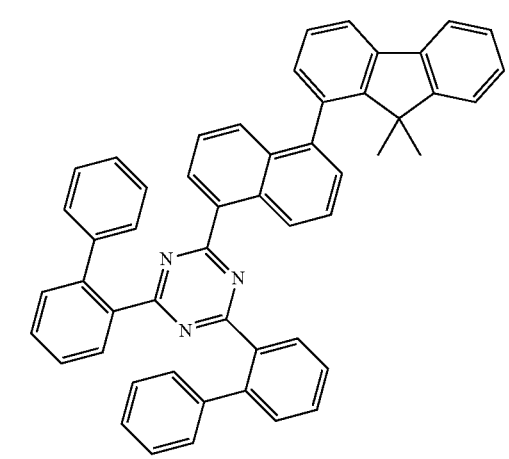

[Compound 78]
[Compound 79]
[Compound 80]
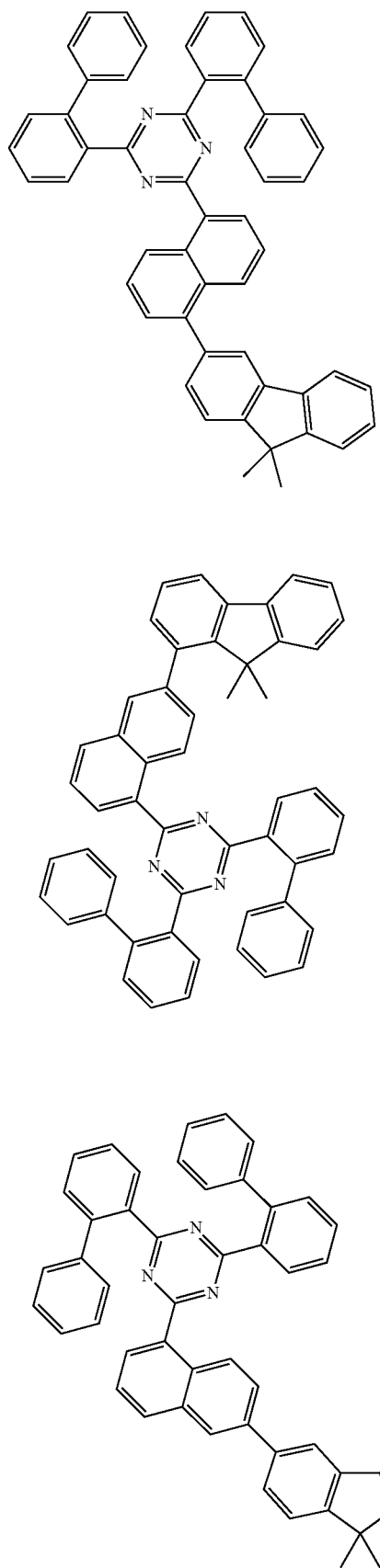
[Compound 81]
[Compound 82]
[Compound 83]
[Compound 84]
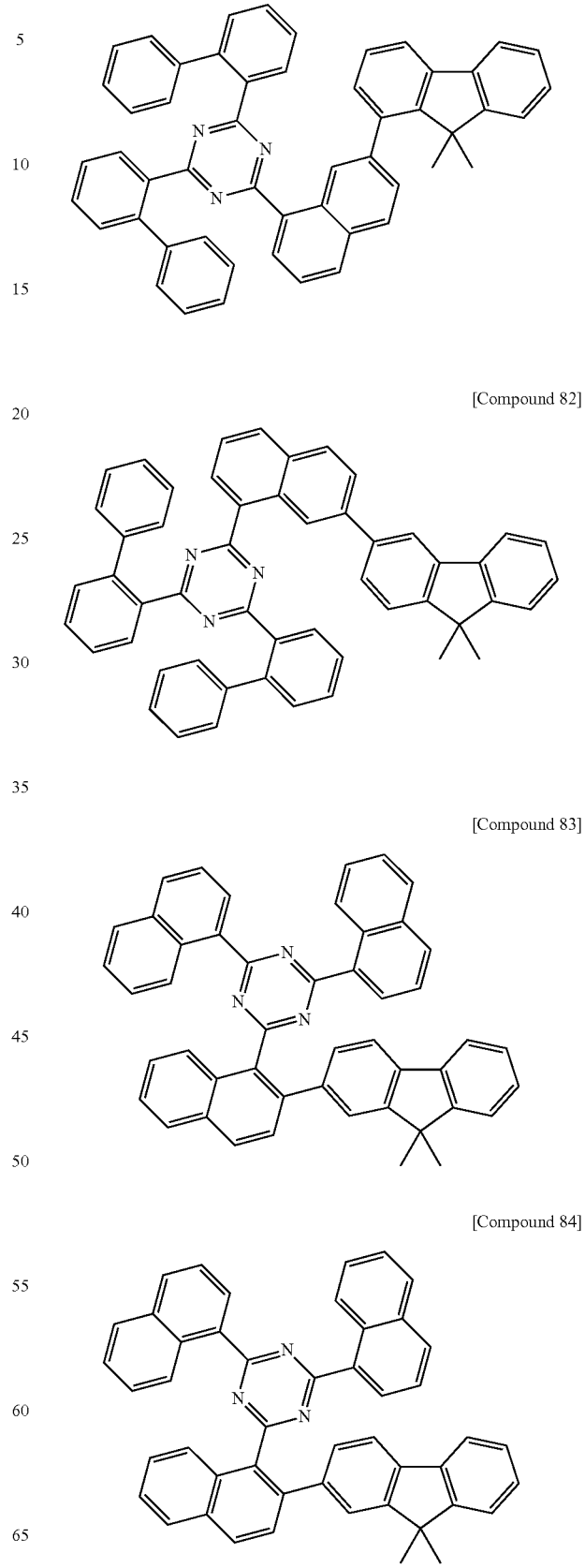

[Compound 85]
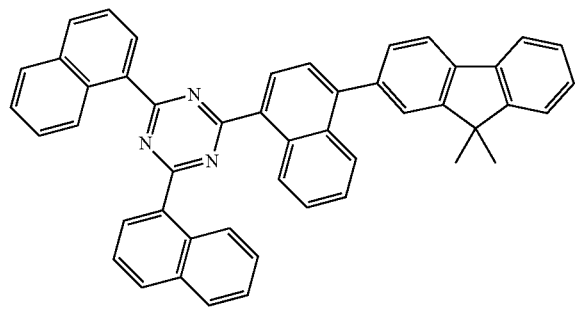
[Compound 86]
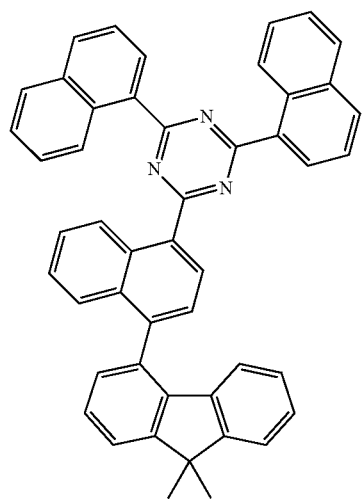
[Compound 87]
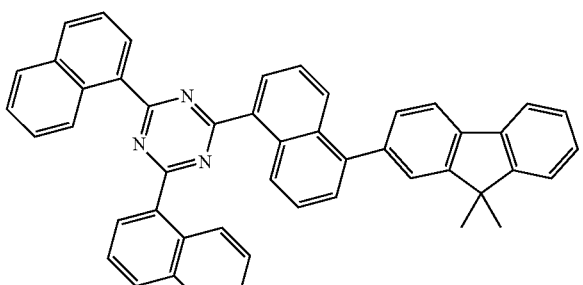
[Compound 88]
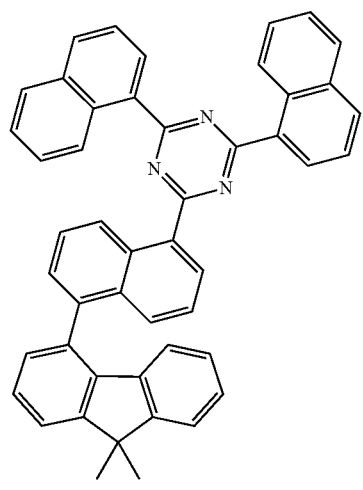
[Compound 89]
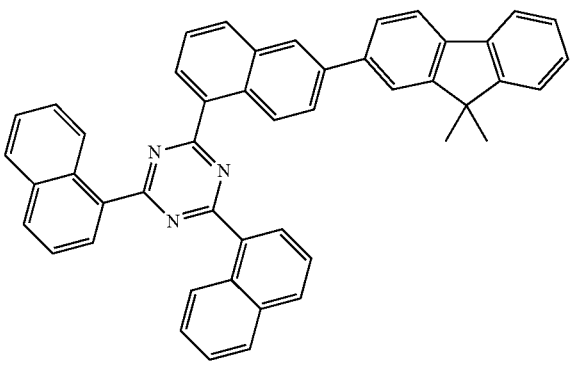
[Compound 90]
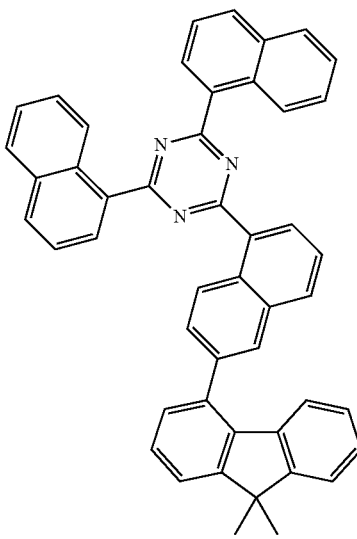
[Compound 91]
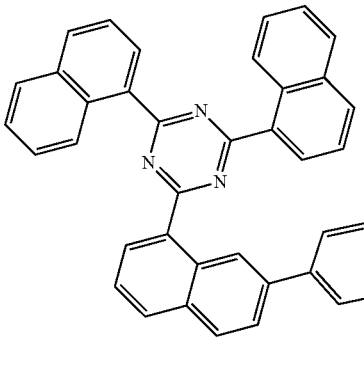

[Compound 92]
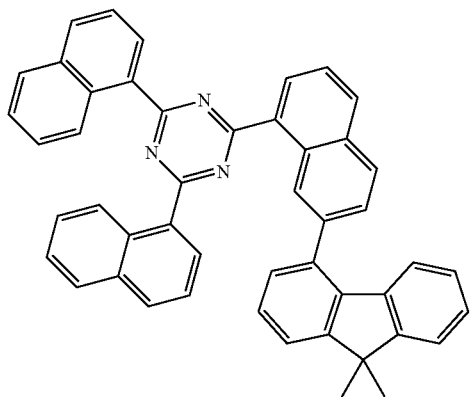
[Compound 93]
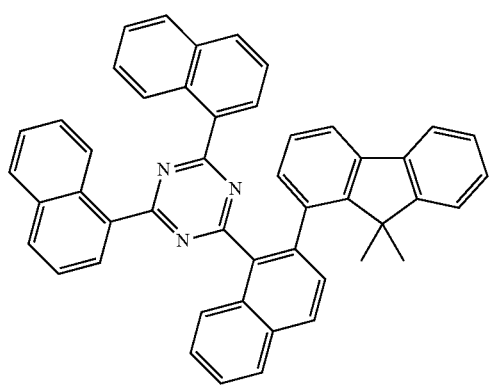
[Compound 94]
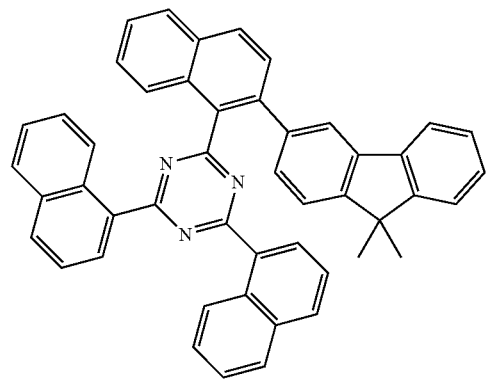
[Compound 95]
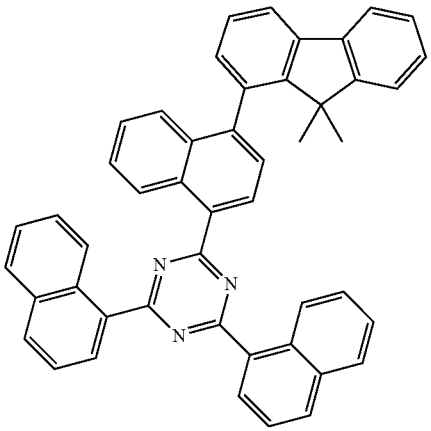
[Compound 96]
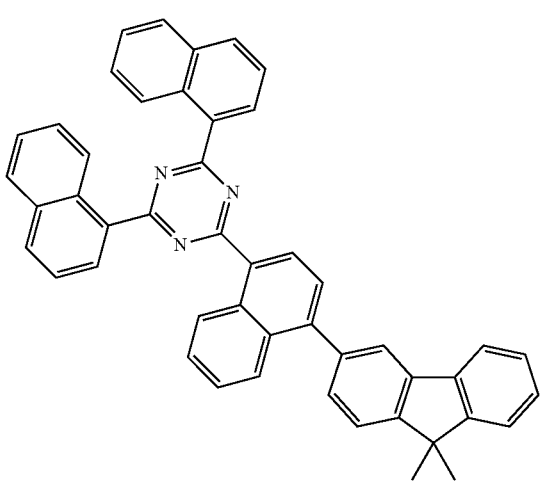
[Compound 97]
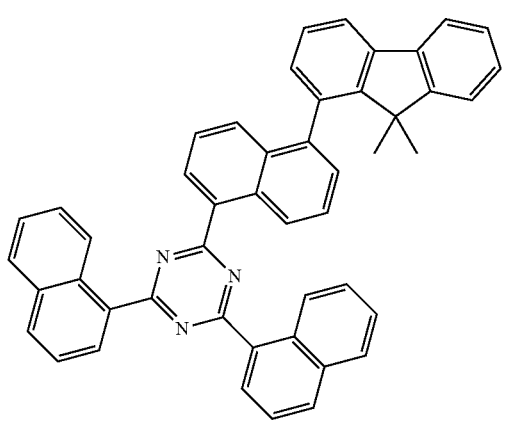

[Compound 98]
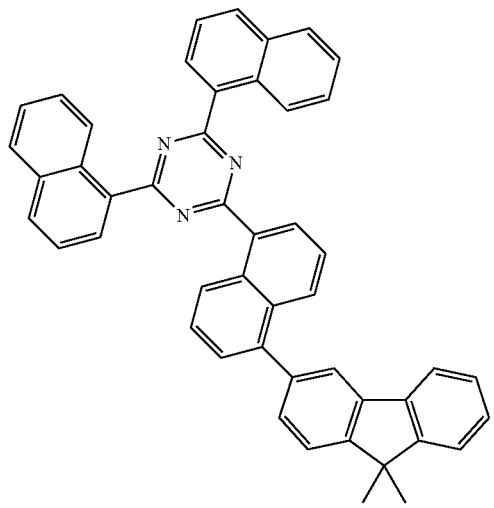
[Compound 99]
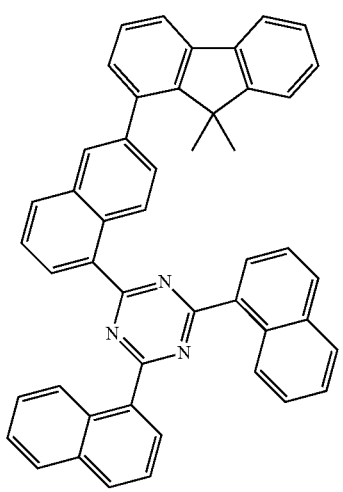
[Compound 100]
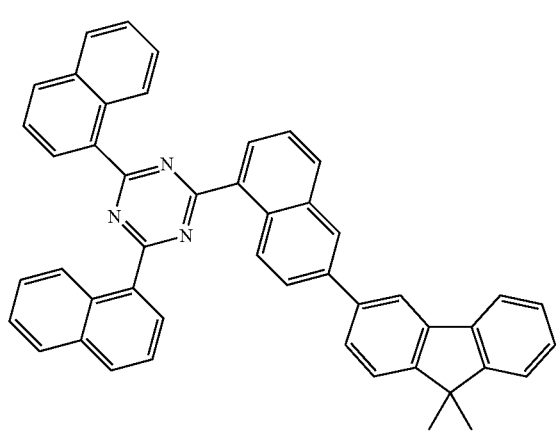
[Compound 101]
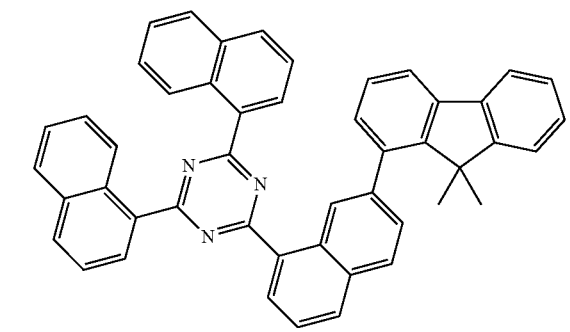
[Compound 102]
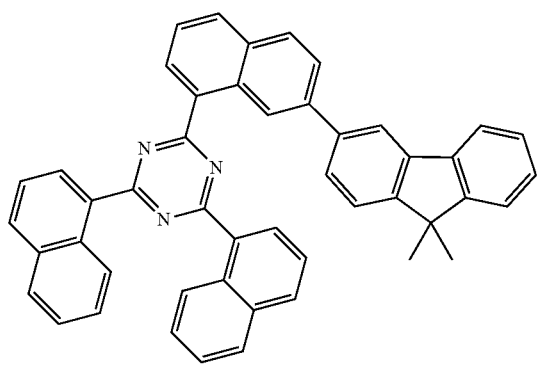
[Compound 103]
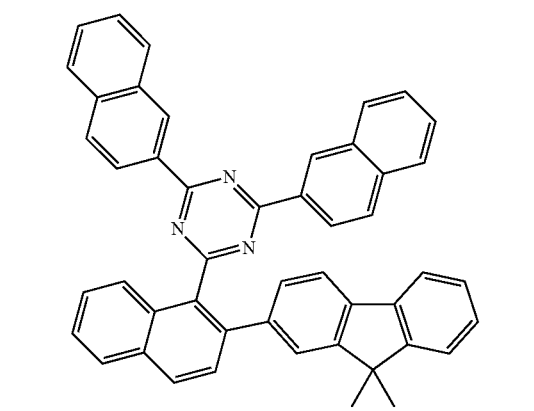
[Compound 104]
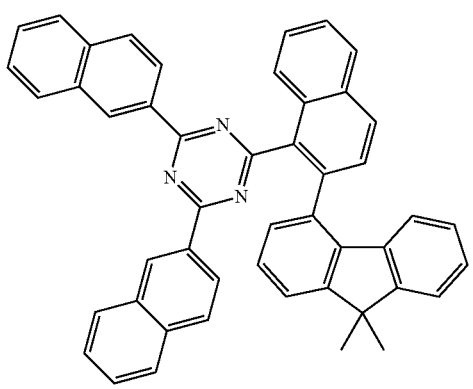

[Compound 105]
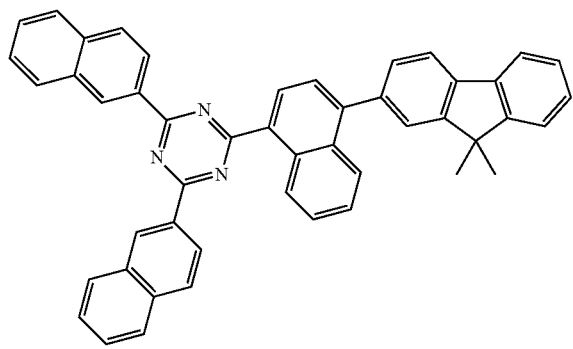
[Compound 106]
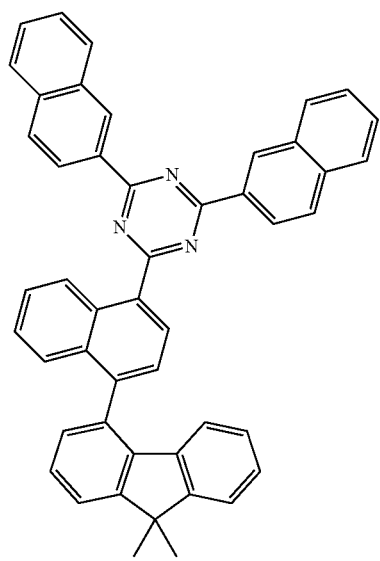
[Compound 107]
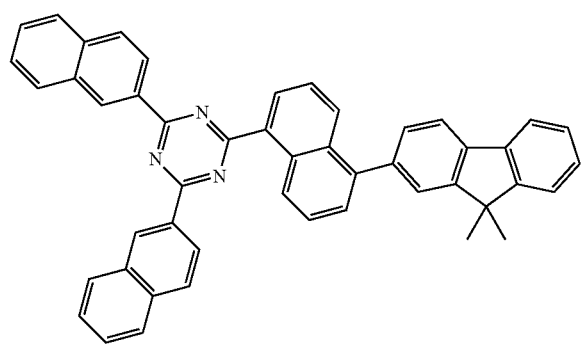
[Compound 108]
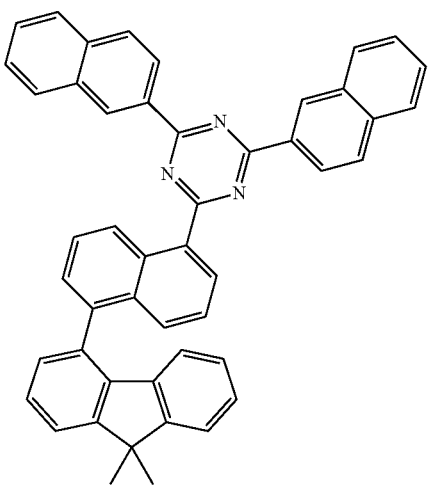
[Compound 109]
[Compound 110]
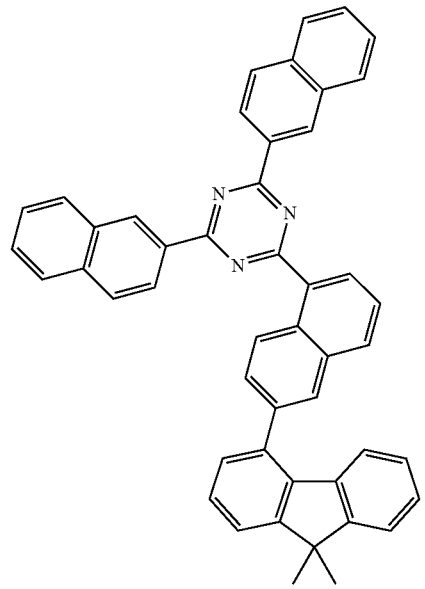

[Compound 111]
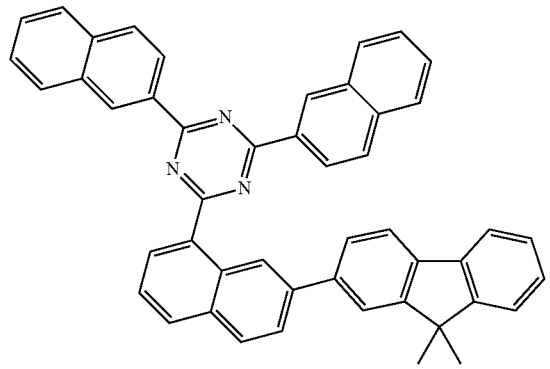
[Compound 112]
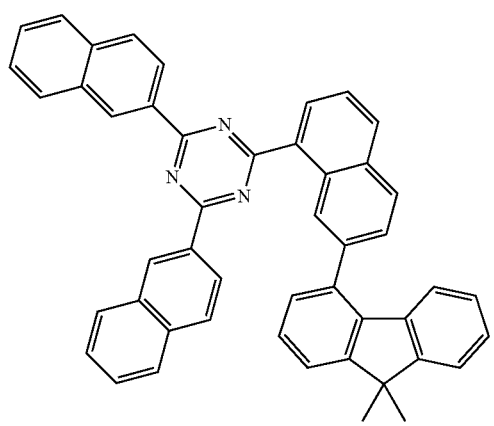
[Compound 113]
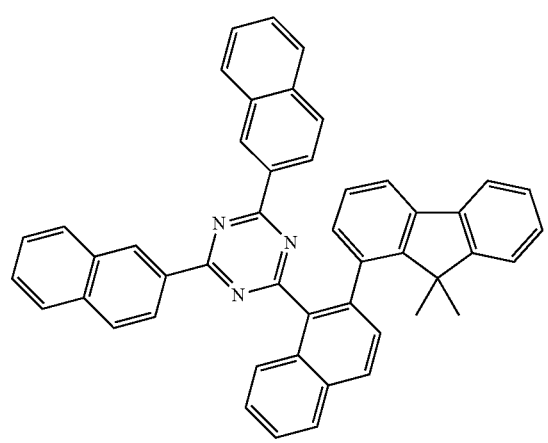
[Compound 114]
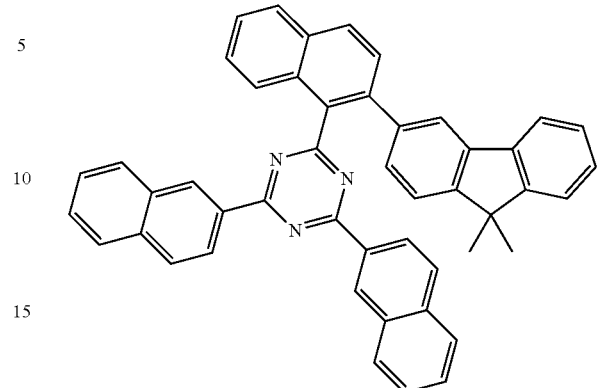
[Compound 115]
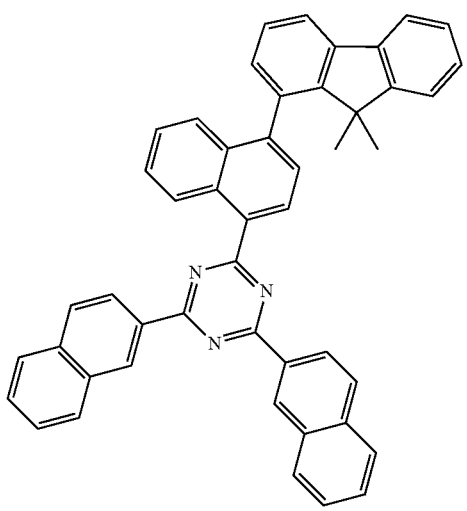
[Compound 116]
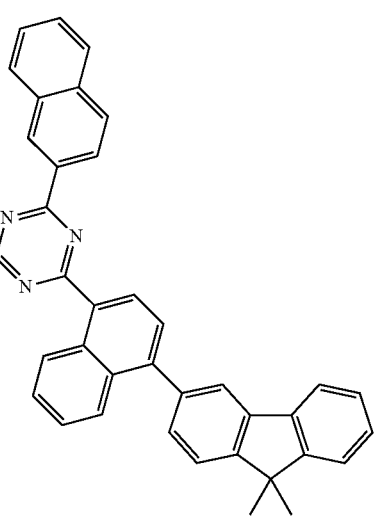

[Compound 117]
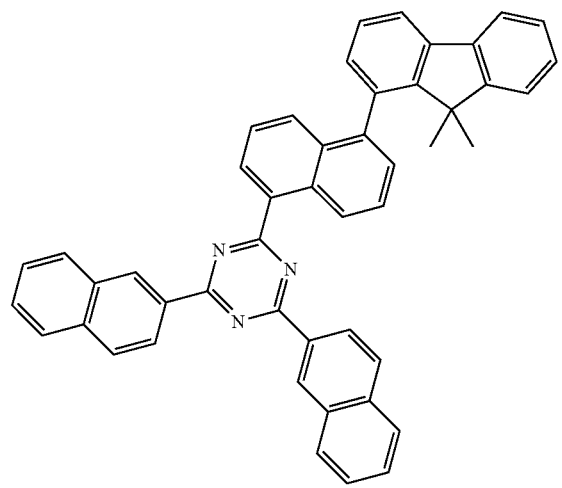
[Compound 118]
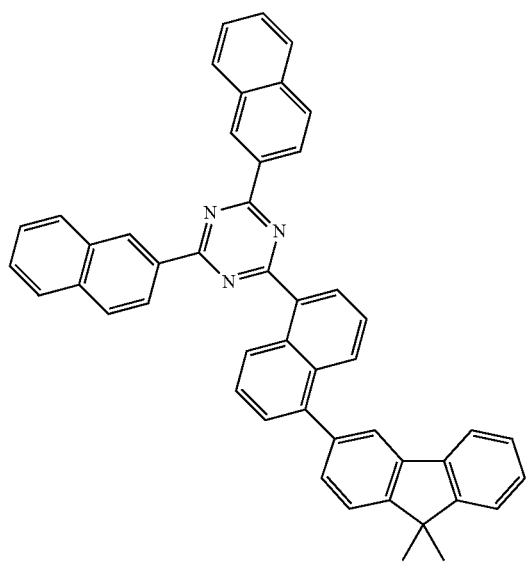
[Compound 119]
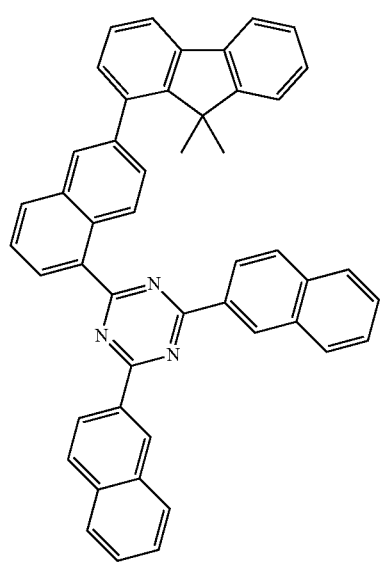
[Compound 120]
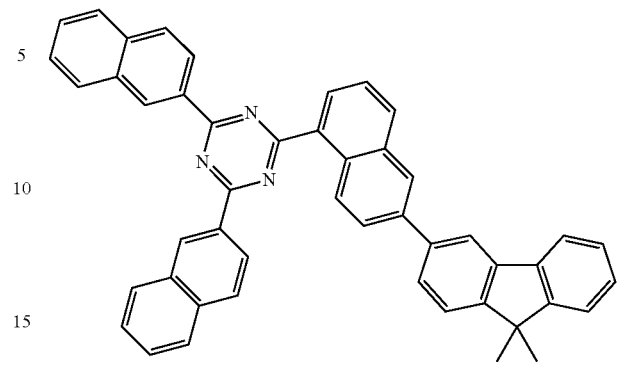
[Compound 121]
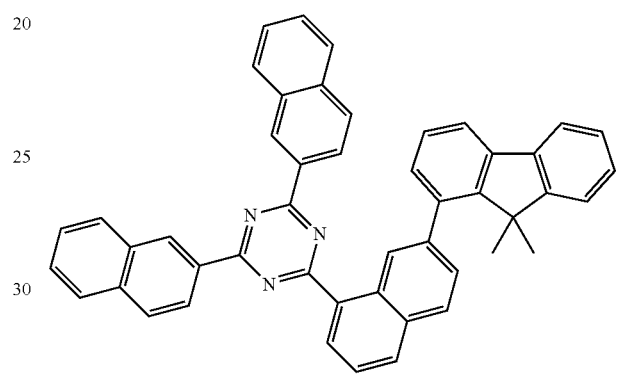
[Compound 122]
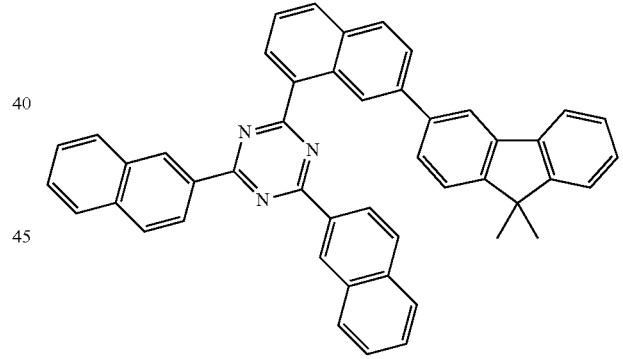
[Compound 123]
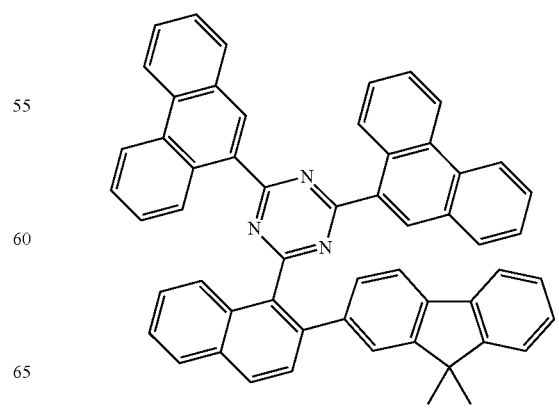

[Compound 124]
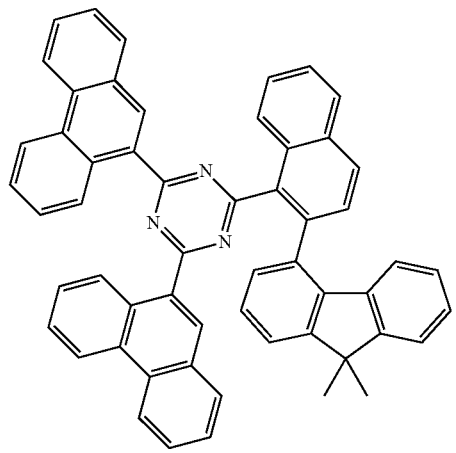
[Compound 125]
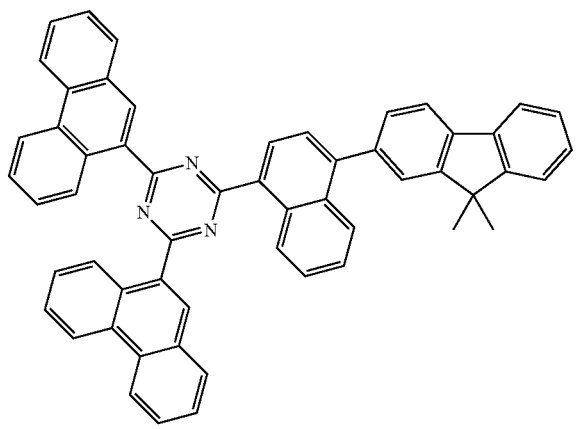
[Compound 126]
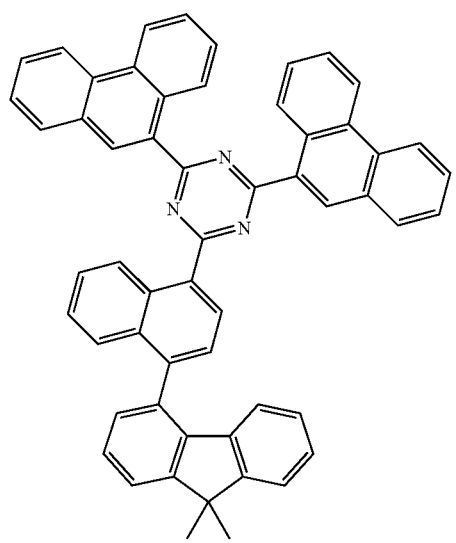
[Compound 127]
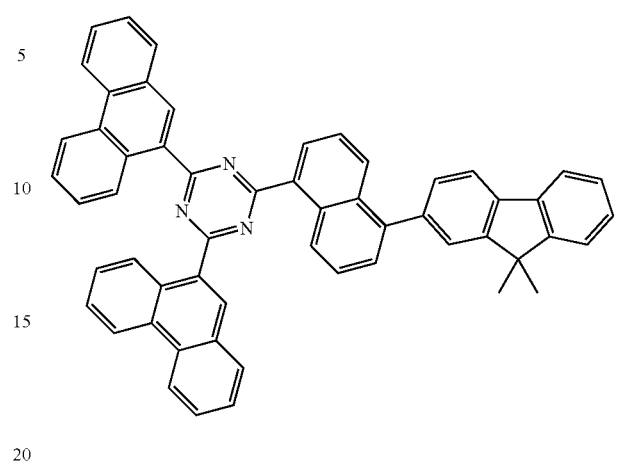
[Compound 128]
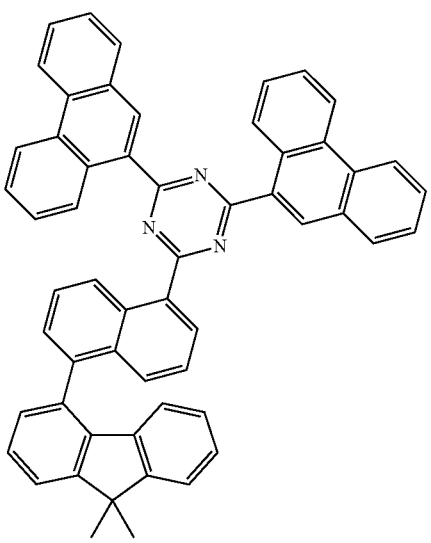
[Compound 129]
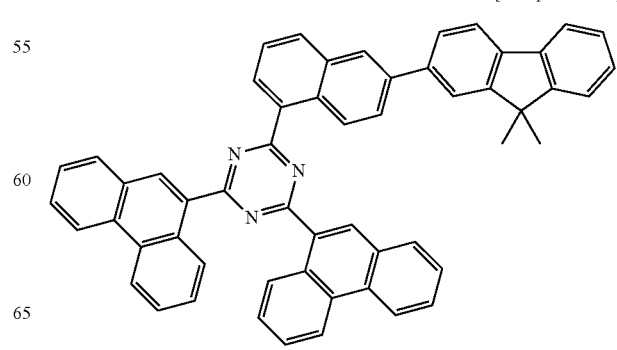

[Compound 130]
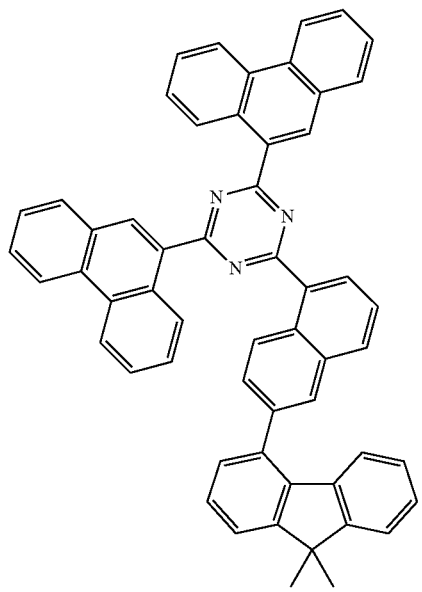
[Compound 131]
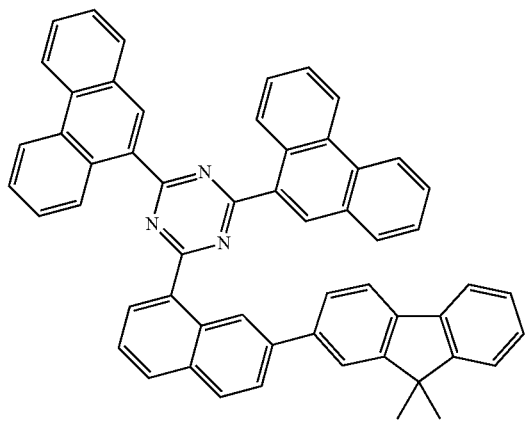
[Compound 132]
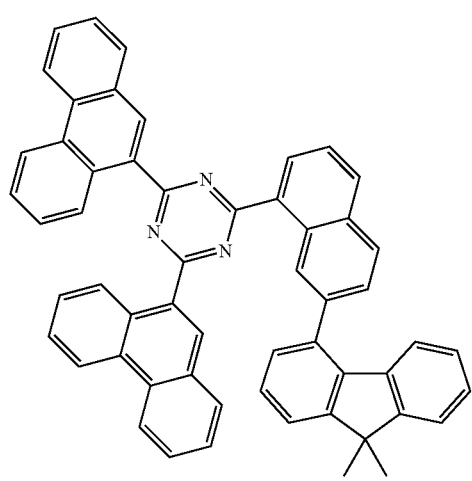
[Compound 133]
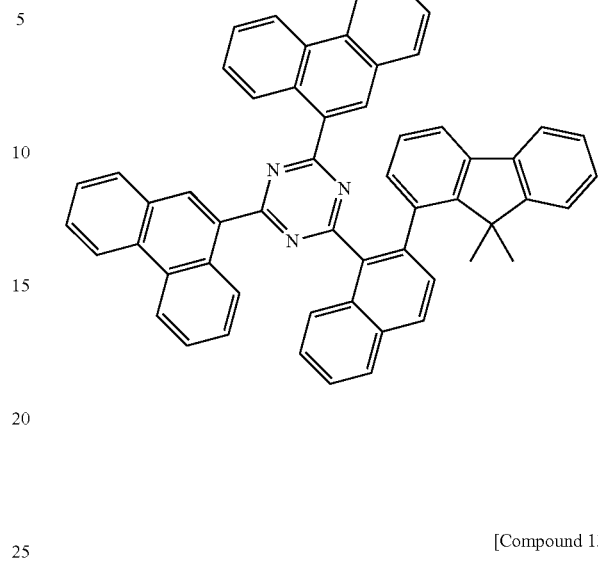
[Compound 134]
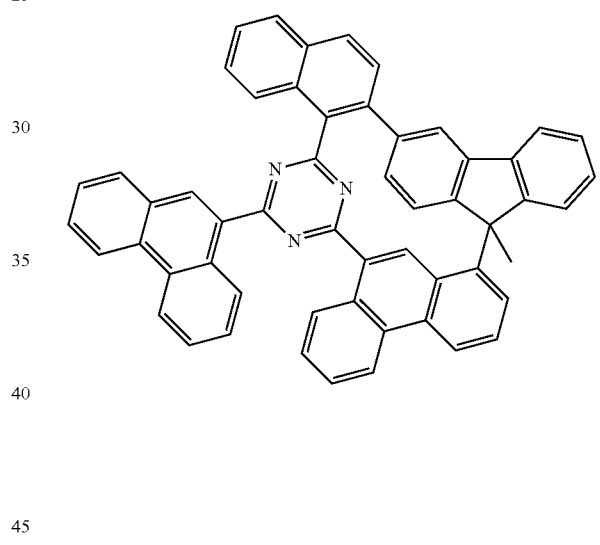
[Compound 135]
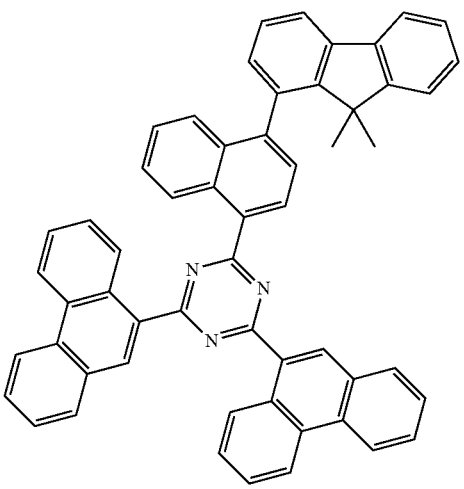

[Compound 136]
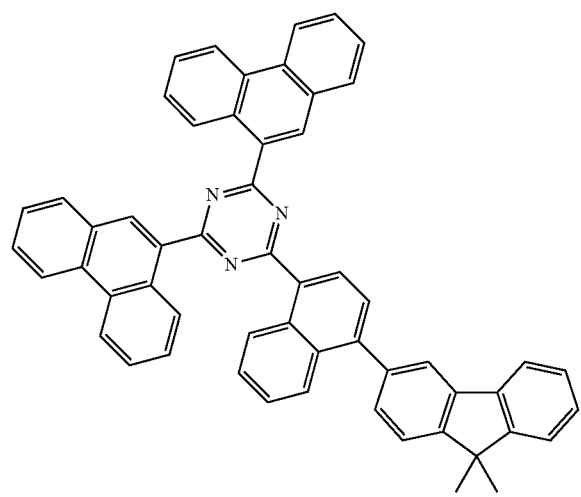
[Compound 137]
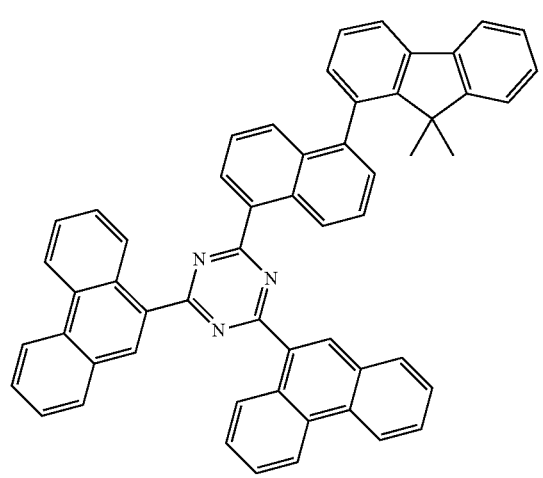
[Compound 138]
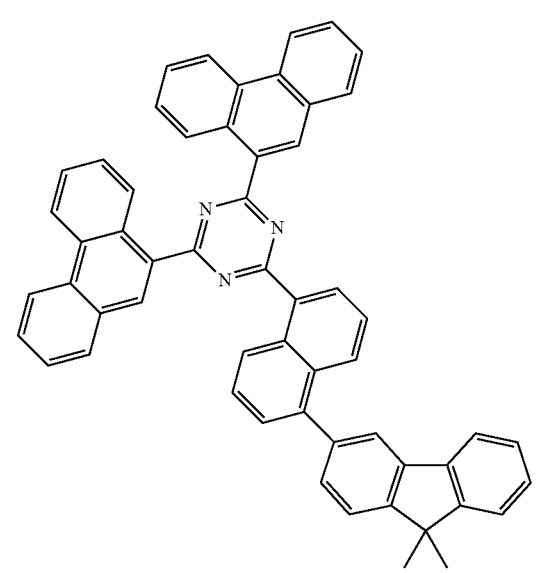
[Compound 139]
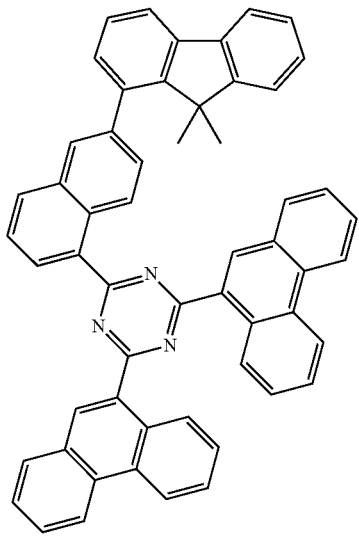
[Compound 140]
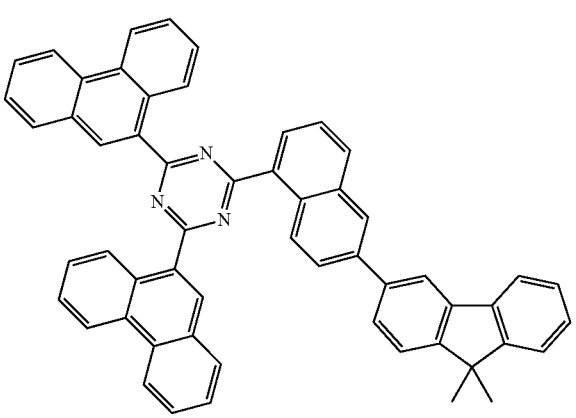
[Compound 141]
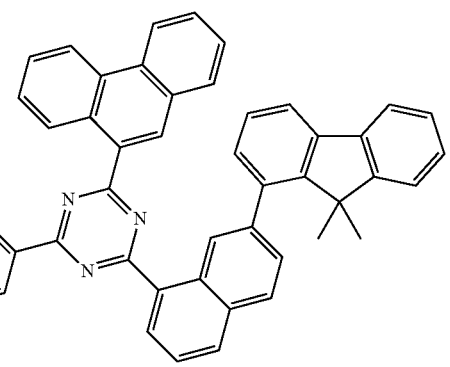

[Compound 142]
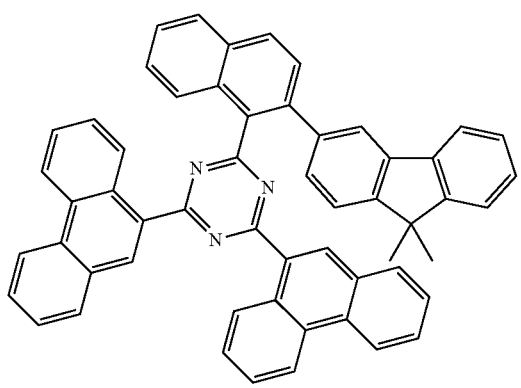
[Compound 143]
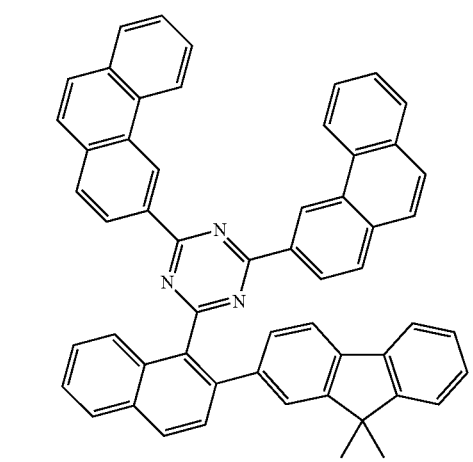
[Compound 144]
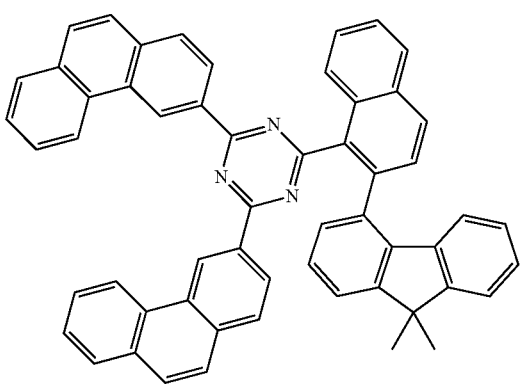
[Compound 145]
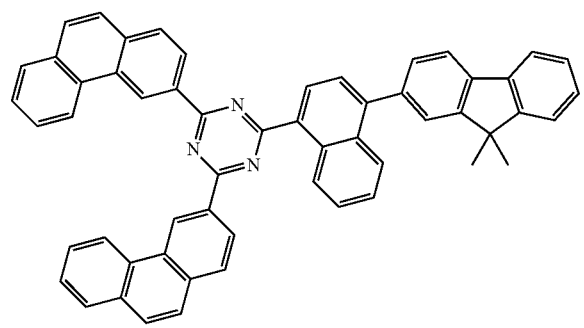
[Compound 146]
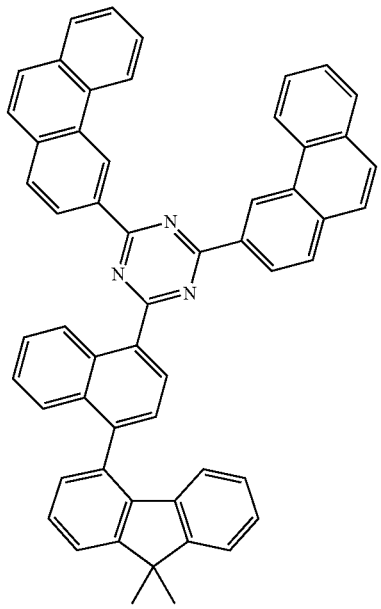
[Compound 147]
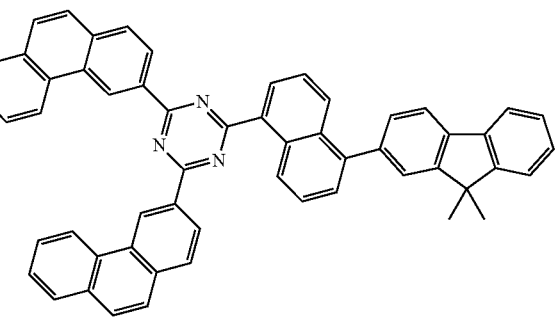
[Compound 148]
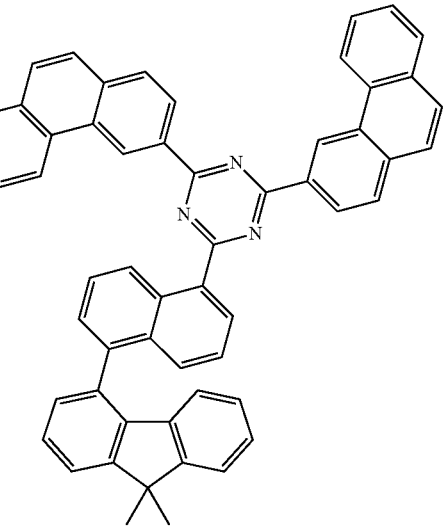

[Compound 149]
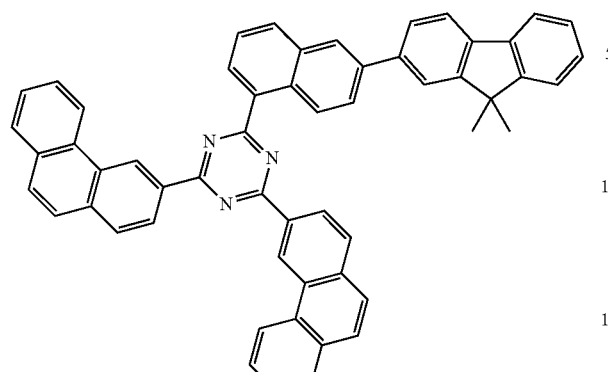
[Compound 152]
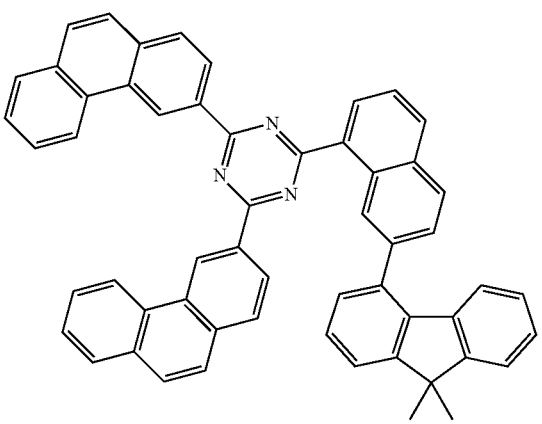
[Compound 150]
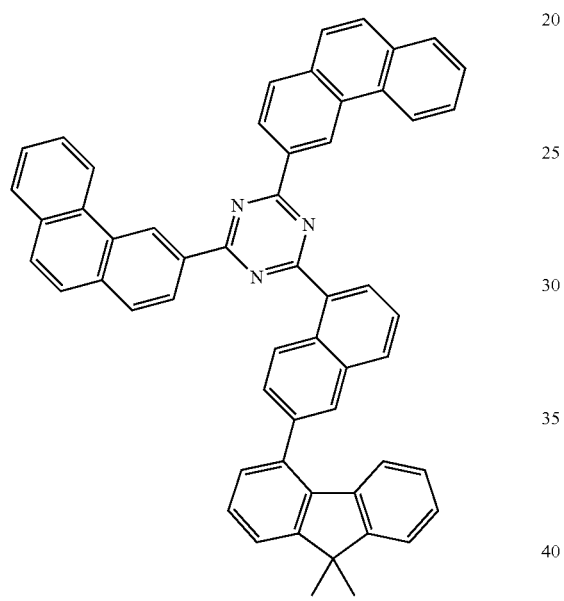
[Compound 153]
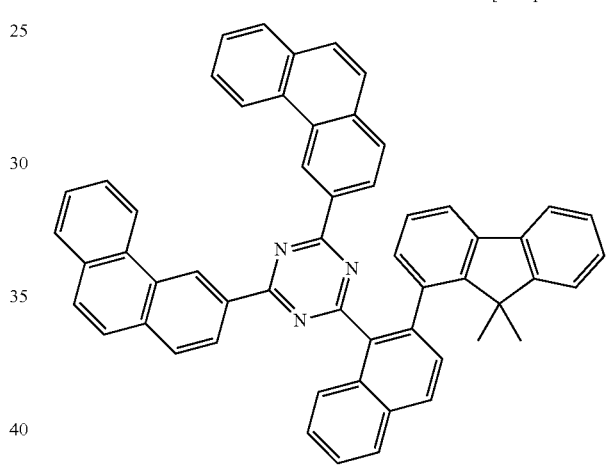
[Compound 151]
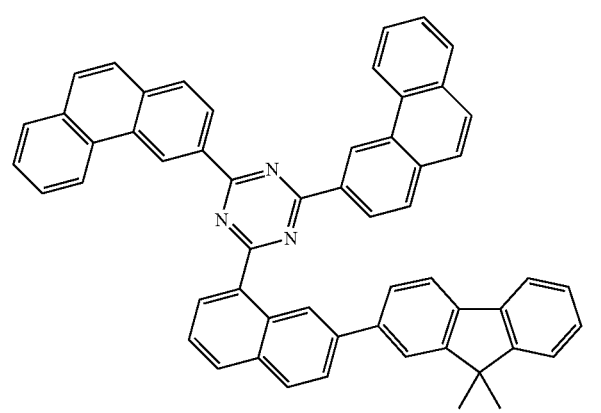
[Compound 154]
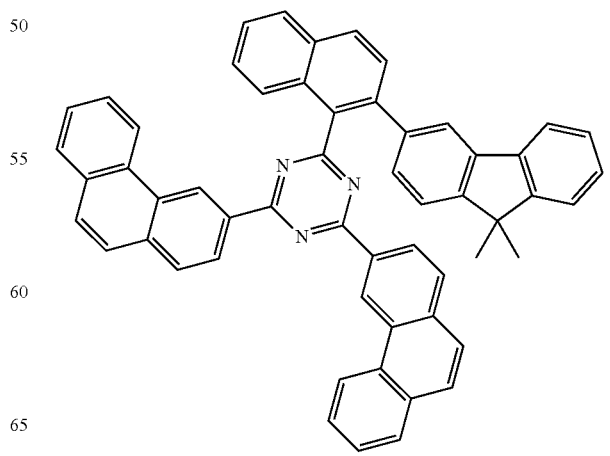

[Compound 155]
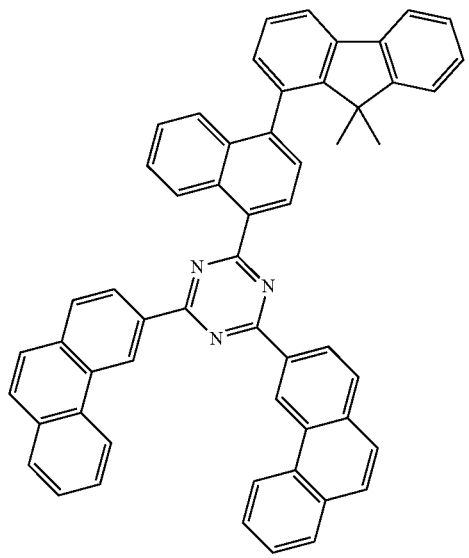
[Compound 156]
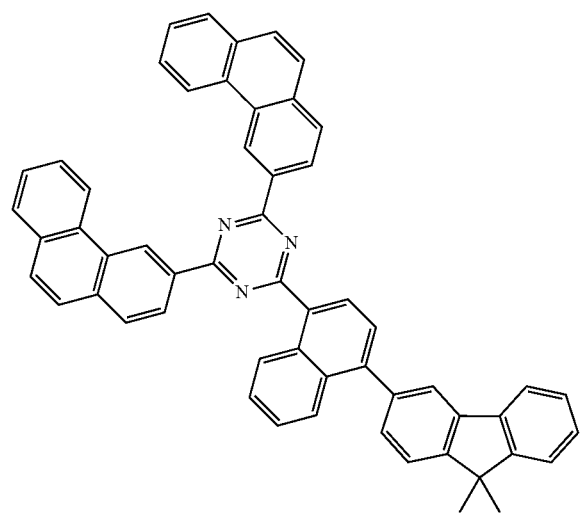
[Compound 157]
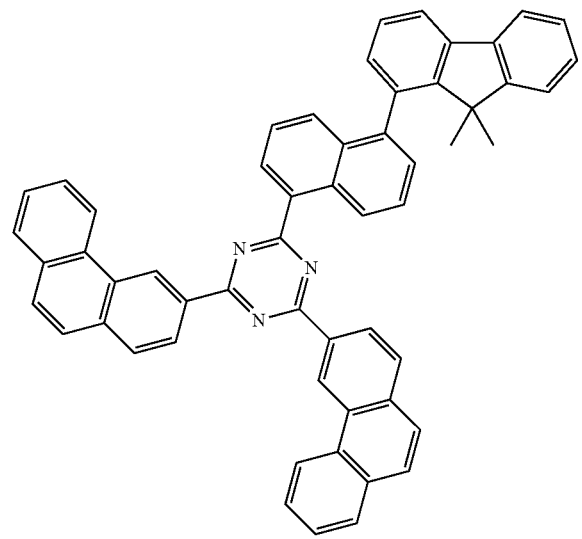
[Compound 158]
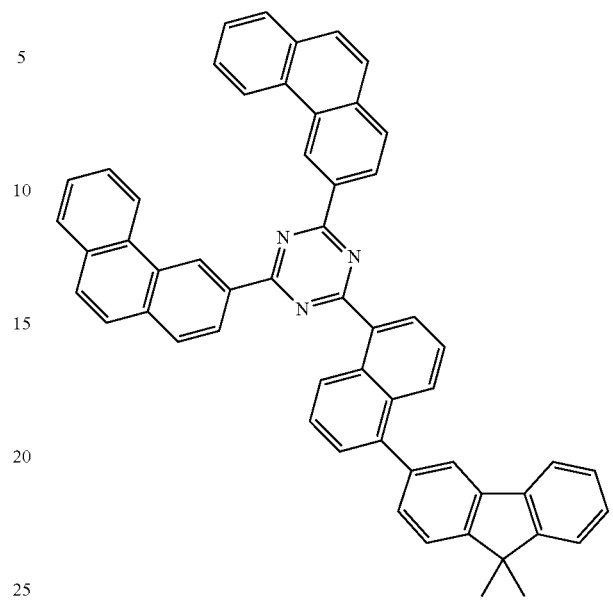
[Compound 159]
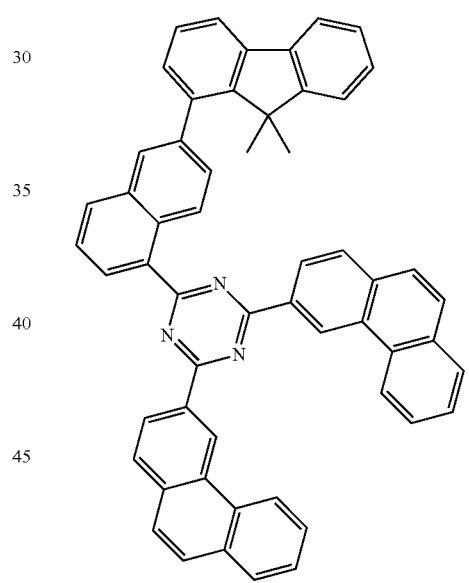
[Compound 160]
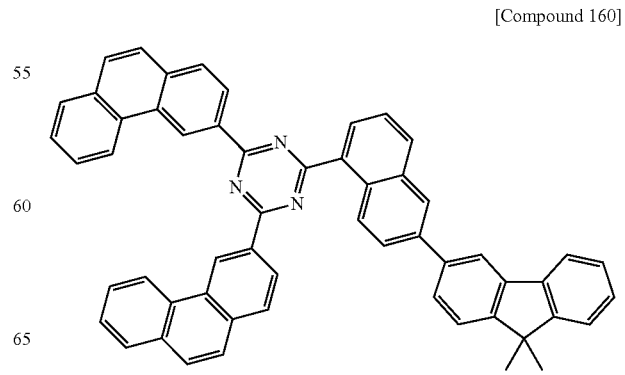

[Compound 161]
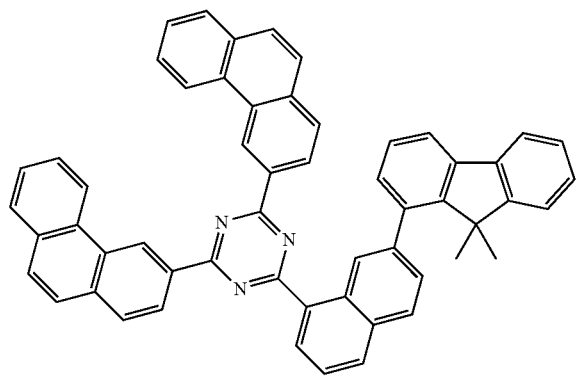
[Compound 164]
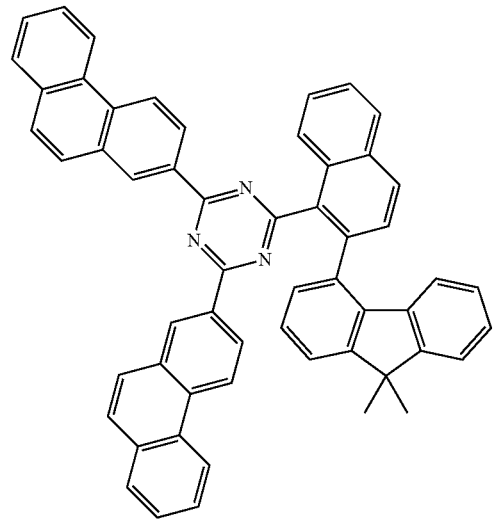
[Compound 162]
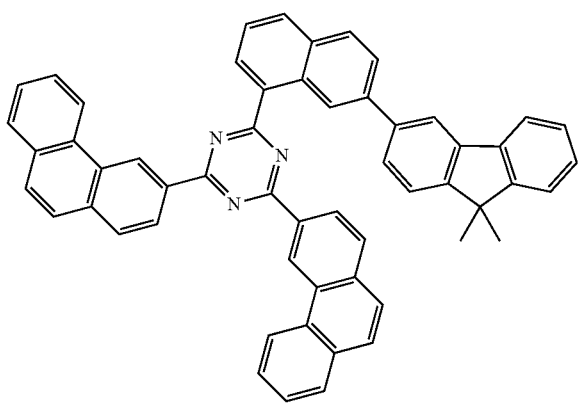
[Compound 165]
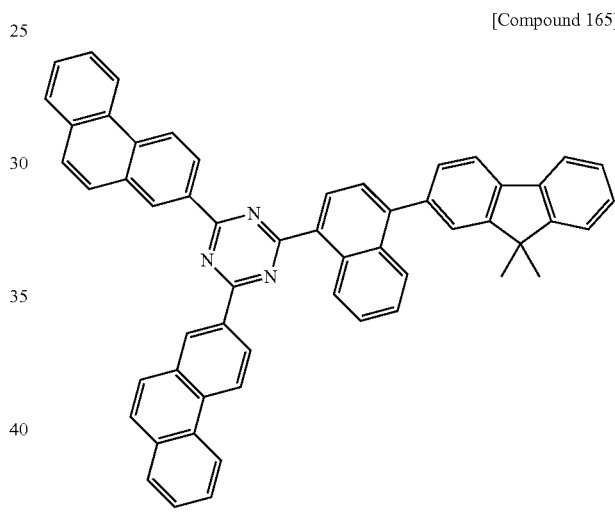
[Compound 163]
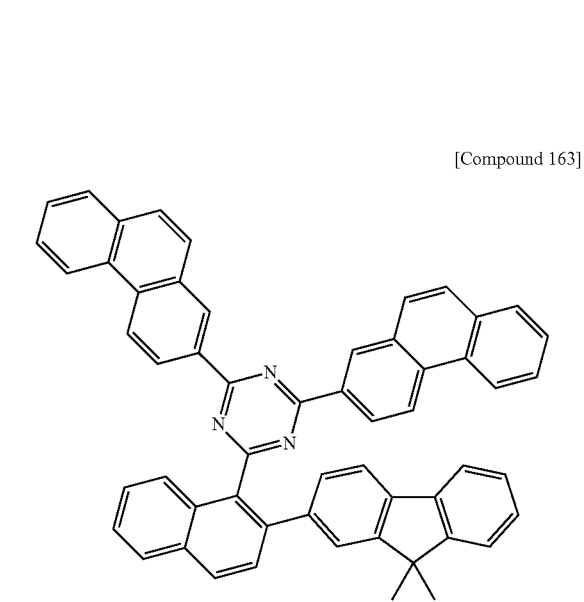
[Compound 166]
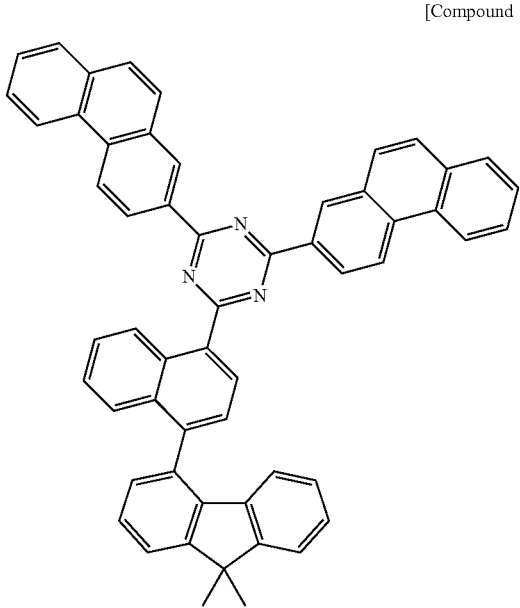

[Compound 167]
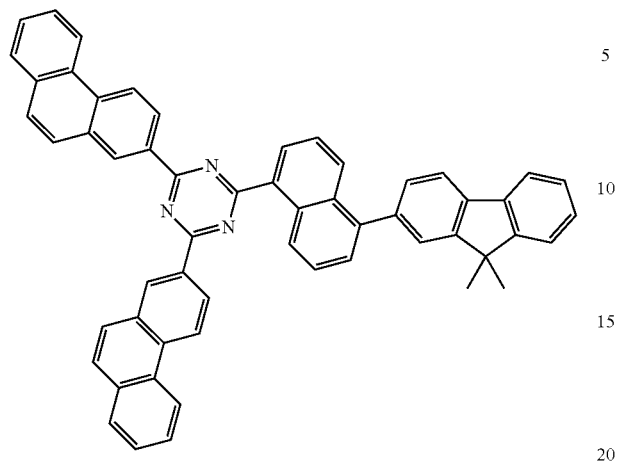
[Compound 168]
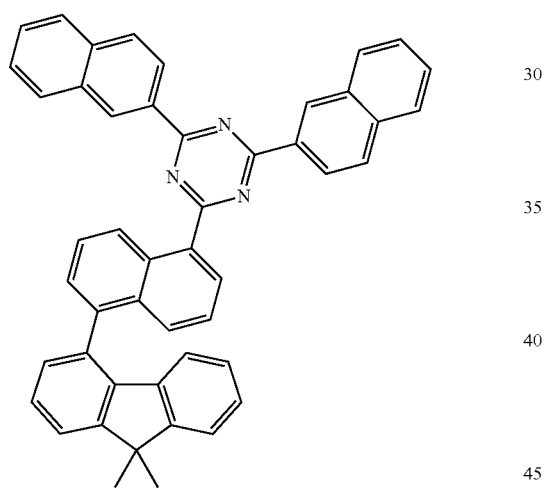
[Compound 169]
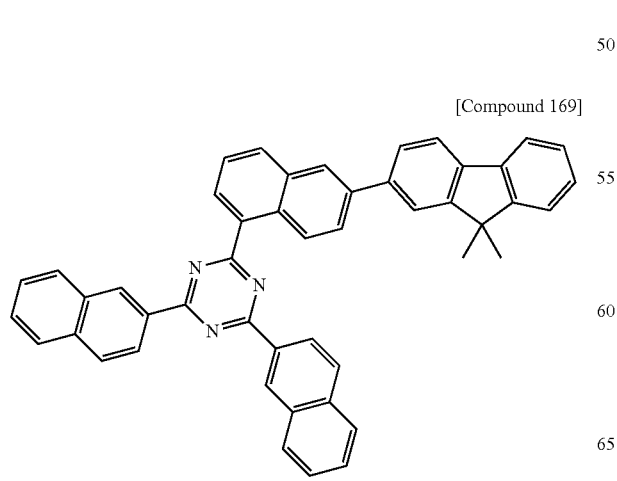
[Compound 170]
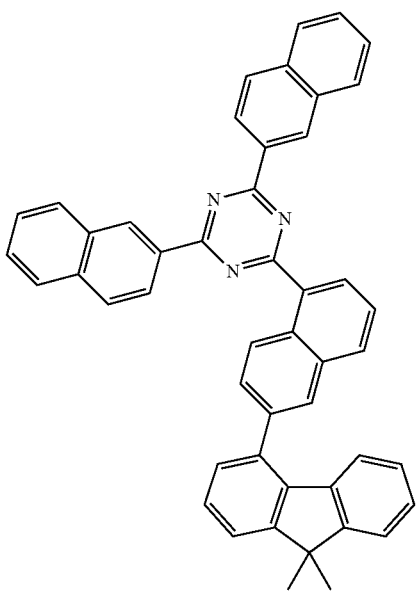
[Compound 171]
[Compound 172]
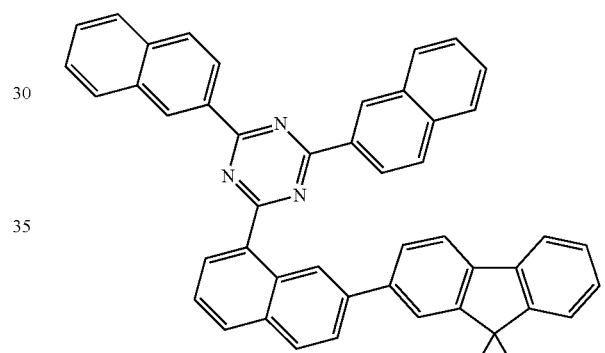

[Compound 173]
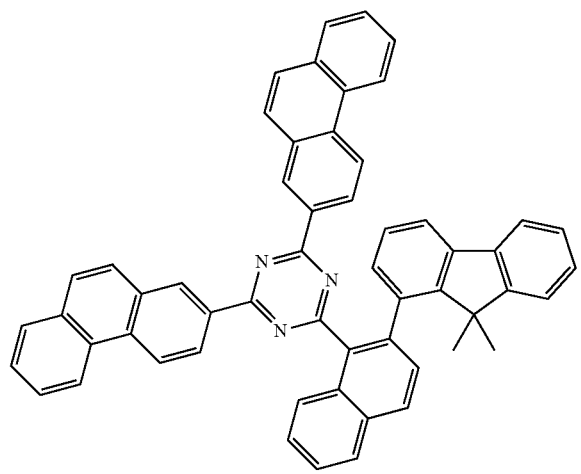
[Compound 174]
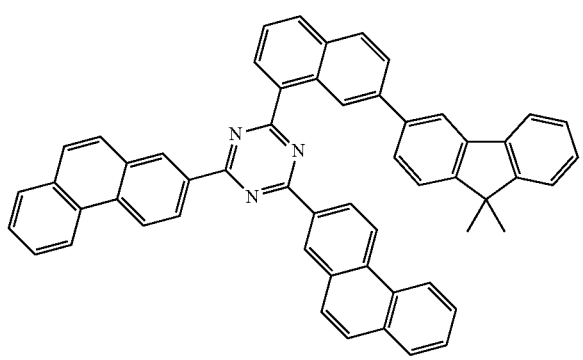
[Compound 175]
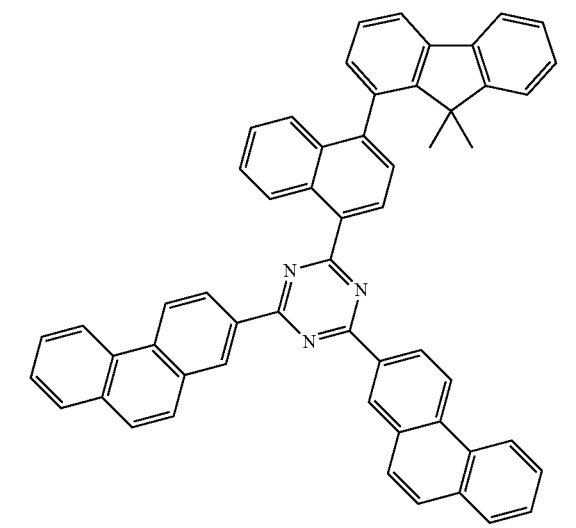
[Compound 176]
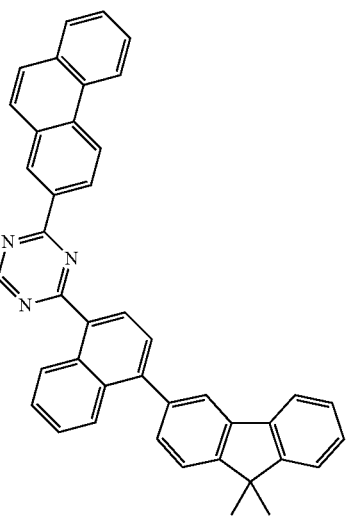
[Compound 177]
[Compound 178]
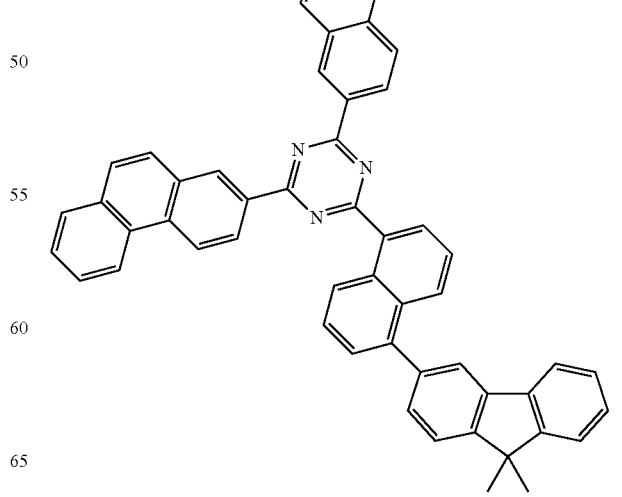

[Compound 179]
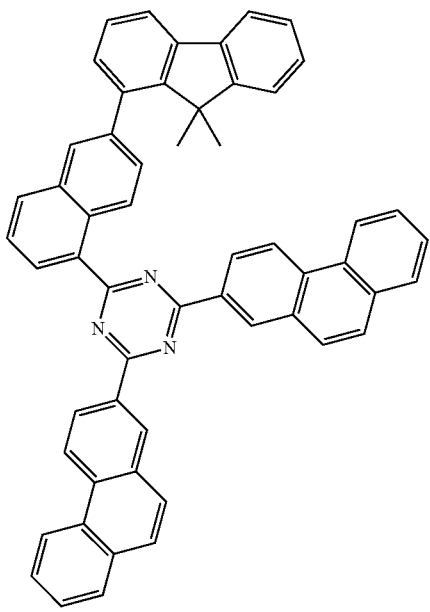
[Compound 182]
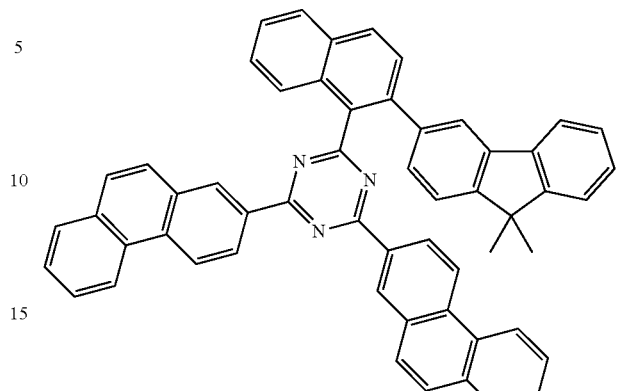
[Compound 183]
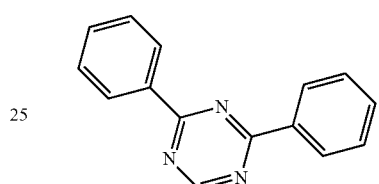
[Compound 180]
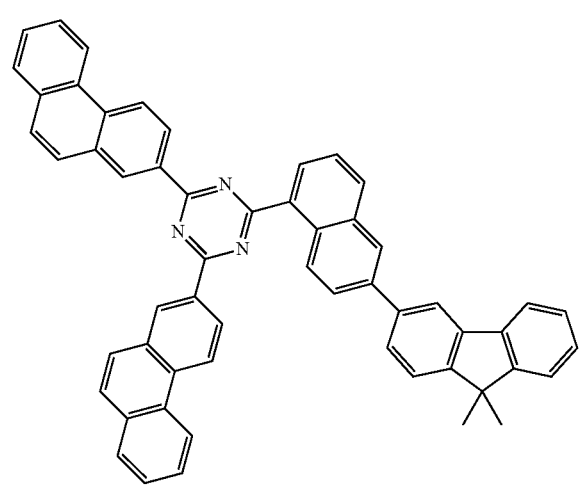
[Compound 184]
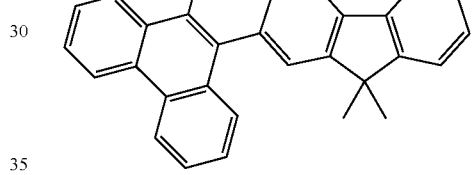
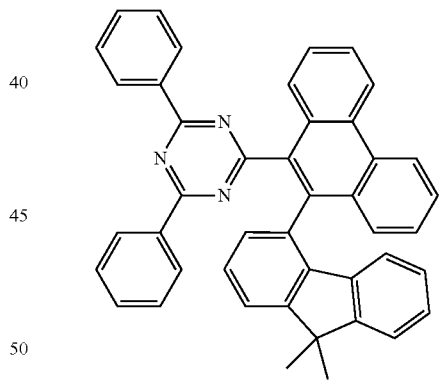
[Compound 181]
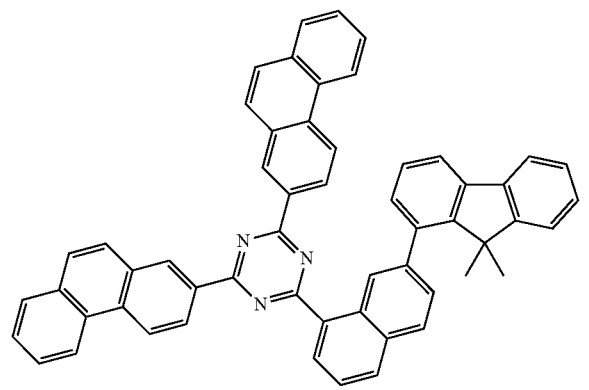
[Compound 185]
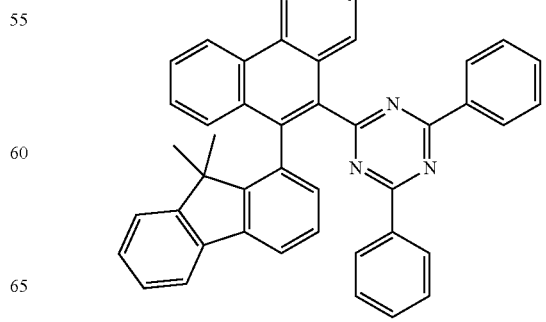

[Compound 186]
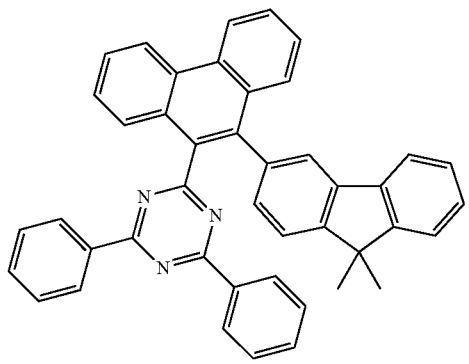
[Compound 187]
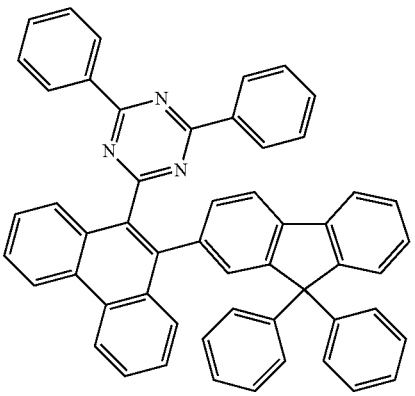
[Compound 188]
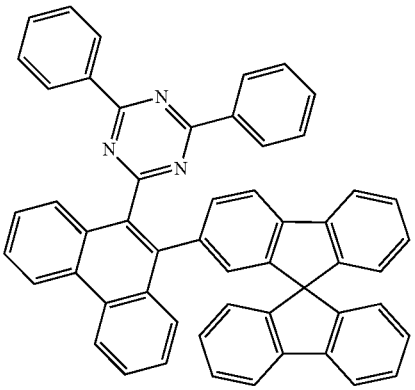
[Compound 189]
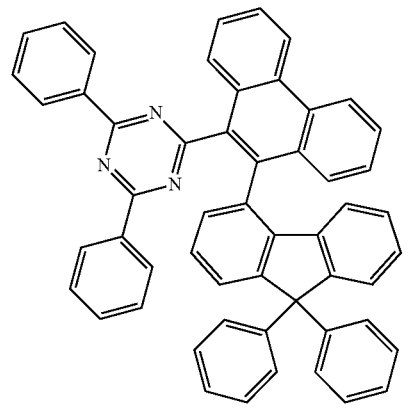
[Compound 190]
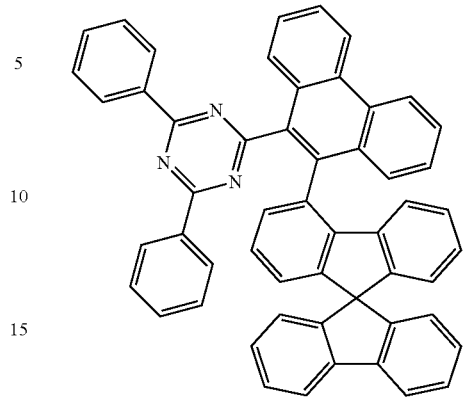
[Compound 191]
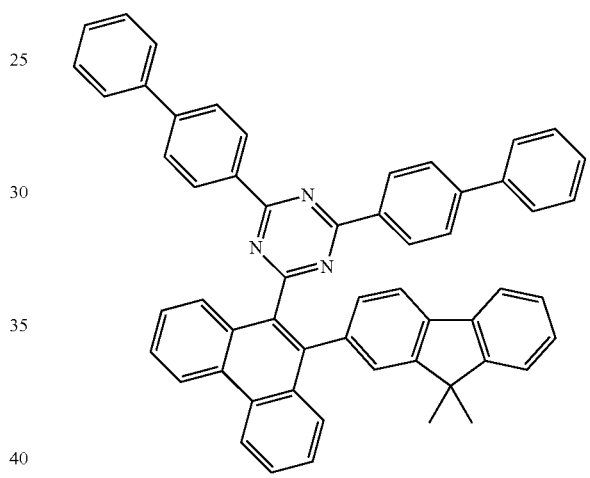
[Compound 192]
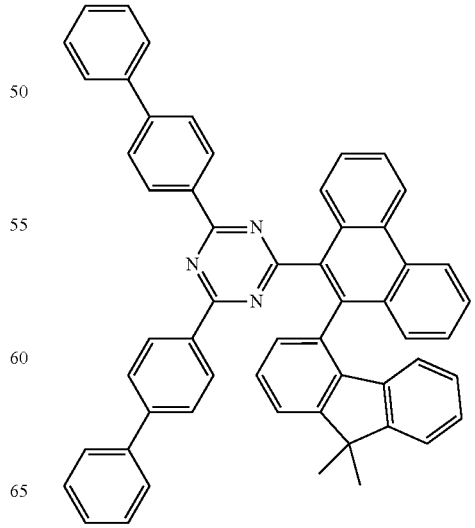

[Compound 193]
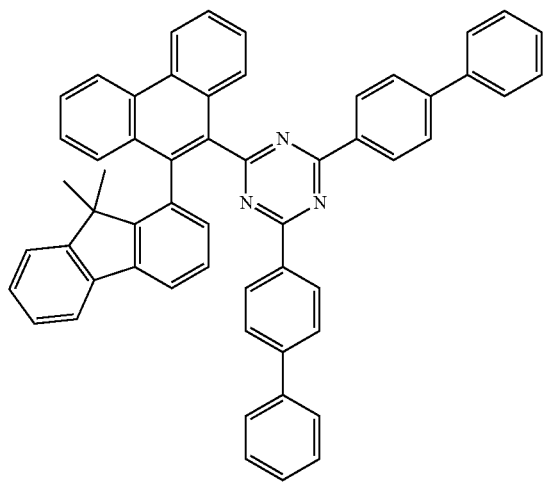
[Compound 194]
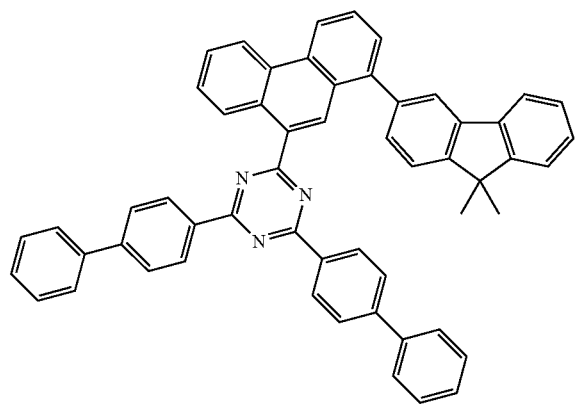
[Compound 195]
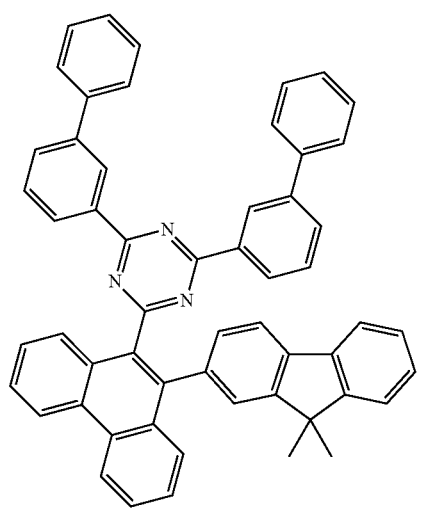
[Compound 196]
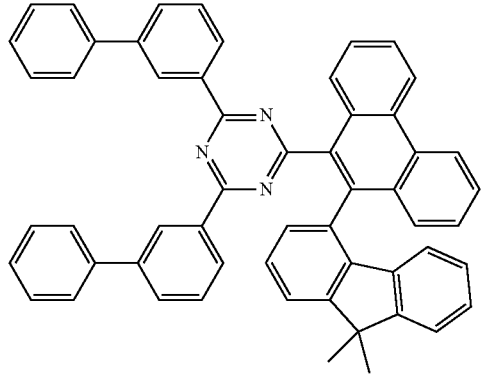
[Compound 197]
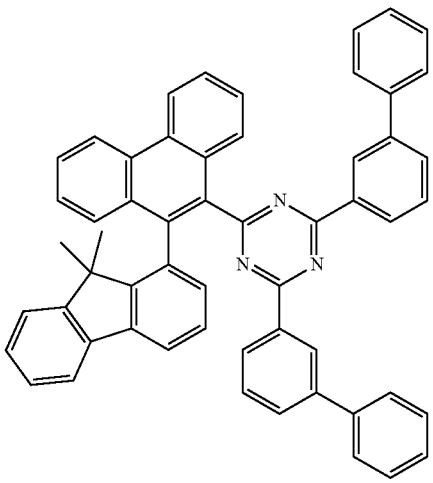
[Compound 198]
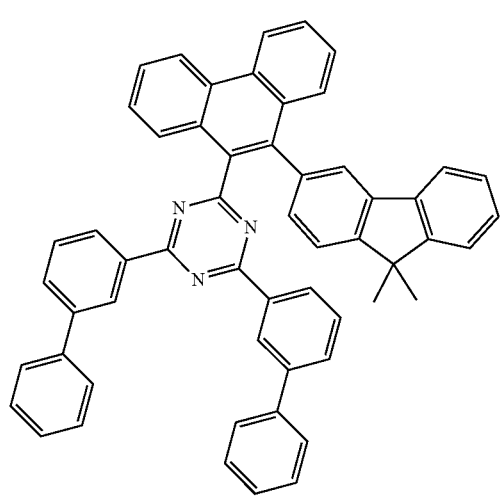

[Compound 199]
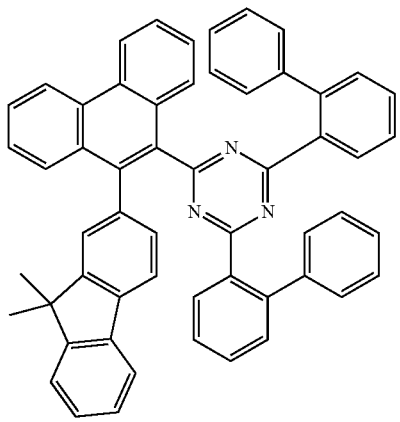
[Compound 200]
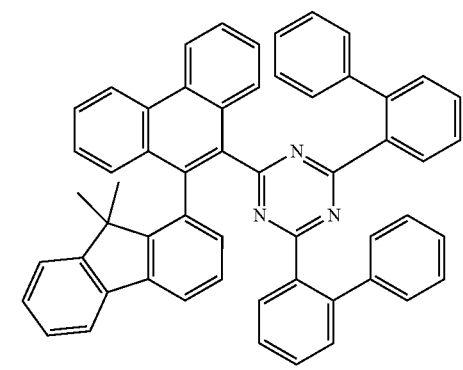
[Compound 201]
[Compound 202]
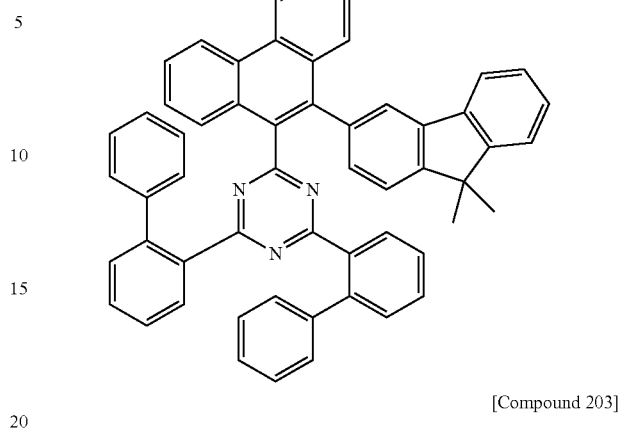
[Compound 203]
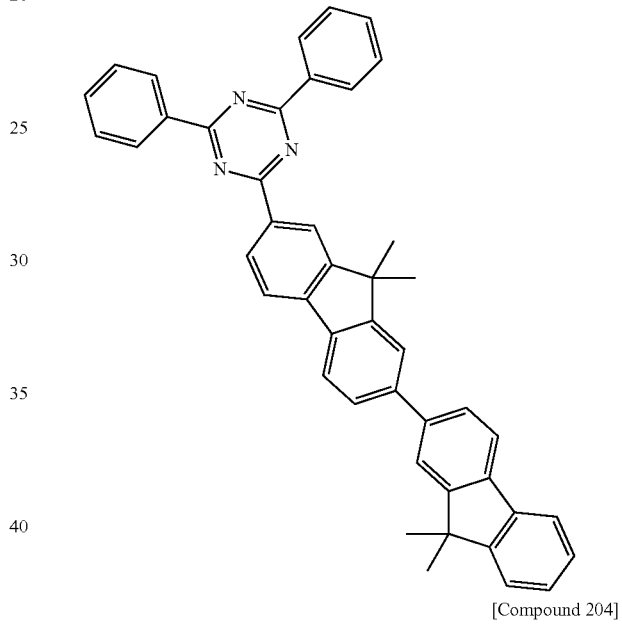
[Compound 204]
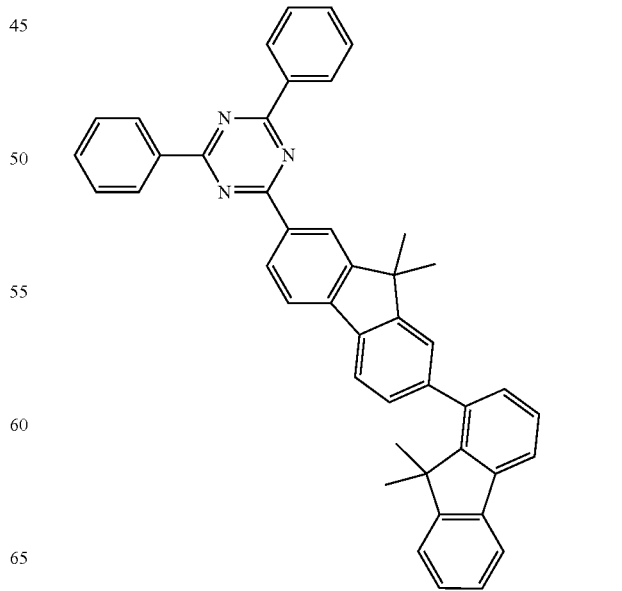

[Compound 205]
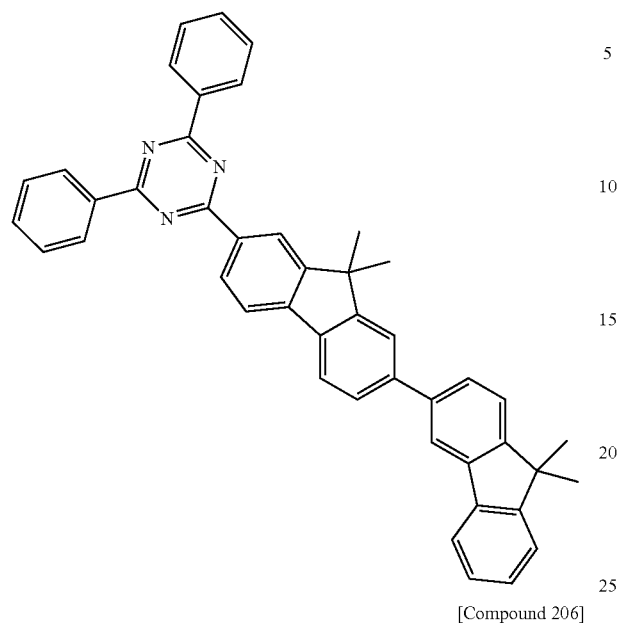
[Compound 206]
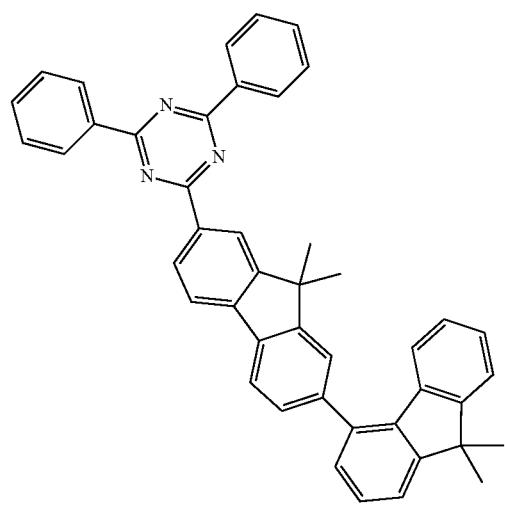
[Compound 207]
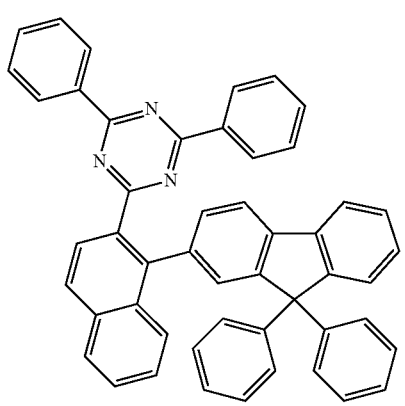
[Compound 208]
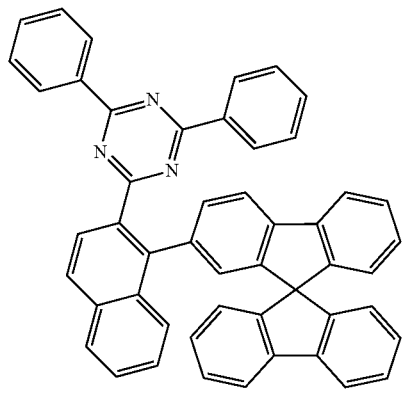
[Compound 209]
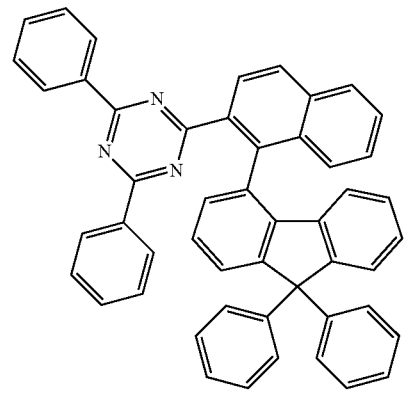
[Compound 210]
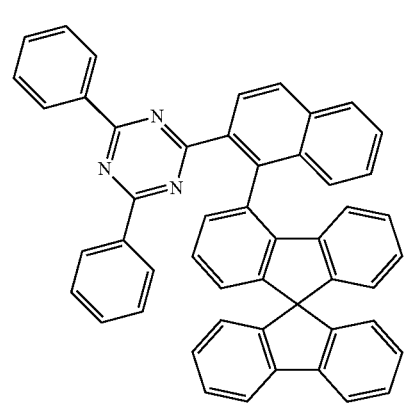

[Compound 211]
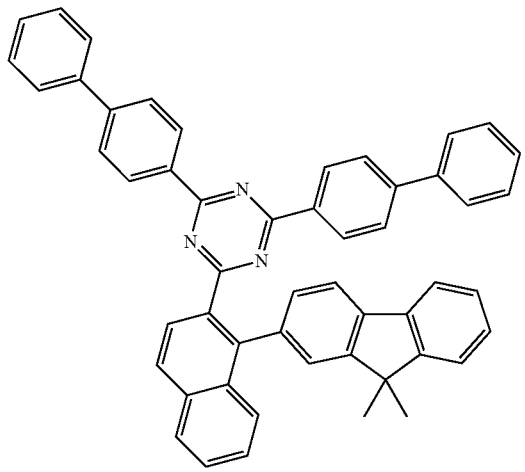
[Compound 212]
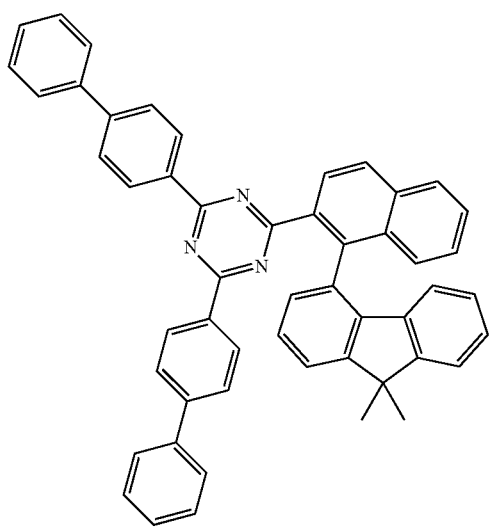
[Compound 213]
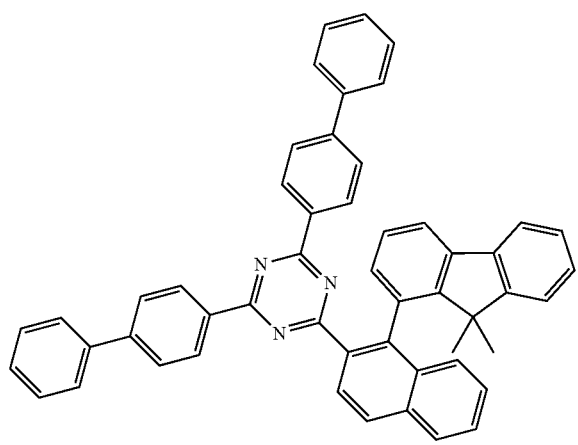
[Compound 214]
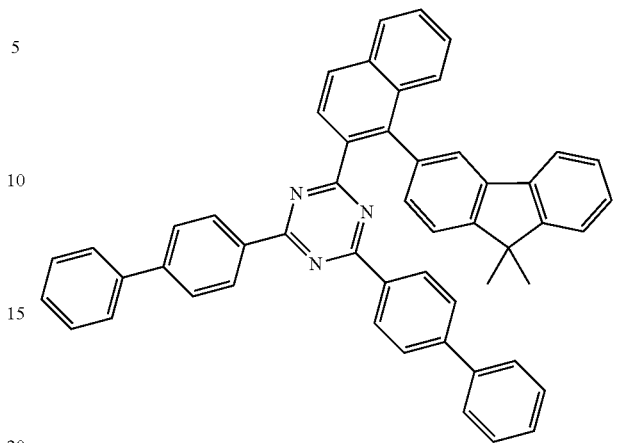
[Compound 215]
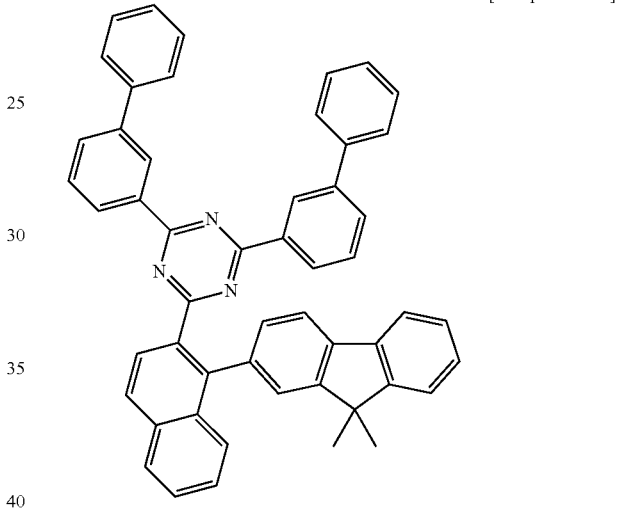
[Compound 216]
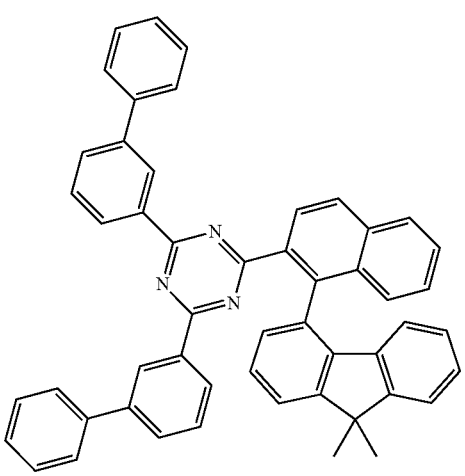

[Compound 217]
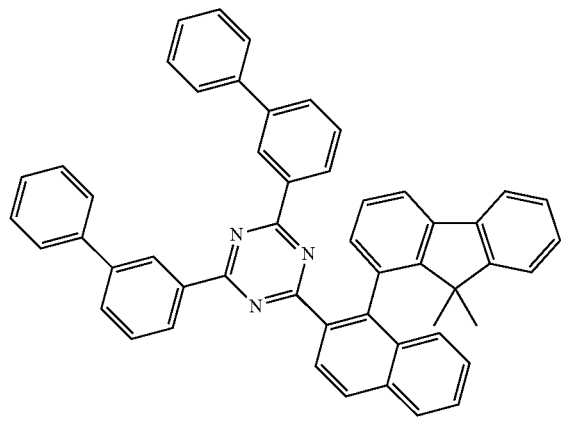
[Compound 218]
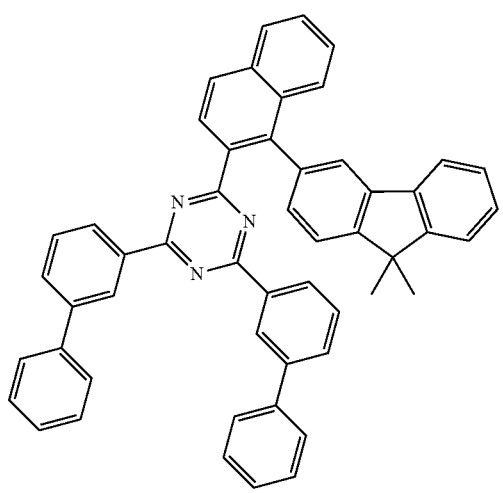
[Compound 219]
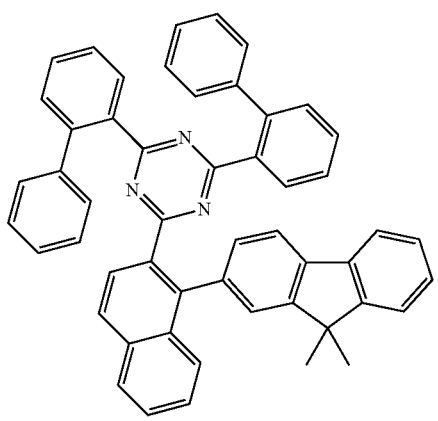
[Compound 220]
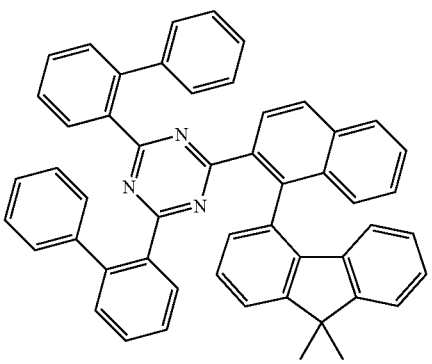
[Compound 221]
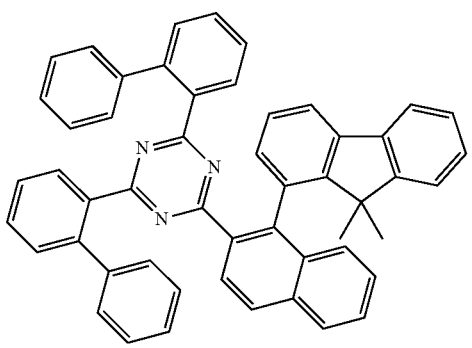
[Compound 222]
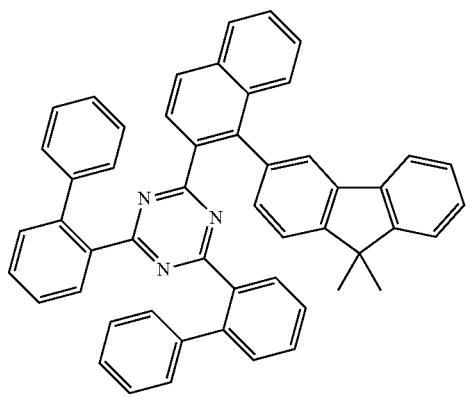
[Compound 223]
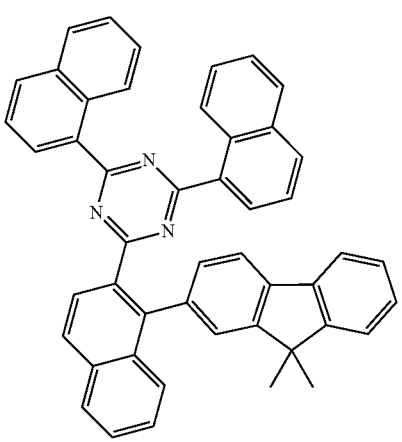

[Compound 224]
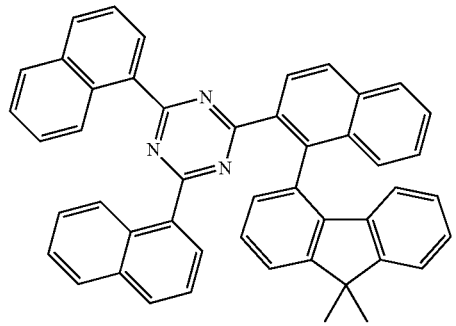
[Compound 225]
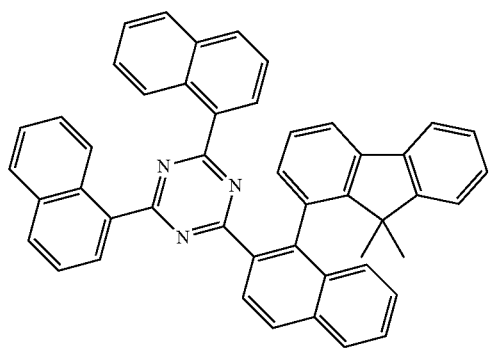
[Compound 226]
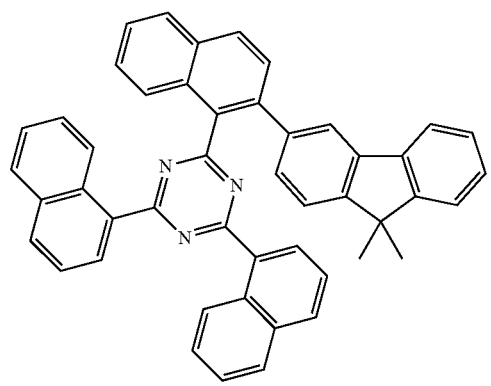
[Compound 227]
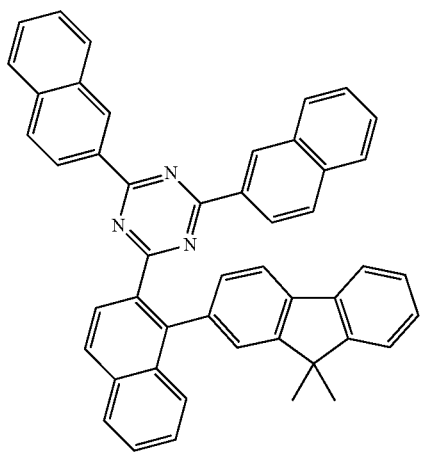
[Compound 228]
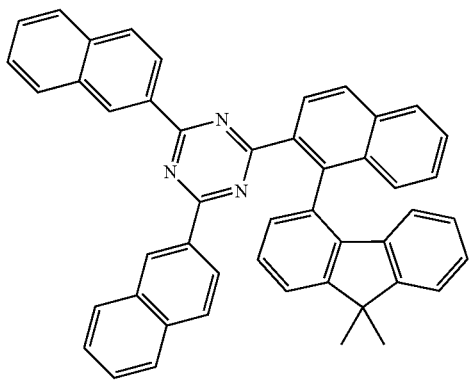
[Compound 229]
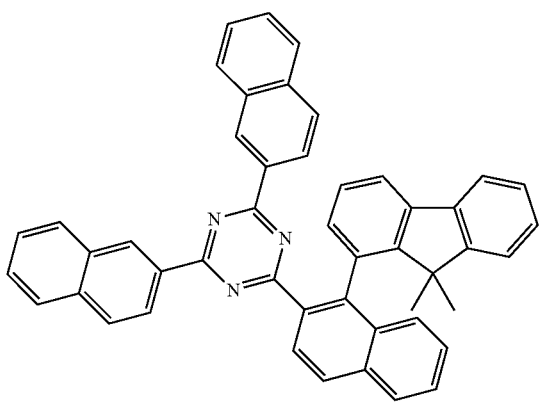
[Compound 230]
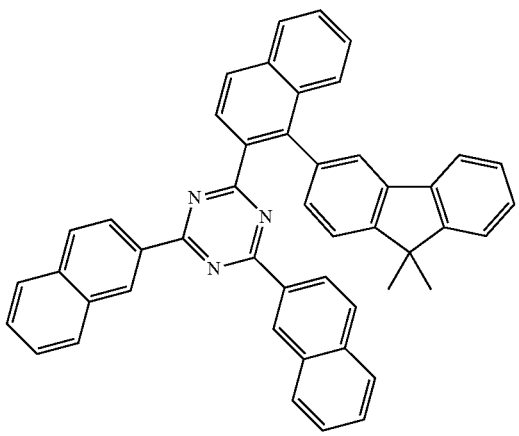

[Compound 231]
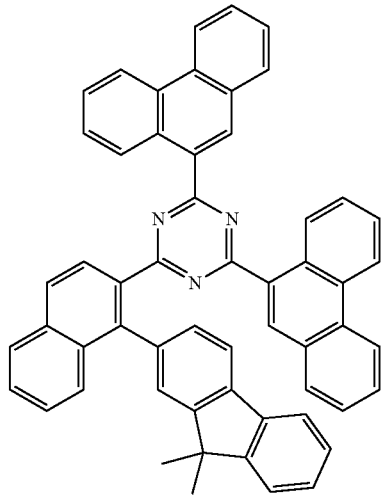
[Compound 234]
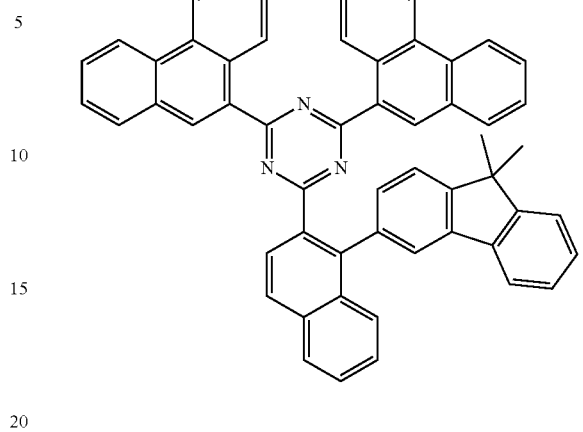
[Compound 232]
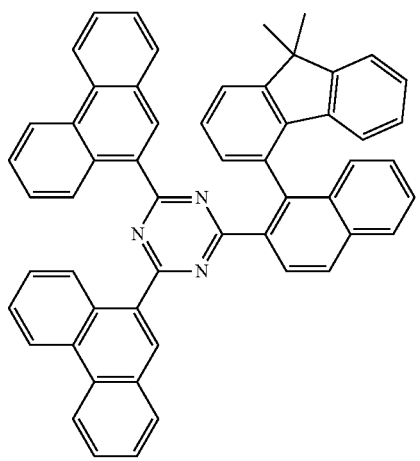
[Compound 235]
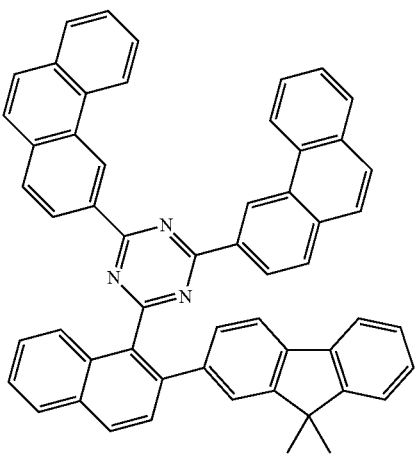
[Compound 233]
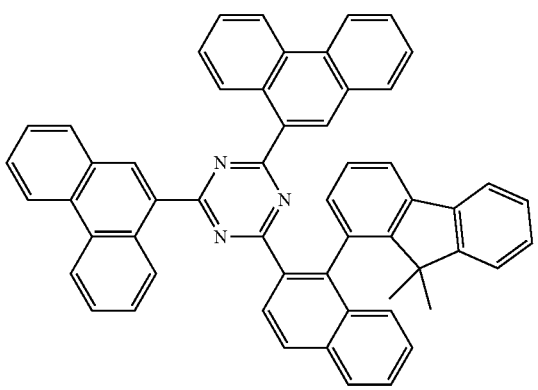
[Compound 236]
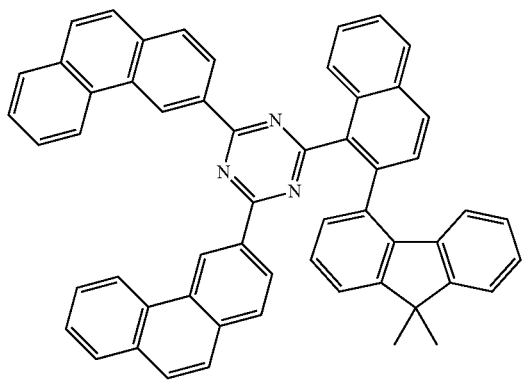

[Compound 237]
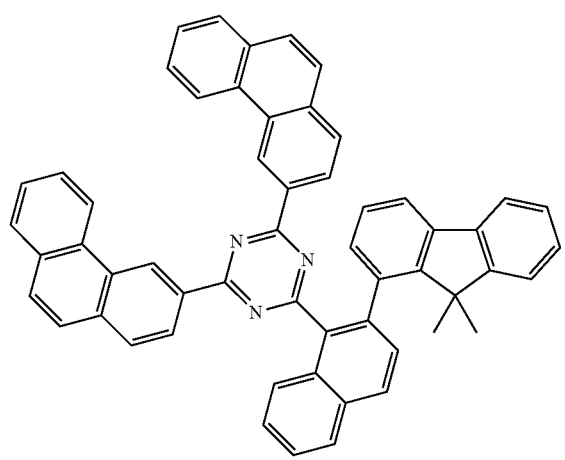
[Compound 238]
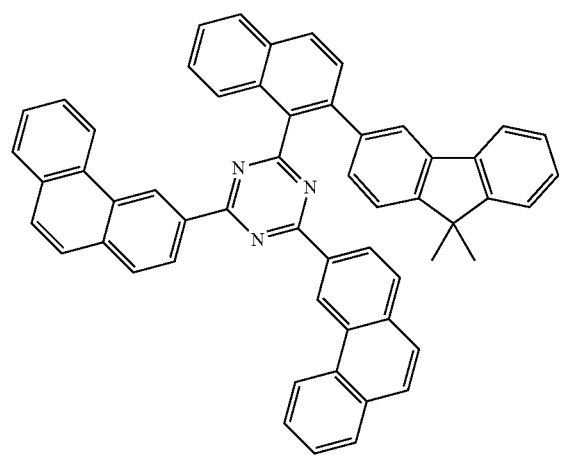
[Compound 239]
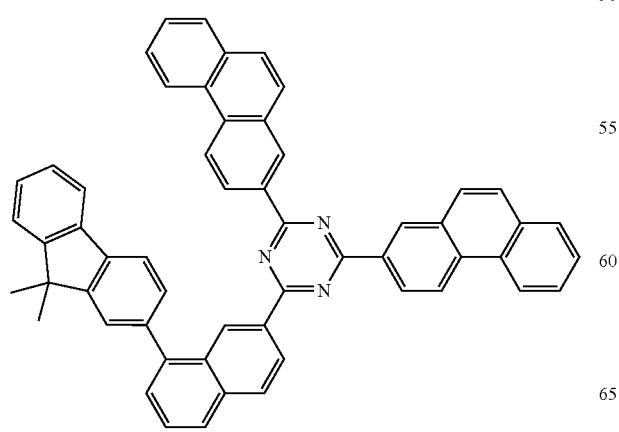
[Compound 240]
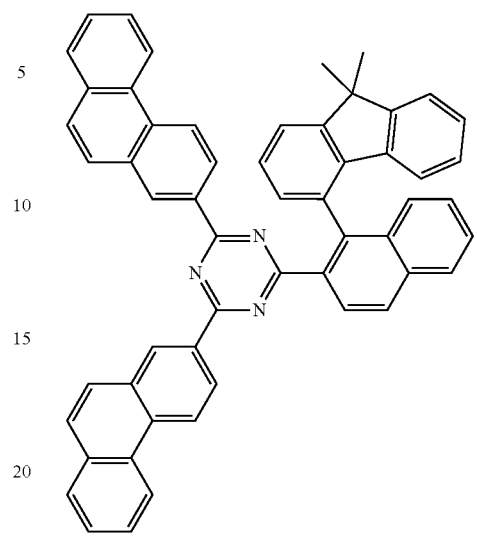
[Compound 241]
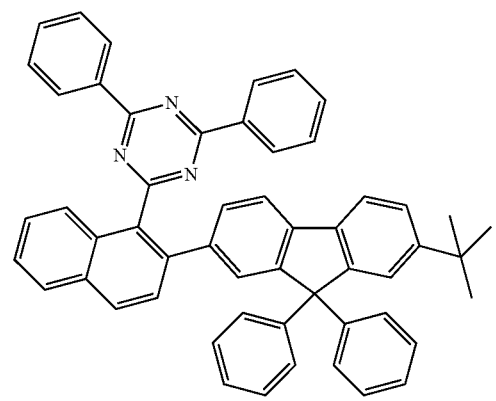
[Compound 242]
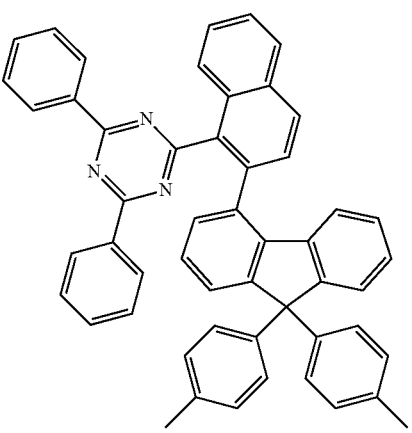

[Compound 243]
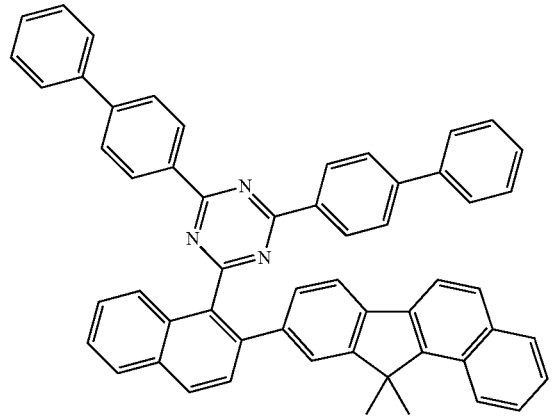
[Compound 244]
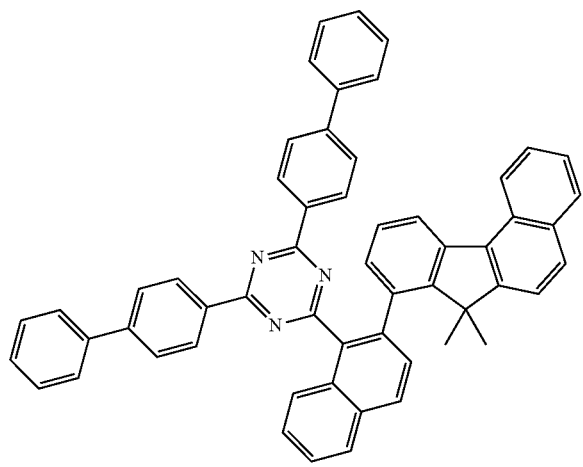
[Compound 245]
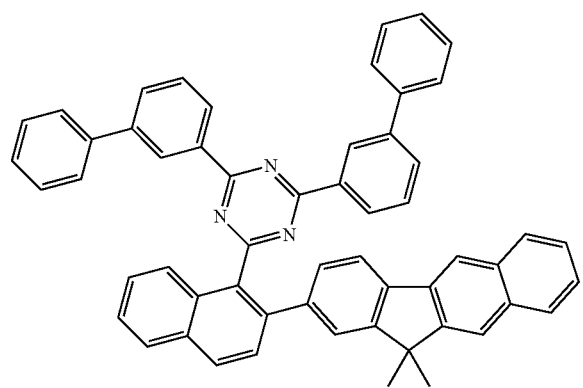
[Compound 246]
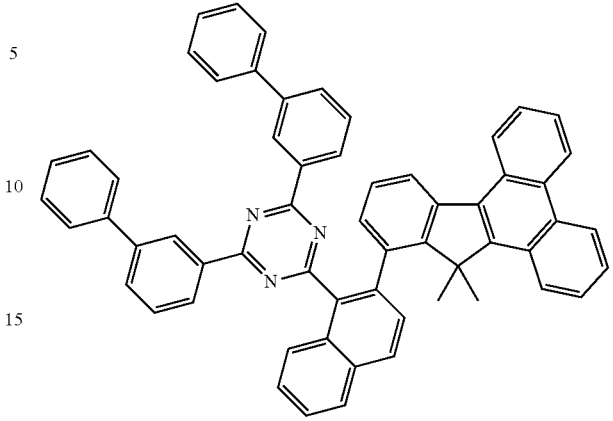
[Compound 247]
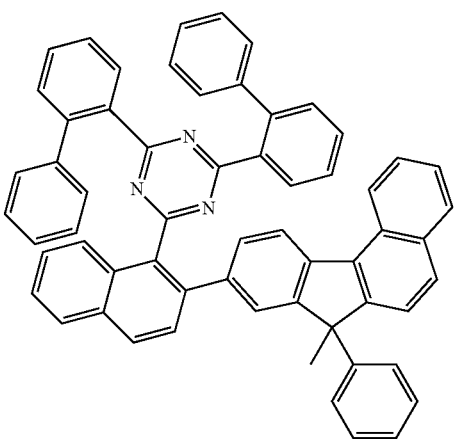
[Compound 248]
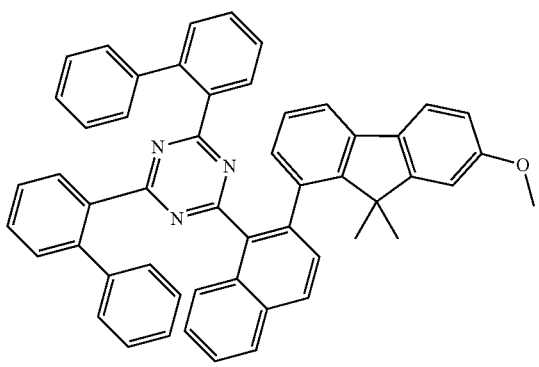
[Compound 249]
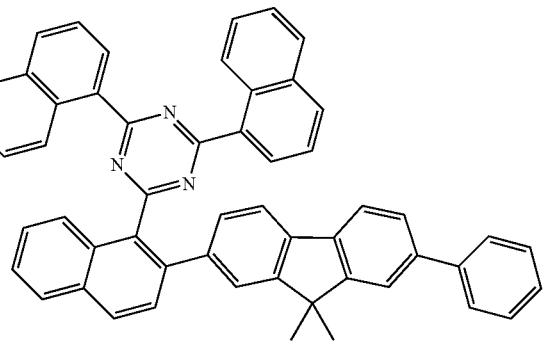

[Compound 250]
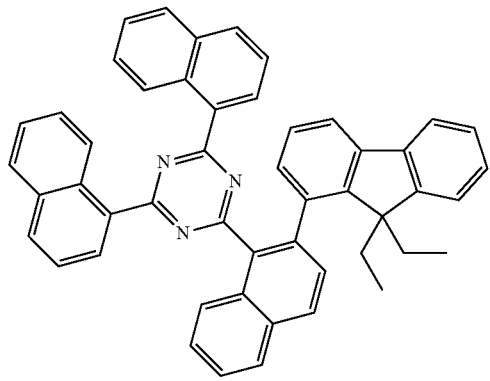
[Compound 251]
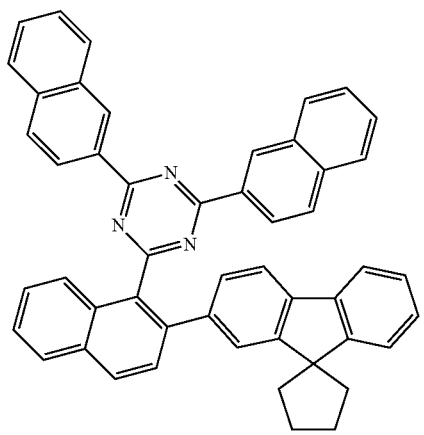
[Compound 252]
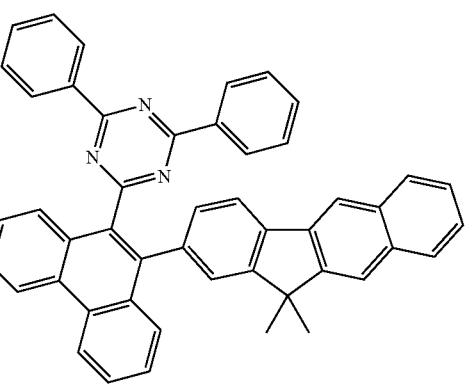
[Compound 253]
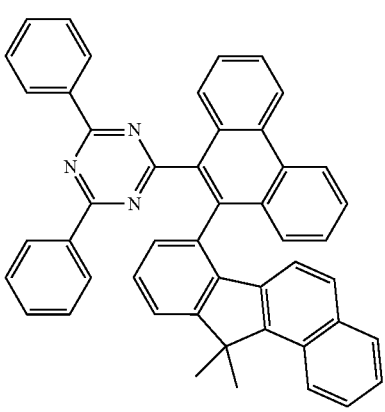
[Compound 254]
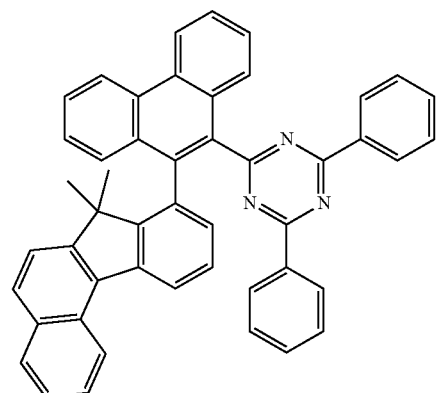
[Compound 255]
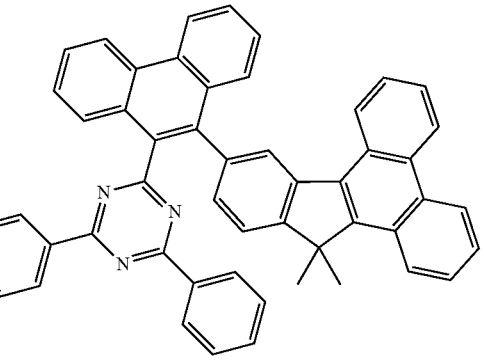
[Compound 256]
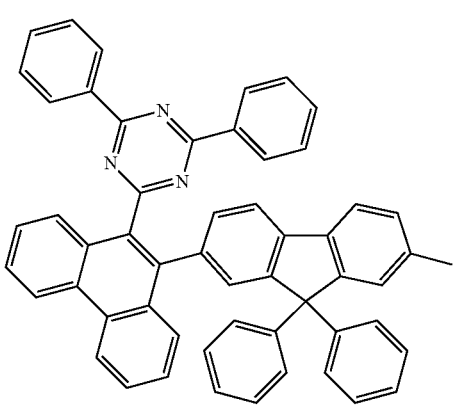

[Compound 257]
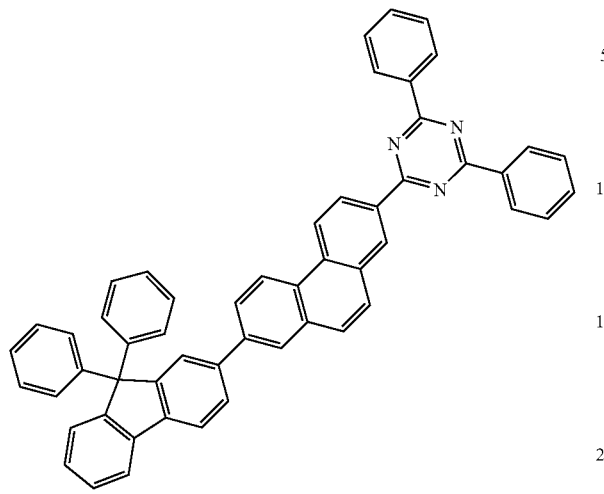
[Compound 258]
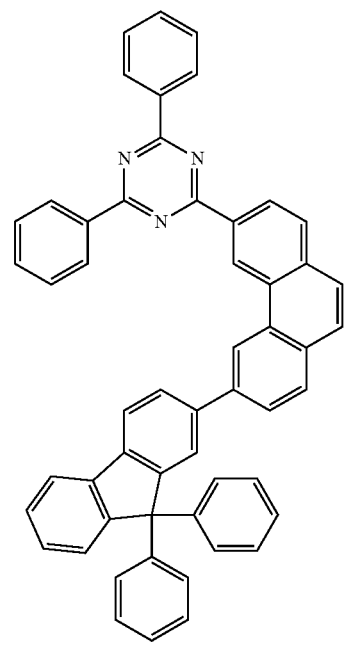
[Compound 259]
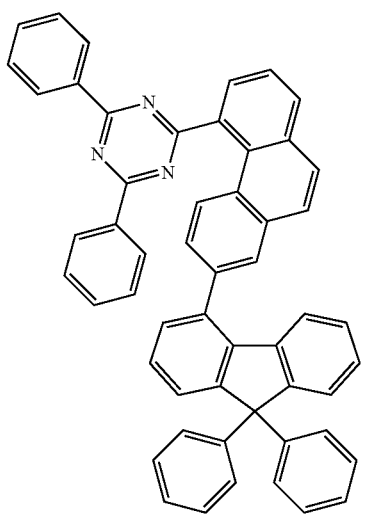
[Compound 260]
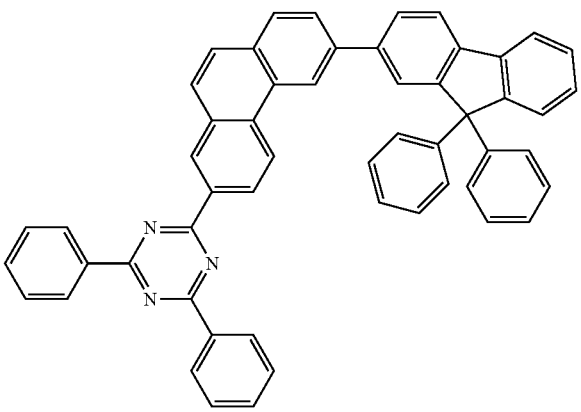
[Compound 261]
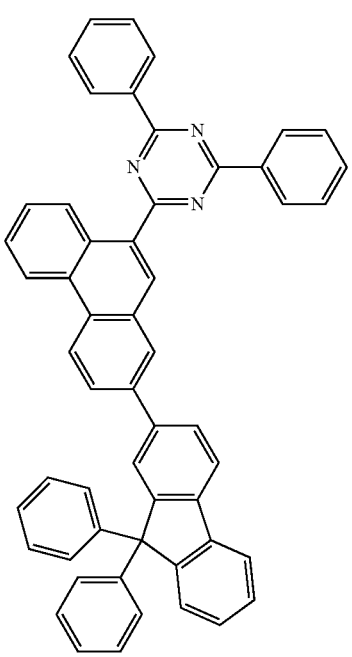

[Compound 262]
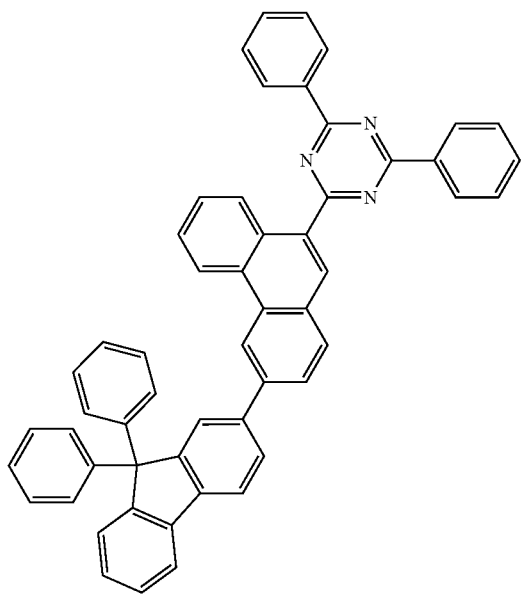
[Compound 264]
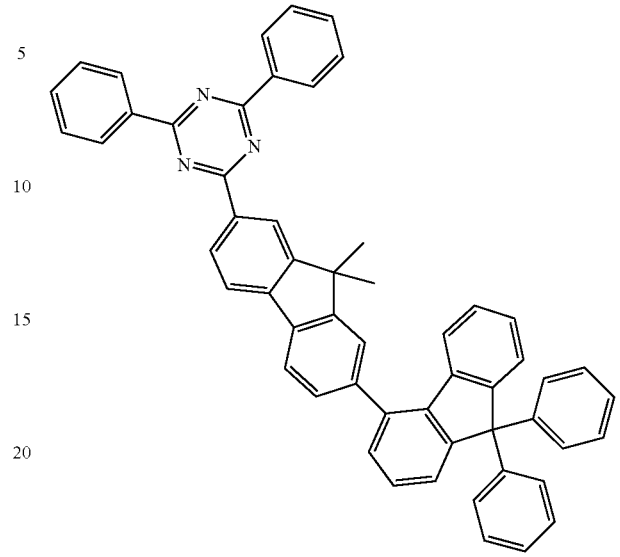
[Compound 263]
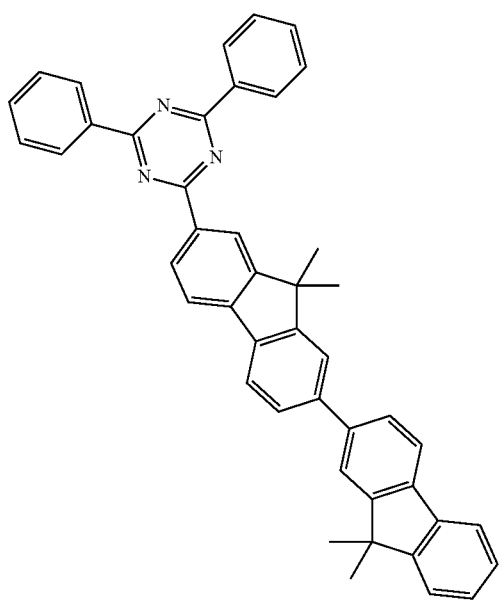
[Compound 265]
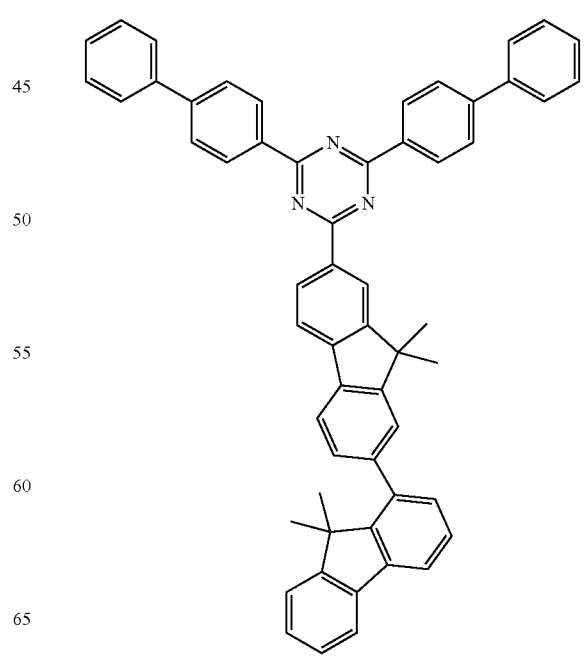

[Compound 266]
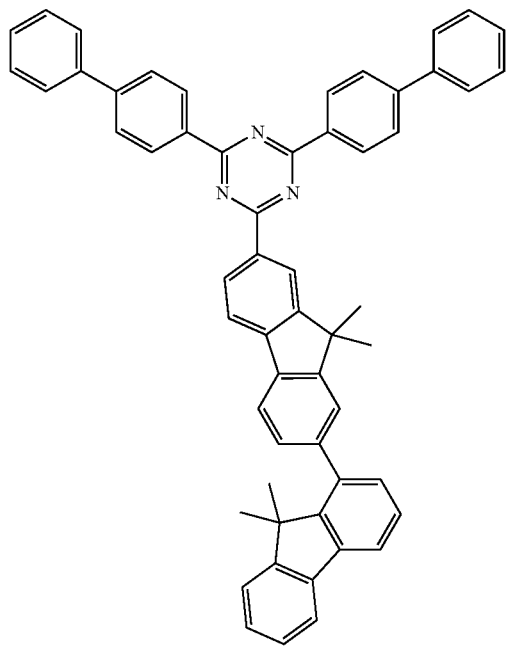
[Compound 268]
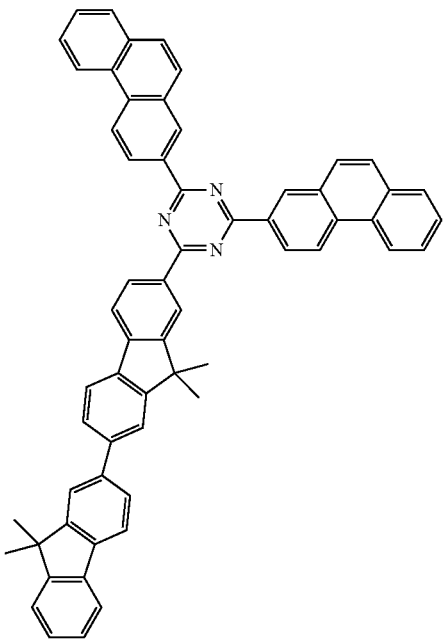
[Compound 267]
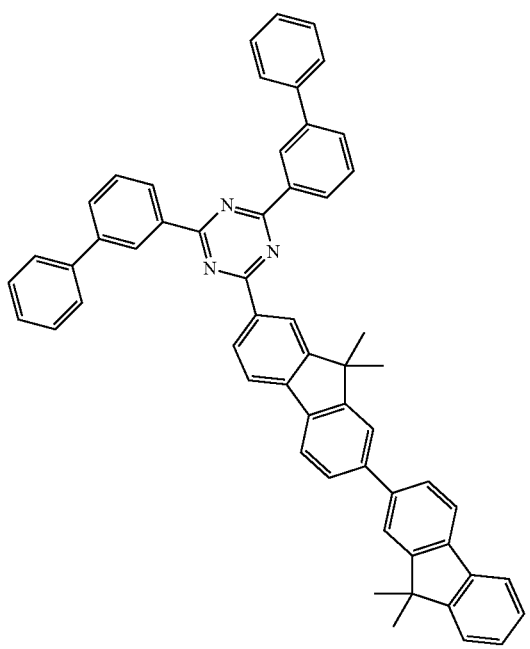
[Compound 269]
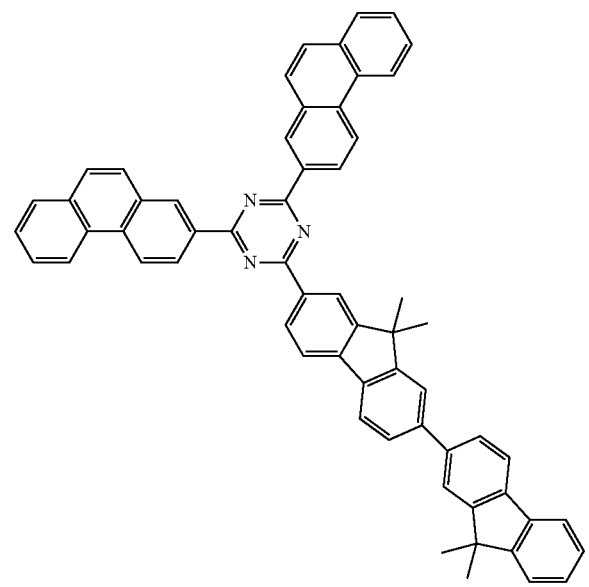

[Compound 270]
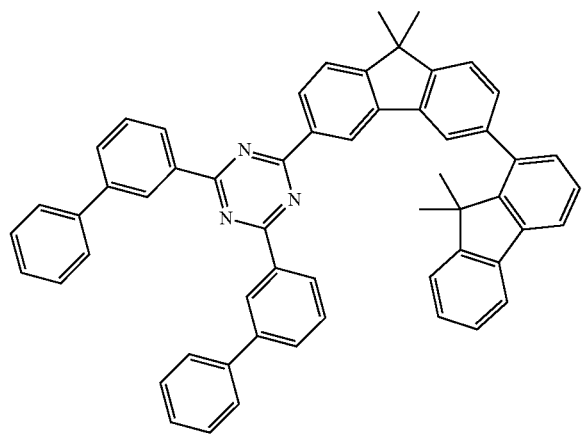
[Compound 271]
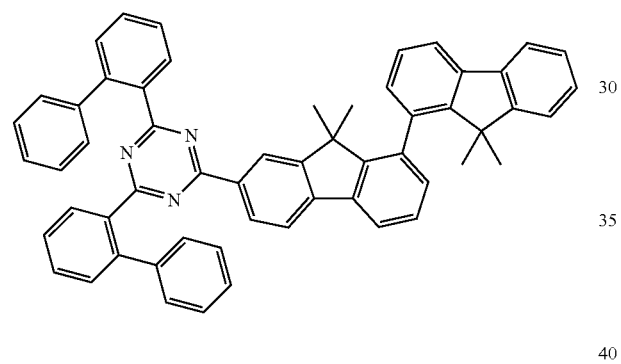
[Compound 272]
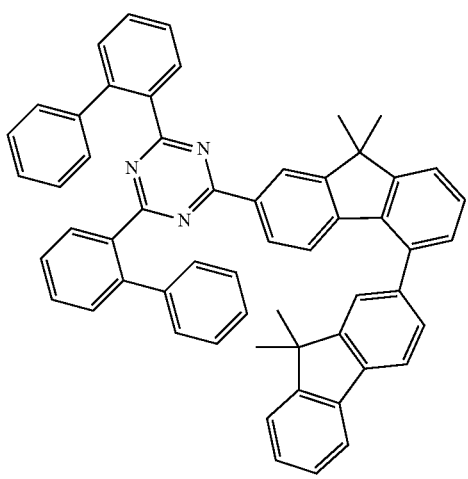
[Compound 273]
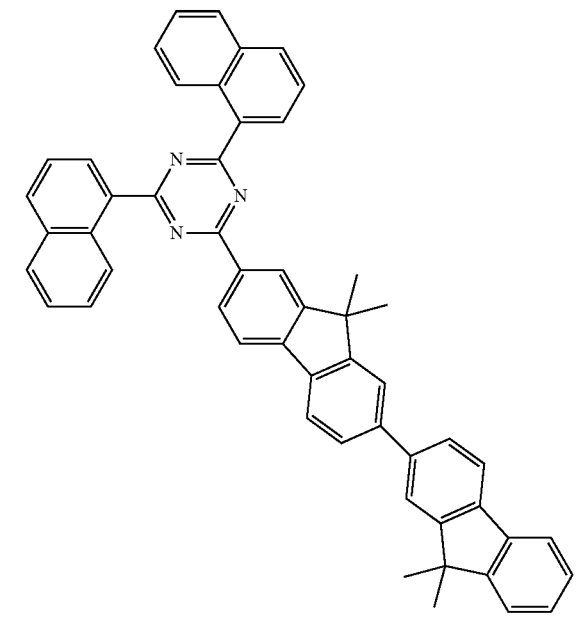
[Compound 274]
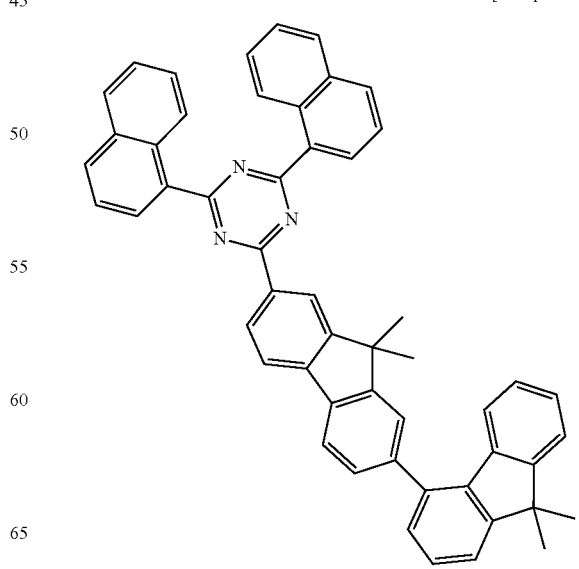

[Compound 275]
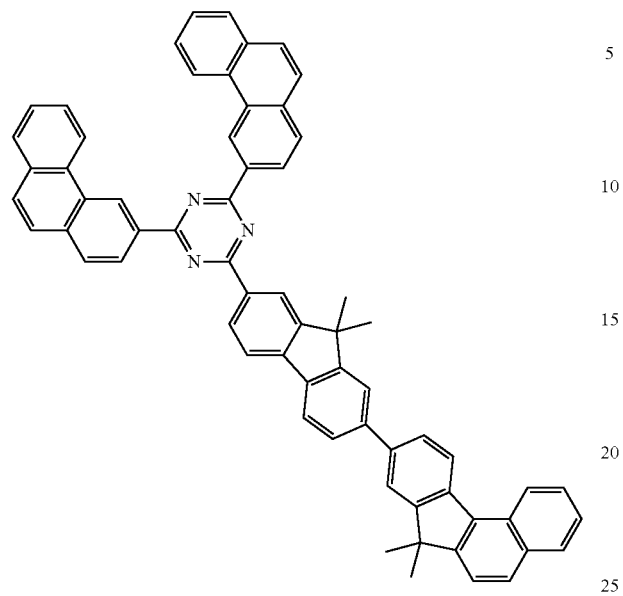
[Compound 276]
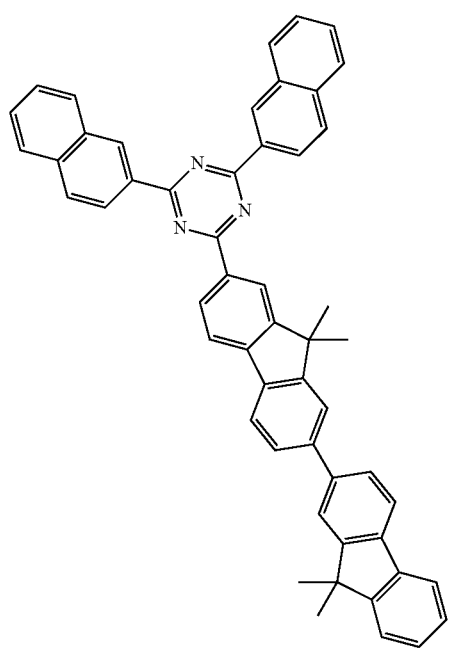
[Compound 277]
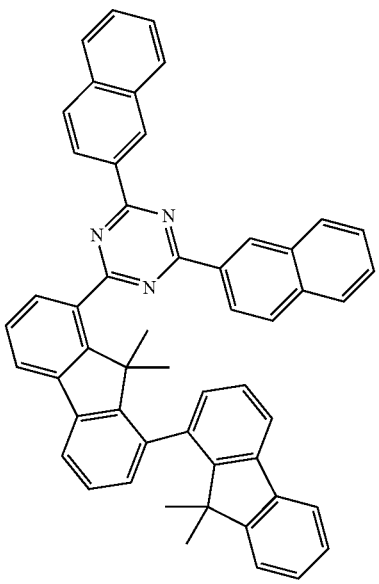
[Compound 278]
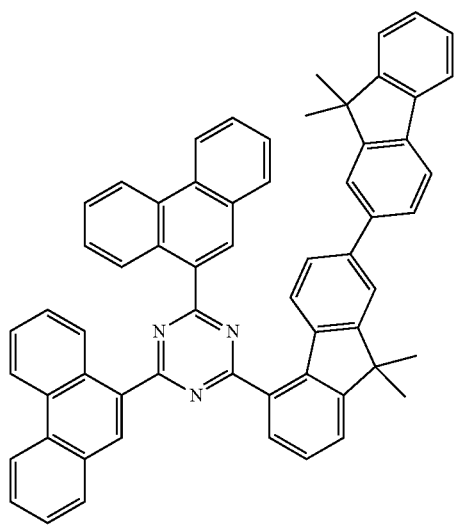

[Compound 279]
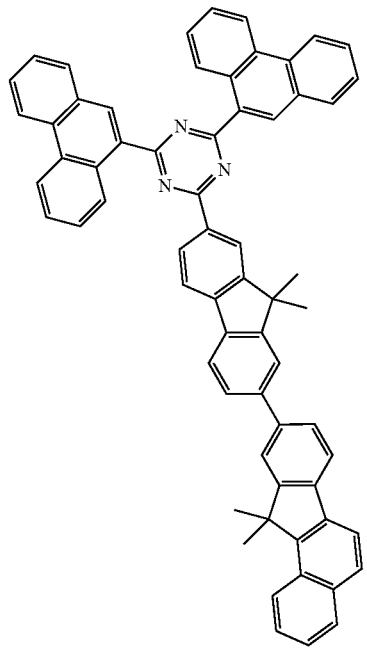
[Compound 280]
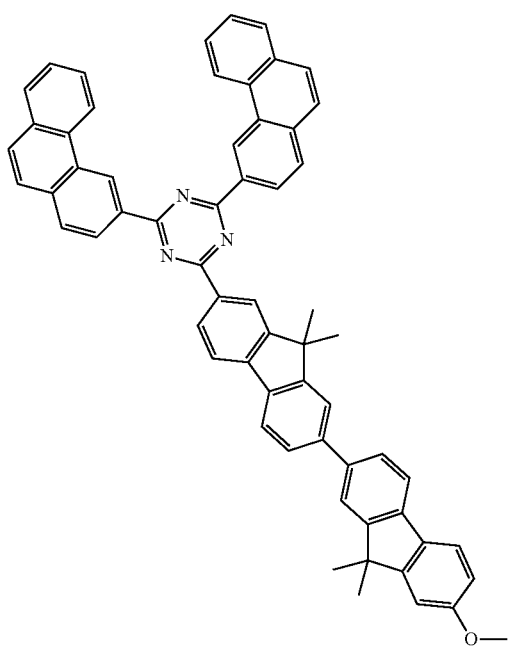
[Compound 281]
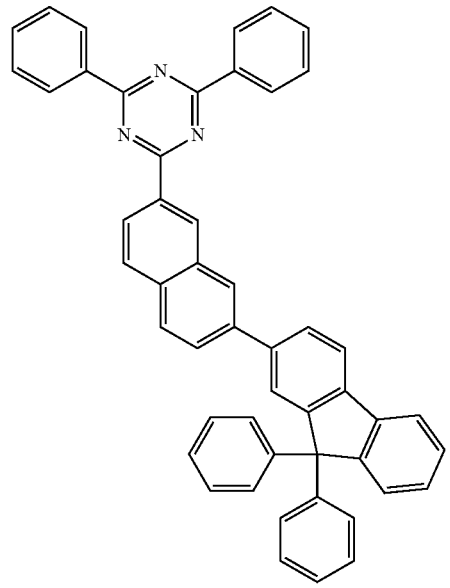
[Compound 282]
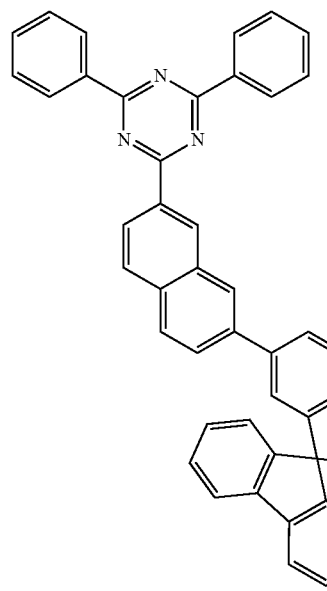

[Compound 283]
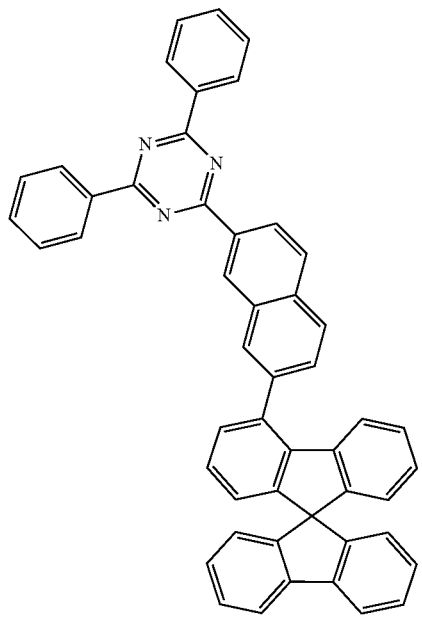
[Compound 284]
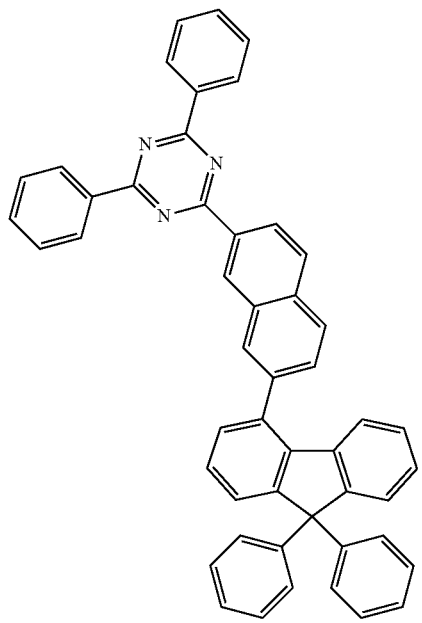
[Compound 285]
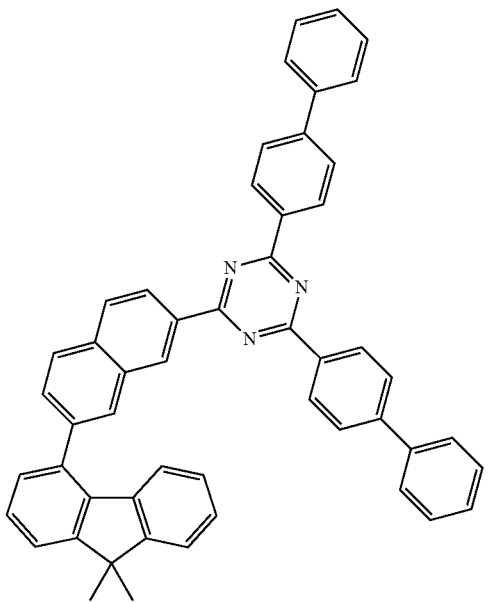
[Compound 286]
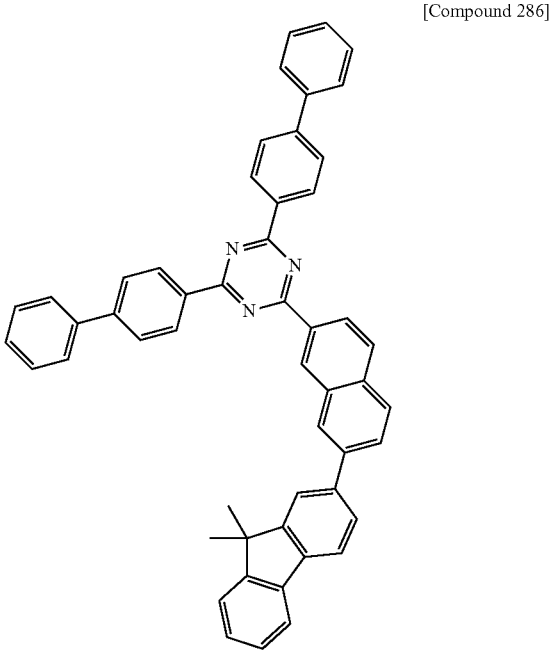

[Compound 287]
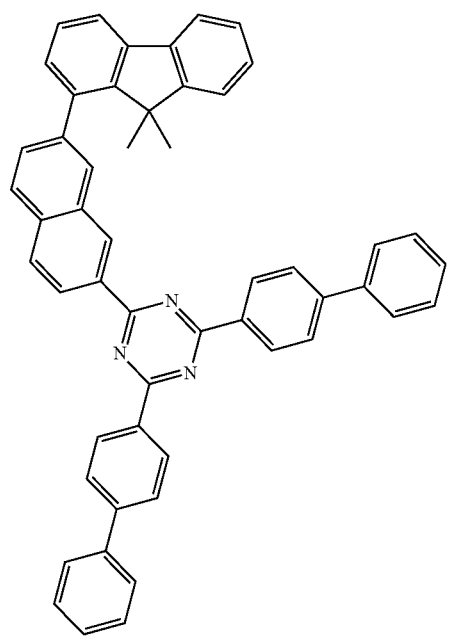
[Compound 289]
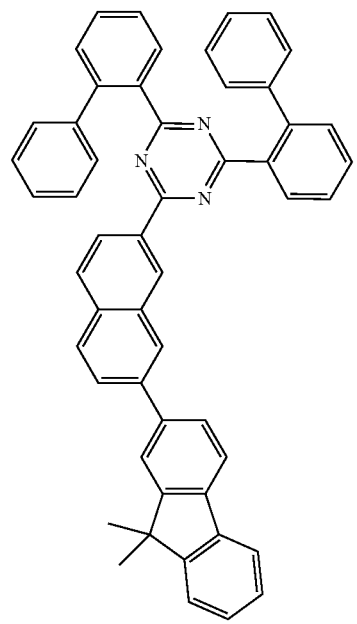
[Compound 288]
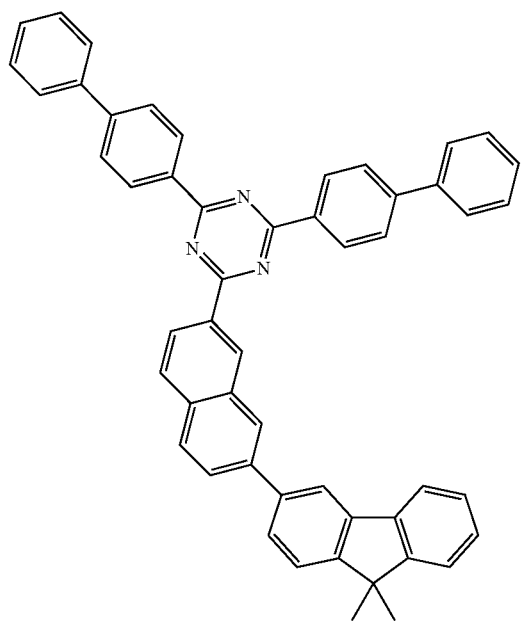
[Compound 290]
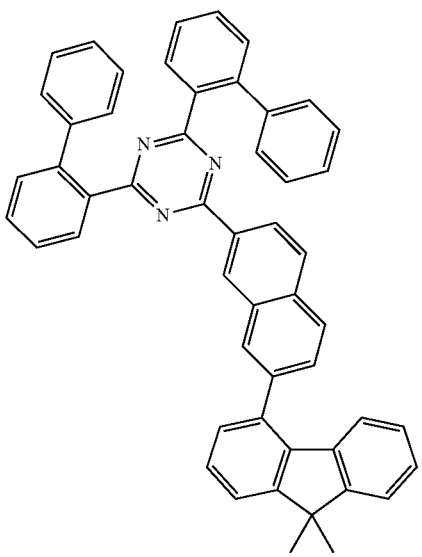

[Compound 291]
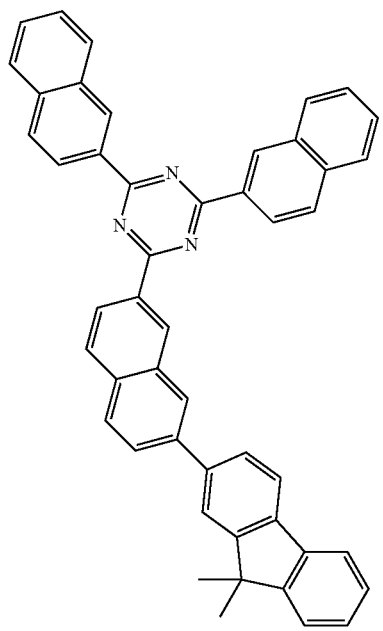
[Compound 292]
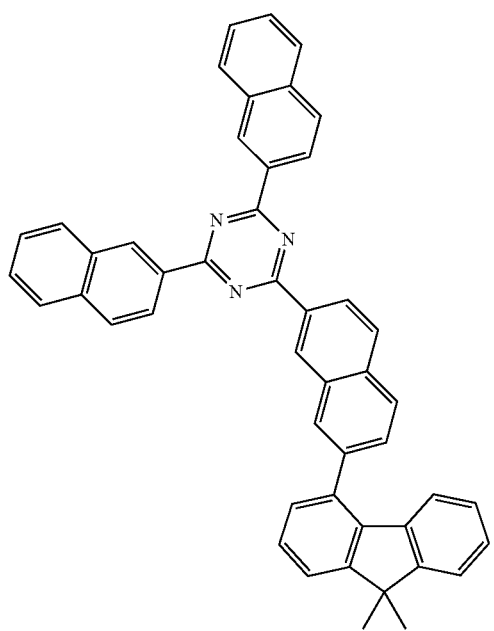
[Compound 293]
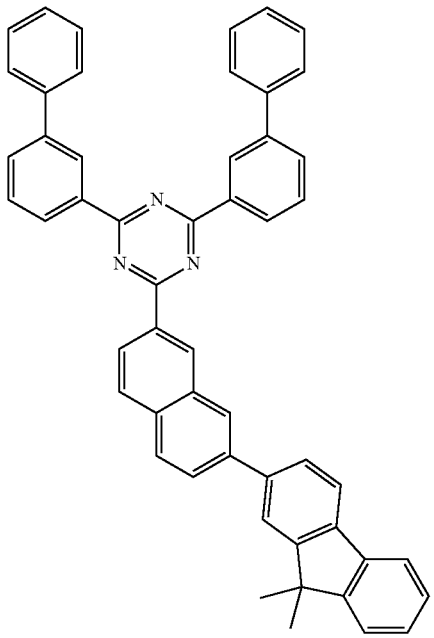
[Compound 294]
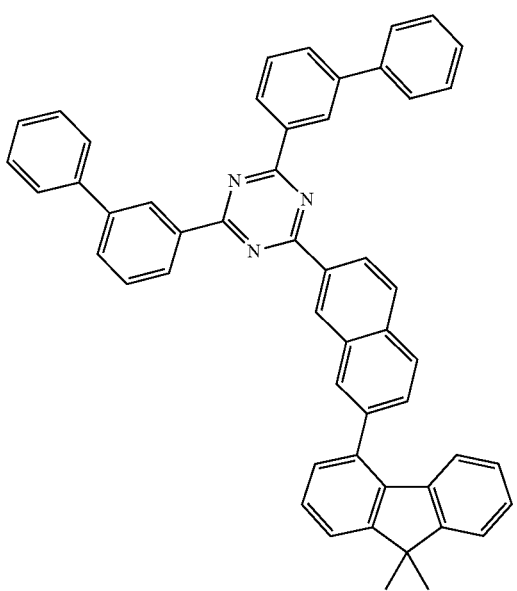

[Compound 295]
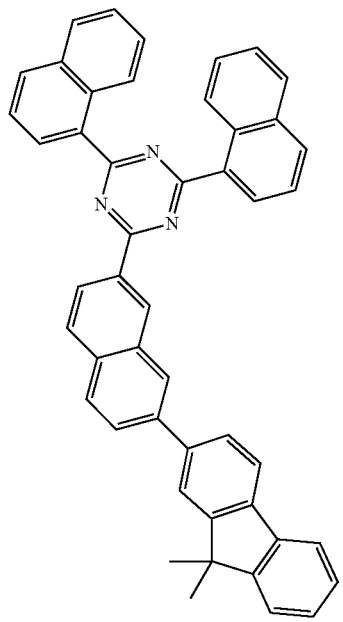
[Compound 297]
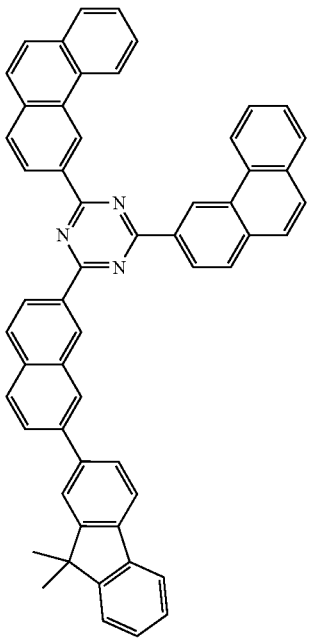
[Compound 296]
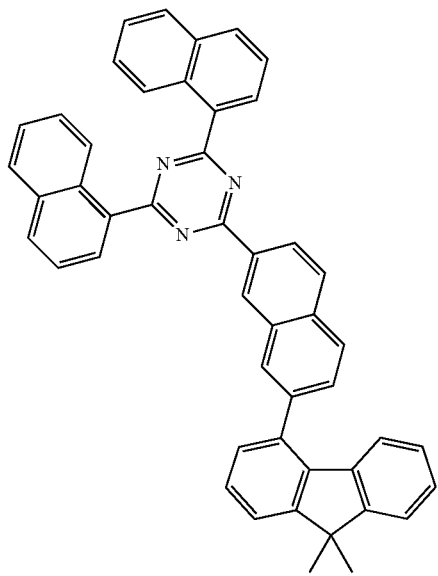
[Compound 298]

[Compound 299]
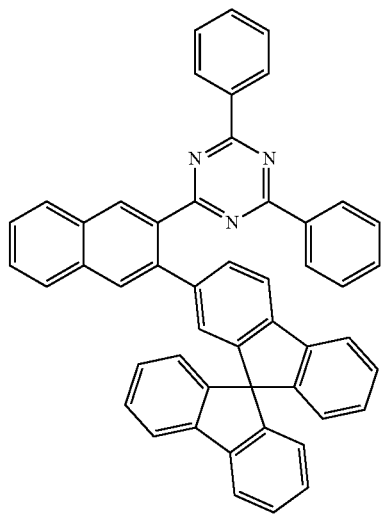
[Compound 302]
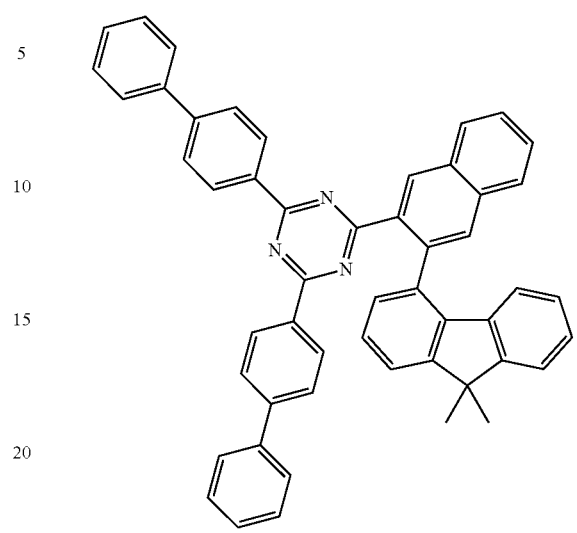
[Compound 300]
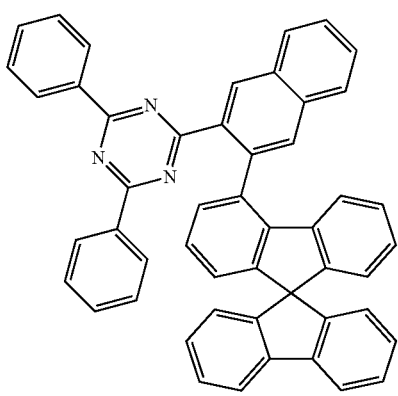
[Compound 301]
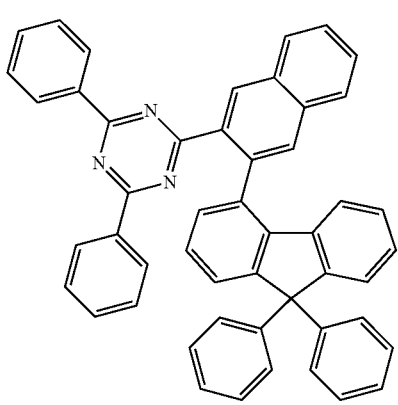
[Compound 303]
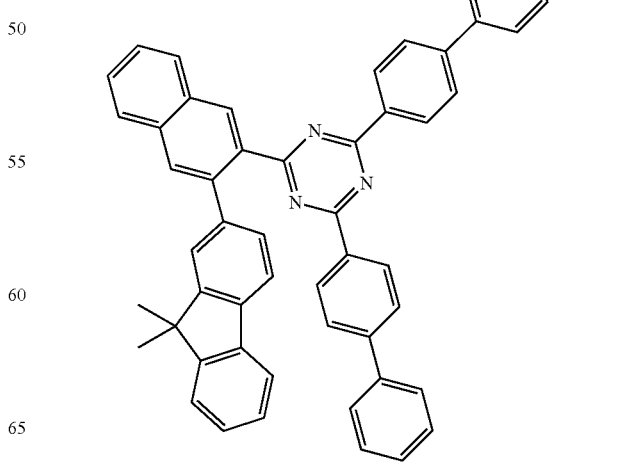

[Compound 304]
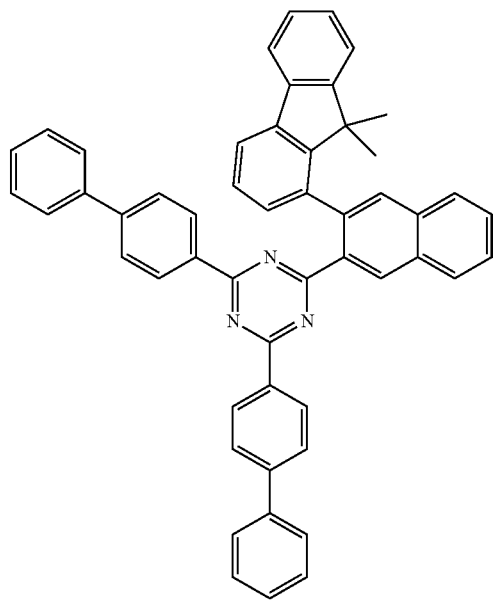
[Compound 305]
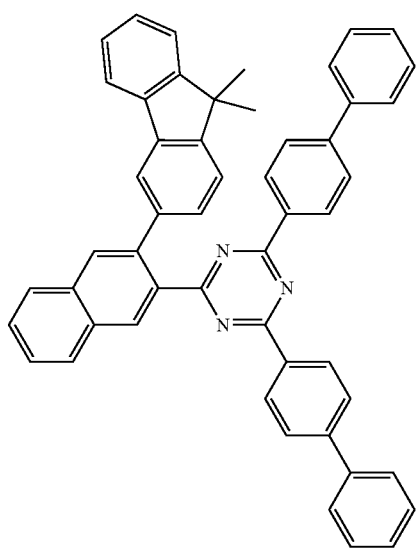
[Compound 306]
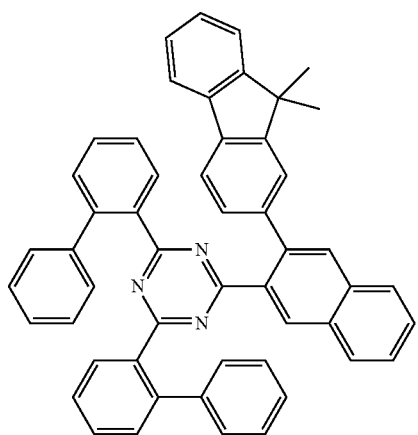
[Compound 307]
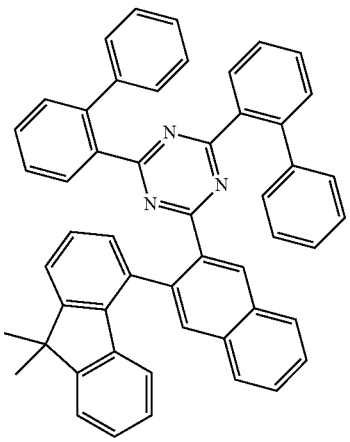
[Compound 308]
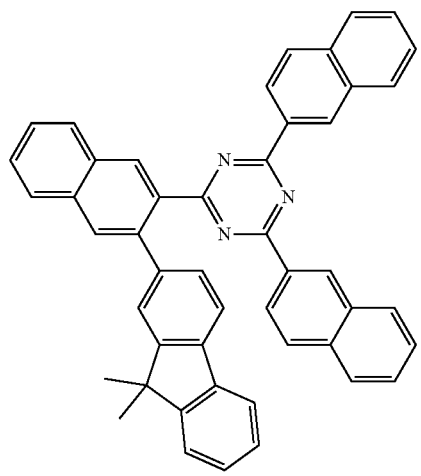
[Compound 309]
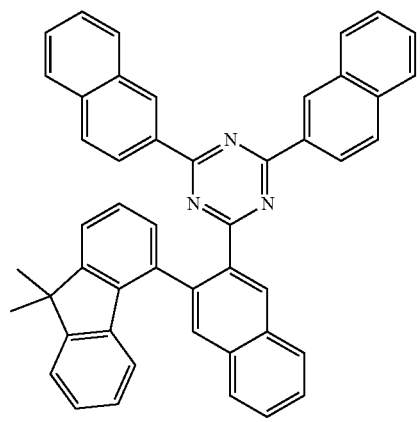

[Compound 310]
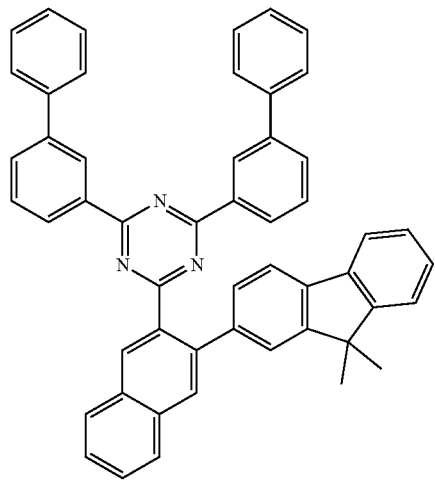
[Compound 311]
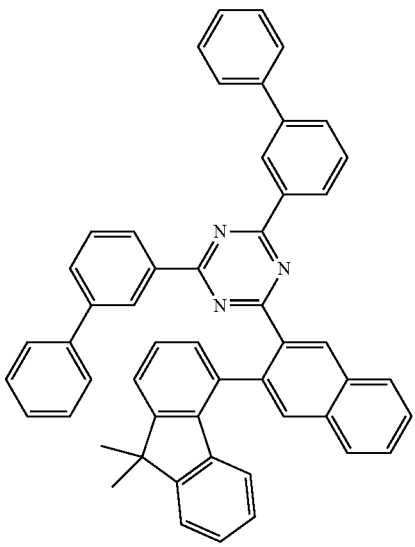
[Compound 312]
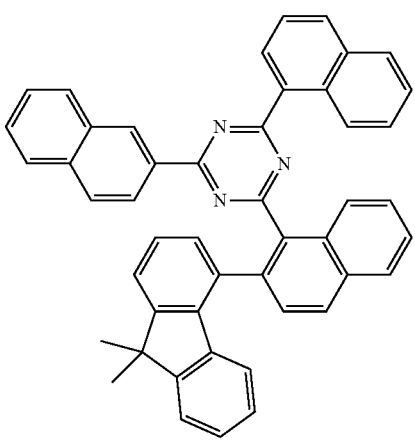
[Compound 313]
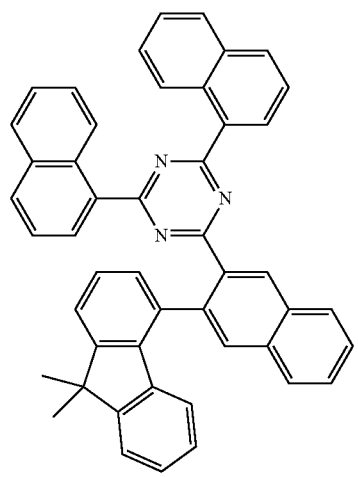
[Compound 313]
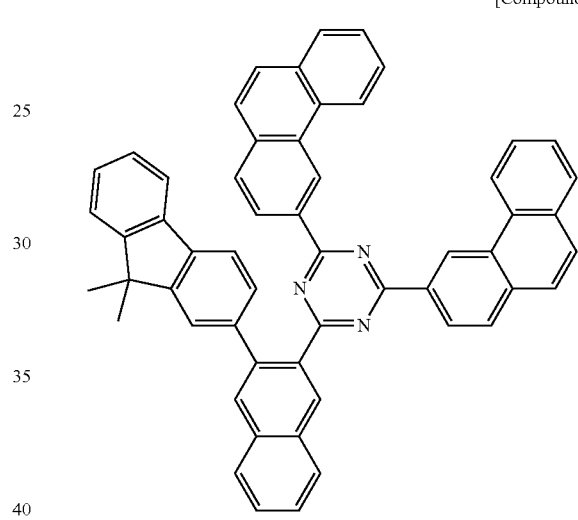
[Compound 314]
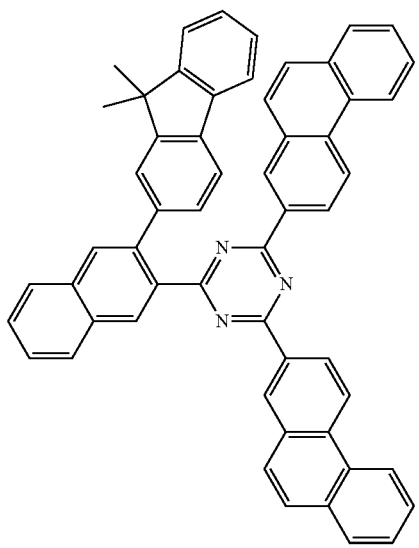

[Compound 316]

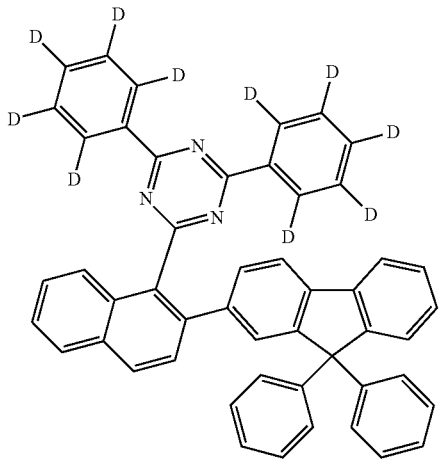

The compound represented by Formula 1 may be prepared based on the Preparation Examples to be described below. According to an exemplary embodiment, the compound may be prepared by the method such as the following Reaction Formula 1.

[Reaction Formula 1]

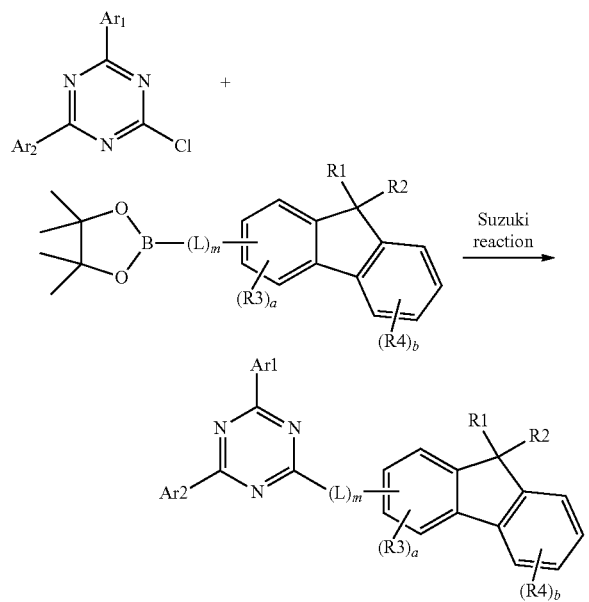

In the reaction formula, the definition of Ar1, Ar2, L, R1, R2, R3, R4, a, b, and m is the same as that in Formula 1.

Specifically, according to an exemplary embodiment of the present specification, the compound of Formula 1 may be prepared by coupling a compound of a triazine derivative substituted with halogen with an aromatic compound substituted with boronic acid or a boronic acid derivative using a palladium catalytic reaction.

Further, the present specification provides an organic light emitting device including the compound represented by Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers includes the compound of Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which simultaneously transports and injects holes, and the hole injection layer, the hole transporting layer, or the layer which simultaneously transports and injects holes includes the compound of Formula 1.

In another exemplary embodiment, the organic material layer includes a light emitting layer, and the light emitting layer includes the compound of Formula 1.

According to an exemplary embodiment of the present specification, the organic material layer includes an electron transporting layer or an electron injection layer, and the electron transporting layer or the electron injection layer includes the compound of Formula 1.

In an exemplary embodiment of the present specification, the electron transporting layer, the electron injection layer, or the layer which simultaneously transports and injects electrons includes the compound of Formula 1.

In another exemplary embodiment, the organic material layer includes a light emitting layer and an electron transporting layer, and the electron transporting layer includes the compound of Formula 1.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 1, a positive electrode 2, a light emitting layer 3, and a negative electrode 4. In the structure, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of Formula 1.

When the organic light emitting device includes a plurality of organic material layers, the organic material layer may be formed of the same material or different materials.

One exemplary embodiment of the present specification is an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the hetero-cyclic compound. In one exemplary embodiment, as the two or more organic material layers, two or more may be selected from the group consisting of an electron transporting layer, an electron injection layer, a layer which simultaneously transports and injects electrons, and a hole blocking layer.

In an exemplary embodiment of the present specification, the organic material layer includes two or more electron transporting layers, and at least one of the two or more electron transporting layers includes the hetero-cyclic compound. Specifically, in an exemplary embodiment of the present specification, the hetero-cyclic compound may also be included in one layer of the two or more electron transporting layers, and may be included in each of the two or more electron transporting layers.

In addition, in an exemplary embodiment of the present specification, when the hetero-cyclic compound is included in each of the two or more electron transporting layers, the other materials except for the hetero-cyclic compound may be the same as or different from each other.

The organic light emitting device of the present specification may be manufactured by the materials and methods known in the art, except that one or more layers of the organic material layers include the compound of Formula 1, that is, the compound represented by Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a negative electrode, thereon. In addition to the method described above, an organic light emitting device may be made by subsequently depositing a negative electrode material, an organic material layer, and a positive electrode material on a substrate.

Further, the compound of Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be manufactured by sequentially stacking a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as $LiF/Al$ or $LiO_2/Al$, and the like, but are not limited thereto.

The hole injection material is a layer which injects holes from an electrode, and is preferably a compound which has a capability of transporting holes, and thus has an effect of injecting holes at positive electrode and an excellent effect of injecting holes for the light emitting layer or the light emitting material, prevents excitons produced from the light emitting layer from moving to an electron injection layer or an electron injection material, and is excellent in forming a thin film. It is preferred that the highest occupied molecular orbital (HOMO) of the hole injection material is between the work function of the positive electrode material and the HOMO of an adjacent organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The electron transporting layer is a layer which receives holes from the hole injection layer and transports holes to the light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex (Alq$_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto. Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like having an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which receives electrons from an electron injection layer and transports electrons to a light emitting layer, and an electron transporting material is a material which may receive electrons well from a negative electrode and may transfer electrons to a light emitting layer, and is suitably a material which has large mobility for the electrons. Specific examples thereof include: an Al complex of 8-hydroxyquinoline; a complex including Alq$_3$; an organic radical compound; and hydroxyflavone-metal complex, but are not limited thereto. The electron transporting layer may be used with any desired cathode material, as used according to the related art. In particular, examples of an appropriate cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to the hole injection layer, and is also excellent in forming a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Formula 1 may be included in an organic solar cell or an organic transistor in addition to the organic light emitting device.

The preparation of the compound represented by Formula 1 and the organic light emitting device including the same will be specifically described in the following Examples. However, the following Examples are provided for illustrating the present specification, and the range of the present specification is not limited thereby.

PREPARATION EXAMPLES

Preparation Example 1

Preparation of [Compound 1]

2-chloro-4,6-diphenyl-1,3,5-triazine (10.0 g, 37.4 mmol) and 2-(2-(9,9-diphenyl-9H-fluoren-2-yl)naphthalen-1 yl)-4,4,5,5-tetramethyl-1,3,2-dioxaborolane (21.3 g, 37.4 mmol) were put into 200 mL of THF. 75 mL of 2.0 M K$_2$CO$_3$ and 0.8 g of Pd(PPh$_3$)$_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 1] (19.4 g, yield 77%, MS: [M+H]$^+$=676).

Preparation Example 2

Preparation of [Compound 6]

2-chloro-4,6-diphenyl-1,3,5-triazine (10.0 g, 37.4 mmol) and 2-(4-(9,9'-spirobi[fluoren]-2-yl)naphthalen-1-yl)-4,4,5,5-tetramethyl-1,3,2-dioxaborolane (21.3 g, 37.4 mmol) were put into 200 mL of THF.

75 mL of 2.0 M K$_2$CO$_3$ and 0.8 g of Pd(PPh$_3$)$_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 6] (18.7 g, yield 74%, MS: [M+H]$^+$=674).

Preparation Example 3

Preparation of [Compound 19]

2-chloro-4,6-diphenyl-1,3,5-triazine (10.0 g, 37.4 mmol) and 2-(7-(9,9-diphenyl-9H-fluoren-4-yl)naphthalen-1-yl)-4, 4,5,5-tetramethyl-1,3,2-dioxaborolane (21.3 g, 37.4 mmol) were put into 200 mL of THF. 75 mL of 2.0 M $K_2CO_3$ and 0.8 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 19] (17.7 g, yield 70%, MS: $[M+H]^+=676$).

Preparation Example 4

Preparation of [Compound 23]

2,4-di([1,1'-biphenyl]-4-yl)-6-chloro-1,3,5-triazine (10.0 g, 23.8 mmol) and 2-(2-(9,9-dimethyl-9H-fluoren-2-yl) naphthalen-1-yl)-4,4,5,5-tetramethyl-1,3,2-dioxaborolane (10.6 g, 23.8 mmol) were put into 200 mL of THF. 75 mL of 2.0 M $K_2CO_3$ and 0.5 g of $Pd(PPh_3)_4$ were put thereinto, and then the resulting mixture was stirred and refluxed for 9 hours. The mixture was cooled to normal temperature, and then a solid produced by filtering the mixture was recrystallized with chloroform and ethanol, thereby preparing [Compound 23] (12.7 g, yield 76%, MS: $[M+H]^+=704$).

Preparation Example 5

Preparation of [Compound 67]

2,4-di([1,1'-biphenyl]-2-yl)-6-chloro-1,3,5-triazine (10.0 g, 23.8 mmol) and 2-(5-(9,9-dimethyl-9H-fluoren-2-yl) naphthalen-1-yl)-4,4,5,5-tetramethyl-1,3,2-dioxaborolane (10.6 g, 23.8 mmol) were put into 200 mL of THF. 75 mL of 2.0 M $K_2CO_3$ and 0.5 g of $Pd(PPh_3)_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 67] (11.9 g, yield 71%, MS: $[M+H]^+=704$).

Preparation Example 6

Preparation of [Compound 89]

2-chloro-4,6-di(naphthalen-1-yl)-1,3,5-triazine (10.0 g, 27.2 mmol) and 2-(6-(9,9-dimethyl-9H-fluoren-2-yl)naphthalen-1-yl)-4,4,5,5-tetramethyl-1,3,2-dioxaborolane (12.1 g, 27.2 mmol) were put into 200 mL of THF. 75 mL of 2.0 M $K_2CO_3$ and 0.5 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 89] (12.2 g, yield 69%, MS: $[M+H]^+=652$).

Preparation Example 7

Preparation of [Compound 112]

2-chloro-4,6-di(naphthalen-2-yl)-1,3,5-triazine (10.0 g, 27.2 mmol) and 2-(7-(9,9-dimethyl-9H-fluoren-2-yl)naphthalen-1-yl)-4,4,5,5-tetramethyl-1,3,2-dioxaborolane (12.1 g, 27.2 mmol) were put into 200 mL of THF. 75 mL of 2.0 M $K_2CO_3$ and 0.5 g of $Pd(PPh_3)_4$ were put thereinto, and then the resulting mixture was stirred and refluxed for 6 hours. The mixture was cooled to normal temperature, and then a solid produced by filtering the mixture was recrys-tallized with chloroform and ethanol, thereby preparing [Compound 112] (13.6 g, yield 77%, MS: $[M+H]^+=652$).

Preparation Example 8

Preparation of [Compound 127]

2-chloro-4,6-di(phenanthren-9-yl)-1,3,5-triazine (10.0 g, 21.4 mmol) and 2-(5-(9,9-dimethyl-9H-fluoren-2-yl)naphthalen-1-yl)-4,4,5,5-tetramethyl-1,3,2-dioxaborolane (9.5 g, 21.4 mmol) were put into 200 mL of THF. 75 mL of 2.0 M $K_2CO_3$ and 0.5 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 127] (10.8 g, yield 67%, MS: $[M+H]^+=752$).

Preparation Example 9

Preparation of [Compound 183]

2-chloro-4,6-diphenyl-1,3,5-triazine (10.0 g, 37.4 mmol) and 2-(10-(9,9-dimethyl-9H-fluoren-2-yl)phenanthren-9-yl)-4,4,5,5-tetramethyl-1,3,2-dioxaborolane (18.6 g, 37.4 mmol) were put into 200 mL of THF. 75 mL of 2.0 M $K_2CO_3$ and 0.8 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 183] (15.3 g, yield 68%, MS: $[M+H]^+=602$).

Preparation Example 10

Preparation of [Compound 263]

2-chloro-4,6-diphenyl-1,3,5-triazine (10.0 g, 37.4 mmol) and 4,4,5,5-tetramethyl-2-(9,9,9',9'-tetramethyl-9H,9'H-[2,2'-bifluoren]-7-yl)-1,3,2-dioxaborolane (19.2 g, 37.4 mmol) were put into 200 mL of THF. 75 mL of 2.0 M $K_2CO_3$ and 0.8 g of $Pd(PPh_3)_4$ were put thereinto, and then the resulting mixture was stirred and refluxed for 6 hours. The mixture was cooled to normal temperature, and then a solid produced by filtering the mixture was recrystallized with chloroform and ethanol, thereby preparing [Compound 263] (16.6 g, yield 72%, MS: $[M+H]^+=618$).

Preparation Example 11

Preparation of [Compound 281]

2-chloro-4,6-diphenyl-1,3,5-triazine (10.0 g, 37.4 mmol) and 2-(7-(9,9-diphenyl-9H-fluoren-2-yl)naphthalen-2-yl)-4,4,5,5-tetramethyl-1,3,2-dioxaborolane (21.3 g, 37.4 mmol) were put into 200 mL of THF. 75 mL of 2.0 M $K_2CO_3$ and 0.8 g of $Pd(PPh_3)_4$ were put thereinto, and then the resulting mixture was stirred and refluxed for 5 hours. The mixture was cooled to normal temperature, and then a solid produced by filtering the mixture was recrystallized with chloroform and ethanol, thereby preparing [Compound 281] (19.7 g, yield 78%, MS: $[M+H]^+=676$).

Preparation Example 12

Preparation of [Compound 299]

2-chloro-4,6-diphenyl-1,3,5-triazine (10.0 g, 37.4 mmol) and 2-(3-(9,9-diphenyl-9H-fluoren-2-yl)naphthalen-2-yl)-4, 4,5,5-tetramethyl-1,3,2-dioxaborolane (21.3 g, 37.4 mmol) were put into 200 mL of THF. 75 mL of 2.0 M $K_2CO_3$ and 0.8 g of $Pd(PPh_3)_4$ were put thereinto, and then the resulting mixture was stirred and refluxed for 7 hours. The mixture was cooled to normal temperature, and then a solid produced by filtering the mixture was recrystallized with chloroform and ethanol, thereby preparing [Compound 299] (18.2 g, yield 72%, MS: $[M+H]^+=676$).

Preparation Example 13

Preparation of [Compound 312]

2-chloro-4,6-di(naphthalen-1-yl)-1,3,5-triazine (10.0 g, 27.2 mmol) and 2-(3-(9,9-dimethyl-9H-fluoren-2-yl)naphthalen-2-yl)-4,4,5,5-tetramethyl-1,3,2-dioxaborolane (12.1 g, 27.2 mmol) were put into 200 mL of THF. 75 mL of 2.0 M $K_2CO_3$ and 0.6 g of $Pd(PPh_3)_4$ were added thereinto, and then the resulting mixture was stirred and refluxed for 8 hours. The mixture was cooled to normal temperature, and then a solid produced by filtering the mixture was recrystallized with chloroform and ethanol, thereby preparing [Compound 312] (13.5 g, yield 76%, MS: $[M+H]^+=652$).

Preparation Example 14

Preparation of [Compound 316]

2-chloro-4,6-bis(phenyl-d5)-1,3,5-triazine (10.0 g, 36.0 mmol) and 2-(2-(9,9-diphenyl-9H-fluoren-2-yl)naphthalen-1-yl)-4,4,5,5-tetramethyl-1,3,2-dioxaborolane (20.5 g 36.0 mmol) were put into 200 mL of THF. 75 mL of 2.0 M $K_2CO_3$ and 0.8 g of $Pd(PPh_3)_4$ were put thereinto, and then the resulting mixture was stirred and refluxed for 8 hours. The mixture was cooled to normal temperature, and then a solid produced by filtering the mixture was recrystallized with chloroform and ethanol, thereby preparing [Compound 361] (16.3 g, yield 66%, MS: $[M+H]^+=686$).

Example

Example 1

A glass substrate thinly coated with indium tin oxide (ITO) to have a thickness of 500 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 minutes, and then transported to a vacuum evaporator.

The following Compound [HI-A] was thermally vacuum deposited to a thickness of 600 Å on the transparent ITO electrode, which was prepared as described above, thereby forming a hole injection layer. Compound [HAT] (50 Å) and the following Compound [HT-A] (600 Å) were sequentially vacuum deposited on the hole injection layer, thereby forming a hole transporting layer.

Subsequently, the following Compounds [BH] and [BD] were vacuum deposited at a weight ratio of 25:1 to have a film thickness of 200 Å on the hole transporting layer, thereby forming a light emitting layer.

[Compound 1] and the following Compound [LiQ] (lithium quinolate) were vacuum deposited at a weight ratio of 1:1 on the light emitting layer, thereby forming an electron injection and transporting layer having a thickness of 350 Å. Lithium fluoride (LiF) and aluminum were subsequently deposited to have a thickness of 10 Å and 1,000 Å, respectively, on the electron injection and transporting layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec, and at 2 Å/sec, respectively, and the degree of vacuum during the deposition was maintained at $1\times10^{-7}$ to $5\times10^{-8}$ torr, thereby manufacturing an organic light emitting device.

[HI-A]

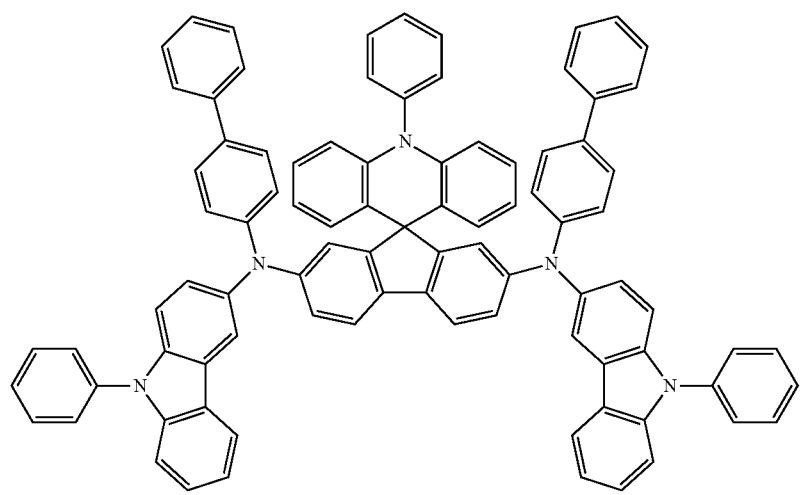

-continued
[BD]
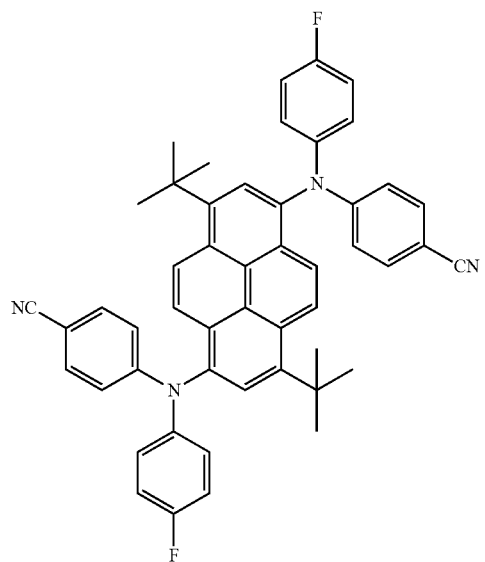
[HT-A]
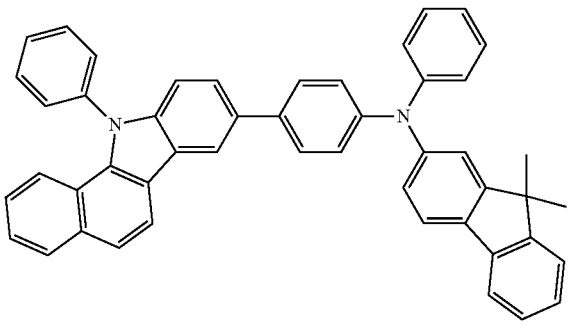
[BH]
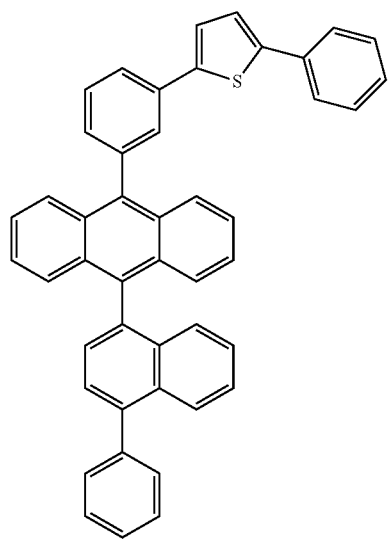
[LiQ]
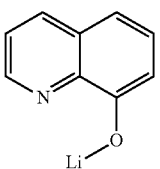
[ET-A]
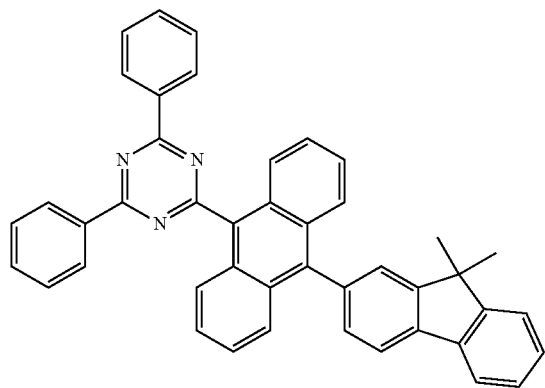

-continued

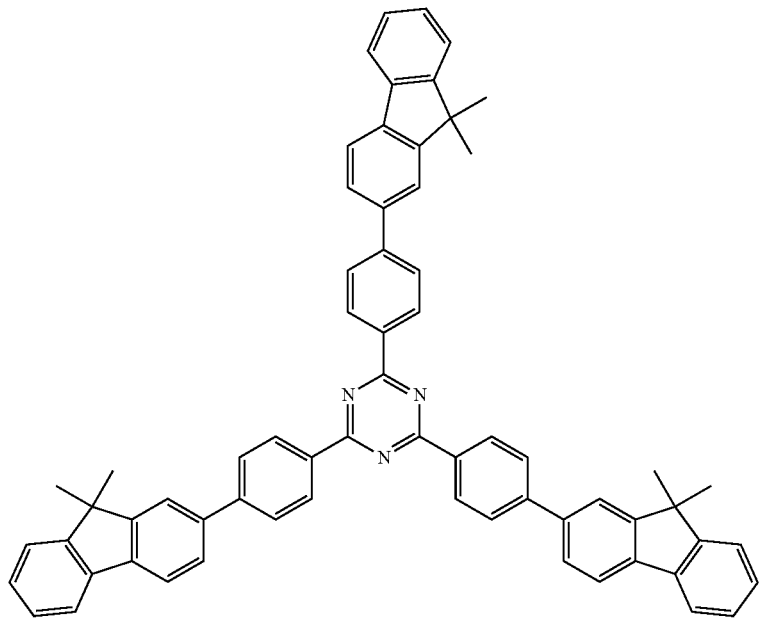
[ET-B]

Example 2

An organic light emitting device was manufactured in the same manner as in [Example 1], except that [Compound 6] was used instead of [Compound 1] of [Example 1].

Example 3

An organic light emitting device was manufactured in the same manner as in [Example 1], except that [Compound 19] was used instead of [Compound 1] of [Example 1].

Example 4

An organic light emitting device was manufactured in the same manner as in [Example 1], except that [Compound 23] was used instead of [Compound 1] of [Example 1].

Example 5

An organic light emitting device was manufactured in the same manner as in [Example 1], except that [Compound 67] was used instead of [Compound 1] of [Example 1].

Example 6

An organic light emitting device was manufactured in the same manner as in [Example 1], except that [Compound 89] was used instead of [Compound 1] of [Example 1].

Example 7

An organic light emitting device was manufactured in the same manner as in [Example 1], except that [Compound 112] was used instead of [Compound 1] of [Example 1].

Example 8

An organic light emitting device was manufactured in the same manner as in [Example 1], except that [Compound 127] was used instead of [Compound 1] of [Example 1].

Example 9

An organic light emitting device was manufactured in the same manner as in [Example 1], except that [Compound 183] was used instead of [Compound 1] of [Example 1].

Example 10

An organic light emitting device was manufactured in the same manner as in [Example 1], except that [Compound 263] was used instead of [Compound 1] of [Example 1].

Example 11

An organic light emitting device was manufactured in the same manner as in [Example 1], except that [Compound 281] was used instead of [Compound 1] of [Example 1].

Example 12

An organic light emitting device was manufactured in the same manner as in [Example 1], except that [Compound 299] was used instead of [Compound 1] of [Example 1].

Example 13

An organic light emitting device was manufactured in the same manner as in [Example 1], except that [Compound 312] was used instead of [Compound 1] of [Example 1].

Example 14

An organic light emitting device was manufactured in the same manner as in [Example 1], except that [Compound 316] was used instead of [Compound 1] of [Example 1].

Comparative Example 1

An organic light emitting device was manufactured in the same manner as in [Example 1], except that [ET-A] was used instead of [Compound 1] of [Example 1].

Comparative Example 2

An organic light emitting device was manufactured in the same manner as in [Example 1], except that [ET-B] was used instead of [Compound 1] of [Example 1].

For the organic light emitting devices manufactured by the above-described method, the driving voltage and the light emitting efficiency were measured at a current density of 10 mA/cm$^2$, and a time (T$_{90}$) for reaching a 90% value compared to the initial luminance was measured at a current density of 20 mA/cm$^2$. The results are shown in the following Table 1.

TABLE 1

| | Voltage (V) | Efficiency (Cd/A) | Color coordinate (x, y) | Service life (h) T$_{90}$ at 20 mA/cm$^2$ |
|---|---|---|---|---|
| Example 1 | 4.50 | 5.28 | (0.143, 0.095) | 198 |
| Example 2 | 4.62 | 5.16 | (0.143, 0.094) | 200 |
| Example 3 | 4.79 | 5.01 | (0.144, 0.096) | 253 |
| Example 4 | 4.55 | 5.12 | (0.144, 0.095) | 185 |
| Example 5 | 4.41 | 5.48 | (0.144, 0.097) | 172 |
| Example 6 | 4.46 | 4.86 | (0.143, 0.098) | 182 |
| Example 7 | 4.51 | 4.99 | (0.143, 0.098) | 221 |
| Example 8 | 4.87 | 4.88 | (0.144, 0.097) | 263 |
| Example 9 | 4.62 | 5.17 | (0.143, 0.098) | 182 |
| Example 10 | 4.81 | 4.93 | (0.144, 0.096) | 213 |
| Example 11 | 4.66 | 5.17 | (0.143, 0.095) | 200 |
| Example 12 | 4.44 | 5.22 | (0.143, 0.098) | 189 |
| Example 13 | 4.50 | 4.99 | (0.144, 0.096) | 196 |
| Example 14 | 4.55 | 5.22 | (0.143, 0.096) | 206 |
| Comparative Example 1 | 5.63 | 4.06 | (0.144, 0.098) | 133 |
| Comparative Example 2 | 5.32 | 4.51 | (0.144, 0.099) | 157 |

From the result of the table, the compound represented by Formula 1 according to the present invention may be used for an organic layer of the organic light emitting device which may simultaneously inject and transport electrons. The organic light emitting device using the same has low driving voltage and high efficiency, and may improve stability of the device by hole stability of the compound.

In particular, the compound represented by Formula 1 according to the present invention is excellent in thermal stability, and may be used in a mixture with an n-type dopant when used in the organic layer which simultaneously injects and transports electrons.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Light emitting layer
8: Electron transporting layer

The invention claimed is:
1. A compound represented by the following Formula 1:

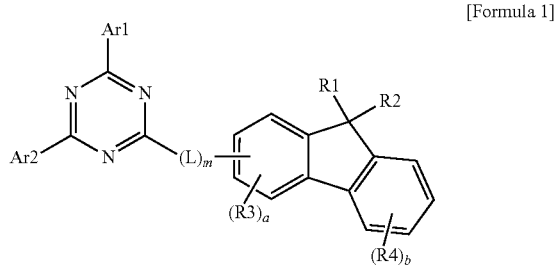

[Formula 1]

in Formula 1,
Ar1 and Ar2 are the same as each other, and each independently an aryl group having 6 to 20 carbon atoms which is unsubstituted or substituted with deuterium,
L is a substituted or unsubstituted naphthylene; a substituted or unsubstituted phenanthrylene; or a substituted or unsubstituted fluorenylene,
R1 and R2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted heterocyclic group, or optionally combine with an adjacent group to form a substituted or unsubstituted hydrocarbon ring,
R3 and R4 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted heterocyclic group, or optionally combine with an adjacent group to form a substituted or unsubstituted monocyclic ring, m is an integer of 1 to 5, a is an integer of 0 to 3, and b is an integer of 0 to 4, and when m, a, and b are each 2 or more, the structures in the parenthesis are the same as or different from each other.

2. The compound of claim 1, wherein Formula 1 is represented by any one of the following Formulae 2 to 4:

[Formula 2]

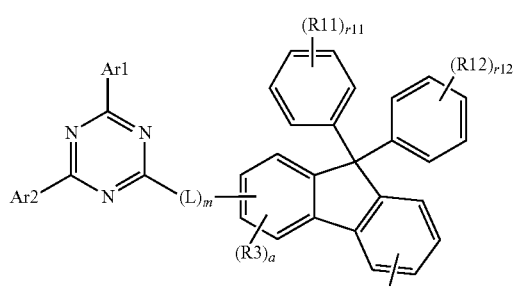

[Formula 3]

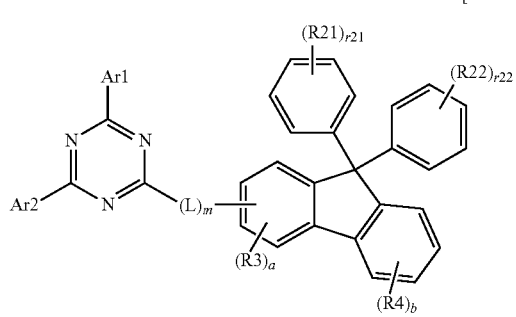

[Formula 4]

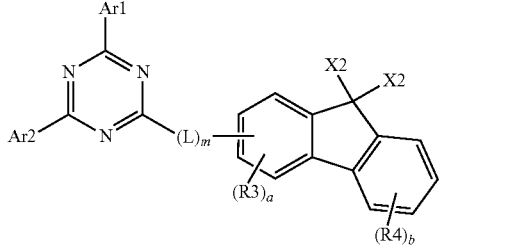

in Formulae 2 to 4, the definition of Ar1, Ar2, L, R3, R4, a, b, and m is the same as defined in Formula 1, the definition of R11, R12, R21, and R22 is the same as the definition of R3 and R4, X1 and X2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted phosphineoxide group; or optionally combine with an adjacent group to form a substituted or unsubstituted hydrocarbon ring, r11 and r12 are the same as or different from each other, and each independently an integer of 0 to 5, r21 and r22 are the same as or different from each other, and each independently an integer of 0 to 4, and when r11, r12, r21, and r22 are each 2 or more, the structures in the parenthesis are the same as or different from each other.

3. The compound of claim 1, wherein Formula 1 is represented by any one of the following Formulae 5 to 8:

[Formula 5]

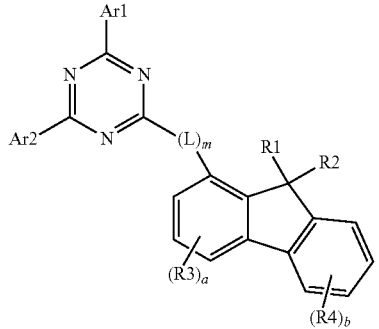

[Formula 6]

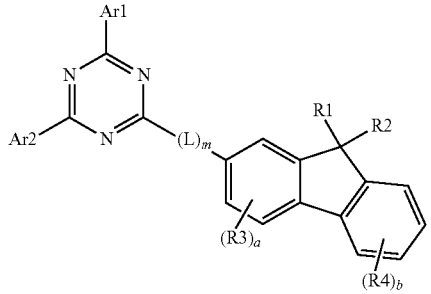

[Formula 7]
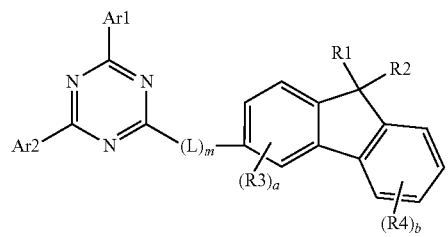
[Formula 8]
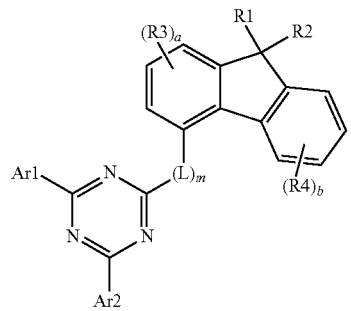
in Formulae 5 to 8,
the definition of Ar1, Ar2, L, R1 to R4, m, a, and b is the same as defined in Formula 1.
4. The compound of claim 1, wherein L is any one selected from the following structures:
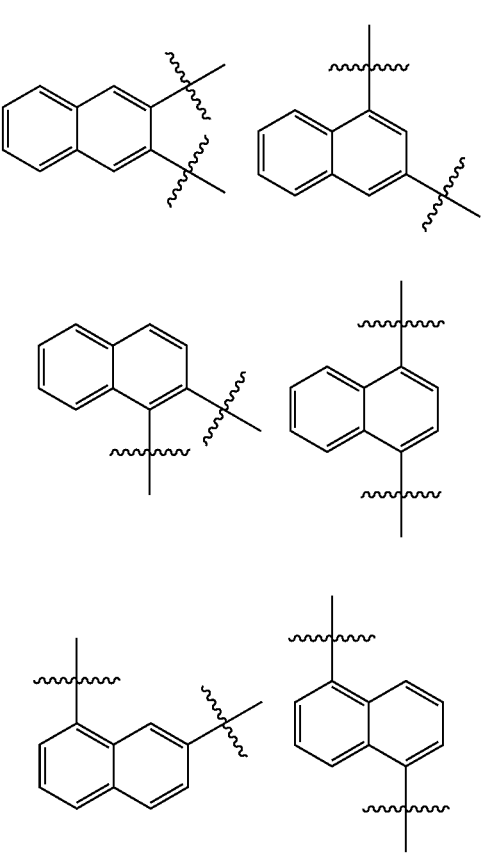
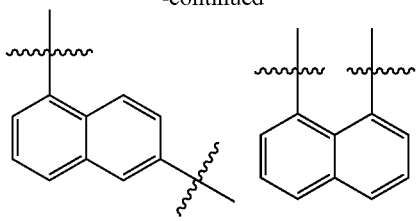
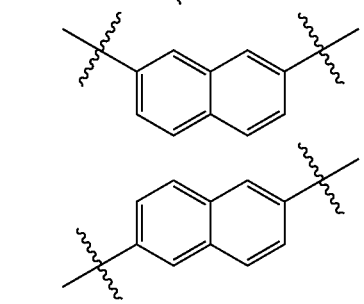
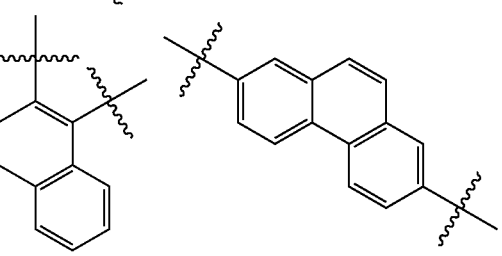
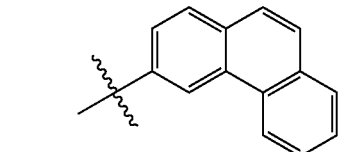
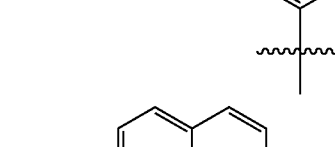
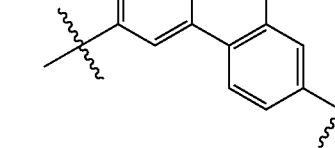
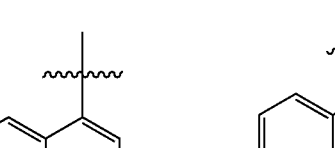
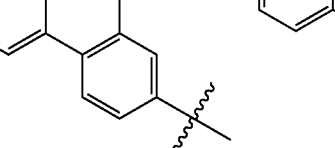
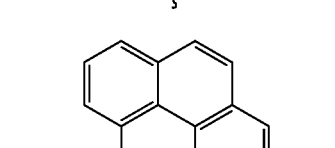
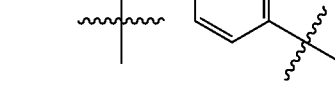

-continued

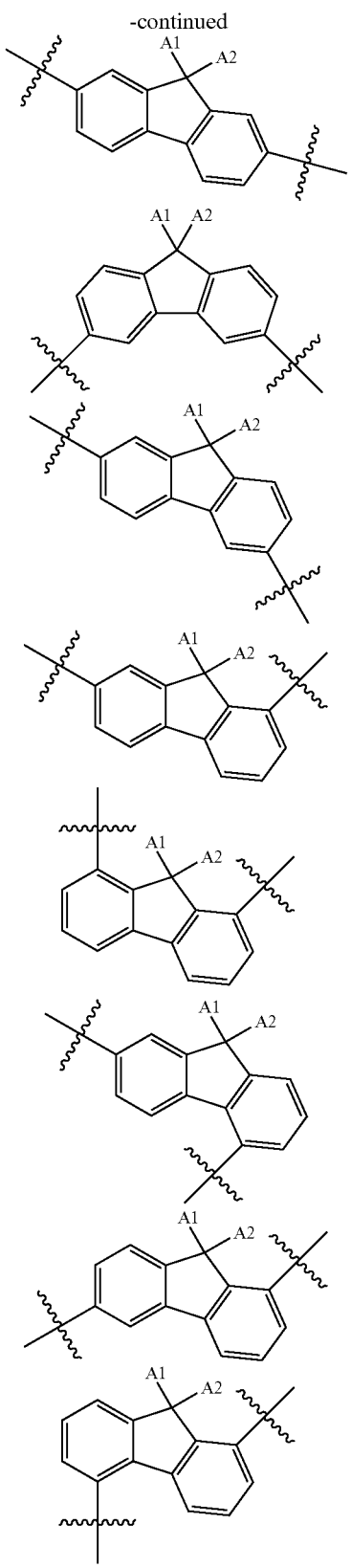

in the structural formulae,
A1 and A2 are the same as or different from each other, and each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphineoxide group; a substituted or unsubstituted aryl group; or a substituted or unsubstituted heterocyclic group, or optionally combine with an adjacent group to form a substituted or unsubstituted ring, and the structures are optionally unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

5. The compound of claim 1, wherein L is naphthylene; phenanthrylene; or fluorenylene substituted with an alkyl group.

6. The compound of claim 1, wherein Ar1 and Ar2 are the same as each other, and a phenyl group; a biphenyl group; a naphthyl group; or a phenanthryl group.

7. The compound of claim 1, wherein R1 and R2 are the same as or different from each other, and each independently an alkyl group; or an aryl group, which is unsubstituted or substituted with one or more substituents selected from the group consisting of deuterium, and an alkyl group, or combine with each other to form a hydrocarbon ring.

8. The compound of claim 1, wherein R3 and R4 are the same as or different from each other, and each independently hydrogen; deuterium; an alkyl group; an alkoxy group; or an aryl group.

9. The compound of claim 1, wherein the

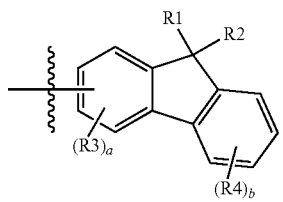

moiety is any one selected from the following structures:

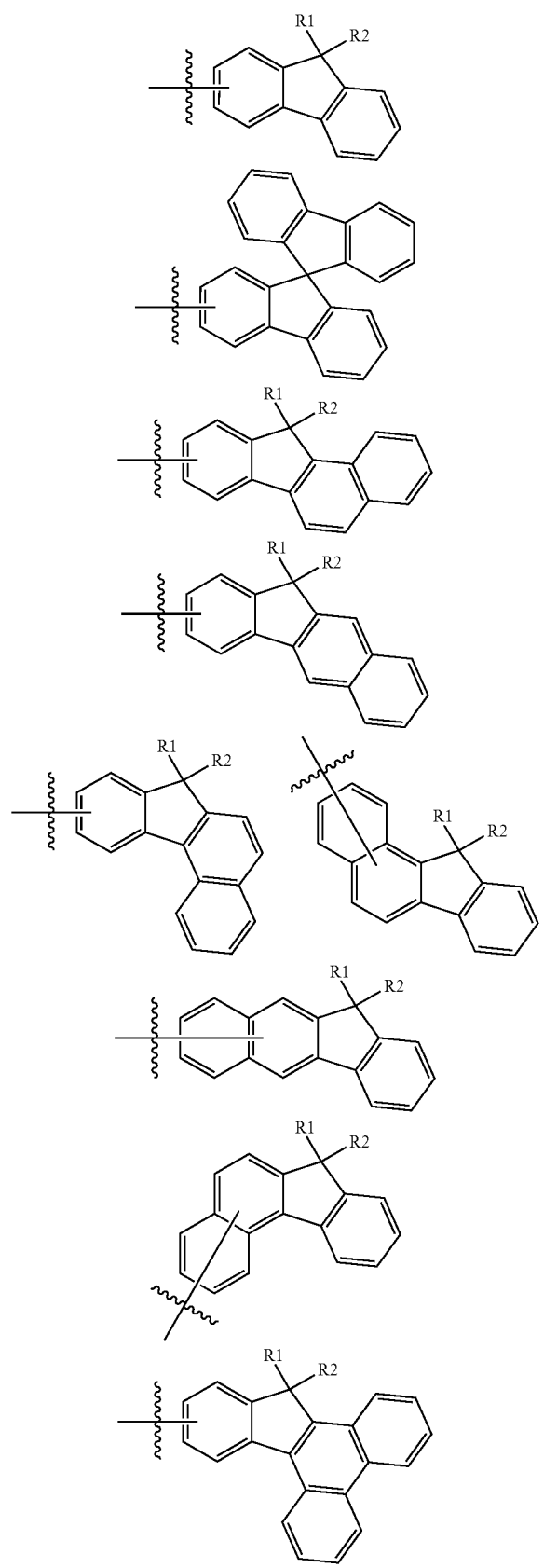

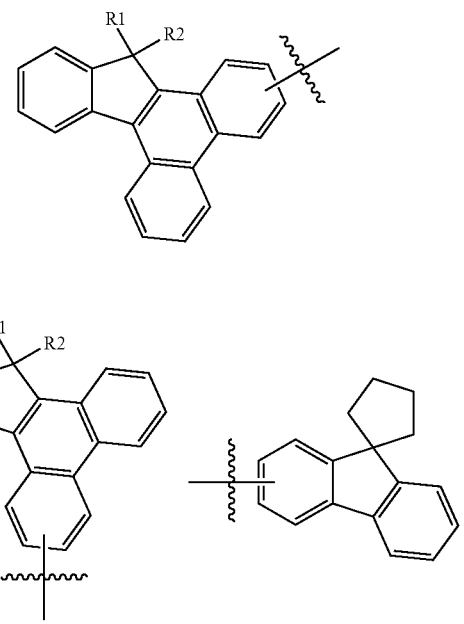

in the structures, the definition of R1 and R2 is the same as defined in Formula 1, and the structures are optionally unsubstituted or substituted with one or more substituents selected from the group consisting of deuterium; a halogen group; a nitrile group; a nitro group; a hydroxy group; a carbonyl group; an ester group; an imide group; an amino group; a phosphineoxide group, an alkoxy group; an aryloxy group; an alkylthioxy group; an arylthioxy group; an alkylsulfoxy group; an arylsulfoxy group; a silyl group; a boron group; an alkyl group;

a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group.

10. The compound of claim 1, wherein the compound of Formula 1 is any one selected from the following compounds:

[Compound 1]

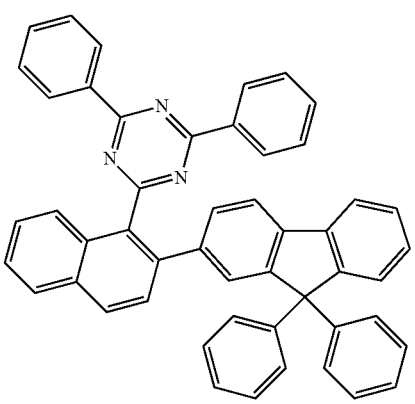

[Compound 2]
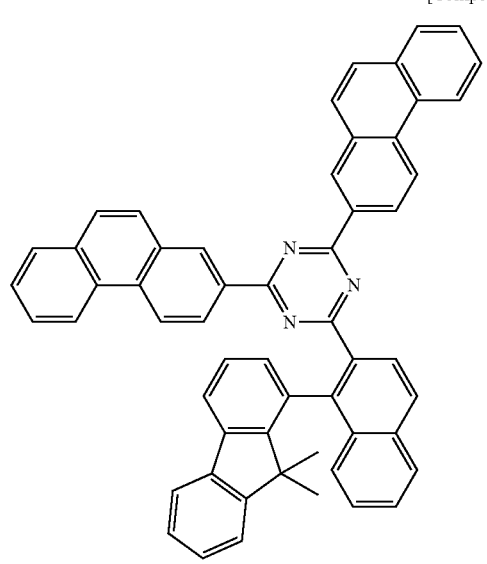
[Compound 5]
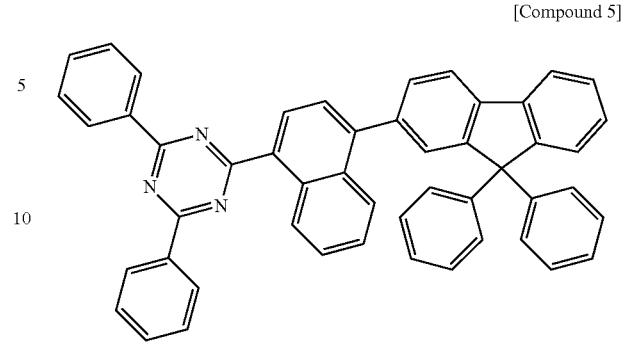
[Compound 3]
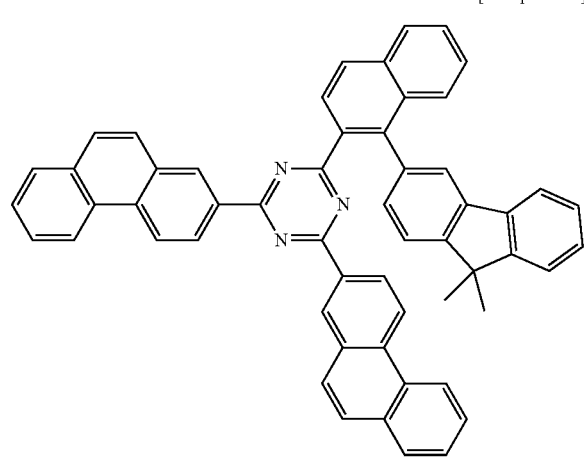
[Compound 6]
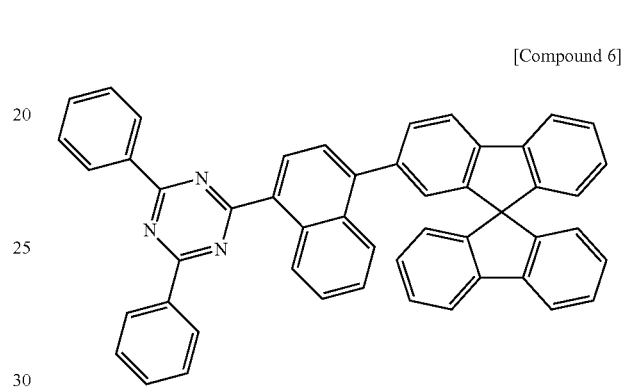
[Compound 7]
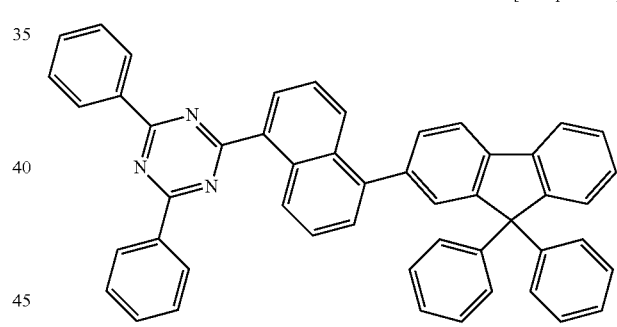
[Compound 4]
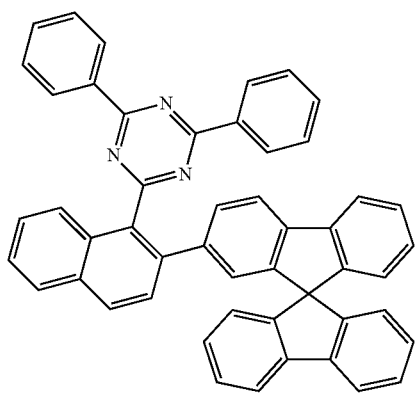
[Compound 8]
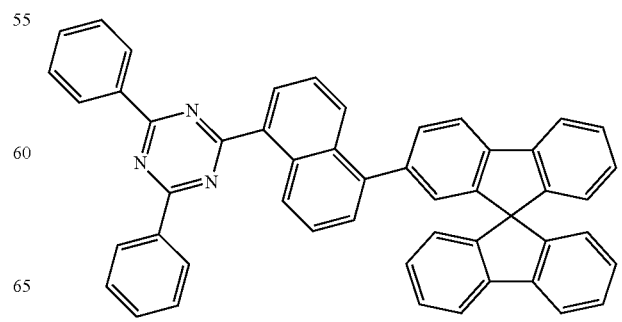

[Compound 9]
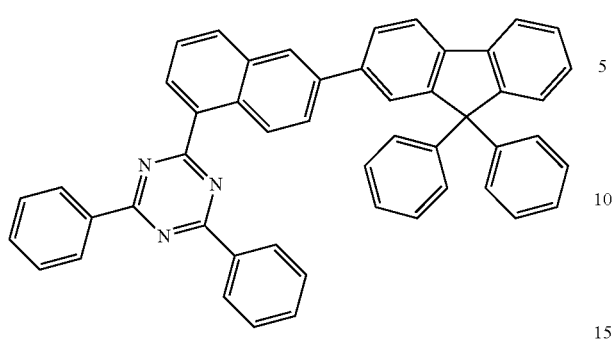
[Compound 10]
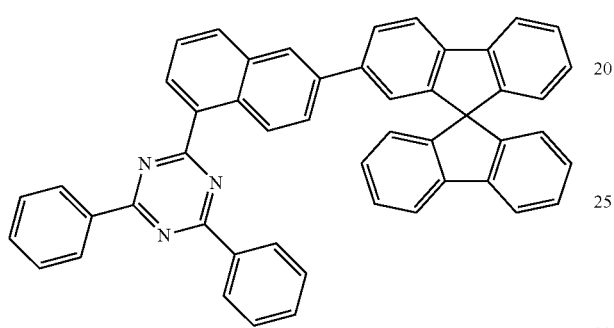
[Compound 11]
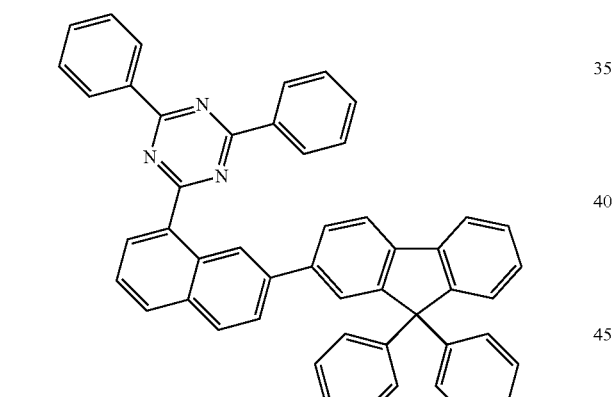
[Compound 12]
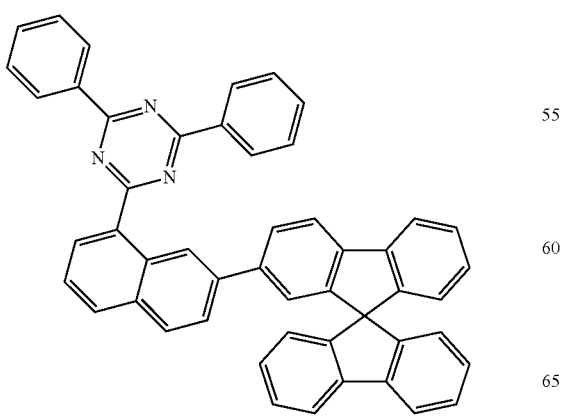
[Compound 13]
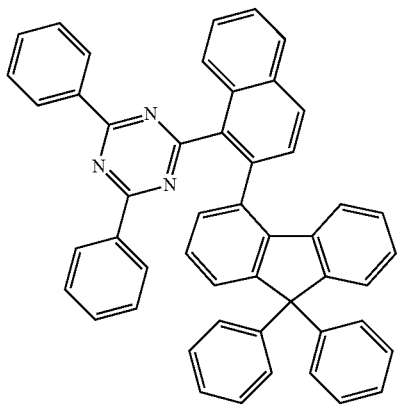
[Compound 14]
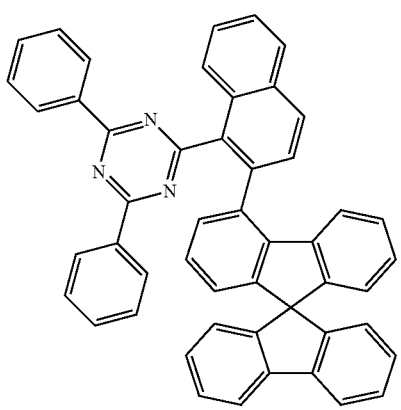
[Compound 15]
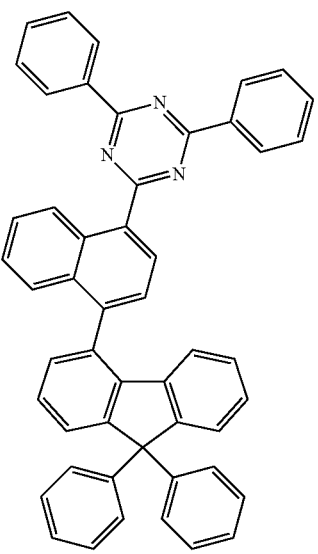

[Compound 16]
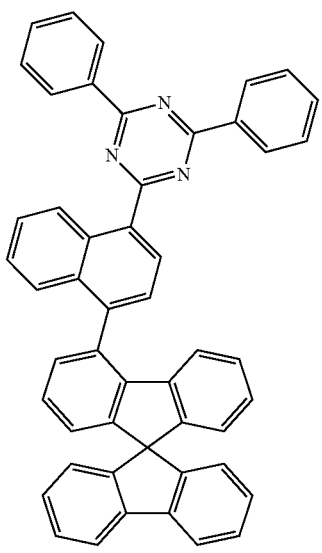
[Compound 17]
[Compound 18]
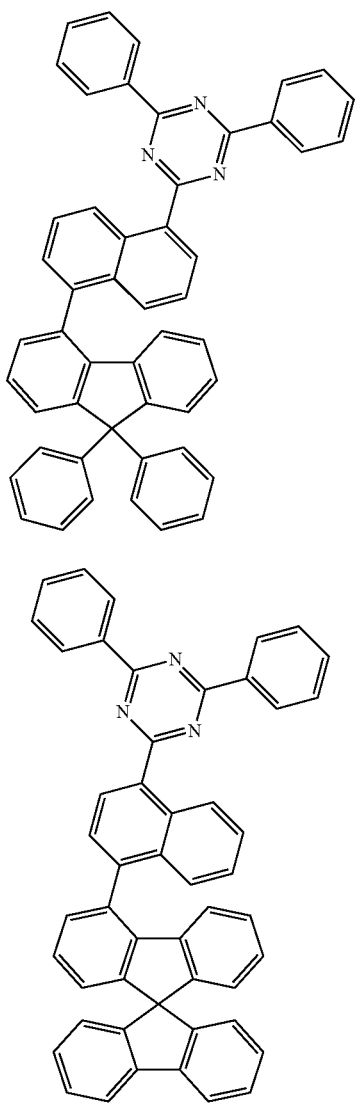
[Compound 19]
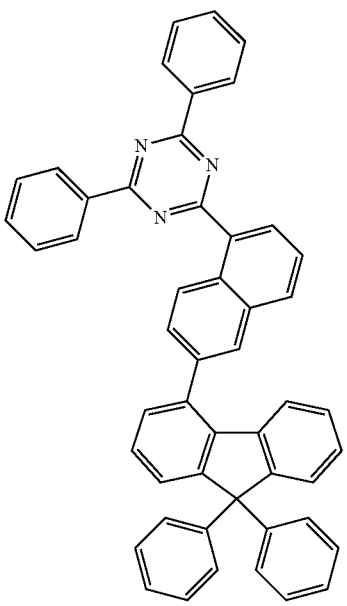
[Compound 20]
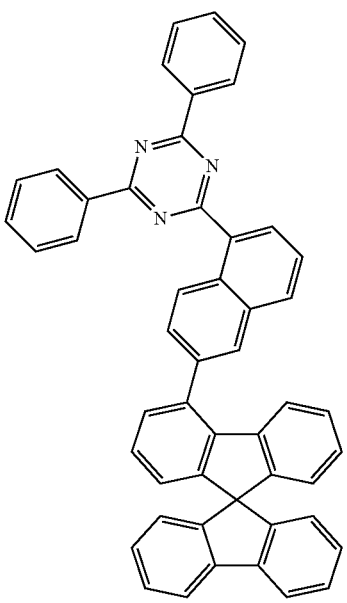
[Compound 21]
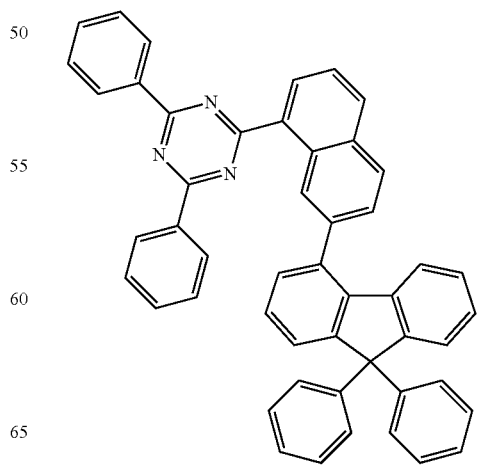

[Compound 22]
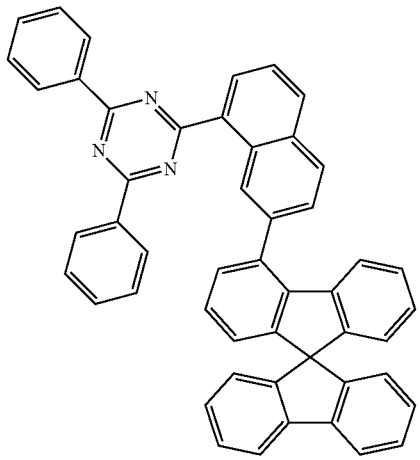
[Compound 23]
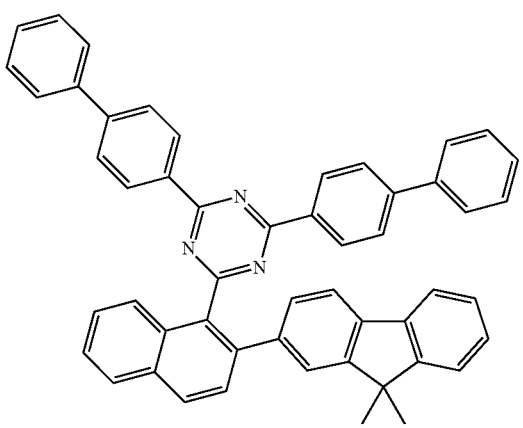
[Compound 24]
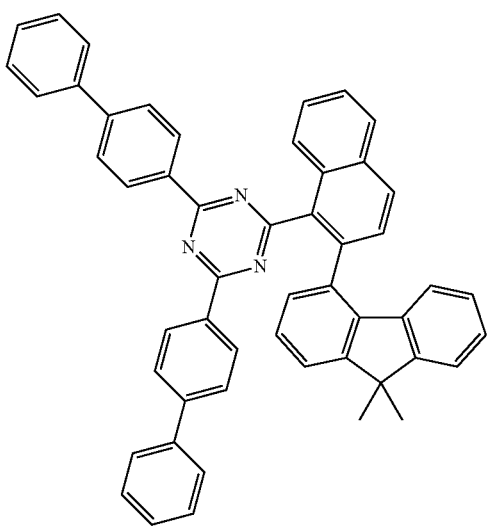
[Compound 25]
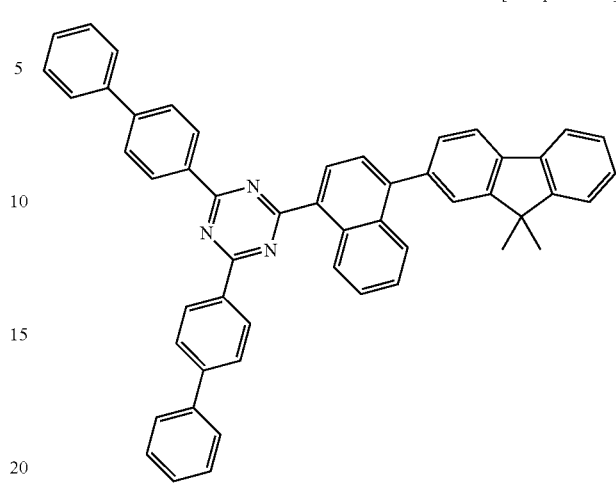
[Compound 26]
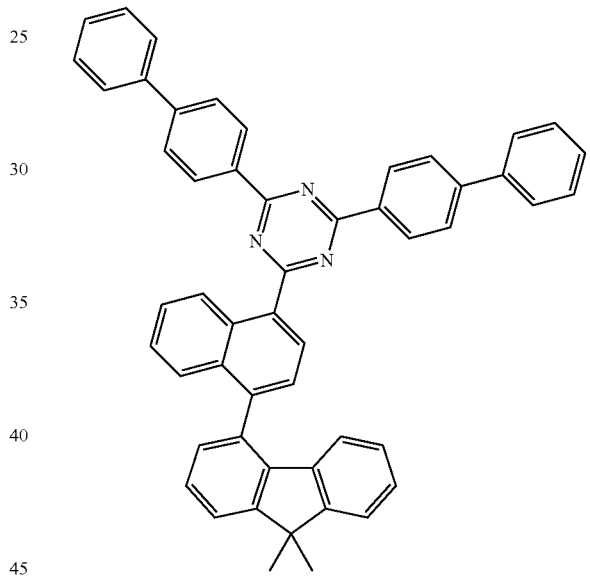
[Compound 27]
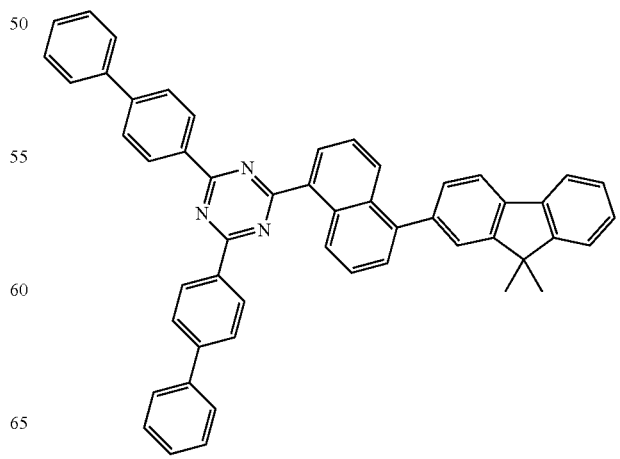

[Compound 28]
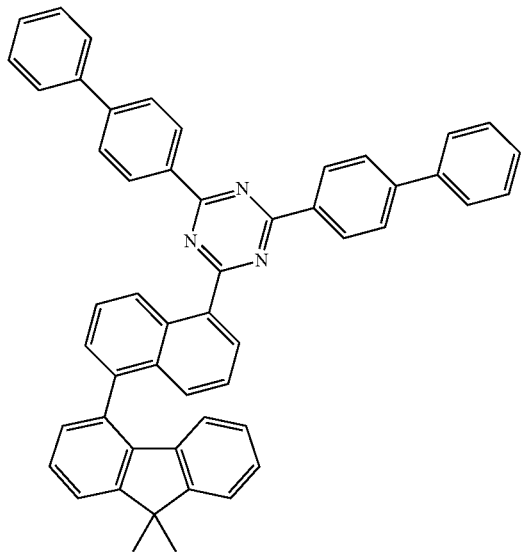
[Compound 29]
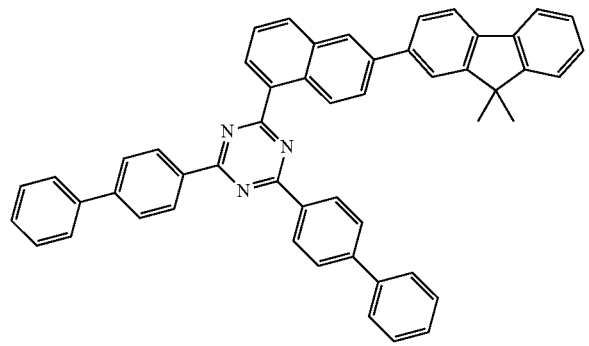
[Compound 30]
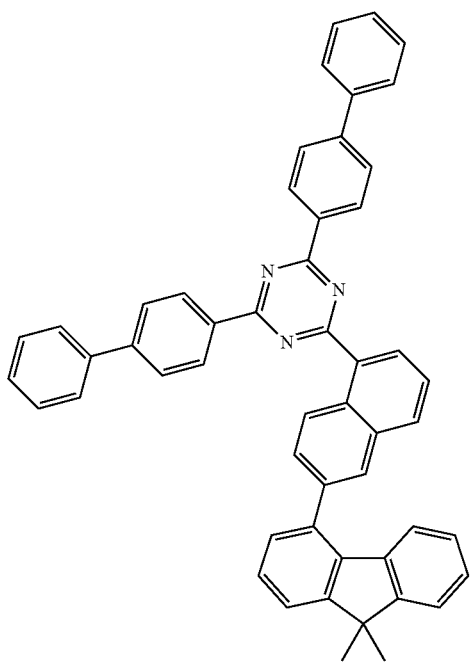
[Compound 31]
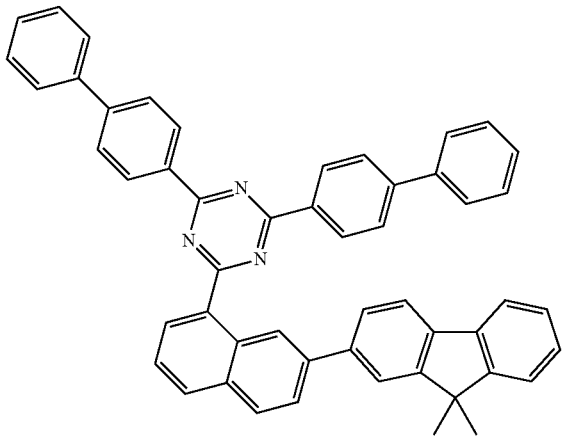
[Compound 32]
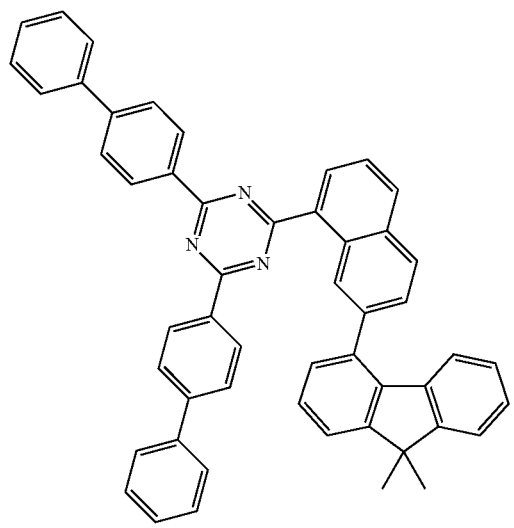
[Compound 33]
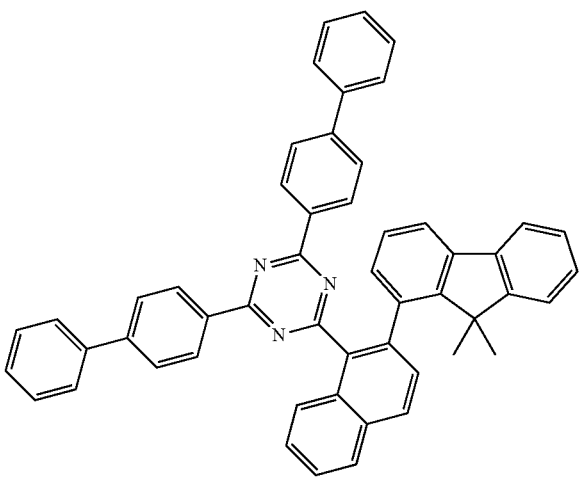

[Compound 34]
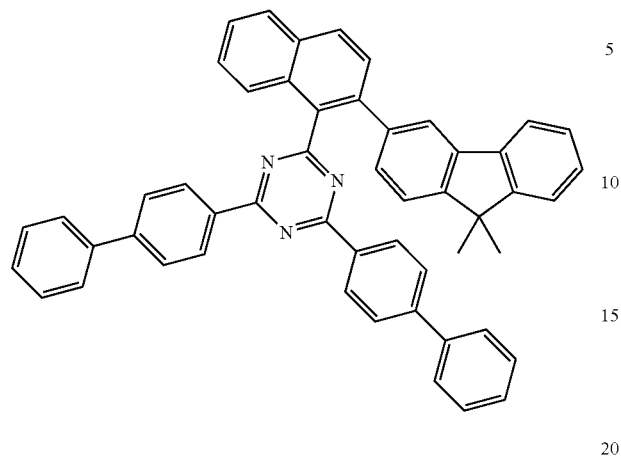
[Compound 35]
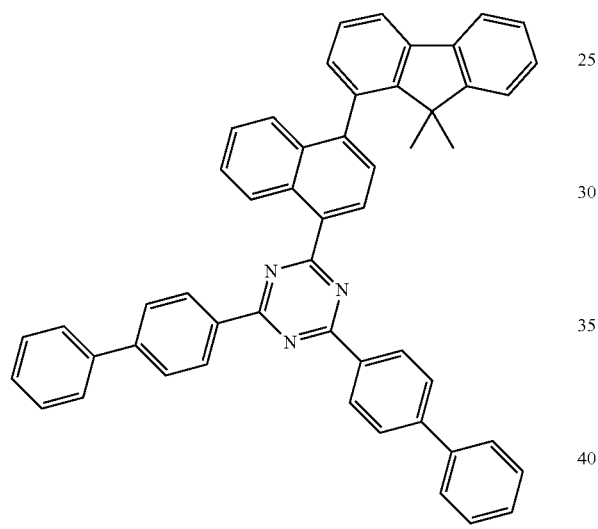
[Compound 36]
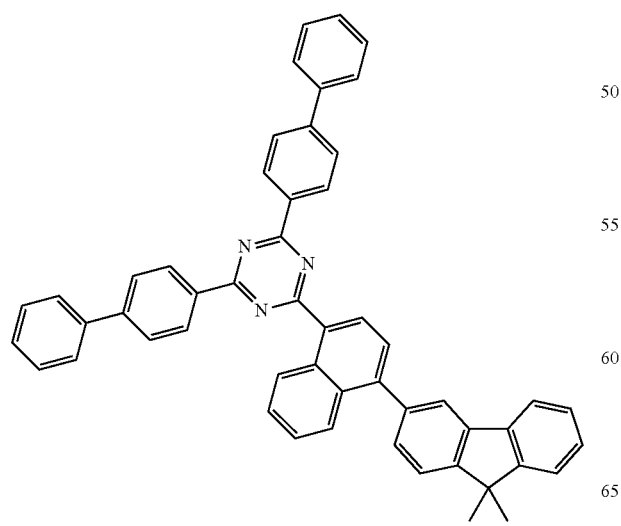
[Compound 37]
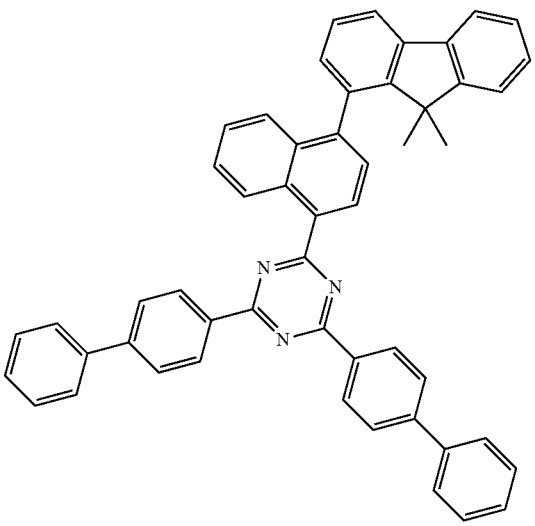
[Compound 38]
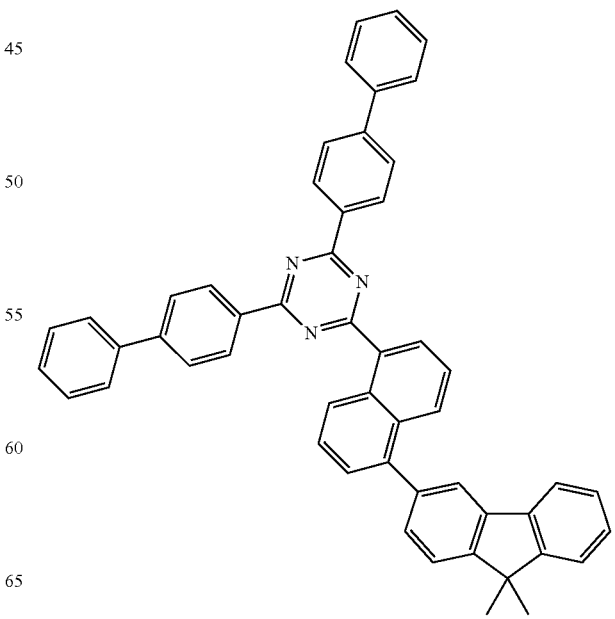

-continued
[Compound 39]
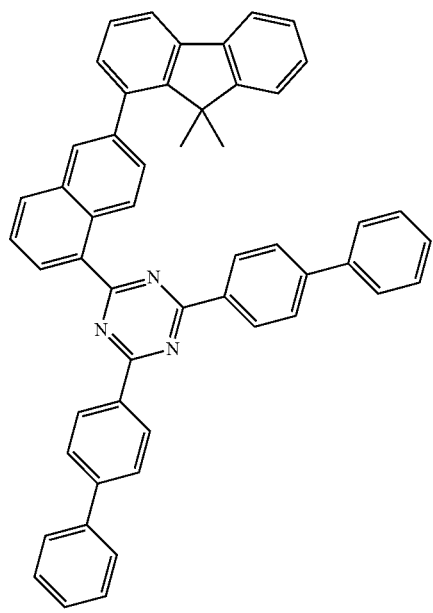
[Compound 40]
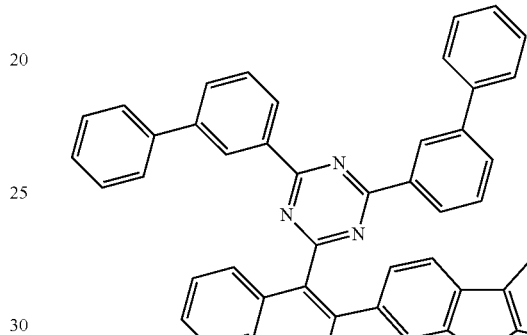
[Compound 41]
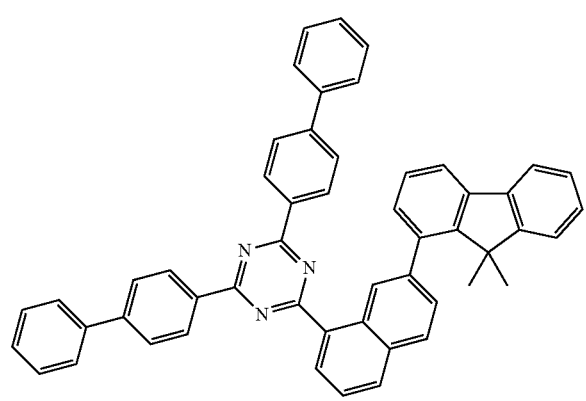
-continued
[Compound 42]
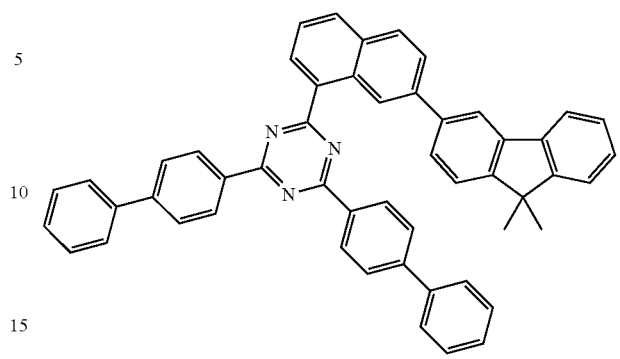
[Compound 43]
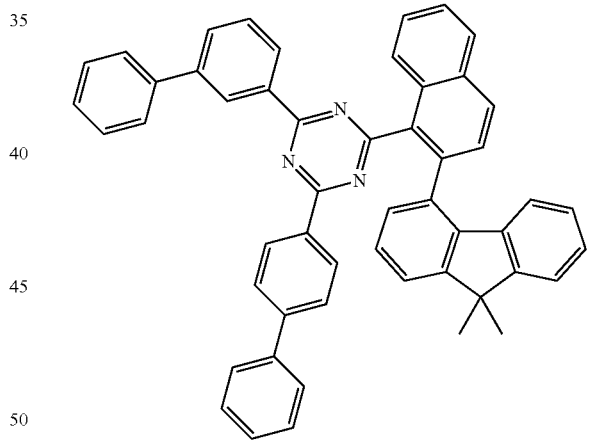
[Compound 44]
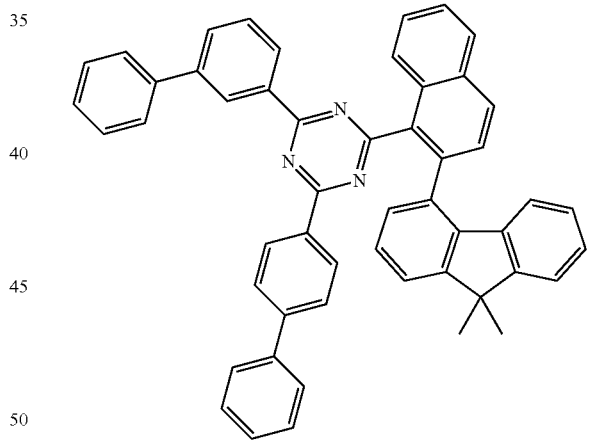
[Compound 45]
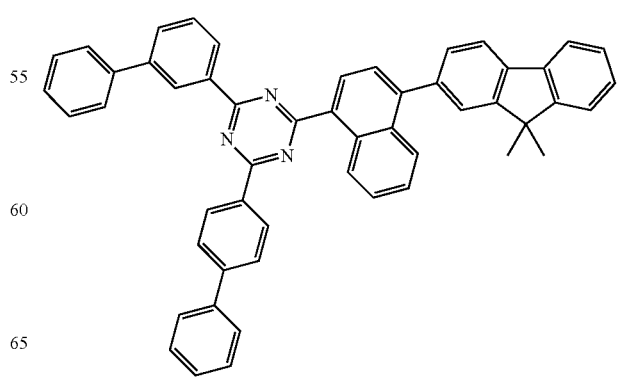

[Compound 46]
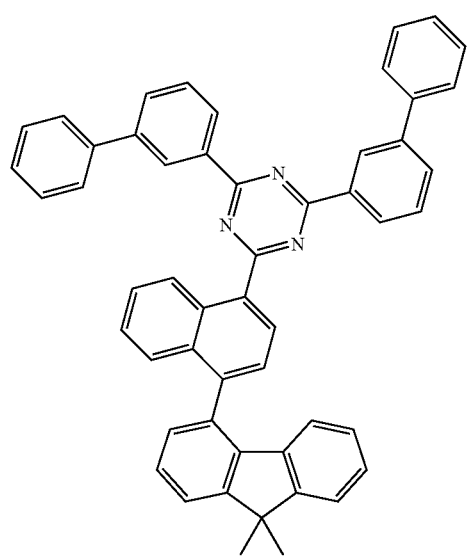
[Compound 47]
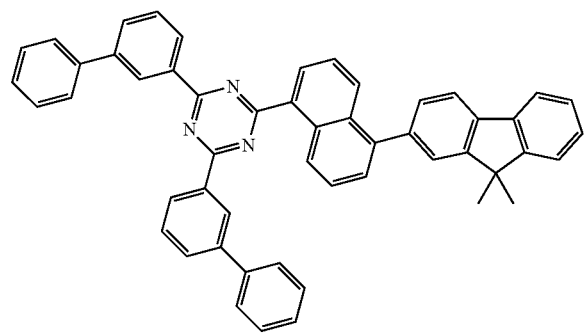
[Compound 48]
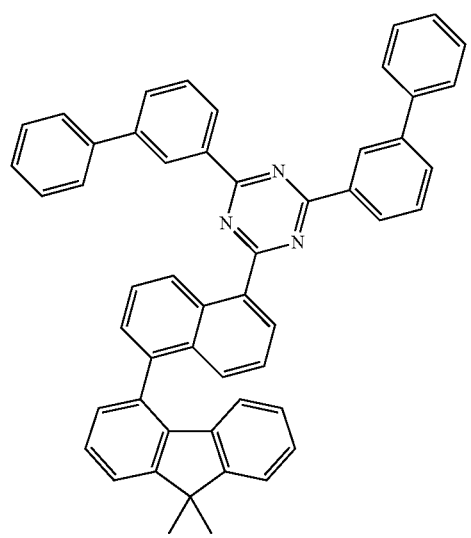
[Compound 49]
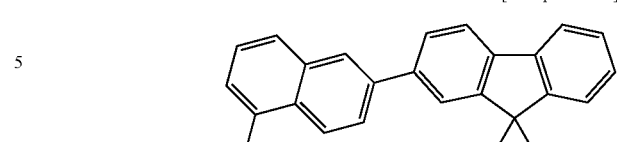
[Compound 50]
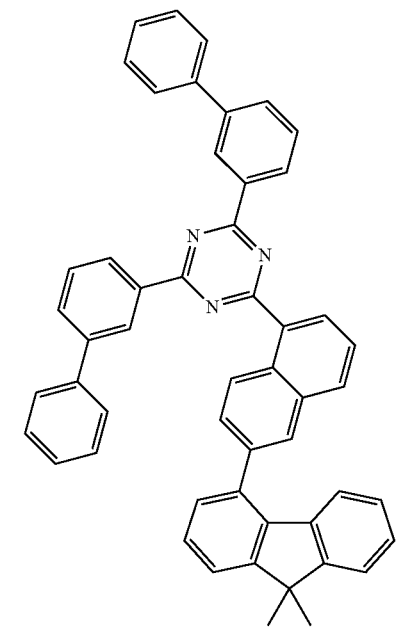
[Compound 51]
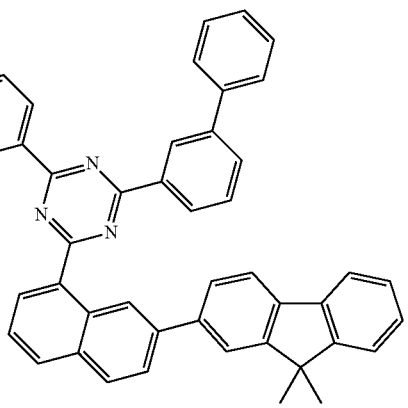

[Compound 52]
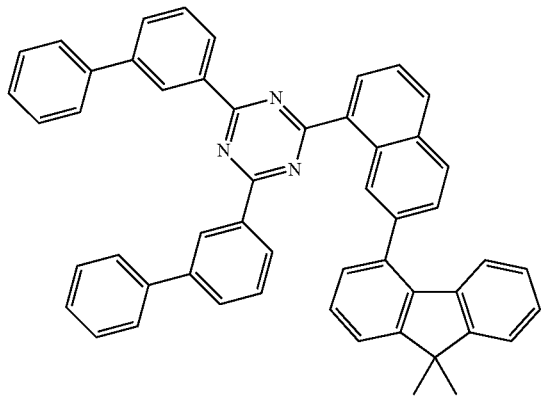
[Compound 53]
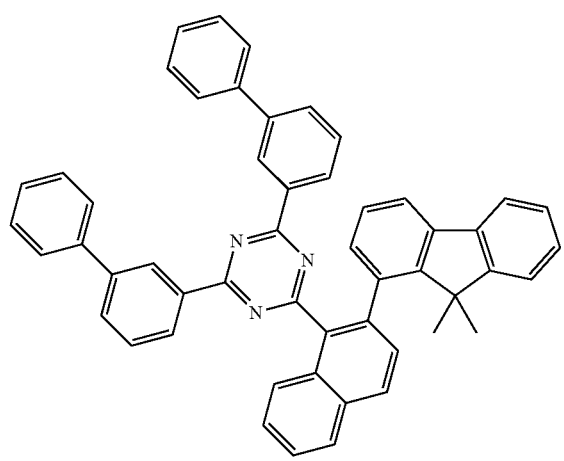
[Compound 54]
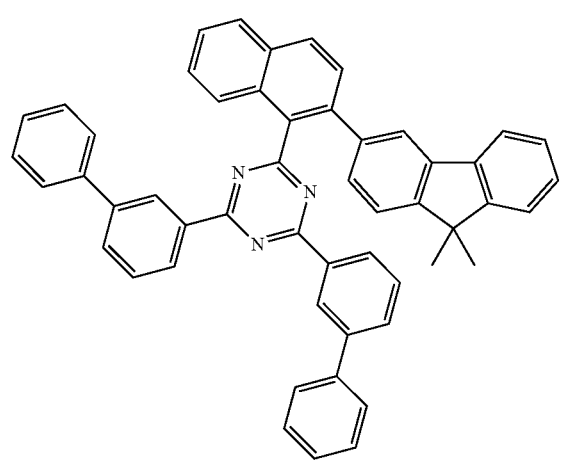
[Compound 55]
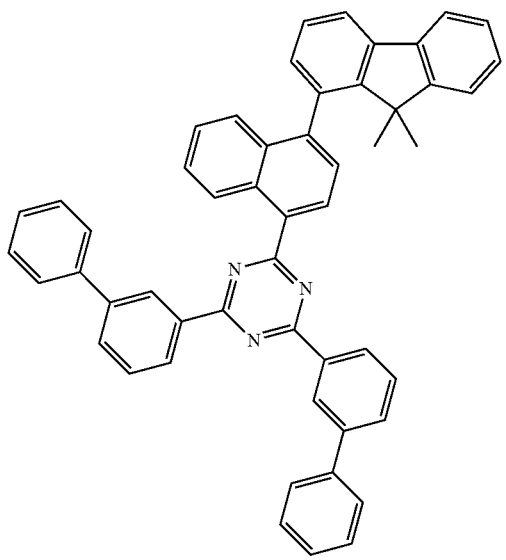
[Compound 56]
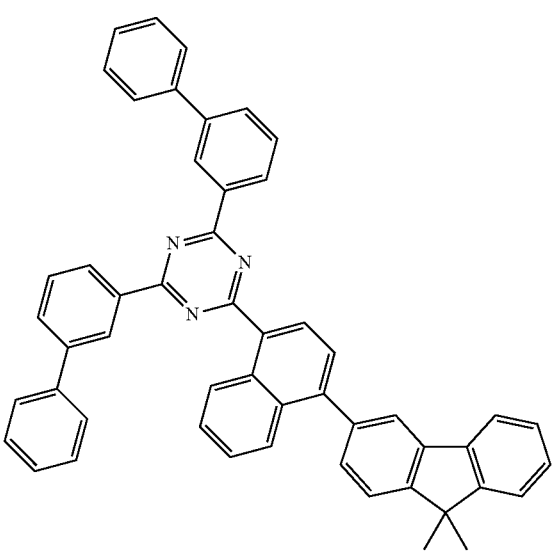

[Compound 57]
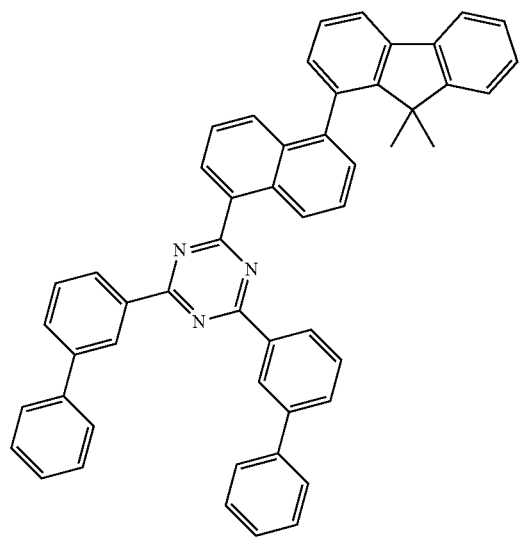
[Compound 60]
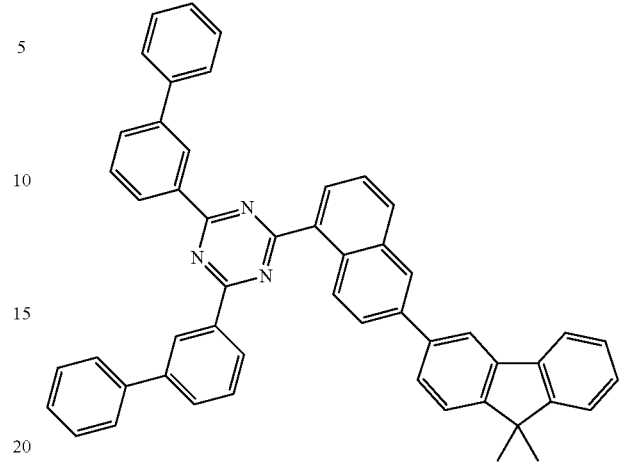
[Compound 58]
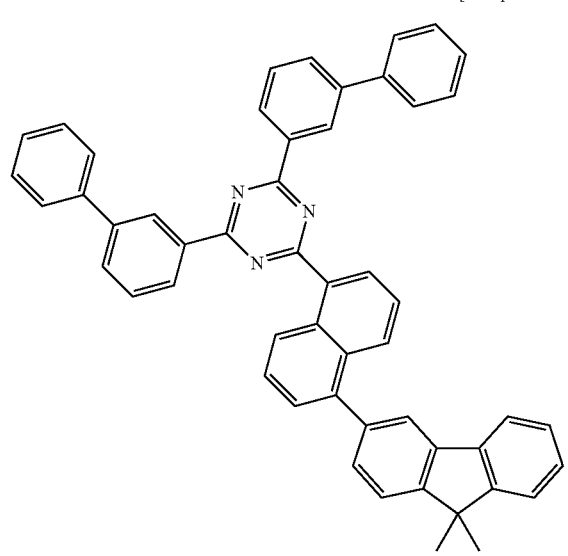
[Compound 61]
[Compound 59]
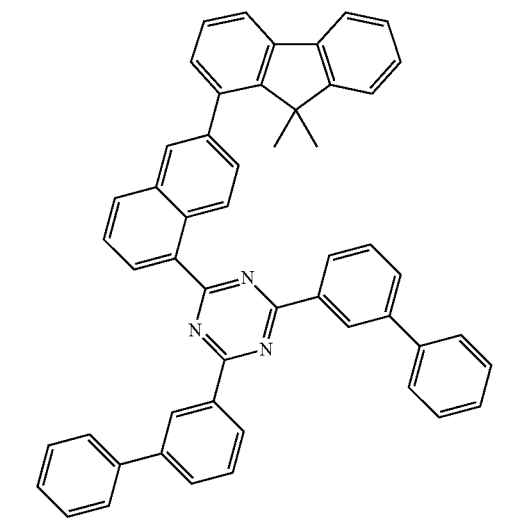
[Compound 62]
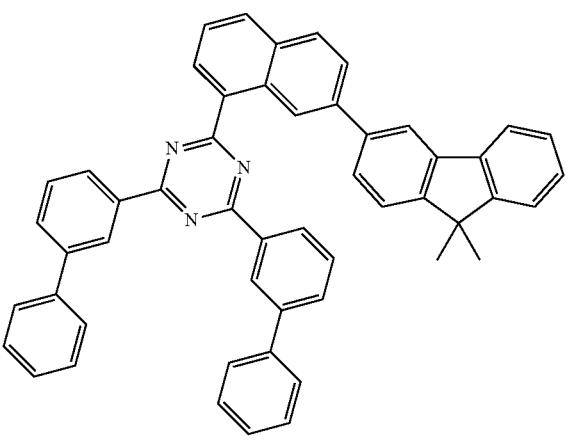

[Compound 63]
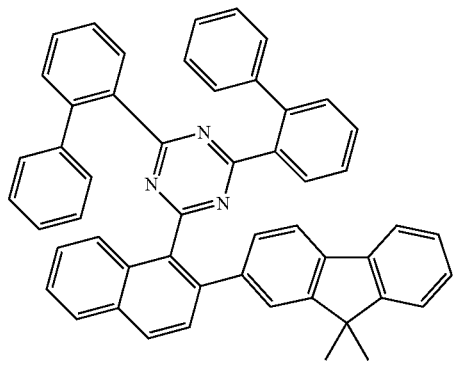
[Compound 64]
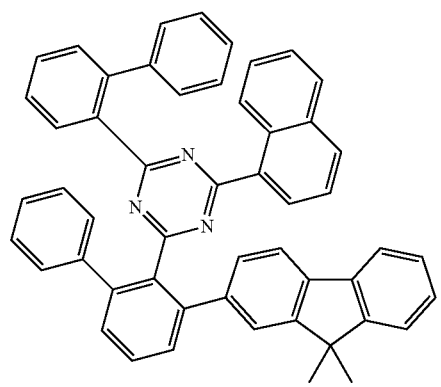
[Compound 65]
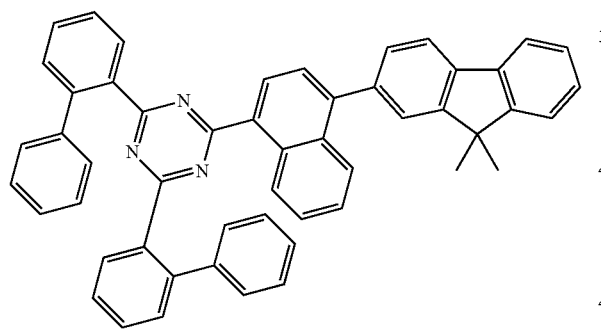
[Compound 66]
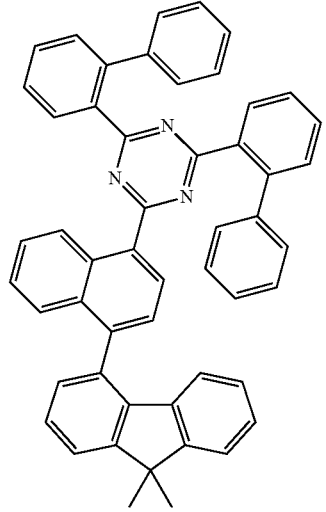
[Compound 67]
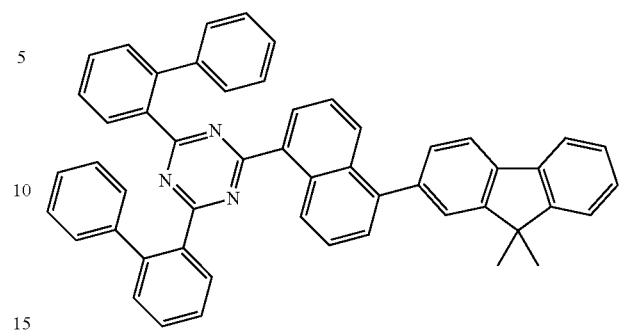
[Compound 68]
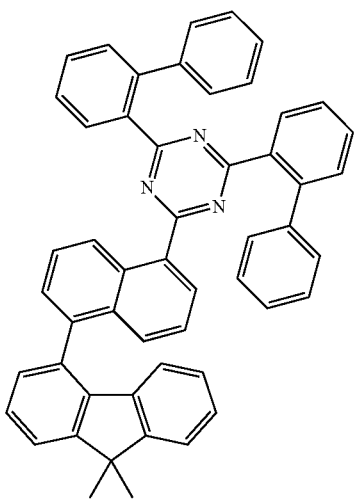
[Compound 69]
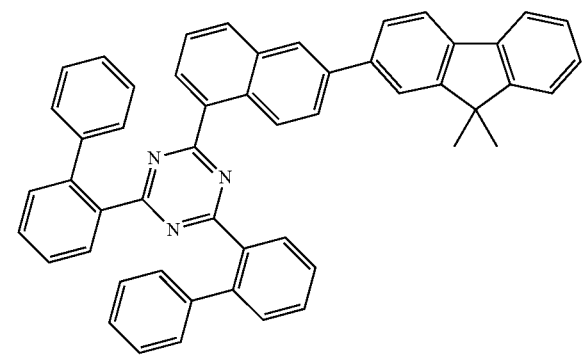

[Compound 70]
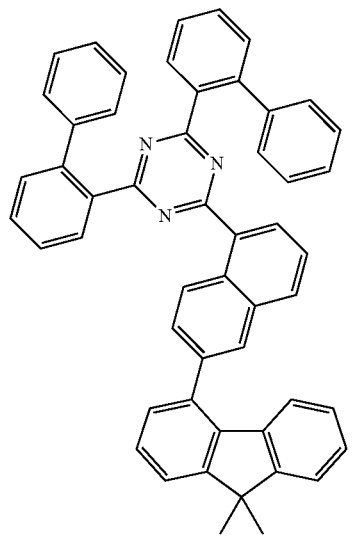
[Compound 71]
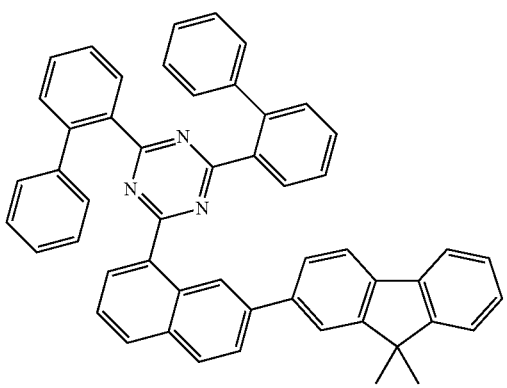
[Compound 72]
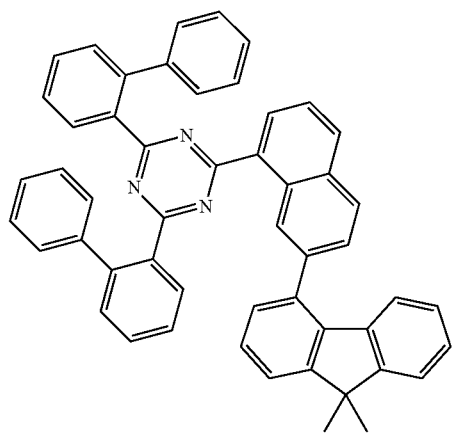
[Compound 73]
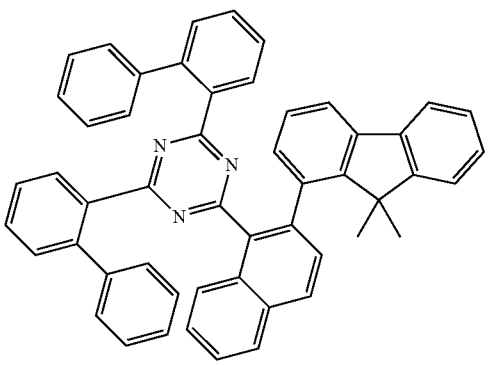
[Compound 74]
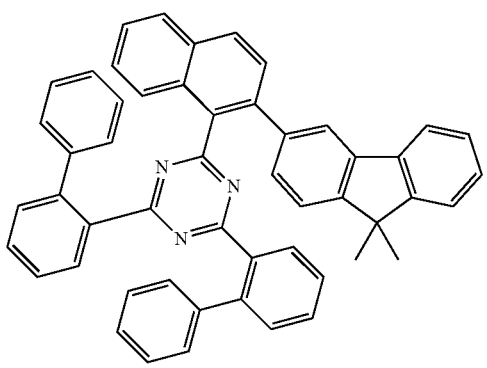
[Compound 75]
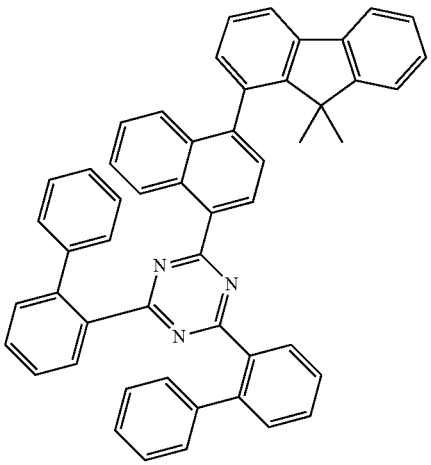

[Compound 76]
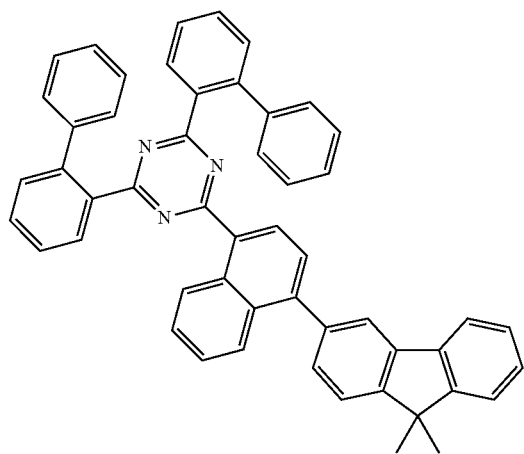
[Compound 79]
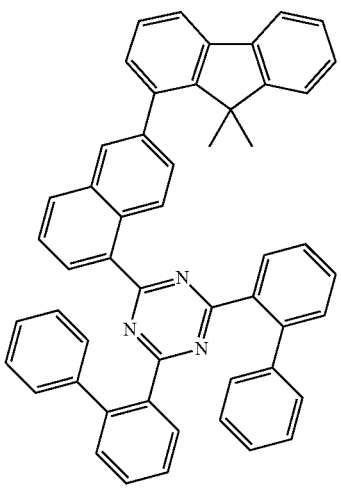
[Compound 77]
[Compound 80]
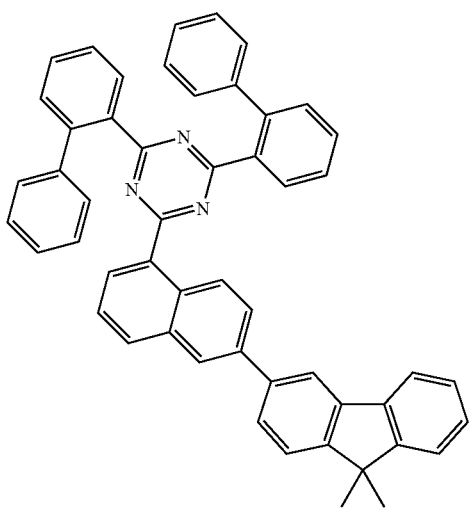
[Compound 78]
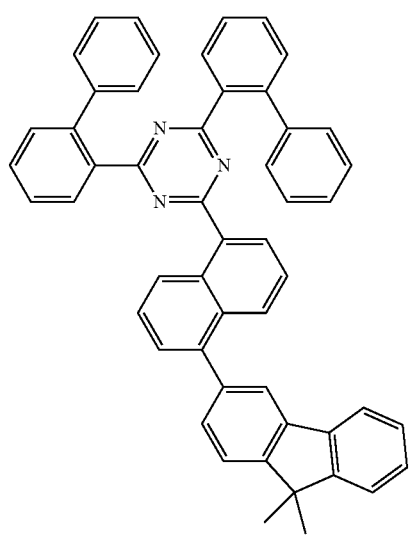
[Compound 81]

[Compound 82]
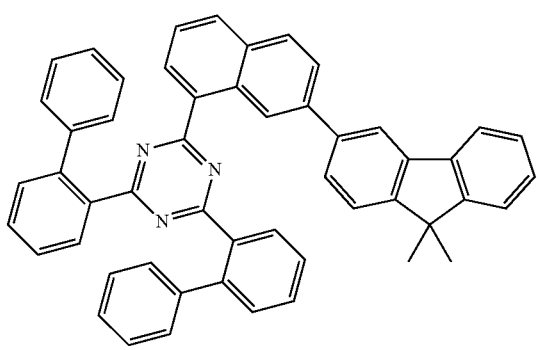
[Compound 83]
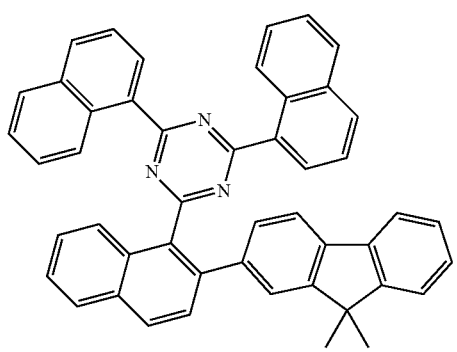
[Compound 84]
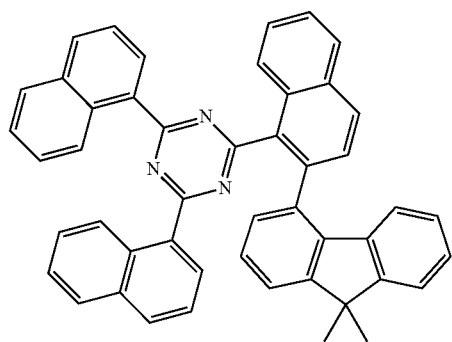
[Compound 85]
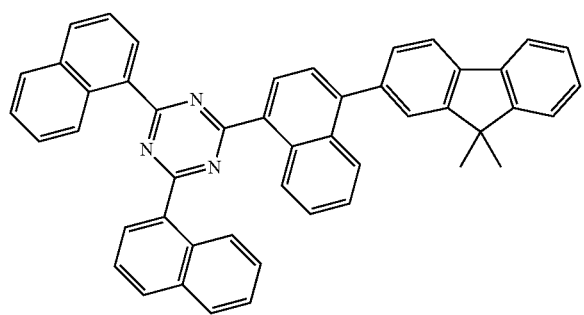
[Compound 86]
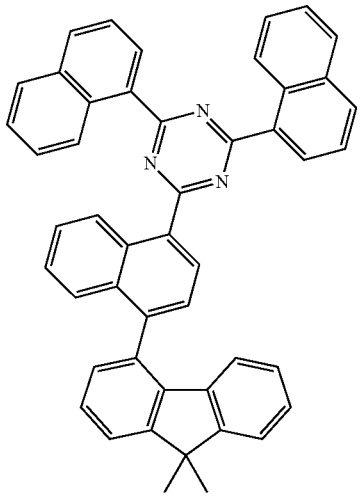
[Compound 87]
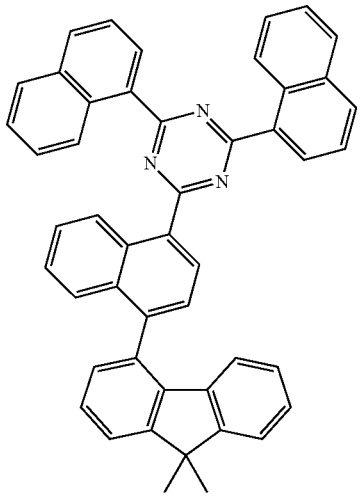
[Compound 88]
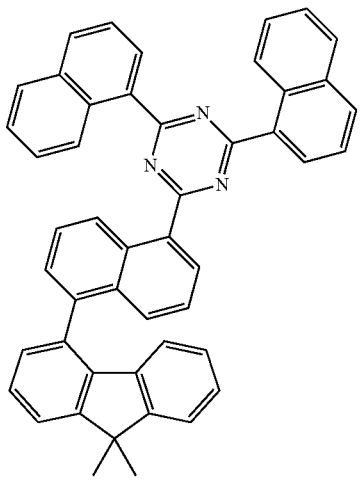

[Compound 89]
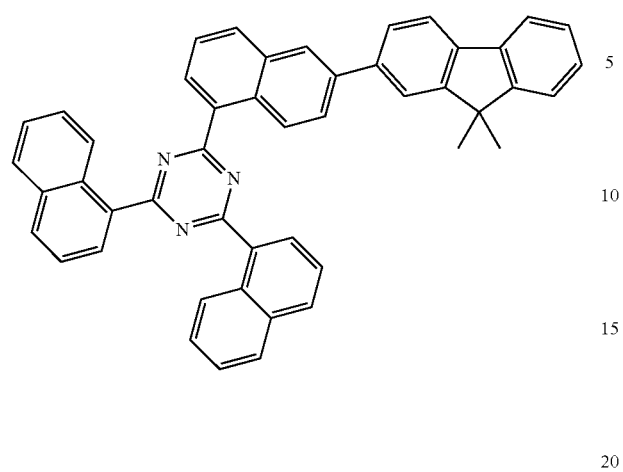
[Compound 92]
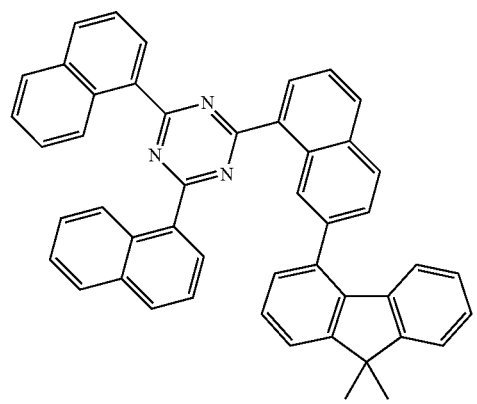
[Compound 90]
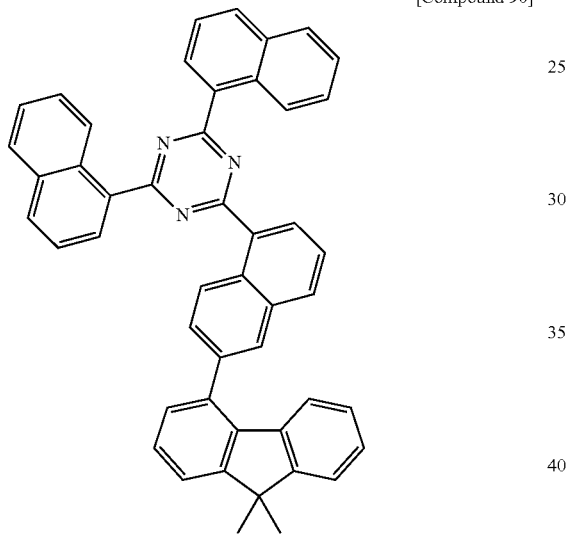
[Compound 93]
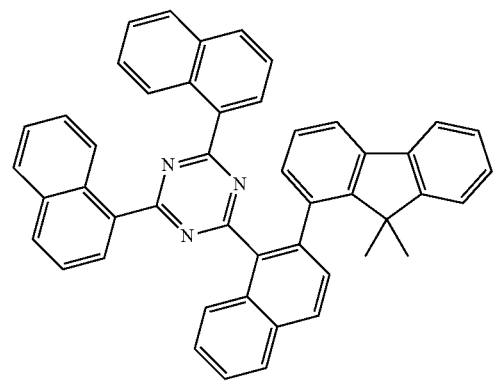
[Compound 91]
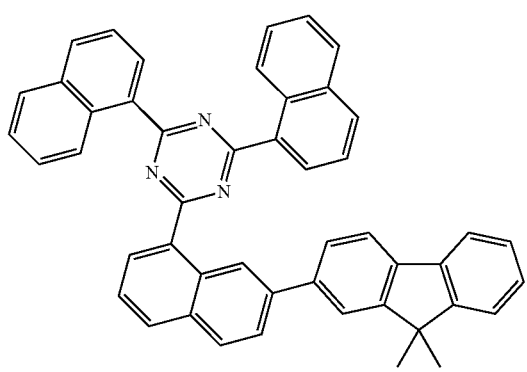
[Compound 94]
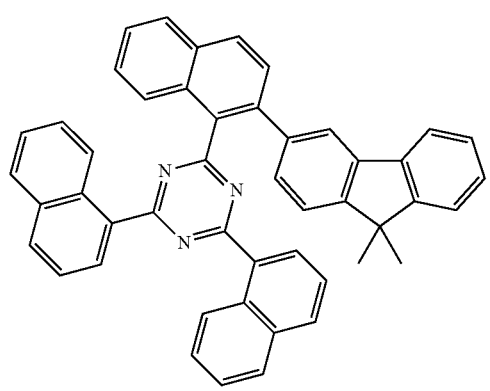

[Compound 95]
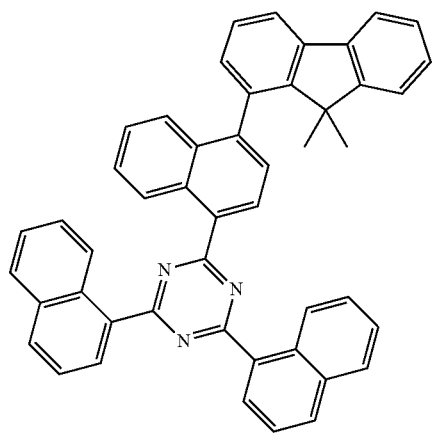
[Compound 96]
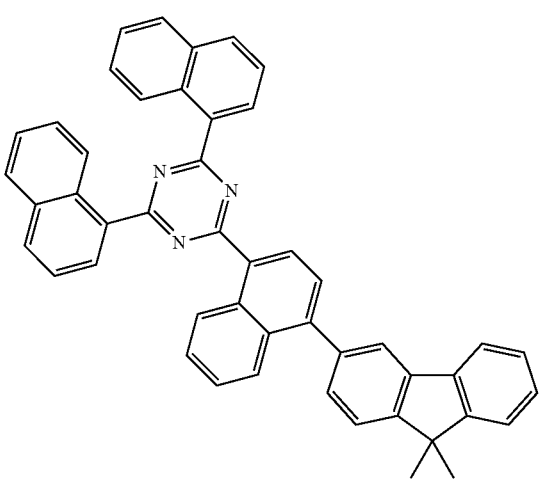
[Compound 97]
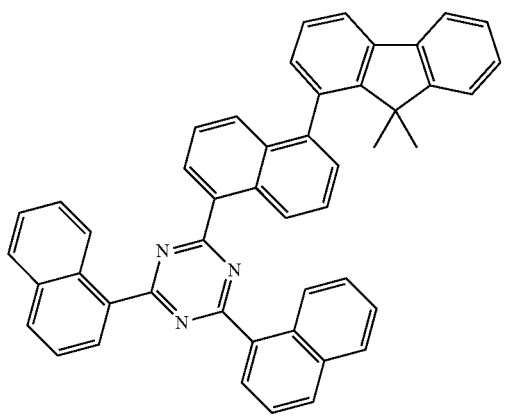
[Compound 98]
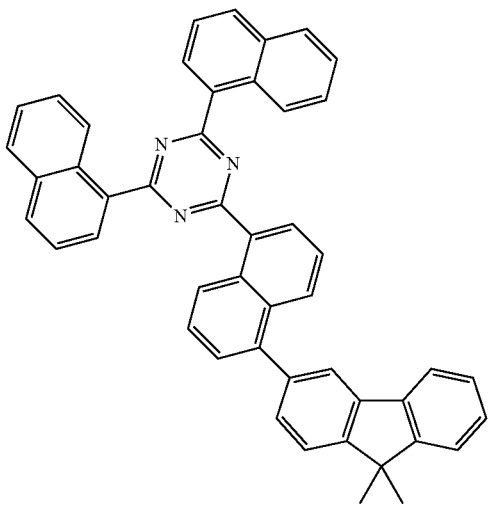
[Compound 99]
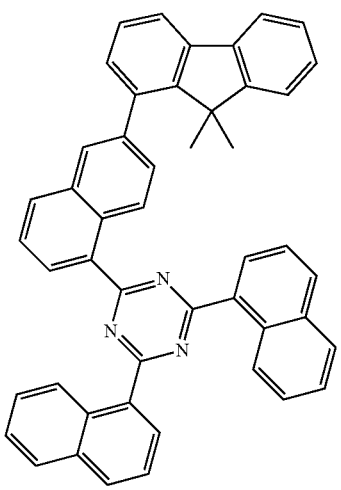
[Compound 100]
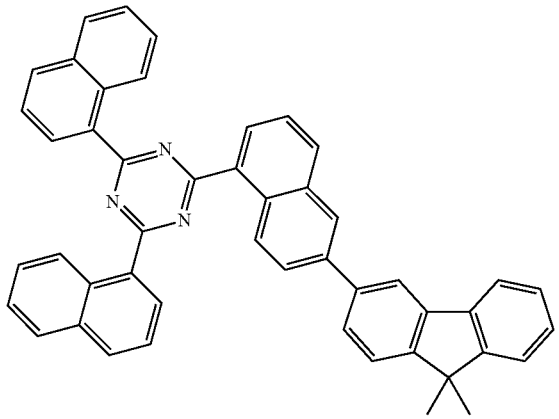

[Compound 101]
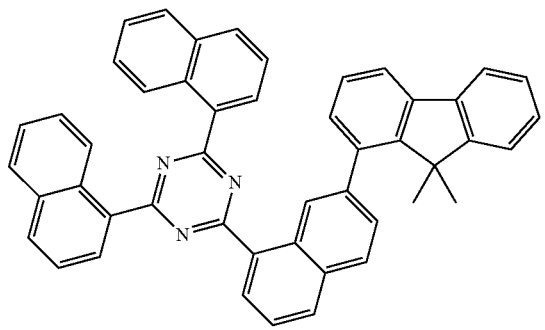
[Compound 105]
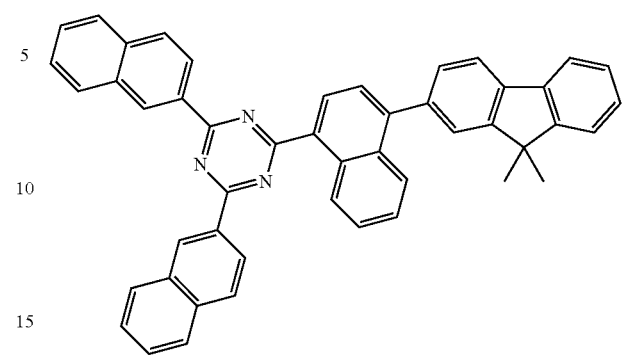
[Compound 102]
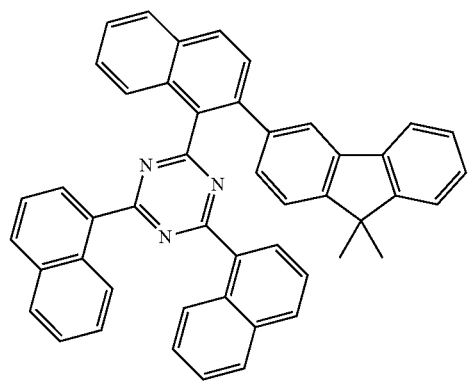
[Compound 106]
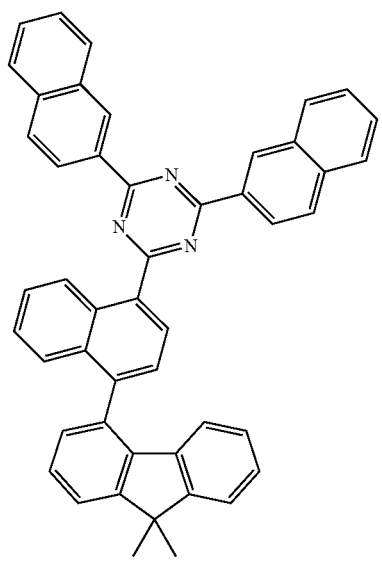
[Compound 103]
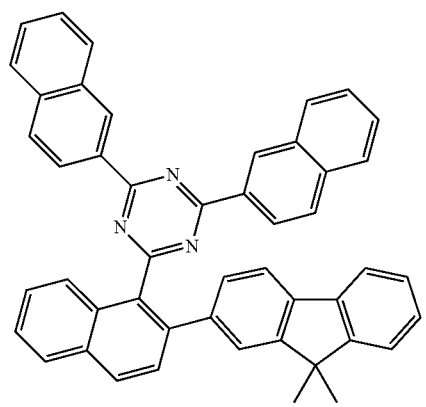
[Compound 104]
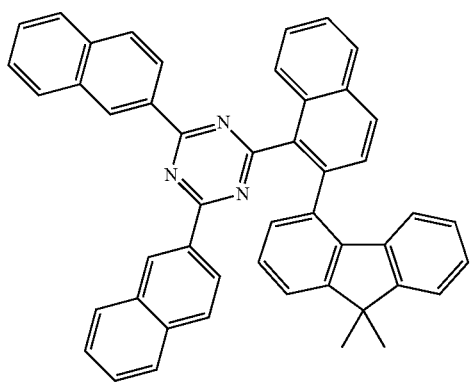
[Compound 107]
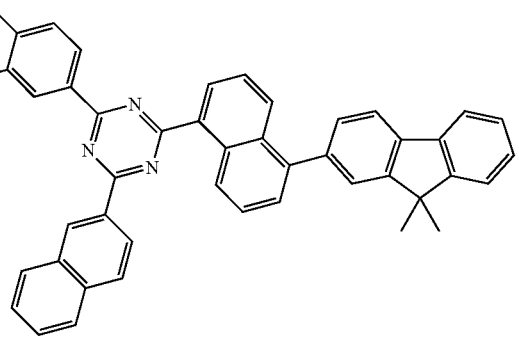

[Compound 108]
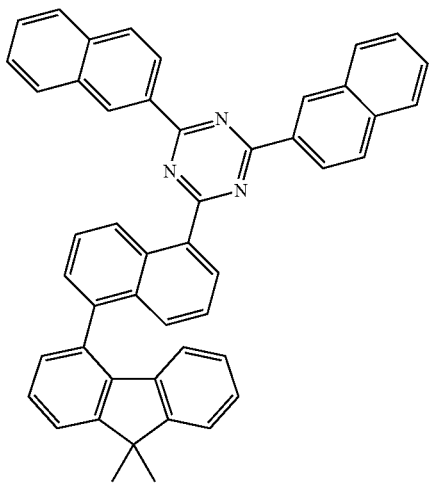
[Compound 109]
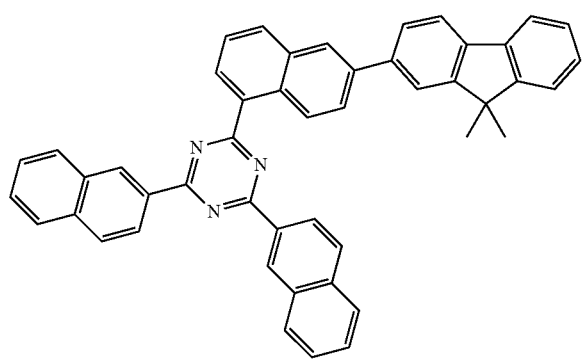
[Compound 110]
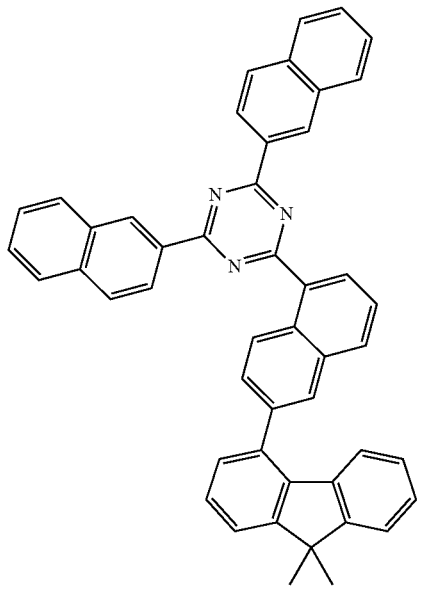
[Compound 111]
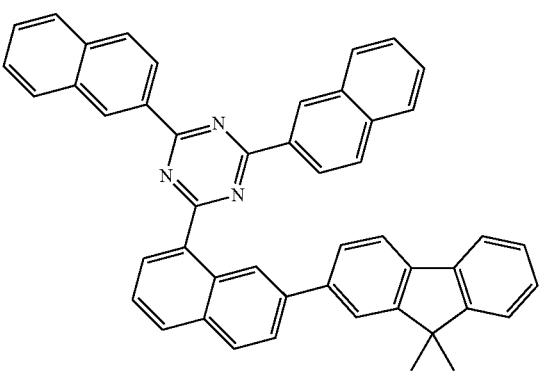
[Compound 112]
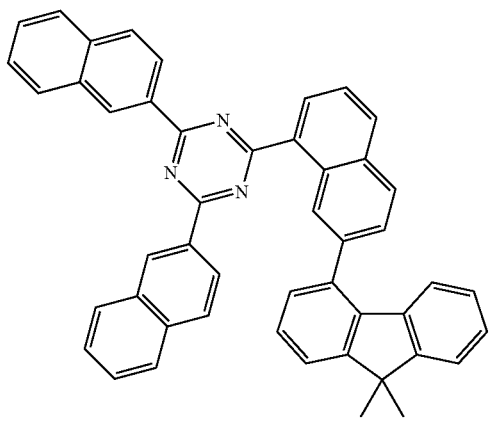
[Compound 113]
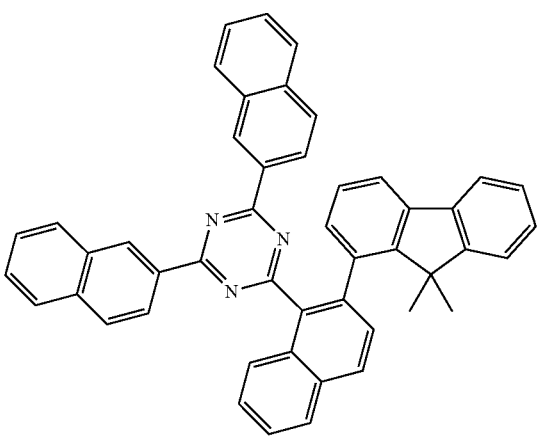

[Compound 114]
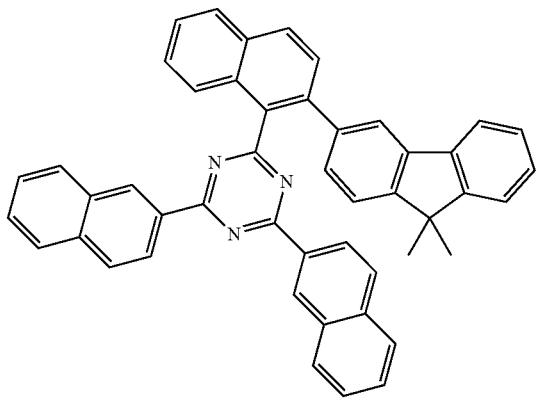
[Compound 117]
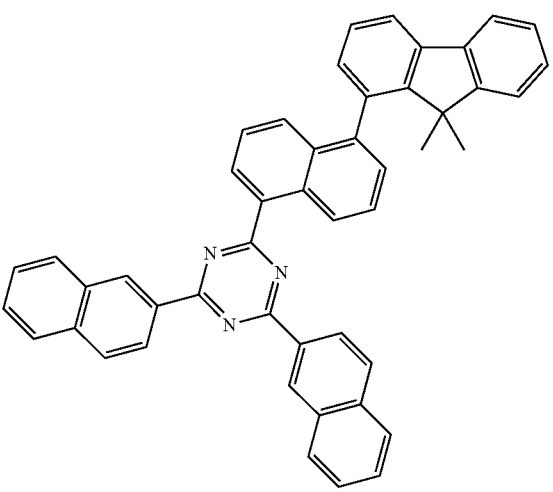
[Compound 115]
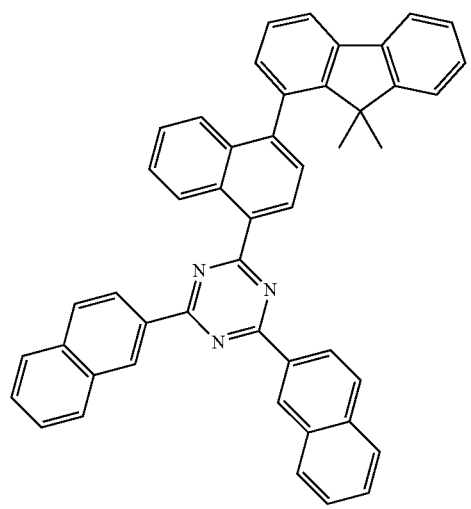
[Compound 118]
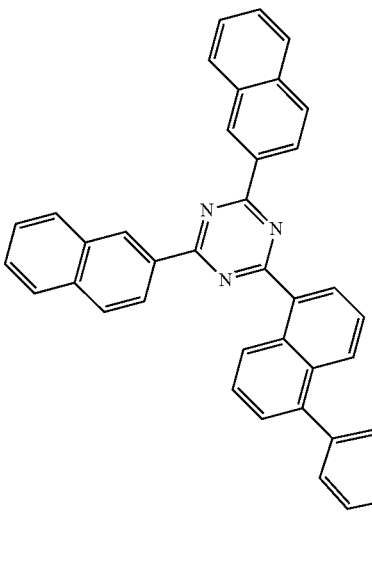
[Compound 116]
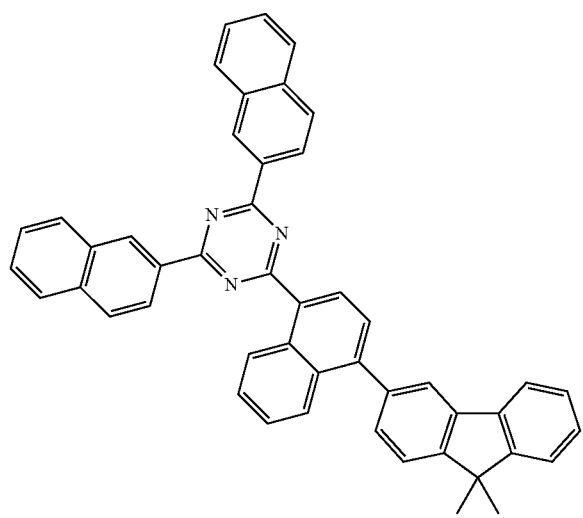
[Compound 119]

[Compound 120]
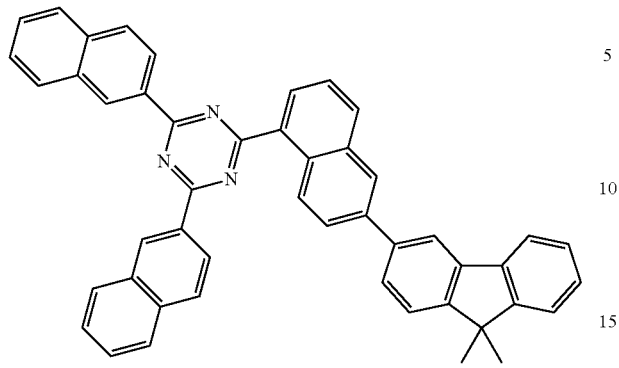
[Compound 121]
[Compound 124]
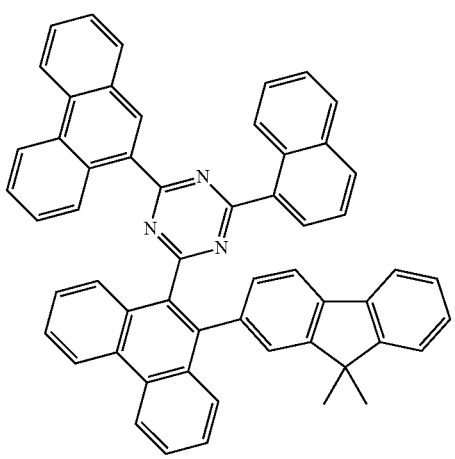
[Compound 122]
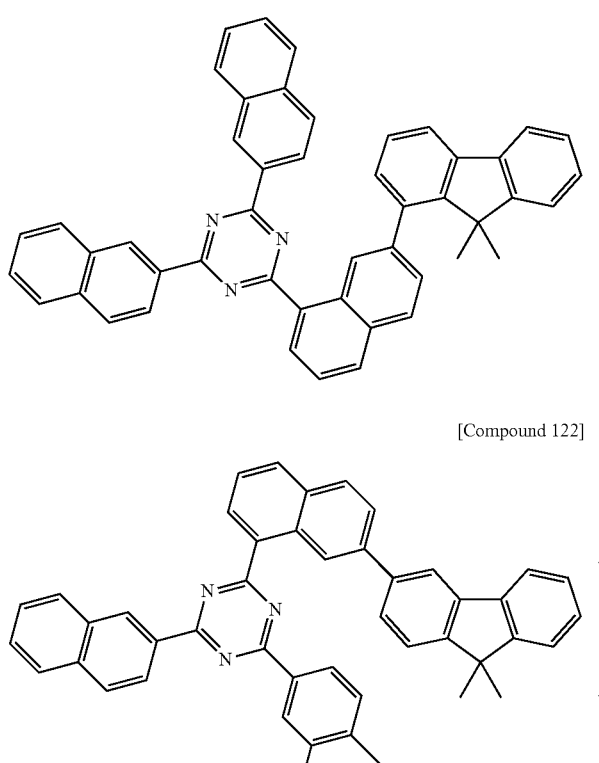
[Compound 125]
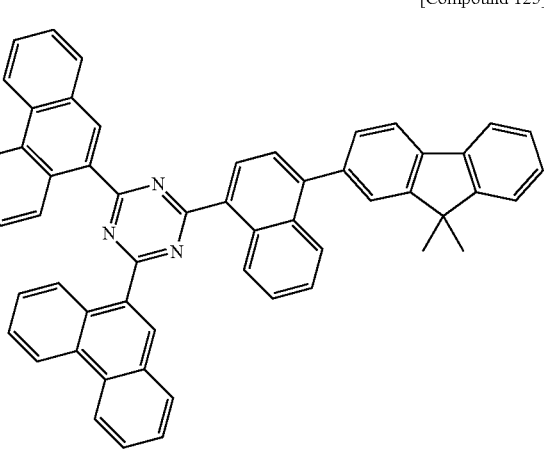
[Compound 123]
[Compound 126]
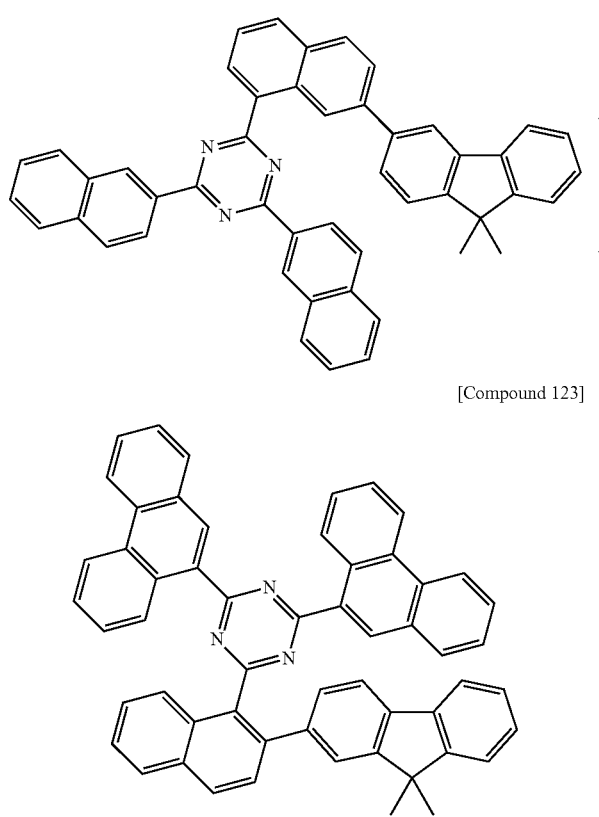
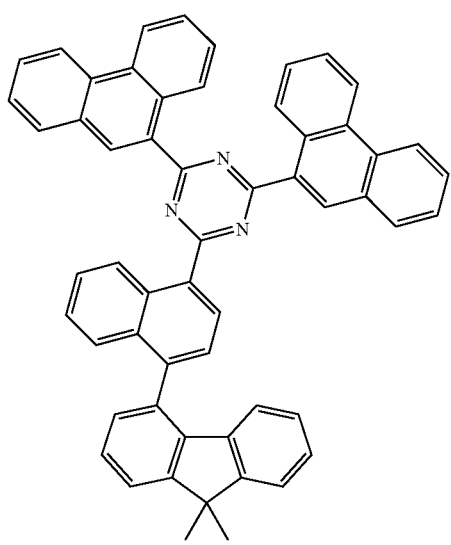

[Compound 127]
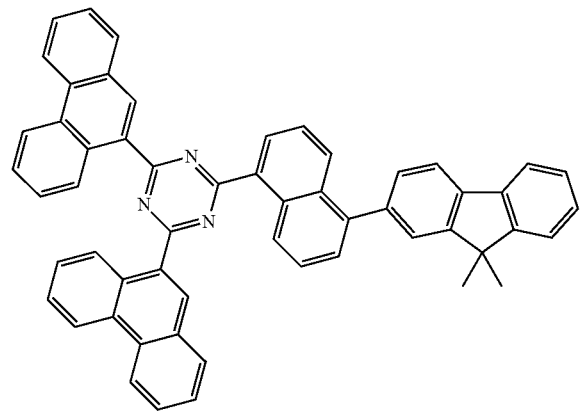
[Compound 128]
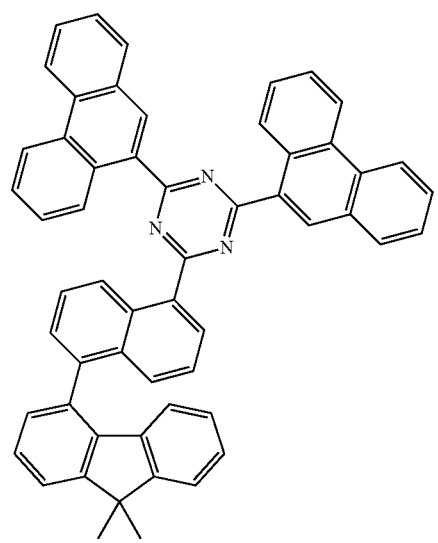
[Compound 129]
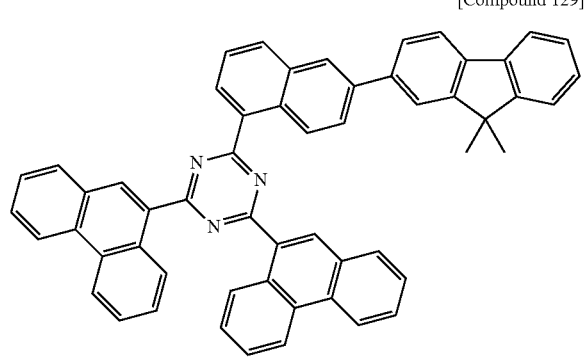
[Compound 130]
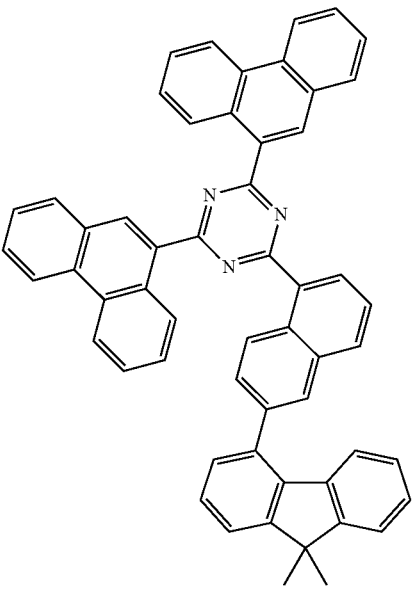
[Compound 131]
[Compound 132]
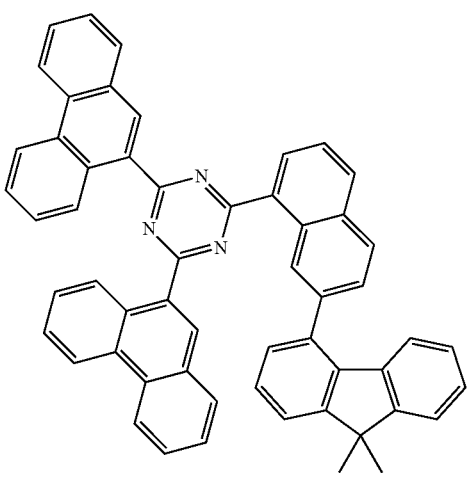

[Compound 133]
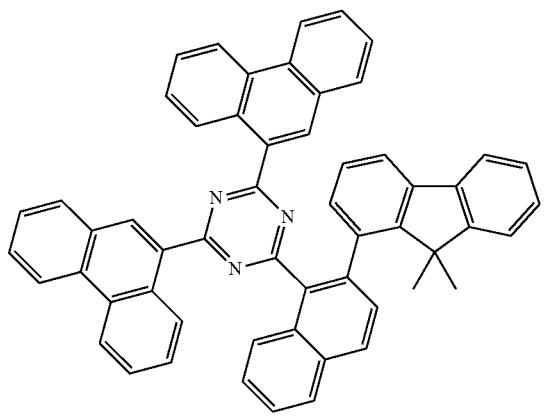
[Compound 134]
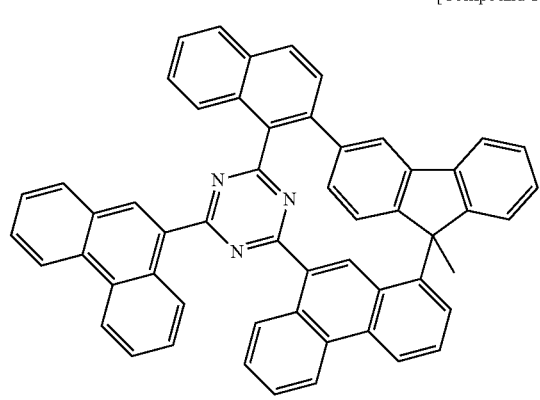
[Compound 135]
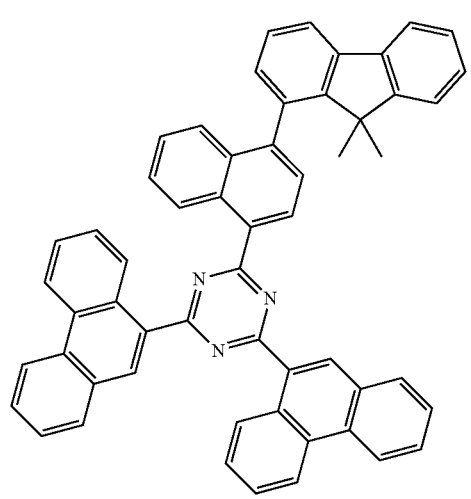
[Compound 136]
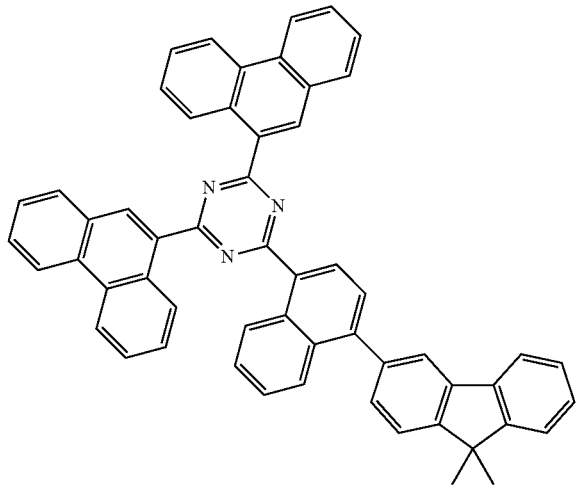
[Compound 137]
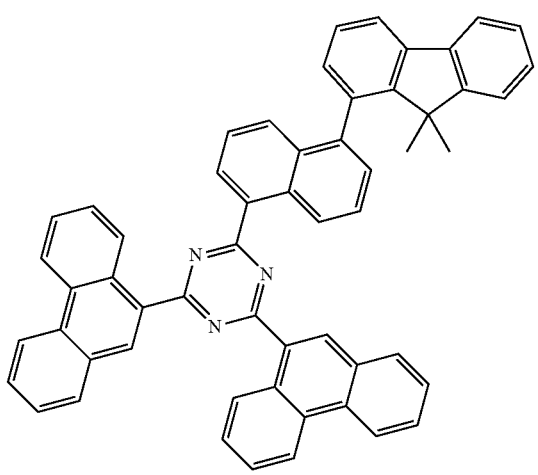
[Compound 138]
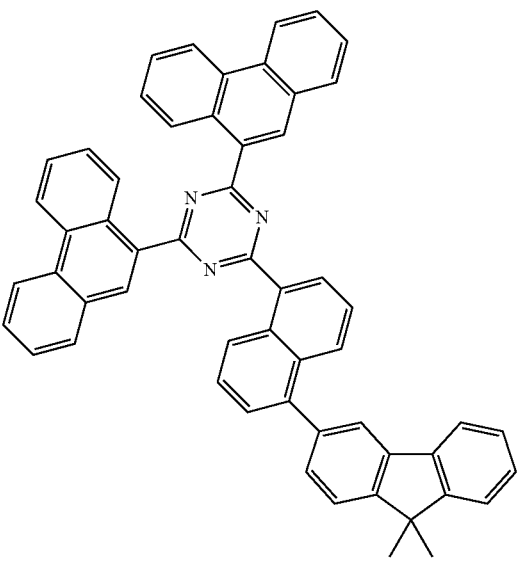

[Compound 139]
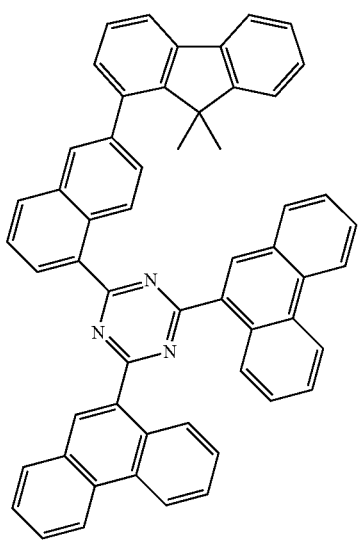
[Compound 140]
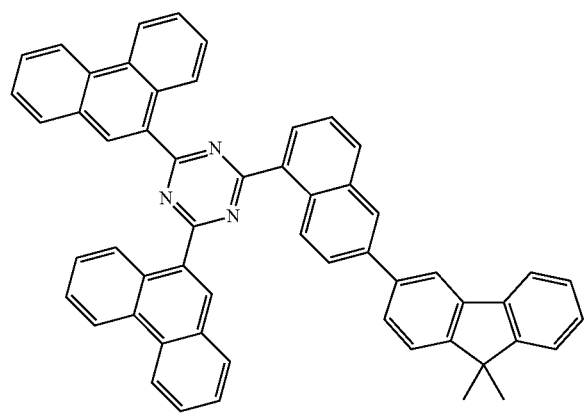
[Compound 141]
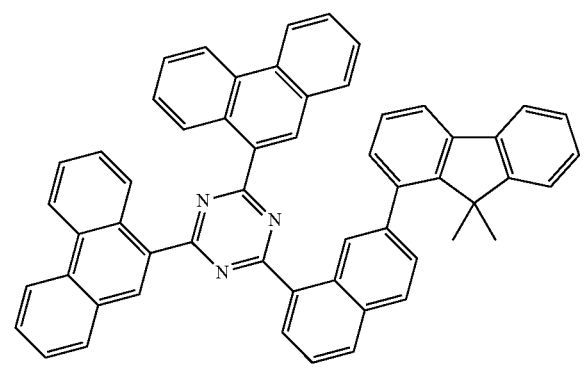
[Compound 142]
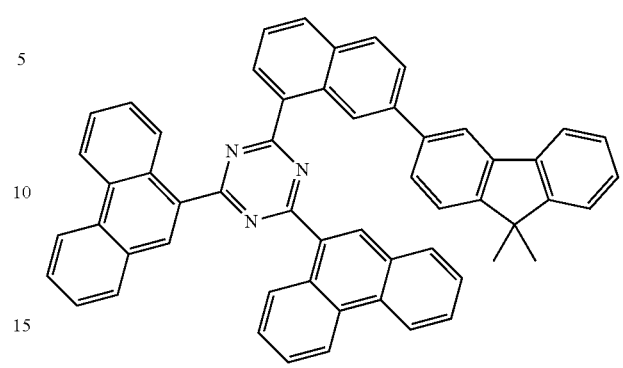
[Compound 143]
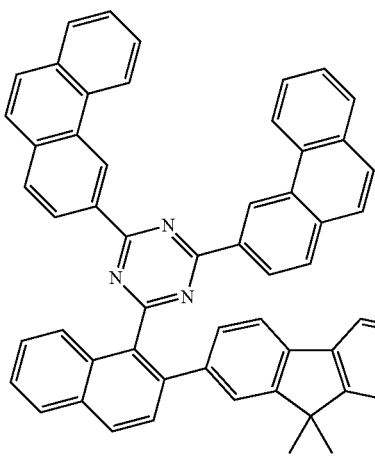
[Compound 144]
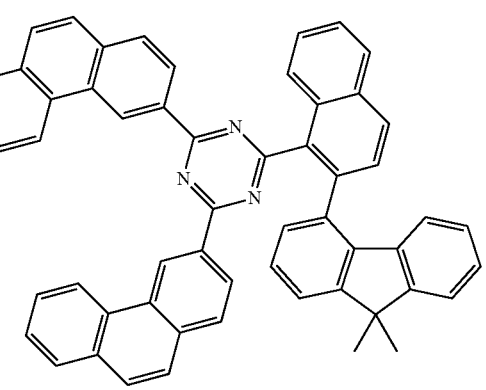
[Compound 145]
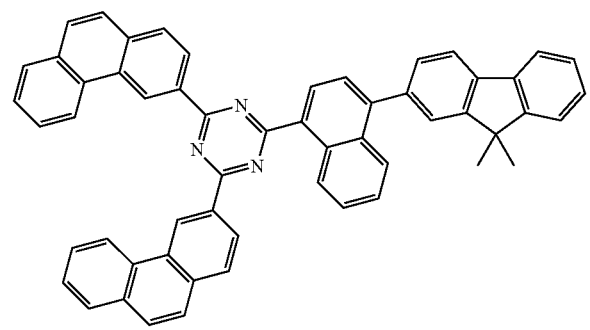

[Compound 146]
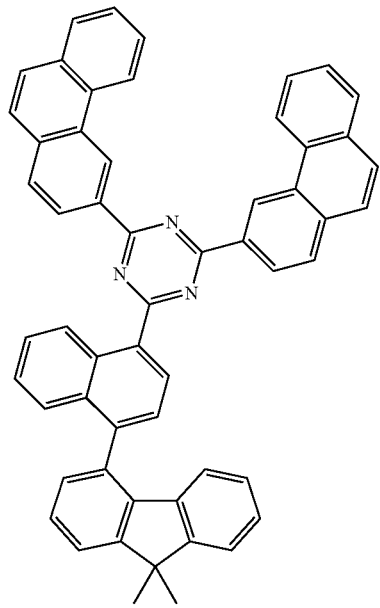
[Compound 147]
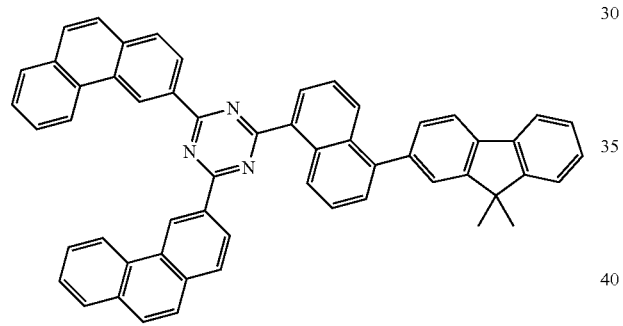
[Compound 148]
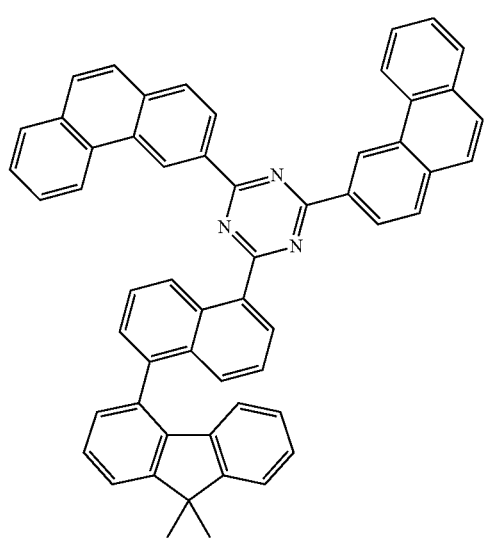
[Compound 149]
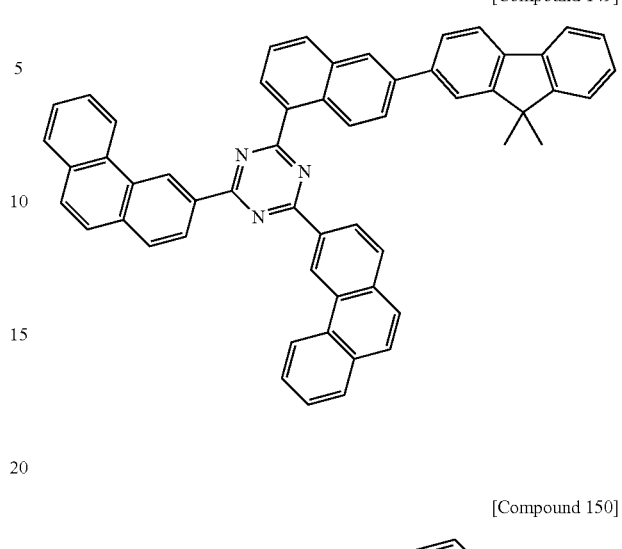
[Compound 150]
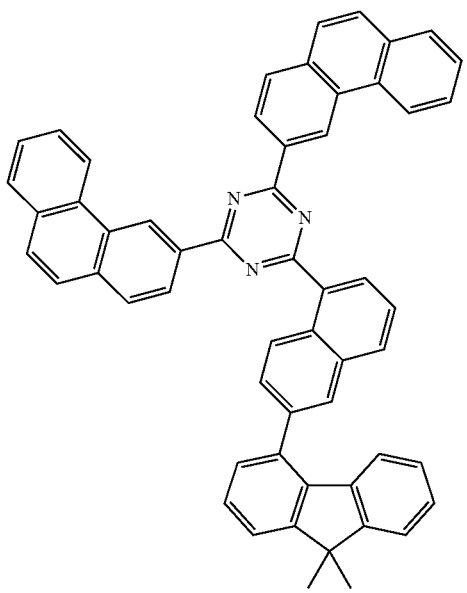
[Compound 151]
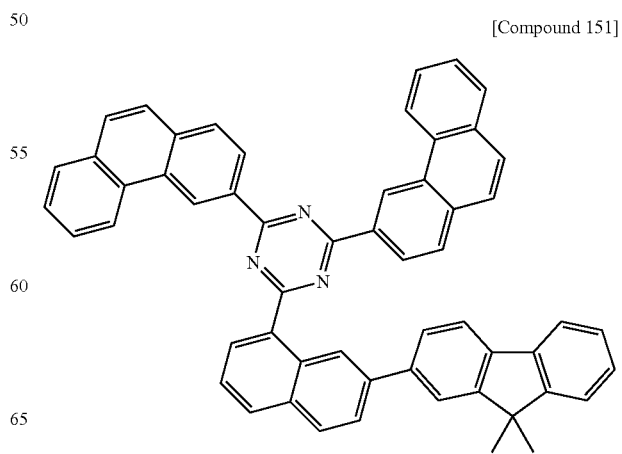

[Compound 152]
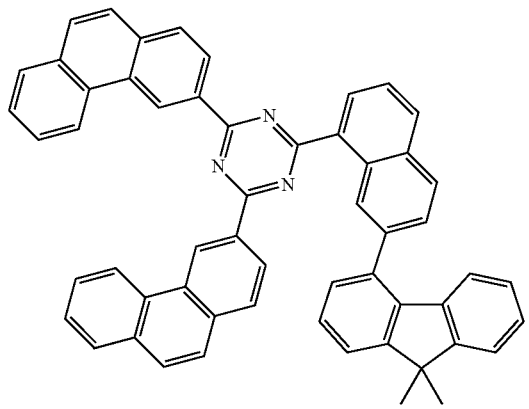
[Compound 153]
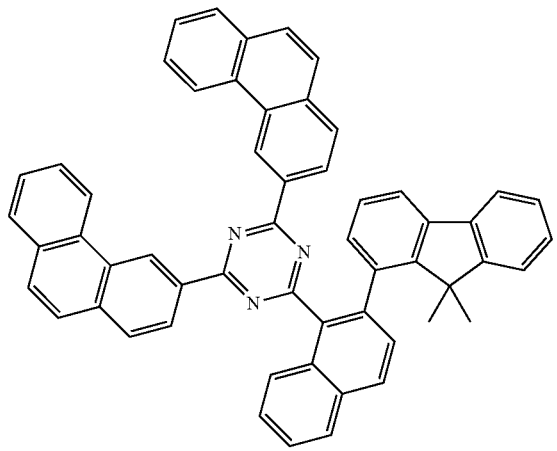
[Compound 154]
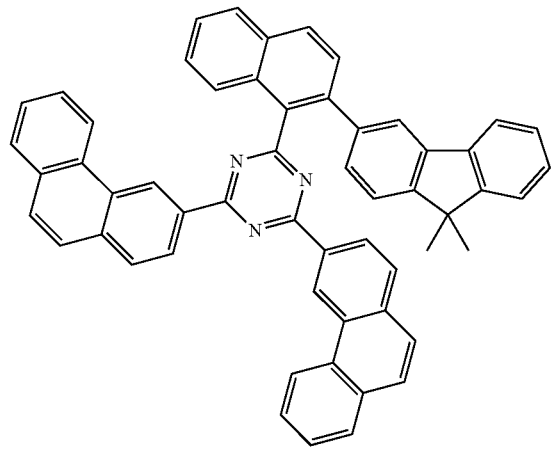
[Compound 155]
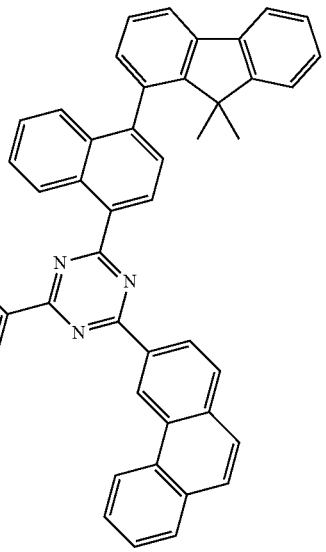
[Compound 156]
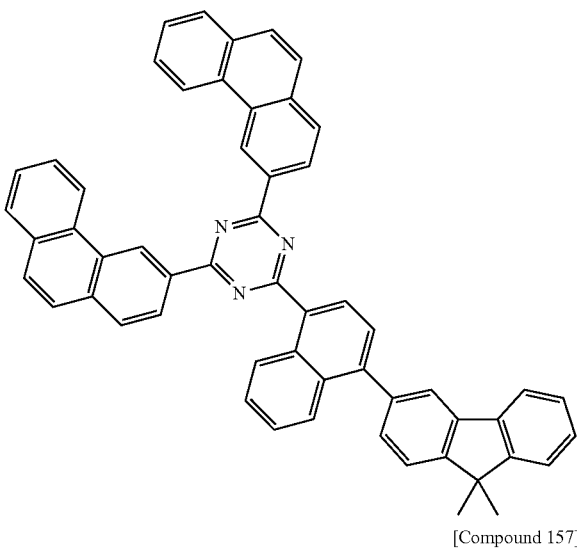
[Compound 157]
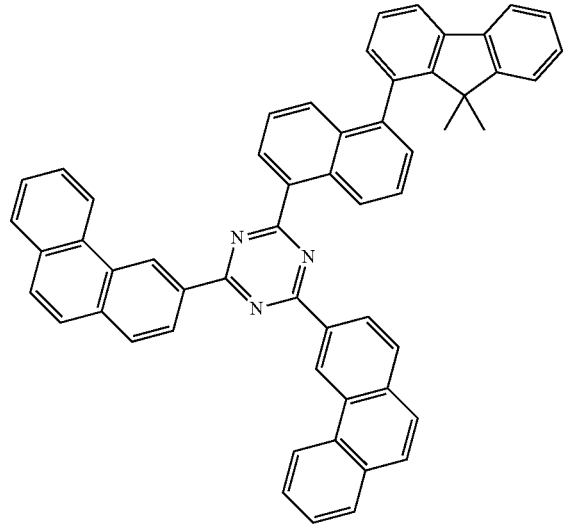

[Compound 158]
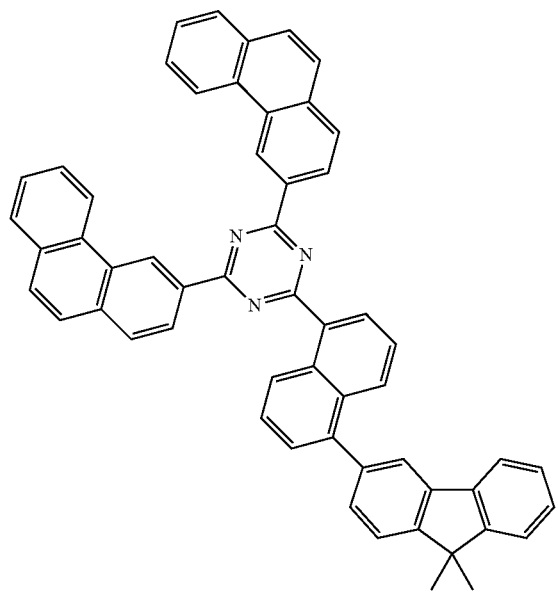
[Compound 161]
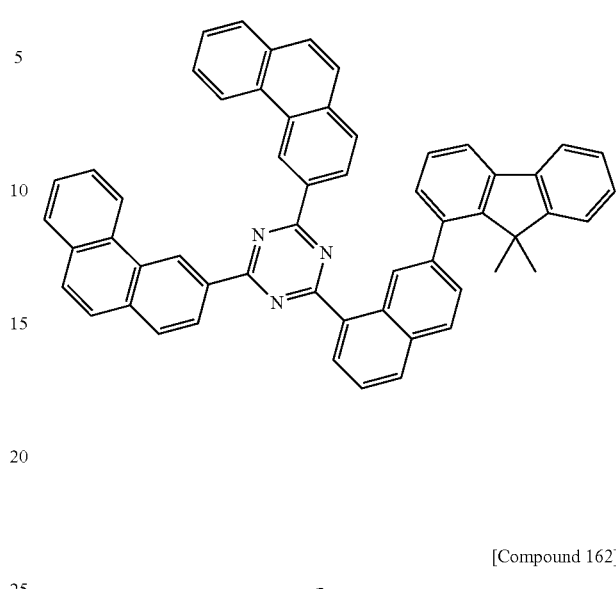
[Compound 159]
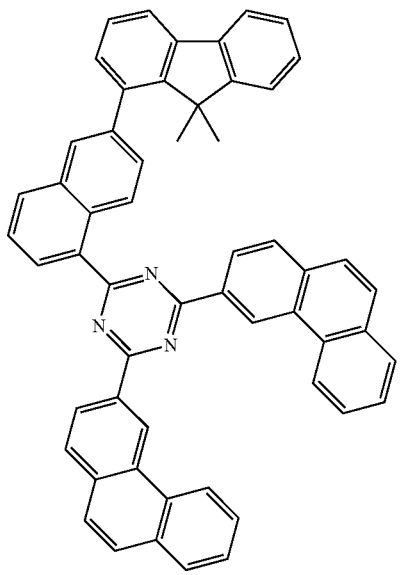
[Compound 162]
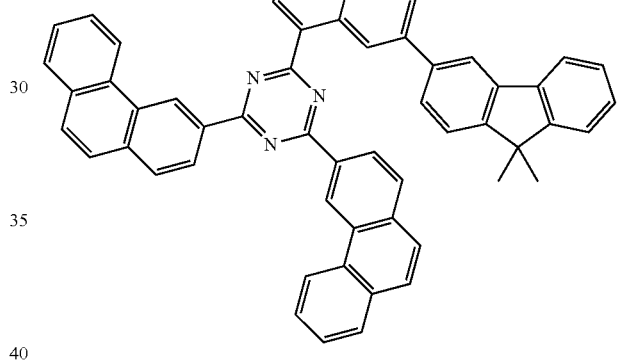
[Compound 160]
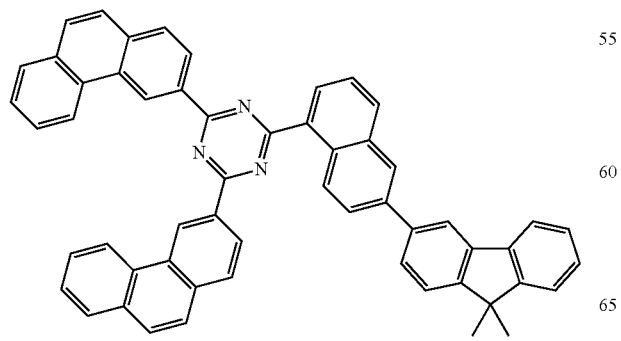
[Compound 163]
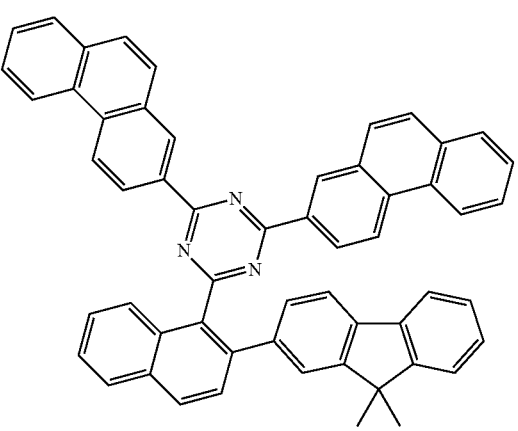

[Compound 164]
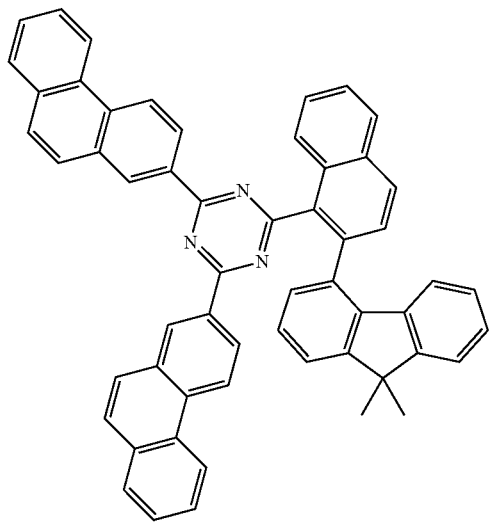
[Compound 165]
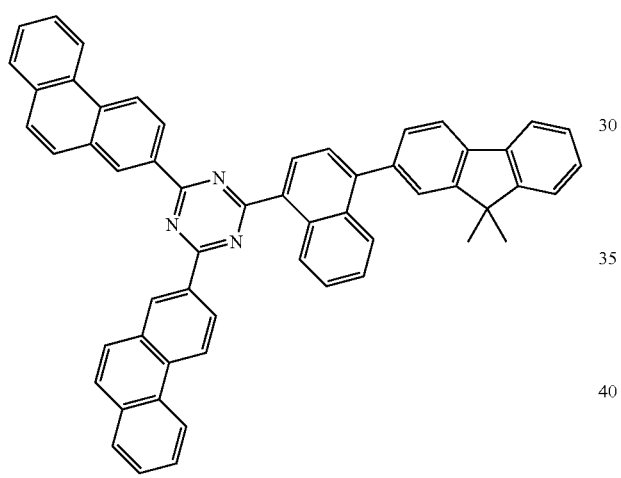
[Compound 166]
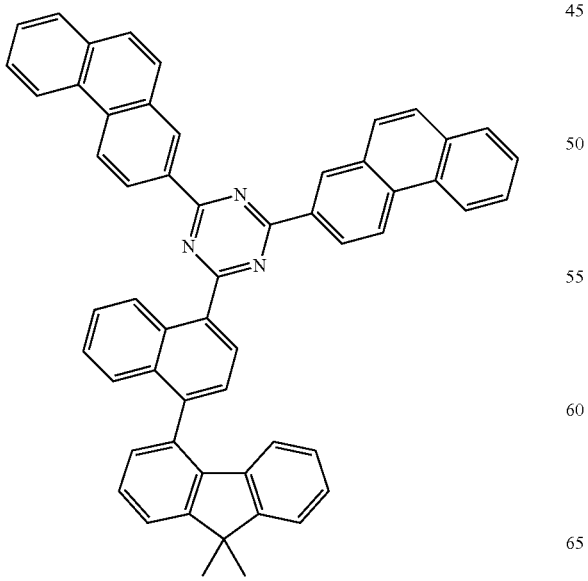
[Compound 167]
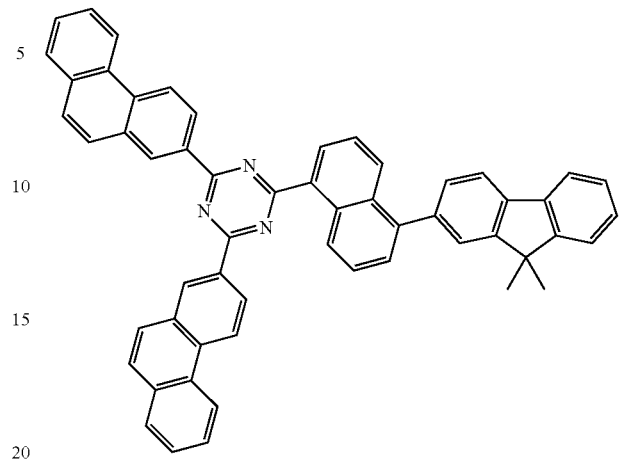
[Compound 168]
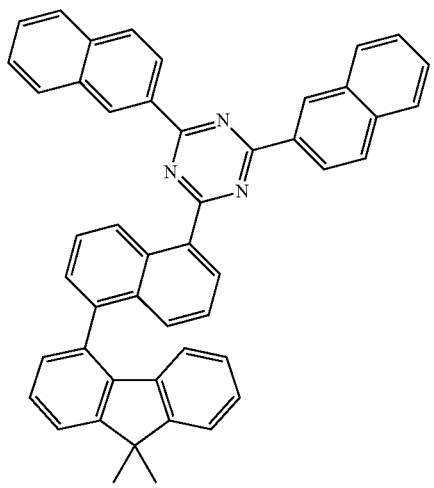
[Compound 169]
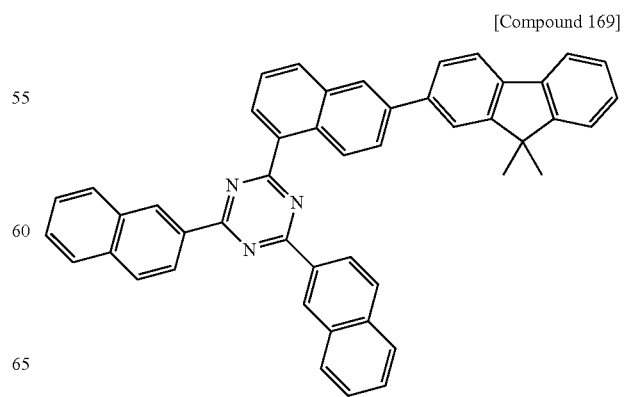

[Compound 170]
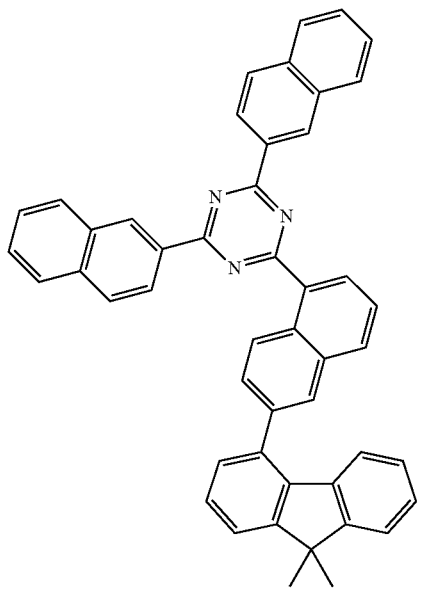
[Compound 171]
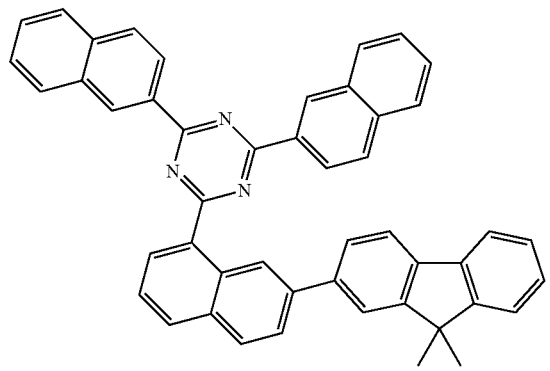
[Compound 172]
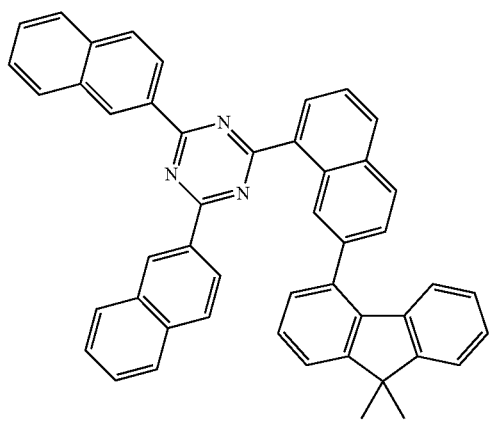
[Compound 173]
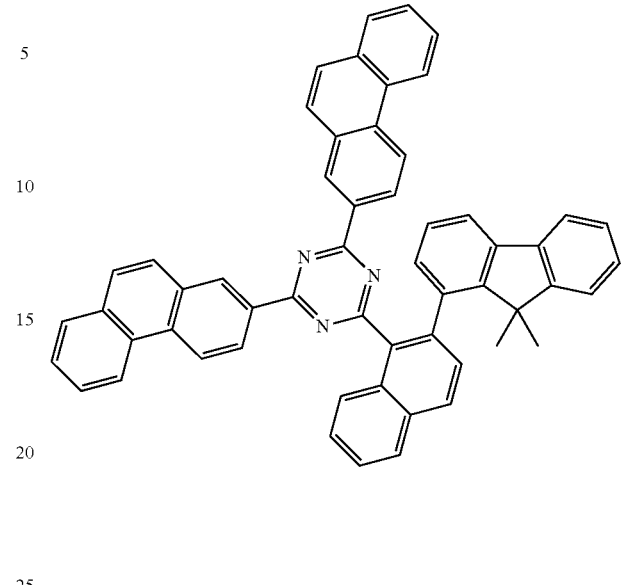
[Compound 174]
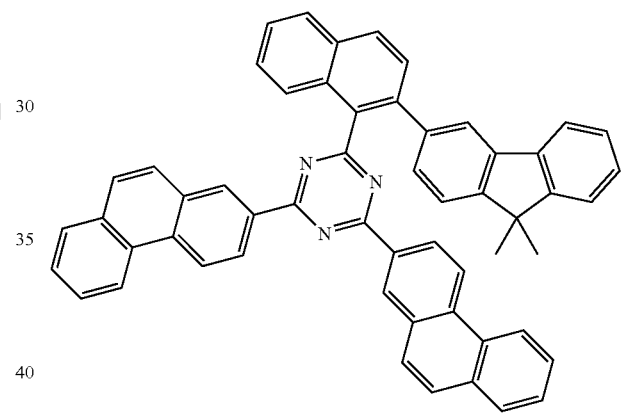
[Compound 175]
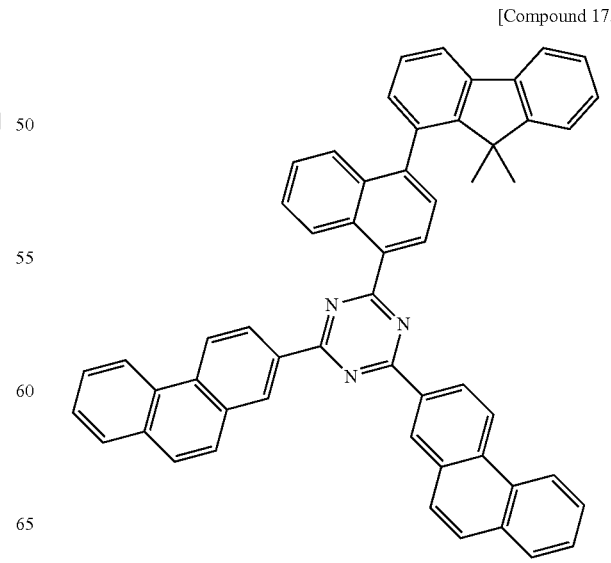

[Compound 176]
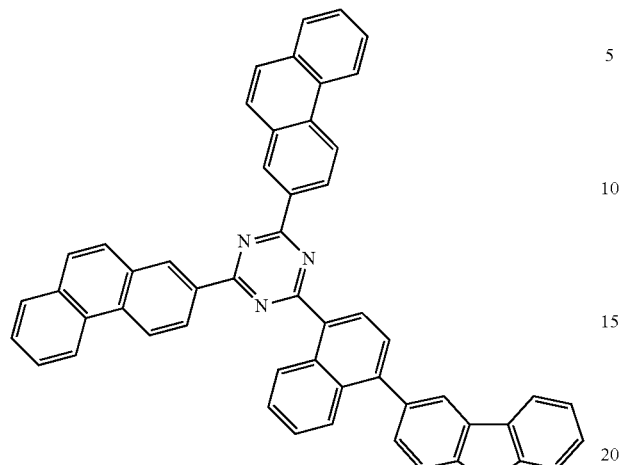
[Compound 177]
[Compound 178]
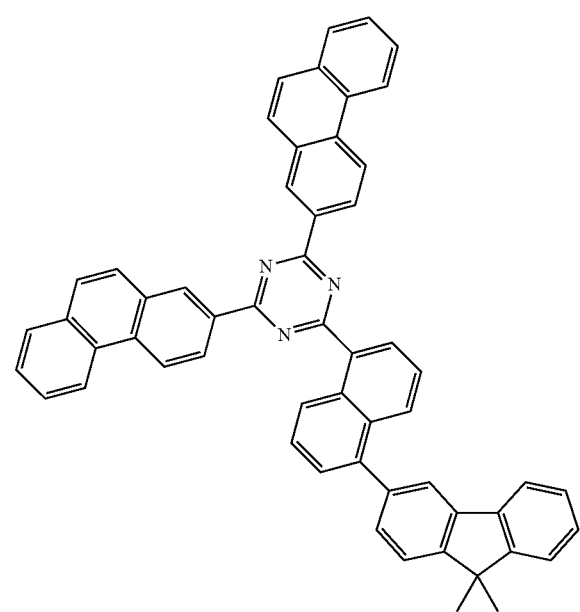
[Compound 179]
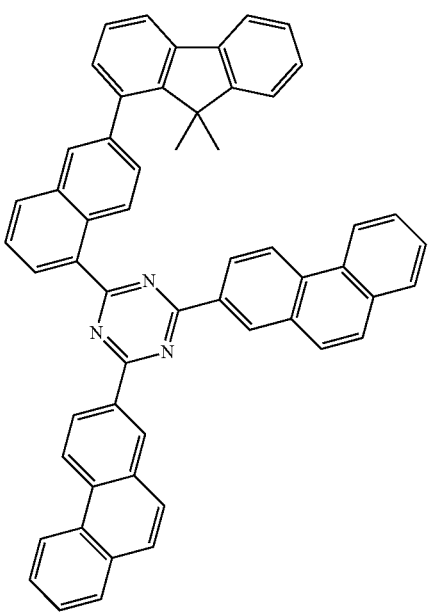
[Compound 180]
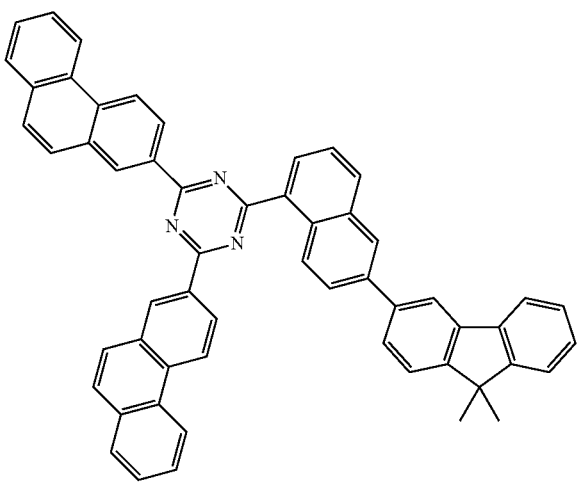
[Compound 181]
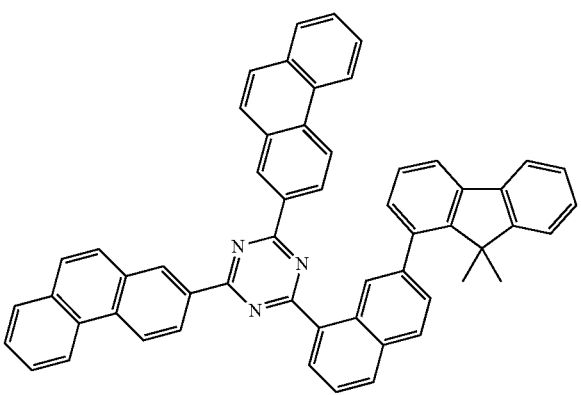

[Compound 182]
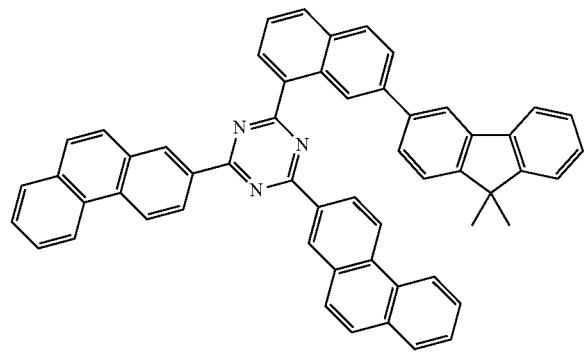
[Compound 186]
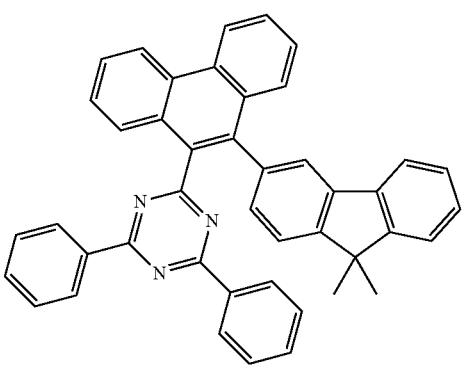
[Compound 183]
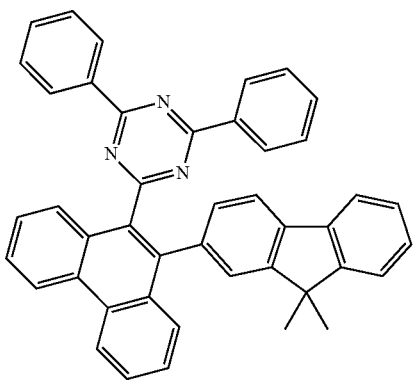
[Compound 187]
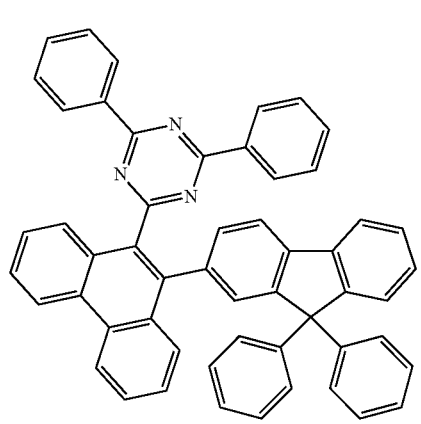
[Compound 184]
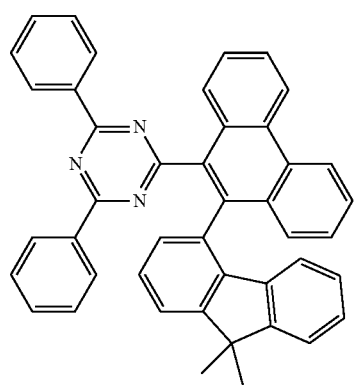
[Compound 188]
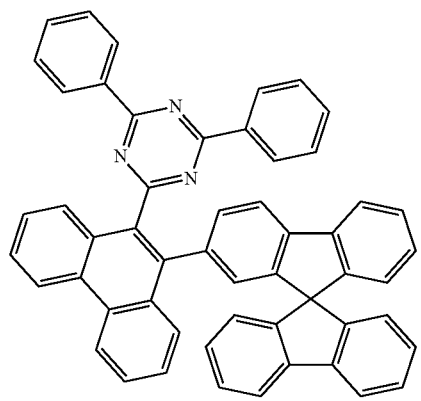
[Compound 185]
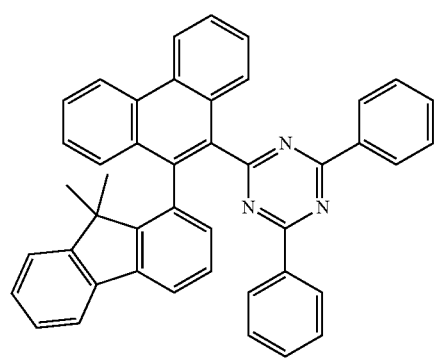
[Compound 189]
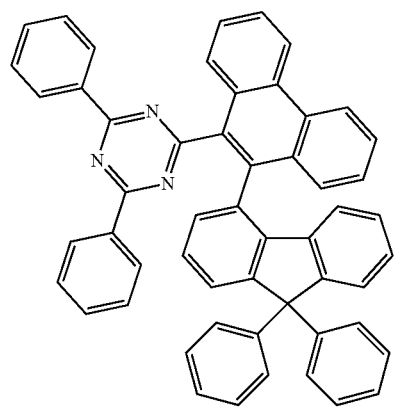

[Compound 190]
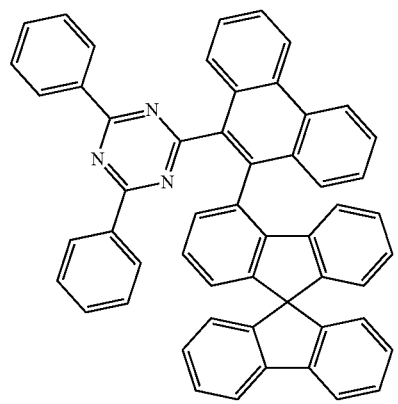
[Compound 193]
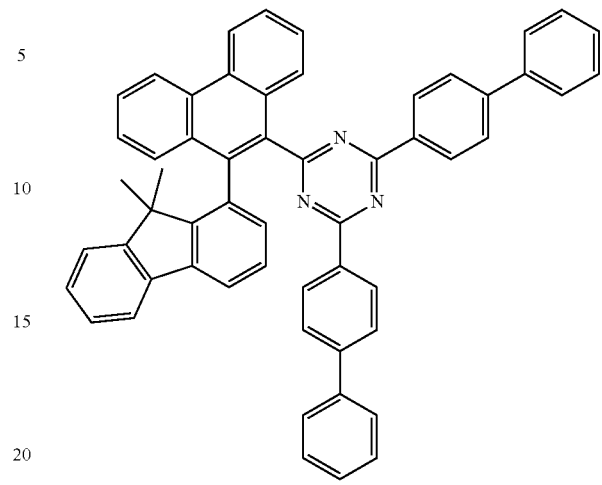
[Compound 191]
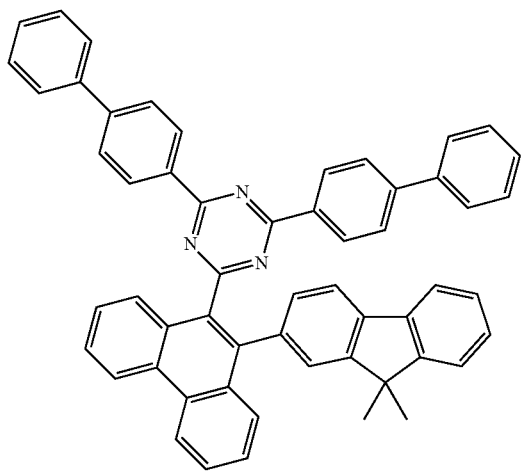
[Compound 194]
[Compound 192]
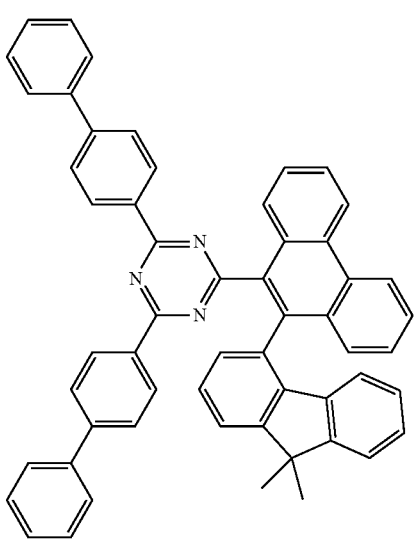
[Compound 195]
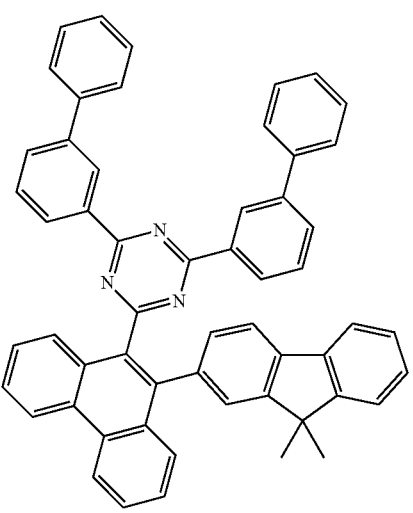

-continued
[Compound 196]
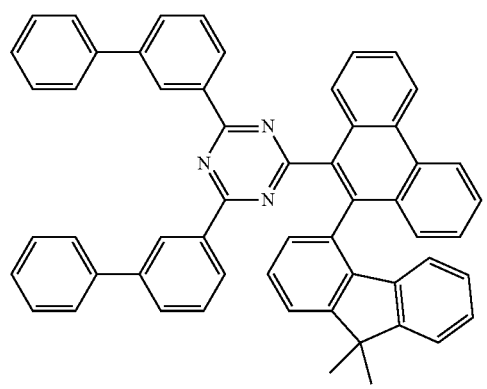
[Compound 197]
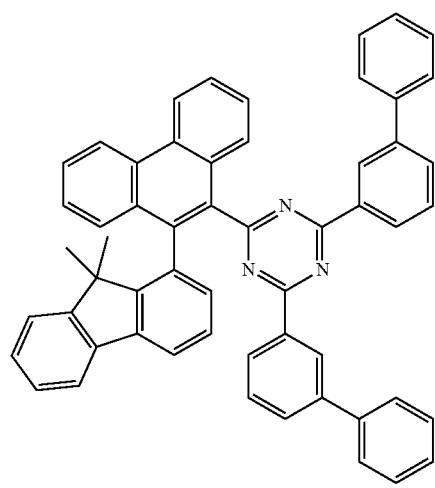
[Compound 198]
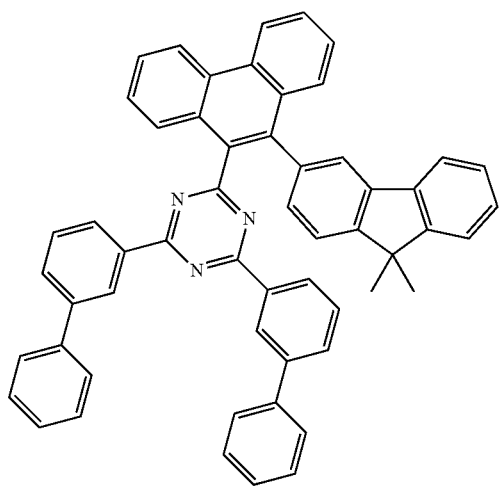
-continued
[Compound 199]
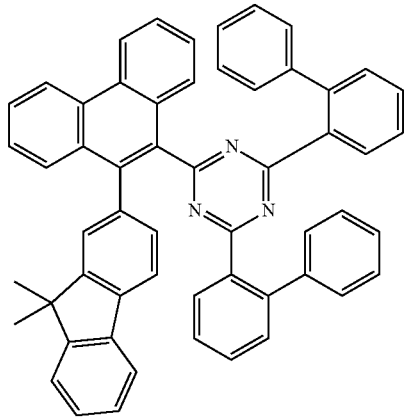
[Compound 200]
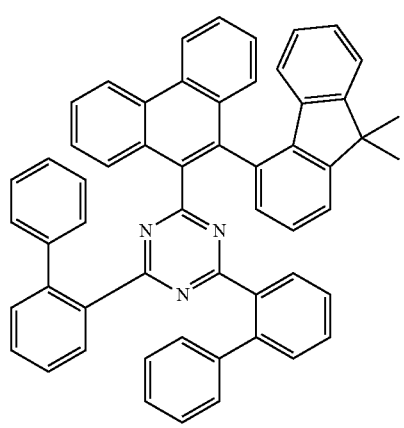
[Compound 201]
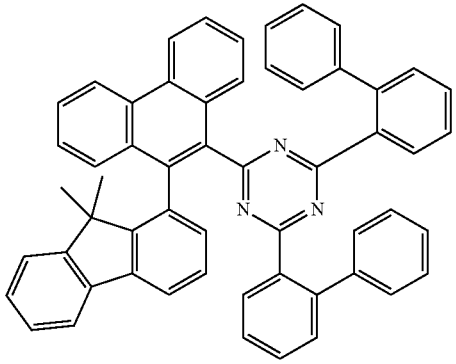

[Compound 202]
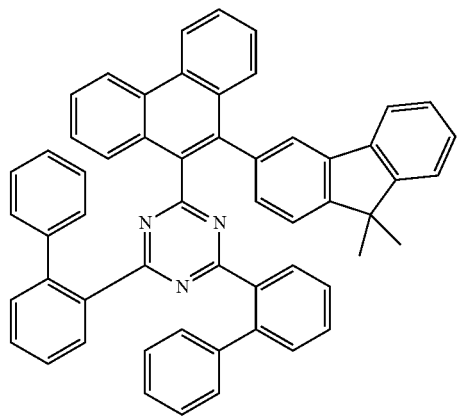
[Compound 203]
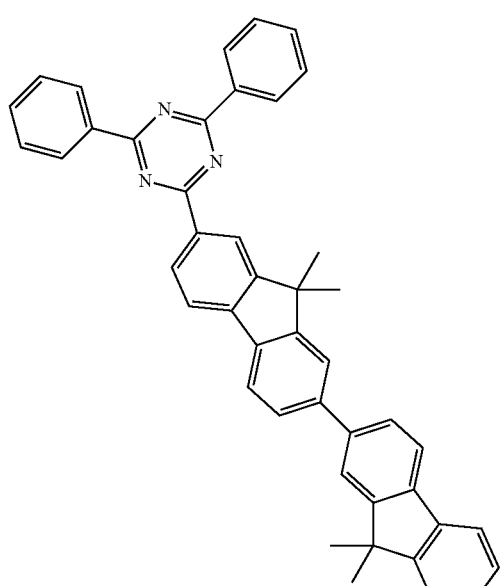
[Compound 204]
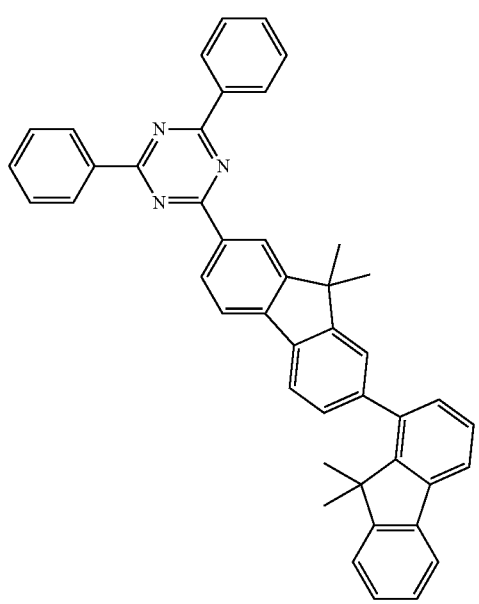
[Compound 205]
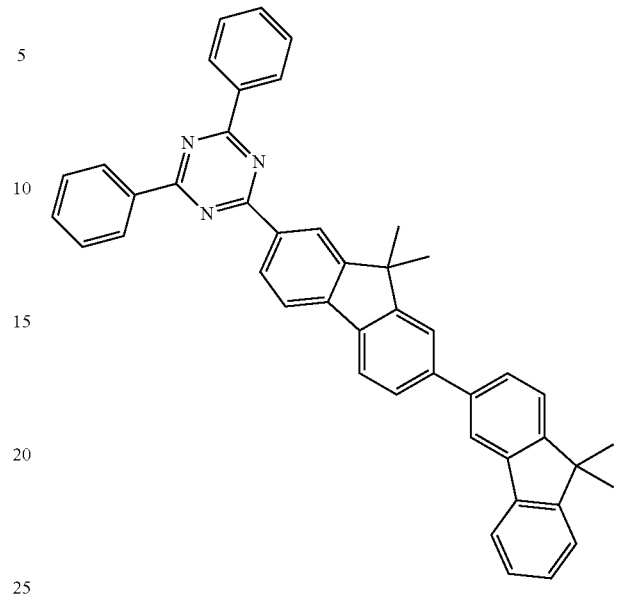
[Compound 206]
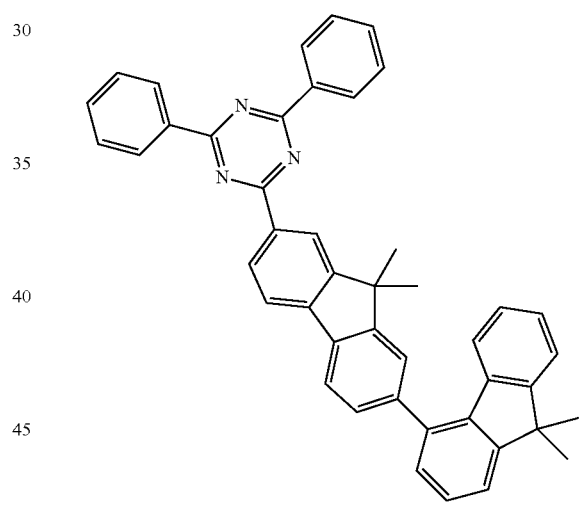
[Compound 207]
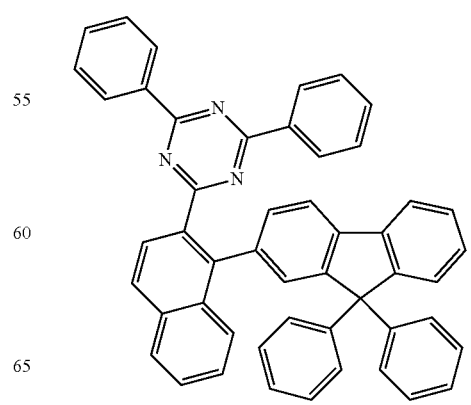

[Compound 208]
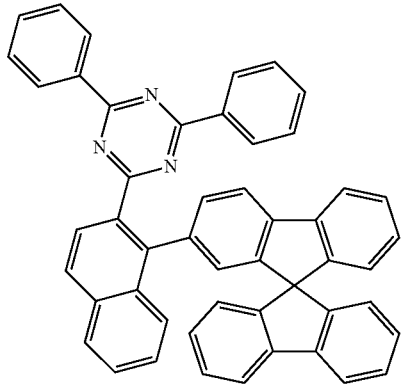
[Compound 209]
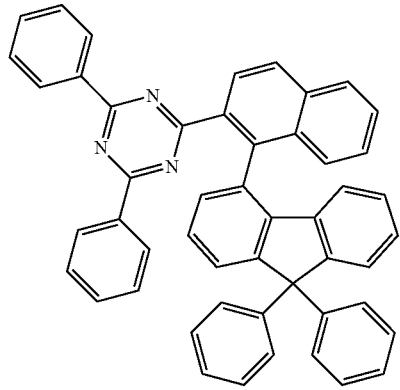
[Compound 210]
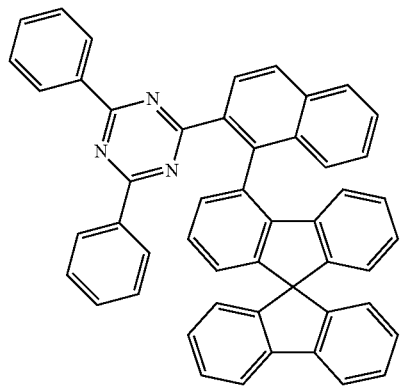
[Compound 211]
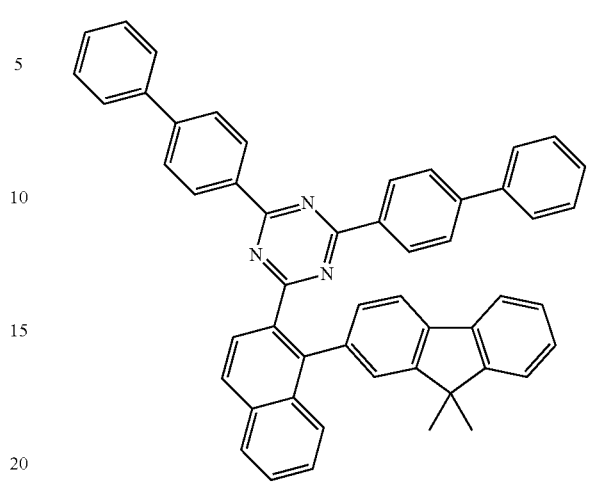
[Compound 212]
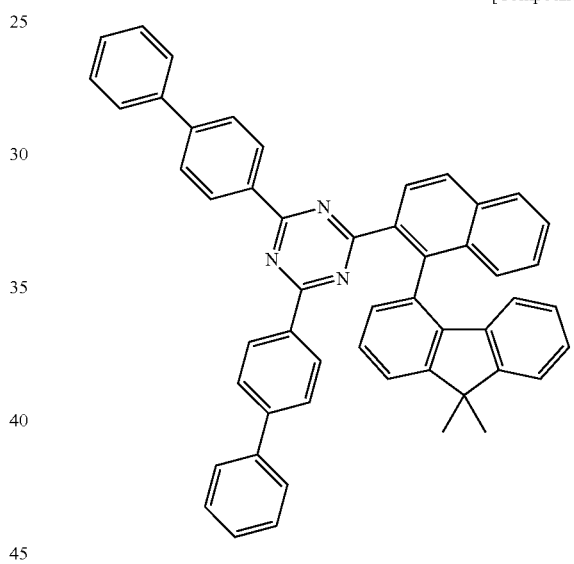
[Compound 213]
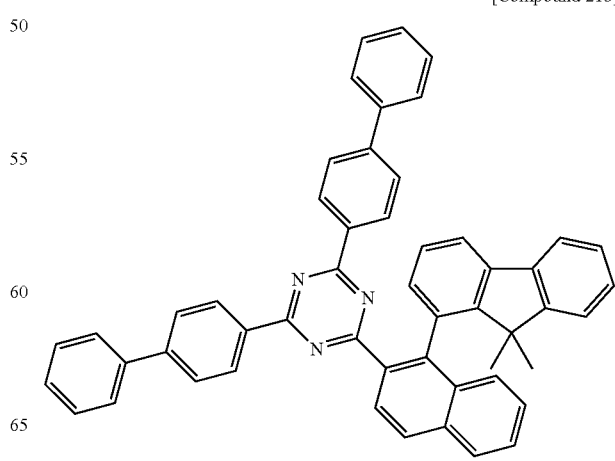

[Compound 214]
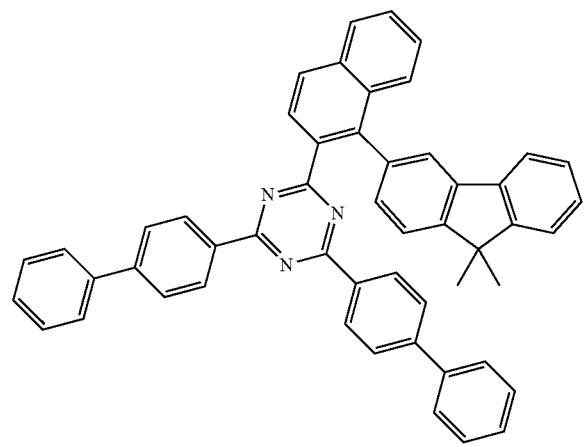
[Compound 217]
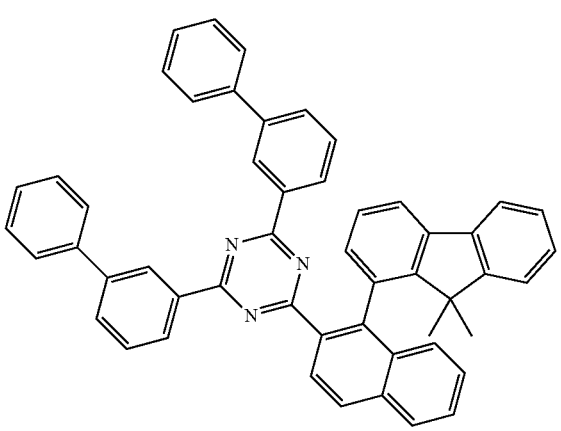
[Compound 215]
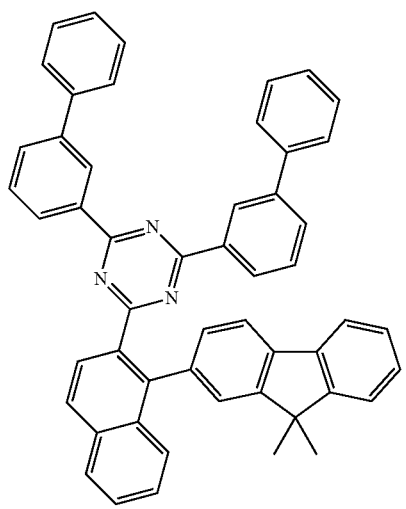
[Compound 218]
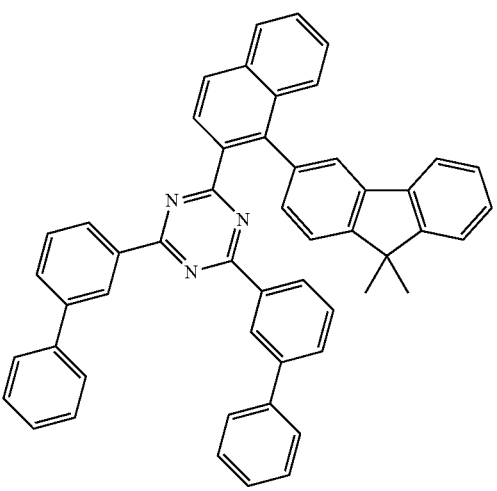
[Compound 216]
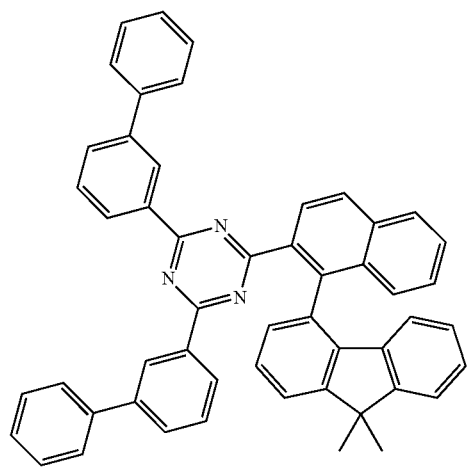
[Compound 219]
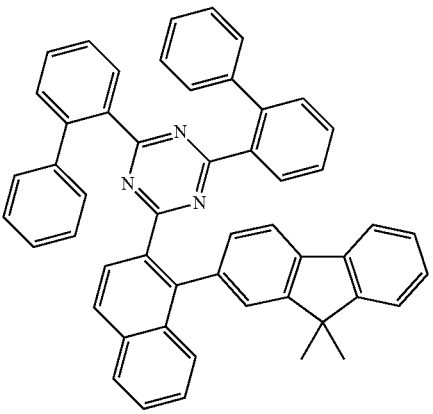

[Compound 220]
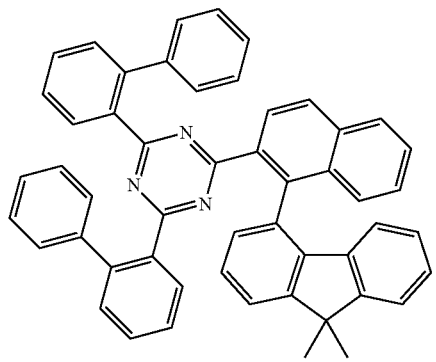
[Compound 221]
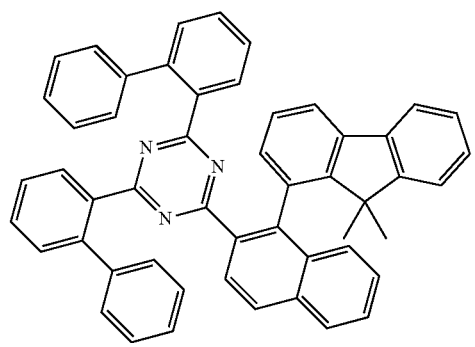
[Compound 222]
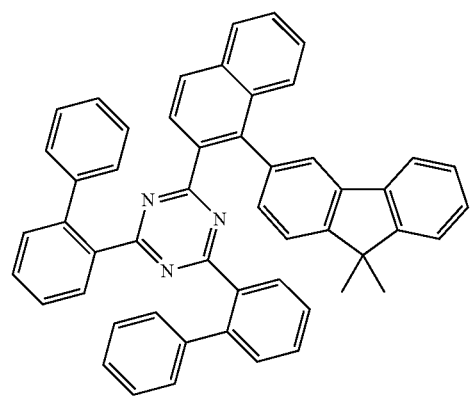
[Compound 223]
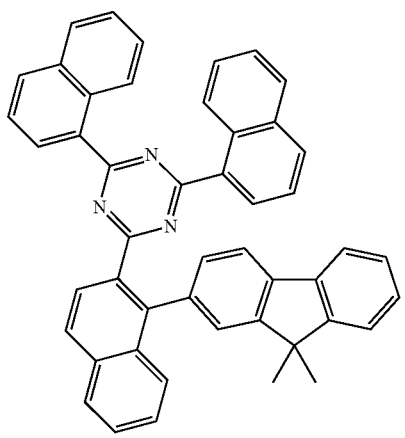
[Compound 224]
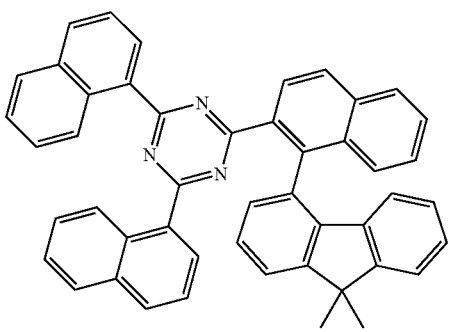
[Compound 225]
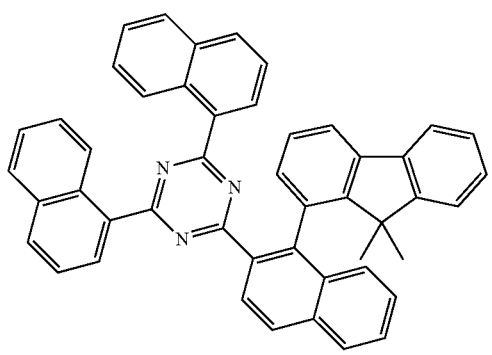
[Compound 226]
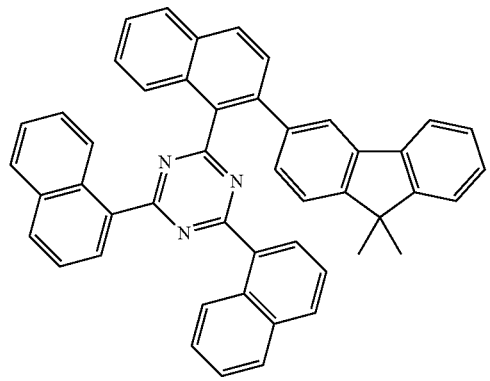
[Compound 227]
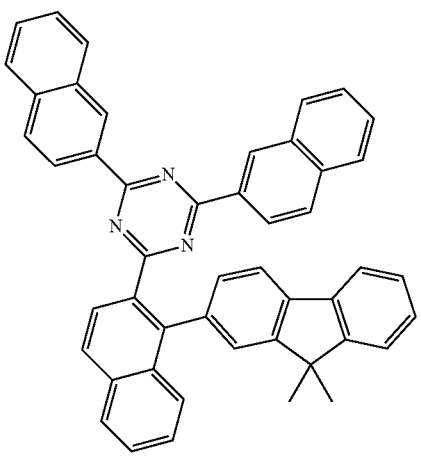

[Compound 228]
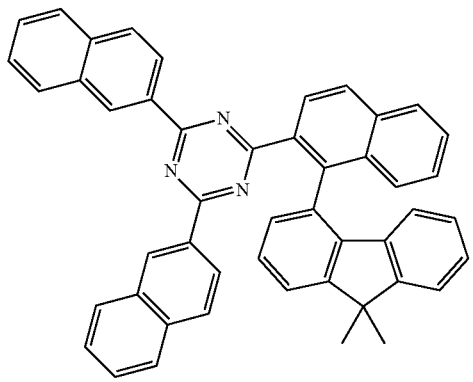
[Compound 231]
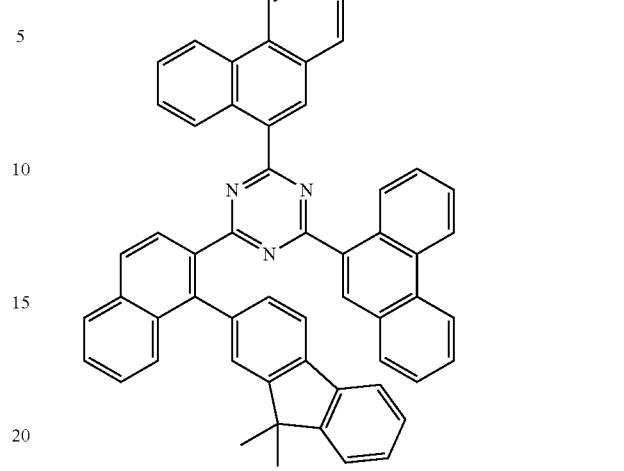
[Compound 229]
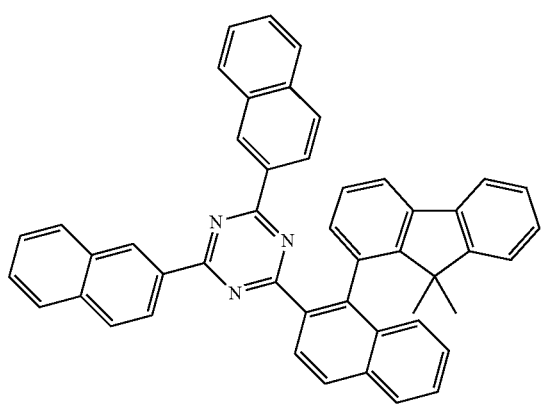
[Compound 232]
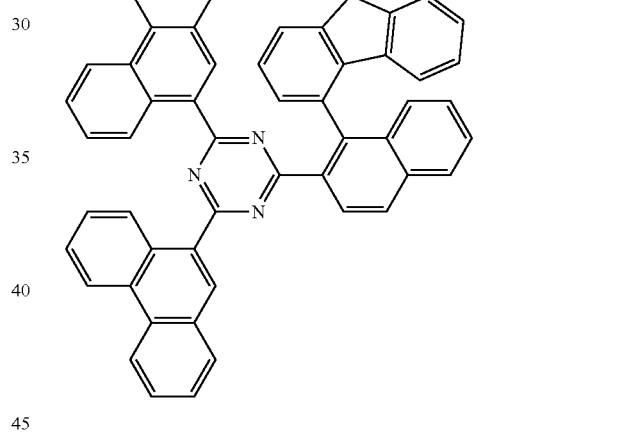
[Compound 230]
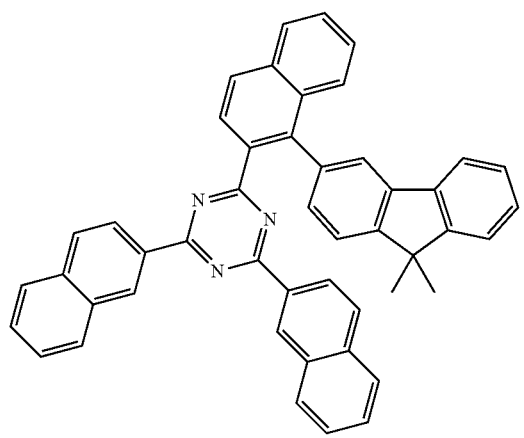
[Compound 233]
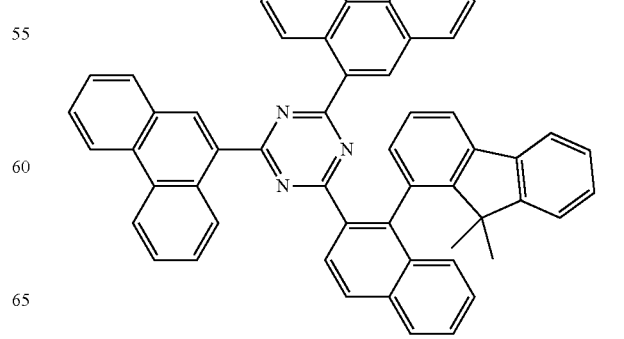

[Compound 234]
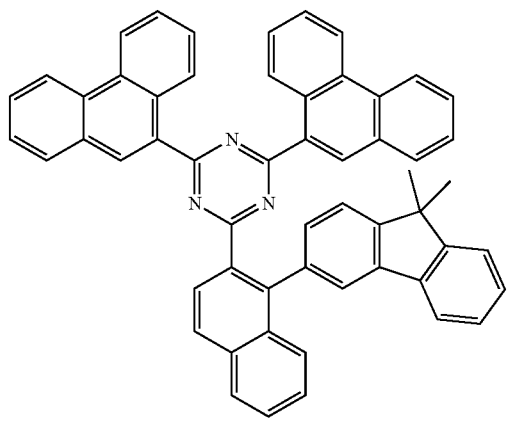
[Compound 237]
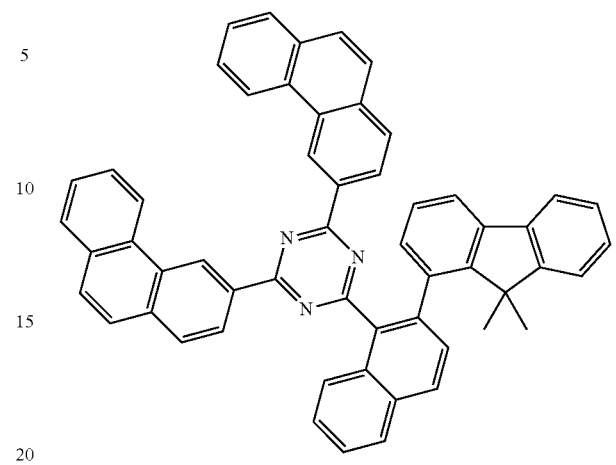
[Compound 235]
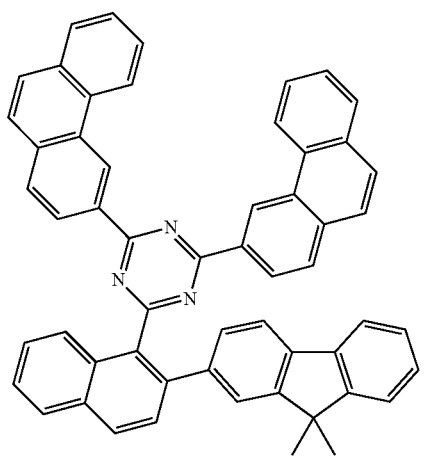
[Compound 238]
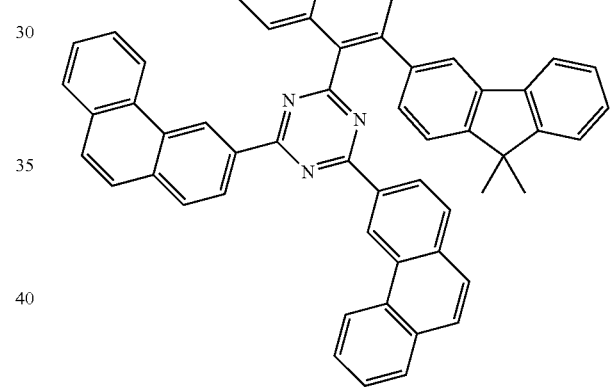
[Compound 236]
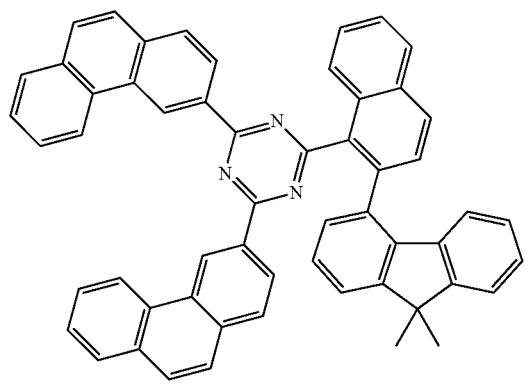
[Compound 239]
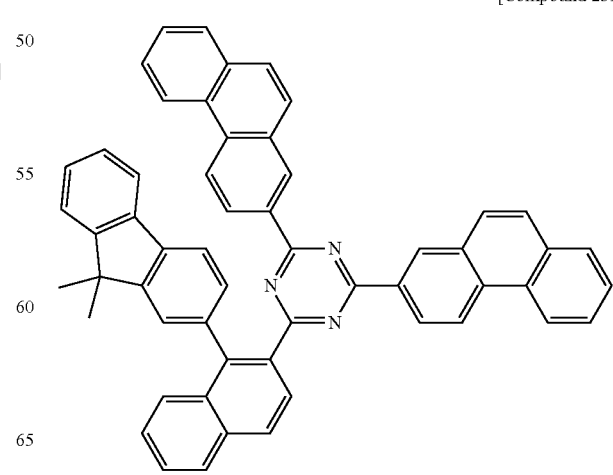

[Compound 240]
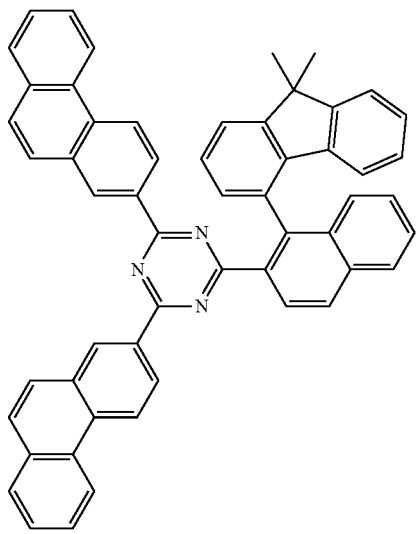
[Compound 243]
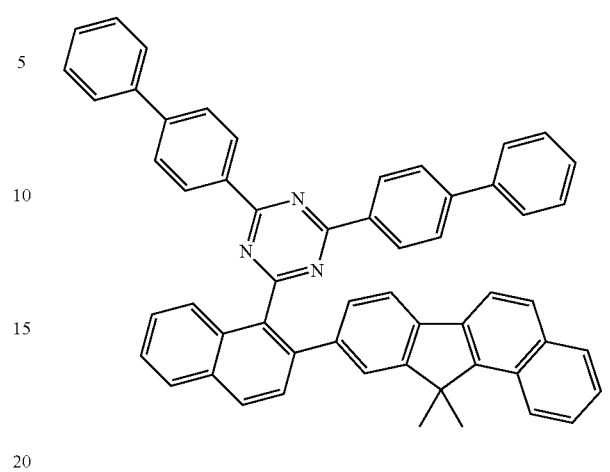
[Compound 241]
[Compound 244]
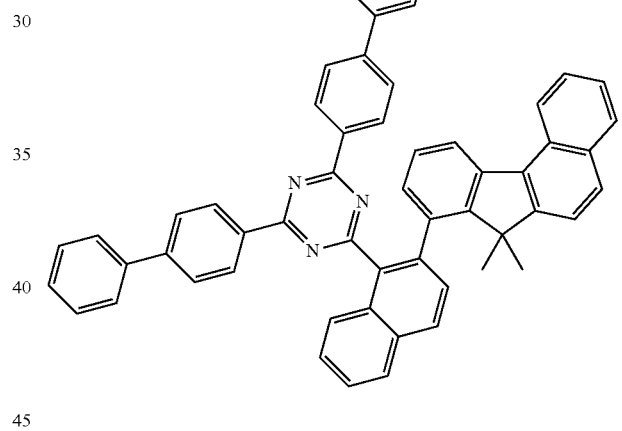
[Compound 242]
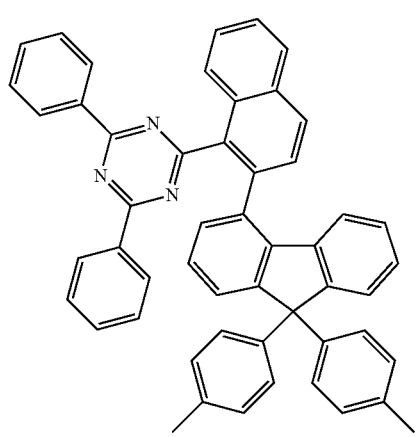
[Compound 245]
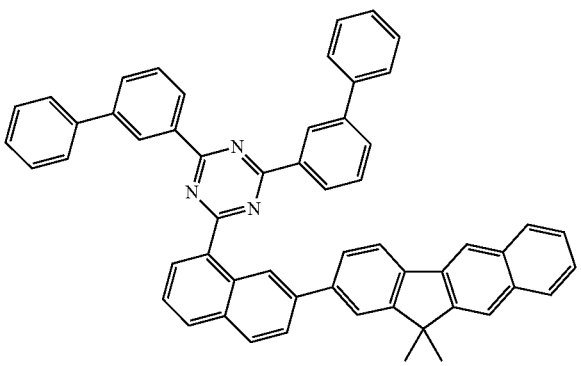

[Compound 246]
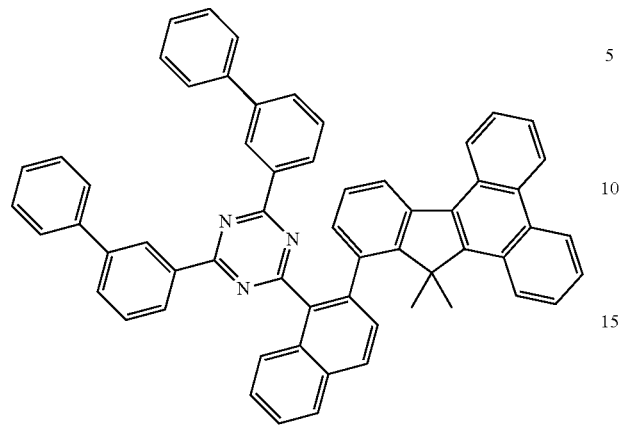
[Compound 247]
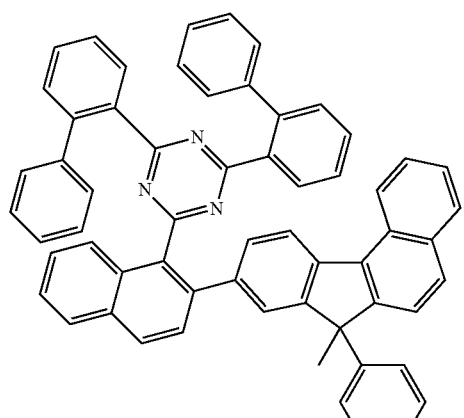
[Compound 248]
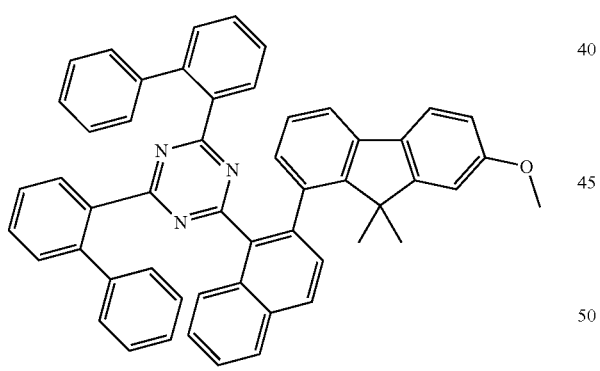
[Compound 249]
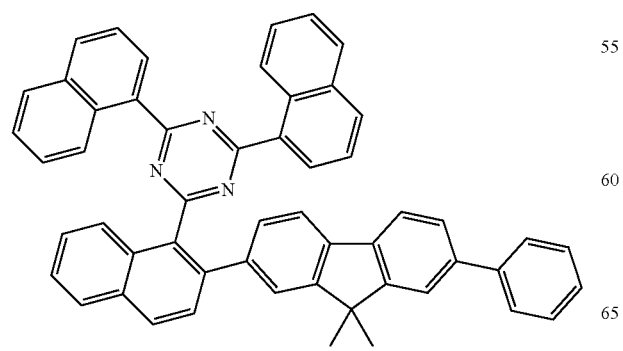
[Compound 250]
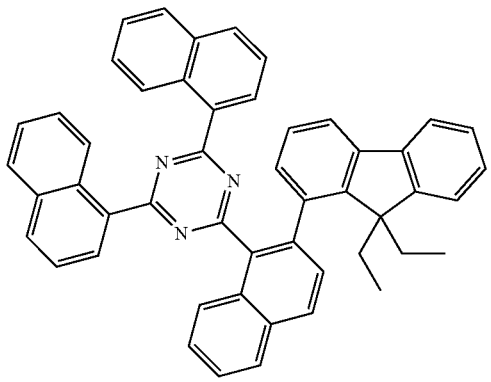
[Compound 251]
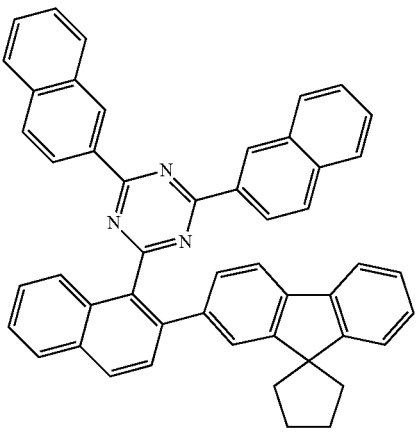
[Compound 252]
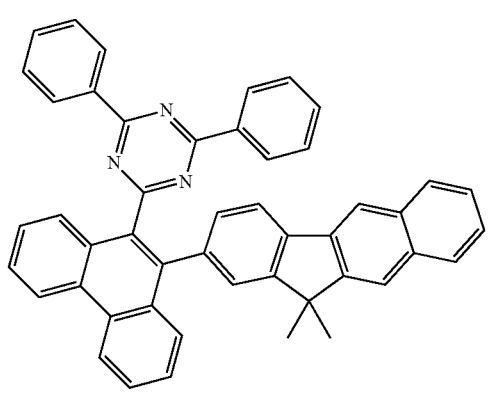
[Compound 253]
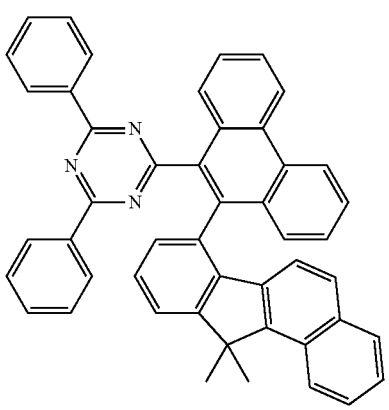

[Compound 254]
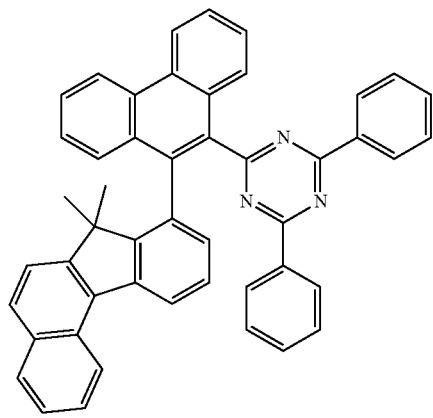
[Compound 257]
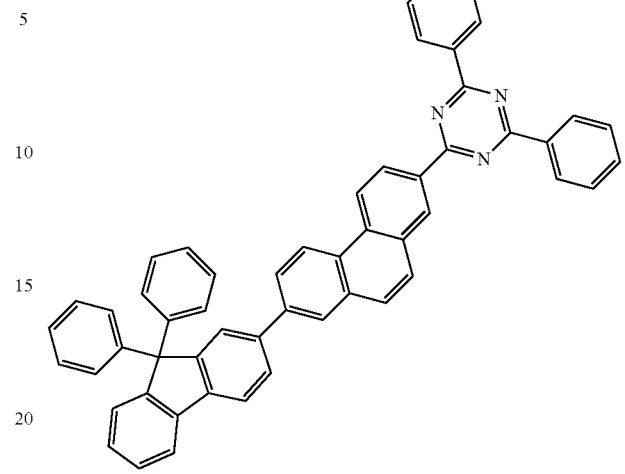
[Compound 255]
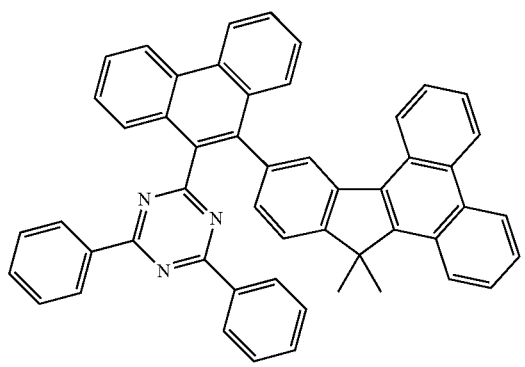
[Compound 258]
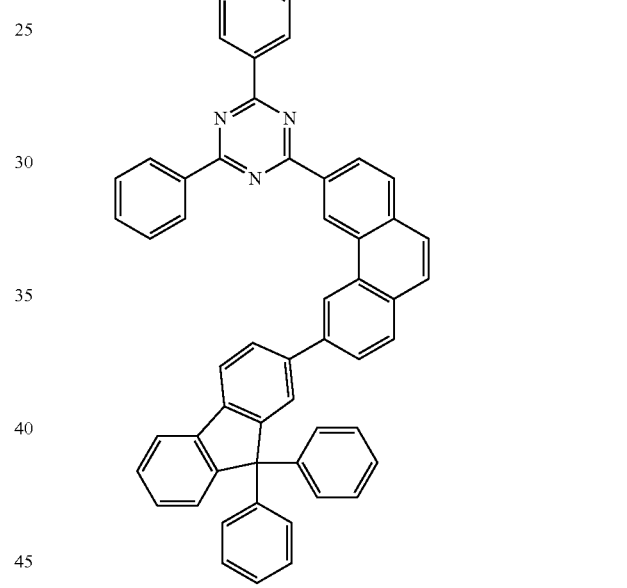
[Compound 256]
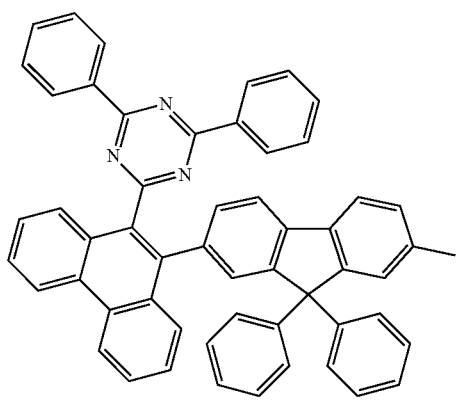
[Compound 259]
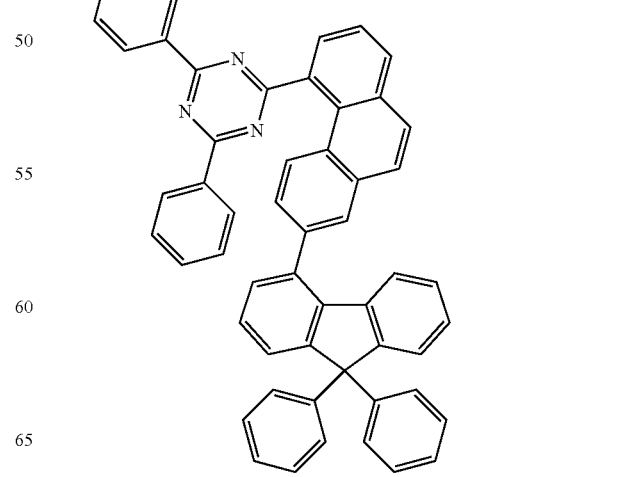

[Compound 260]
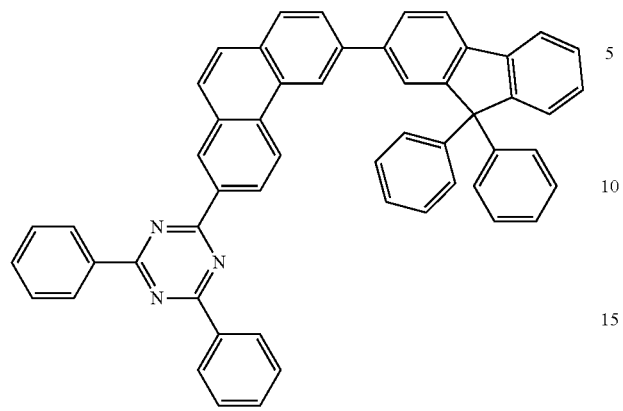
[Compound 262]
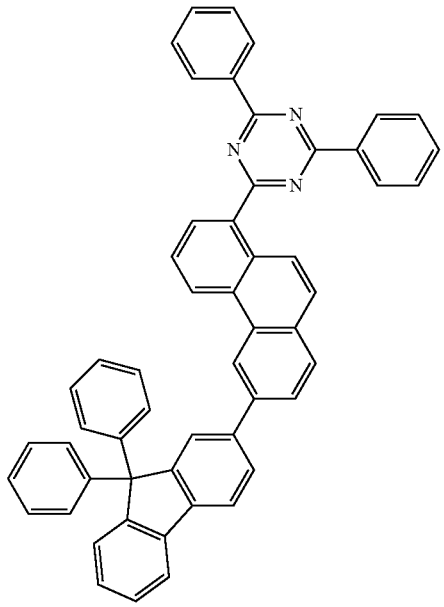
[Compound 261]
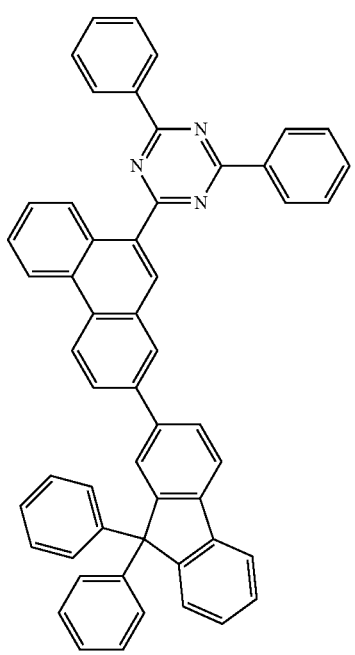
[Compound 263]
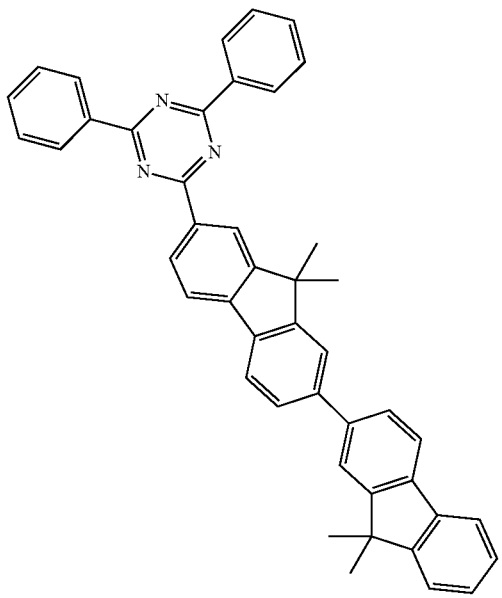

[Compound 264]
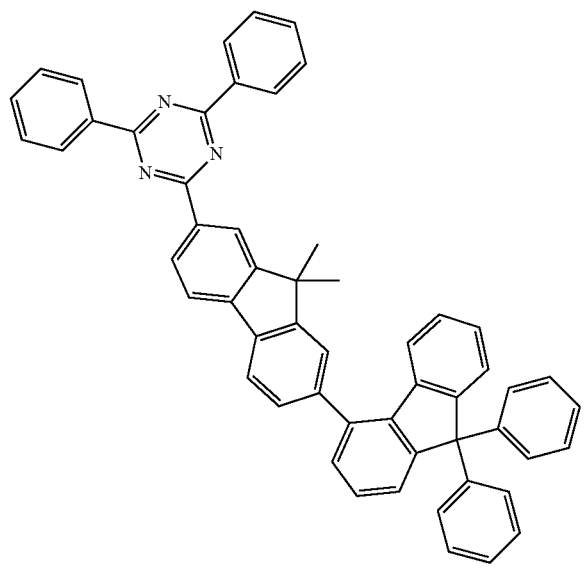
[Compound 266]
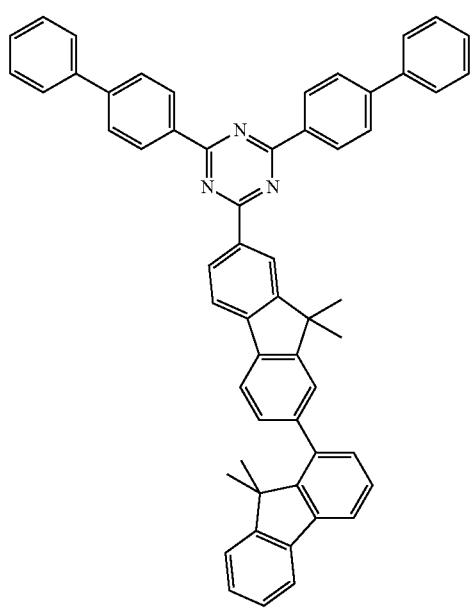
[Compound 265]
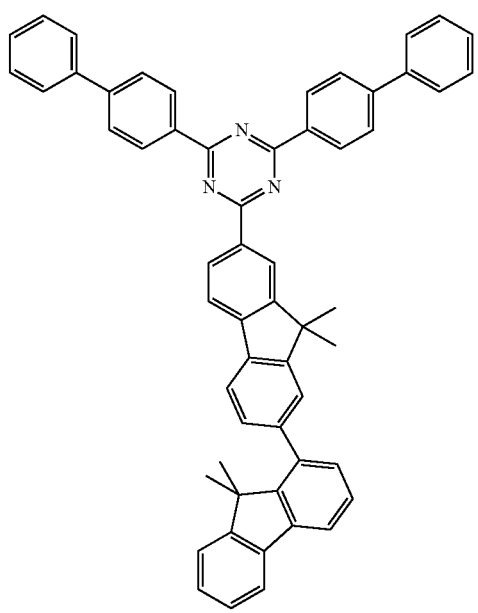
[Compound 267]
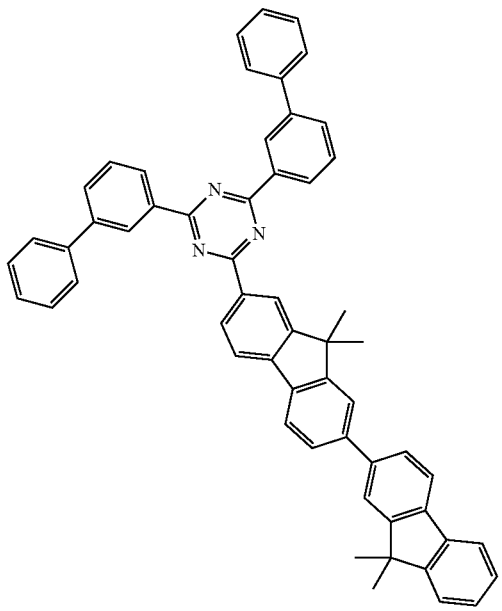

[Compound 268]
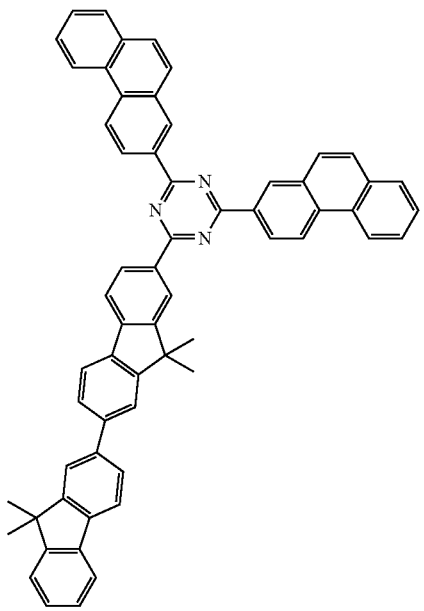
[Compound 269]
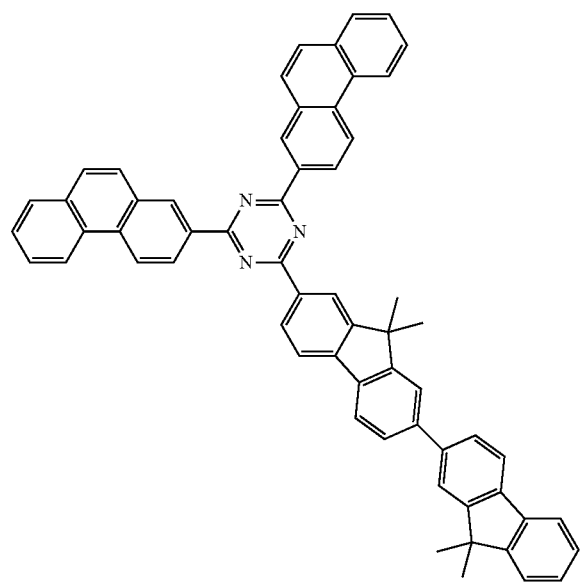
[Compound 270]
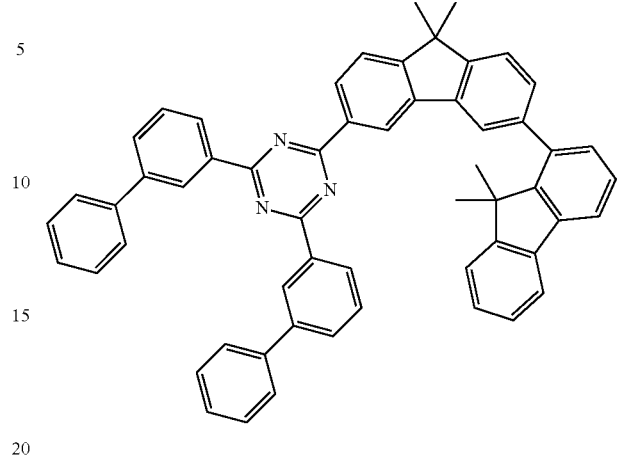
[Compound 271]
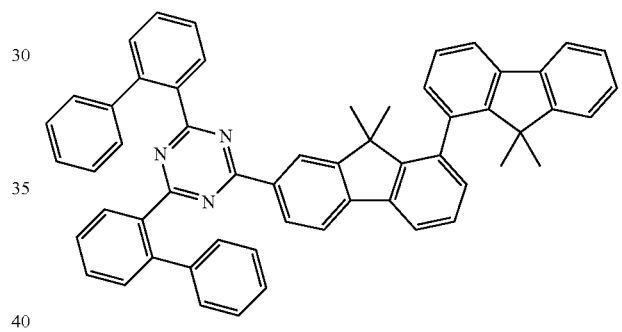
[Compound 272]
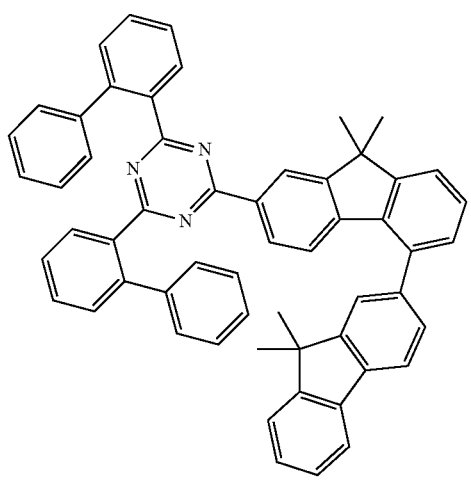

[Compound 273]
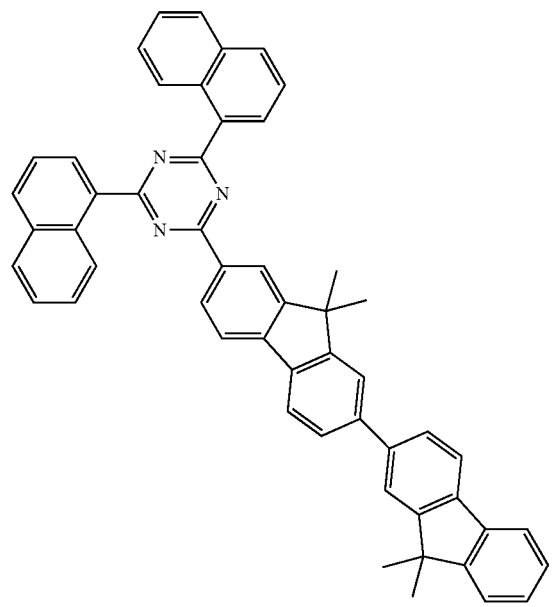
[Compound 274]
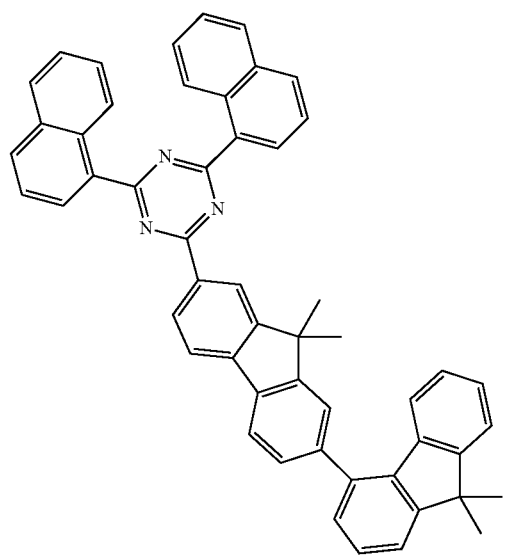
[Compound 275]
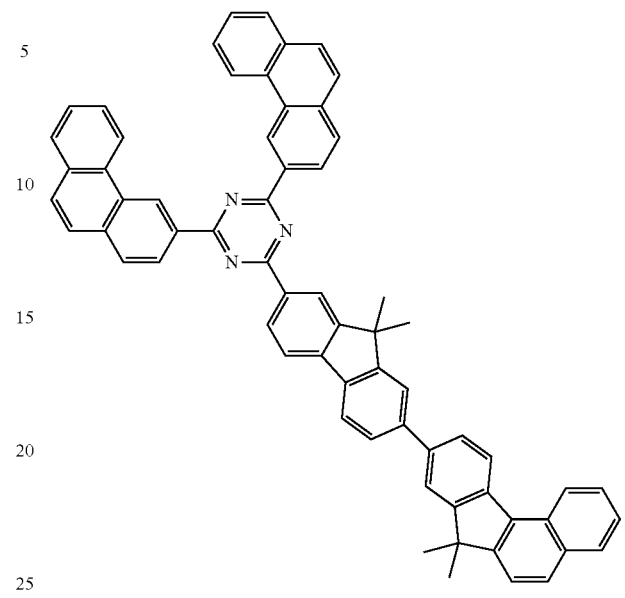
[Compound 276]
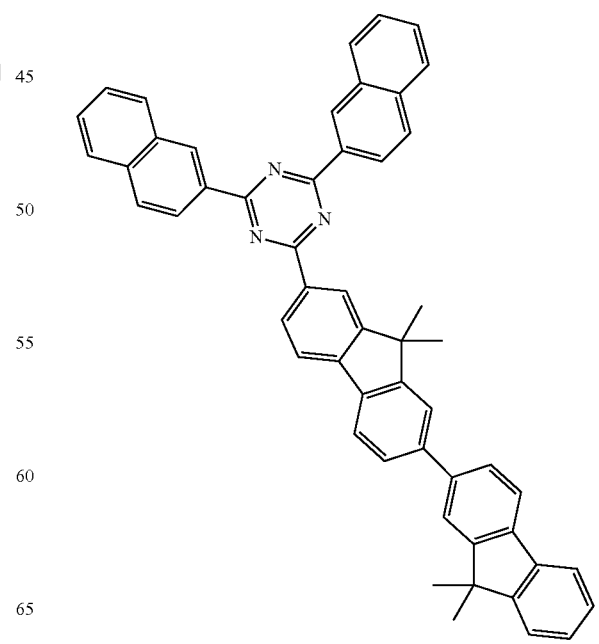

[Compound 277]
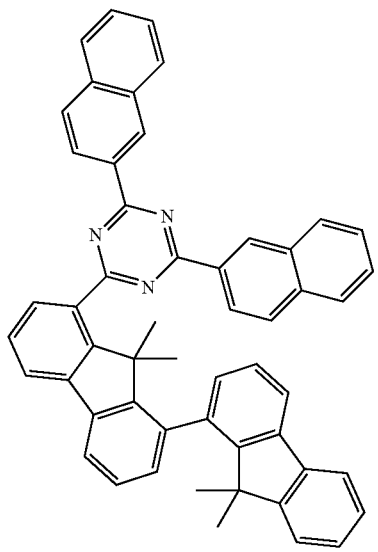
[Compound 278]
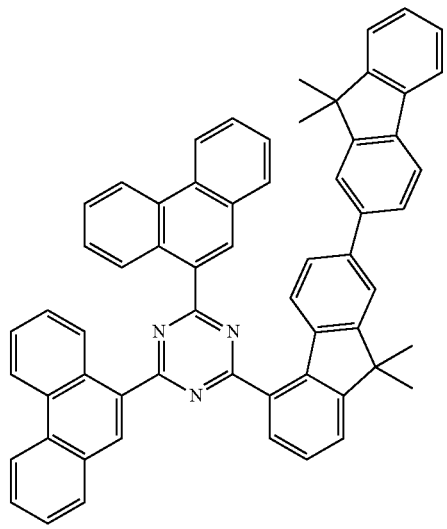
[Compound 279]
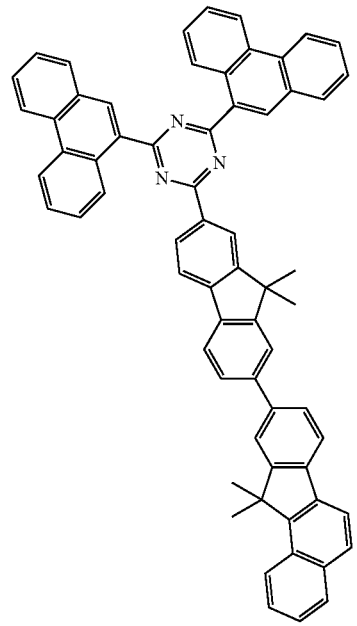
[Compound 280]
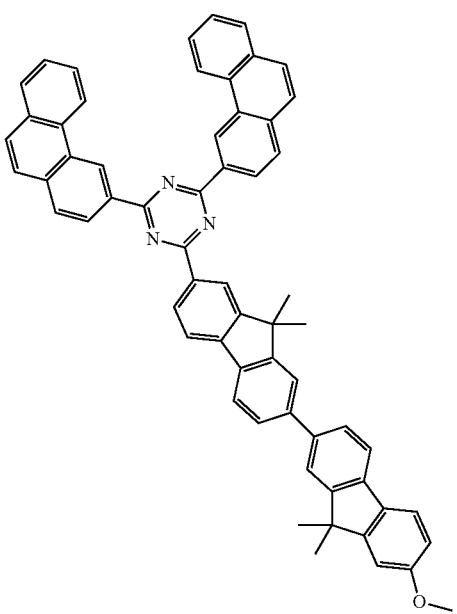

[Compound 281]
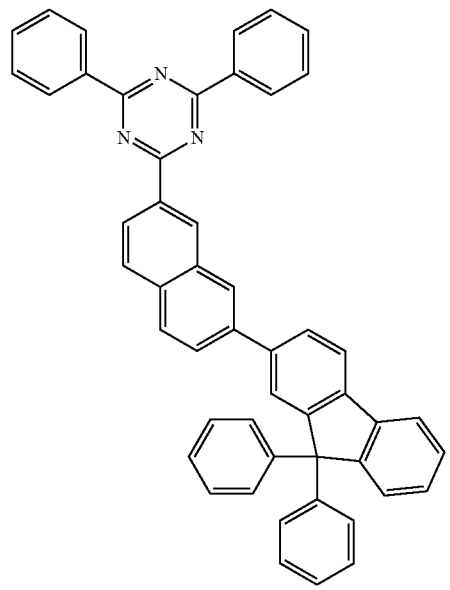
[Compound 283]
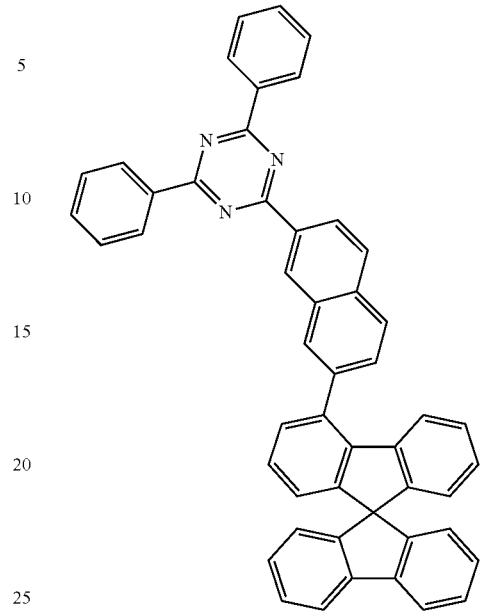
[Compound 282]
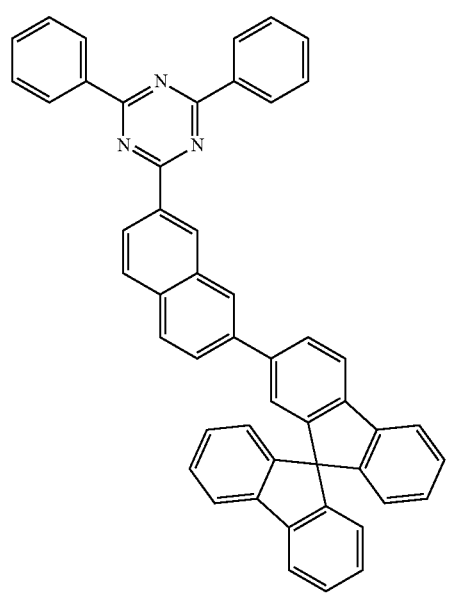
[Compound 284]
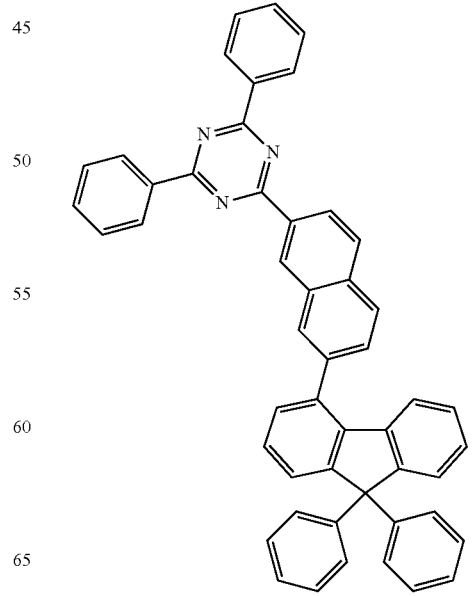

[Compound 285]
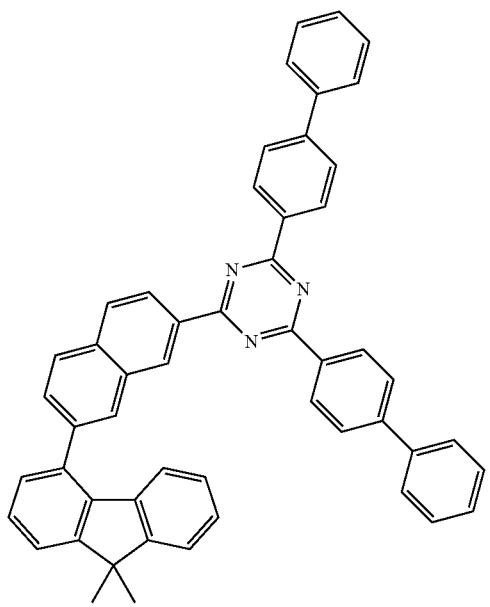
[Compound 287]
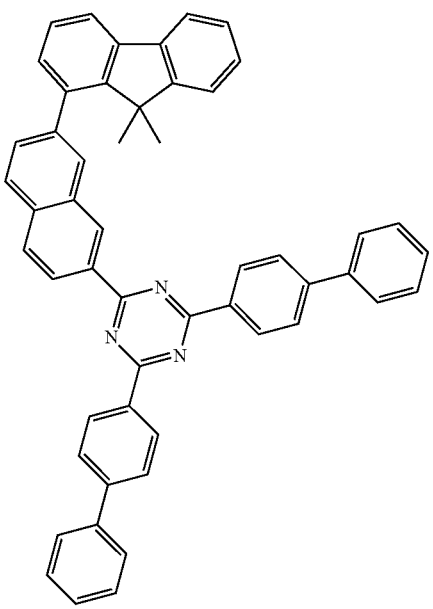
[Compound 286]
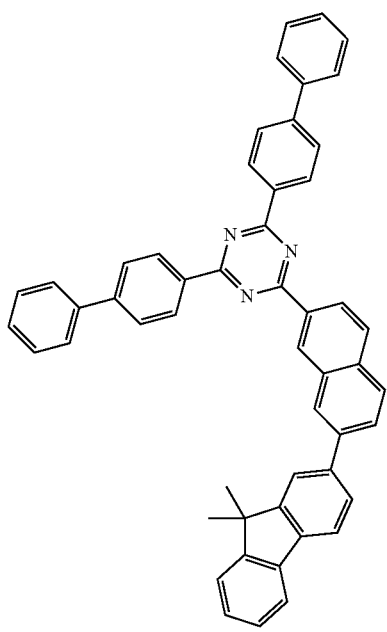
[Compound 288]

[Compound 289]
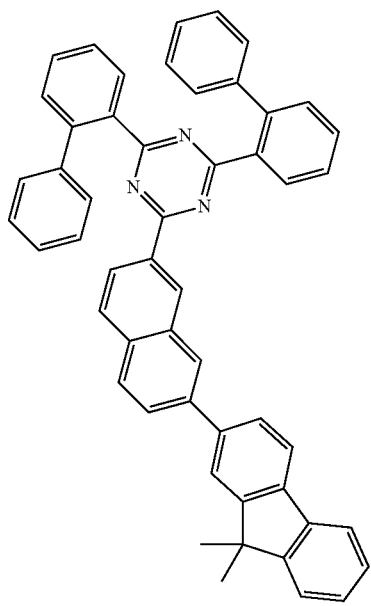
[Compound 291]
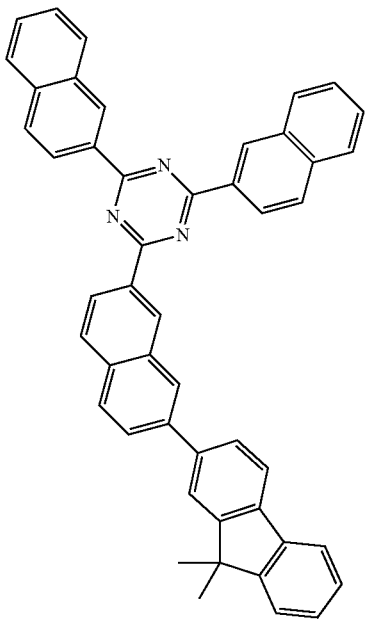
[Compound 290]
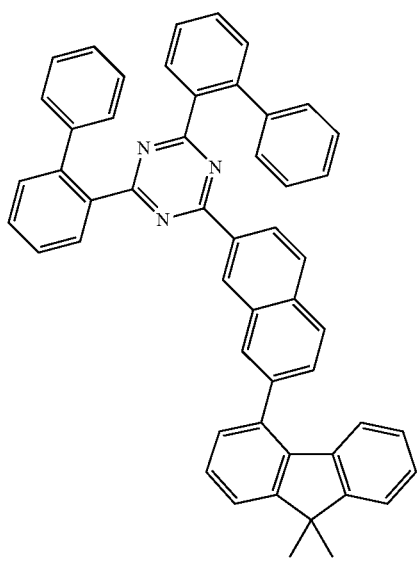
[Compound 292]
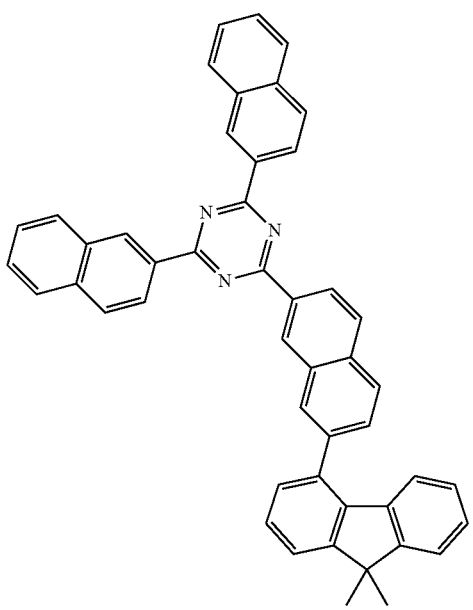

[Compound 293]
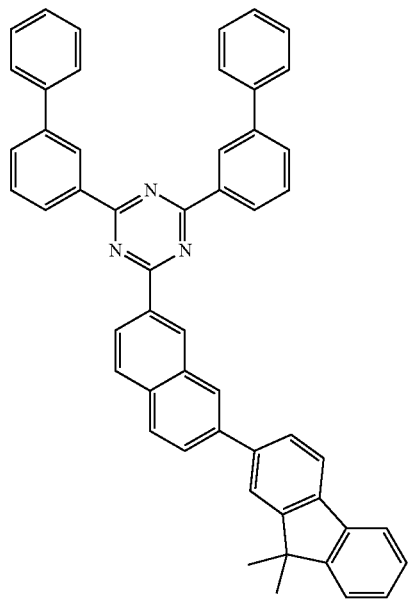
[Compound 294]
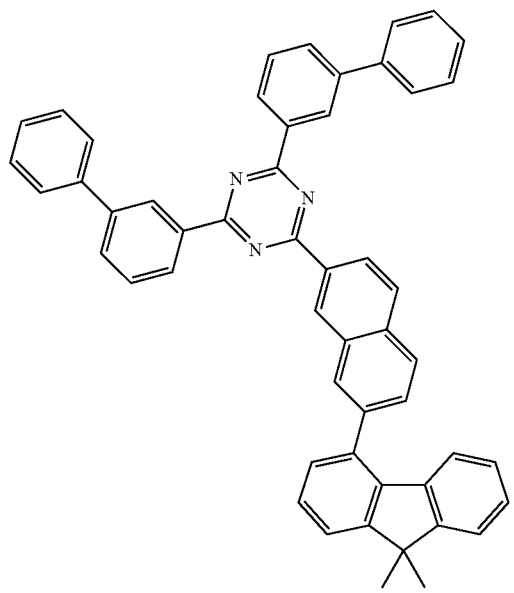
[Compound 295]
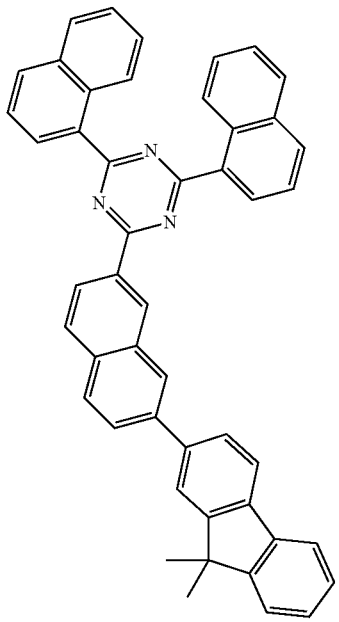
[Compound 296]
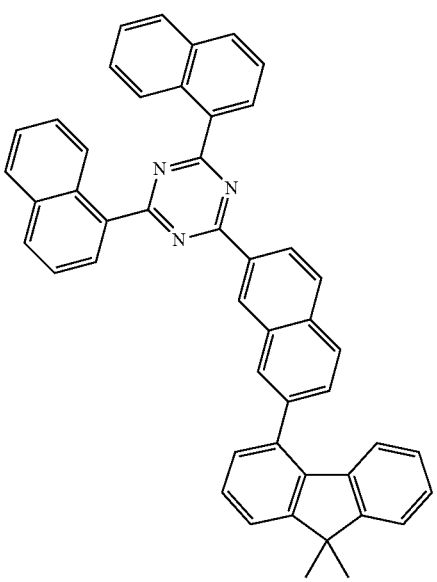

[Compound 297]
[Compound 298]
[Compound 299]
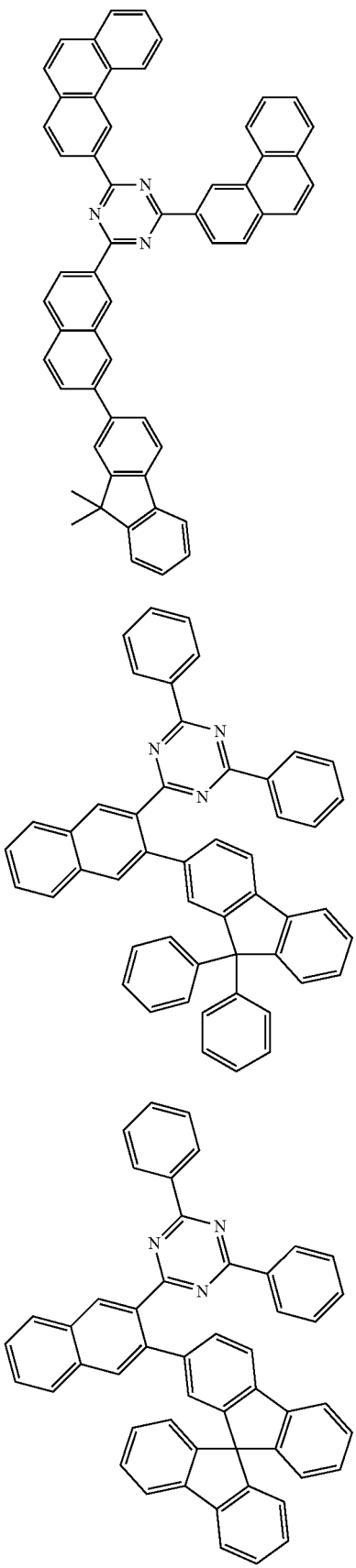
[Compound 300]
[Compound 301]
[Compound 302]
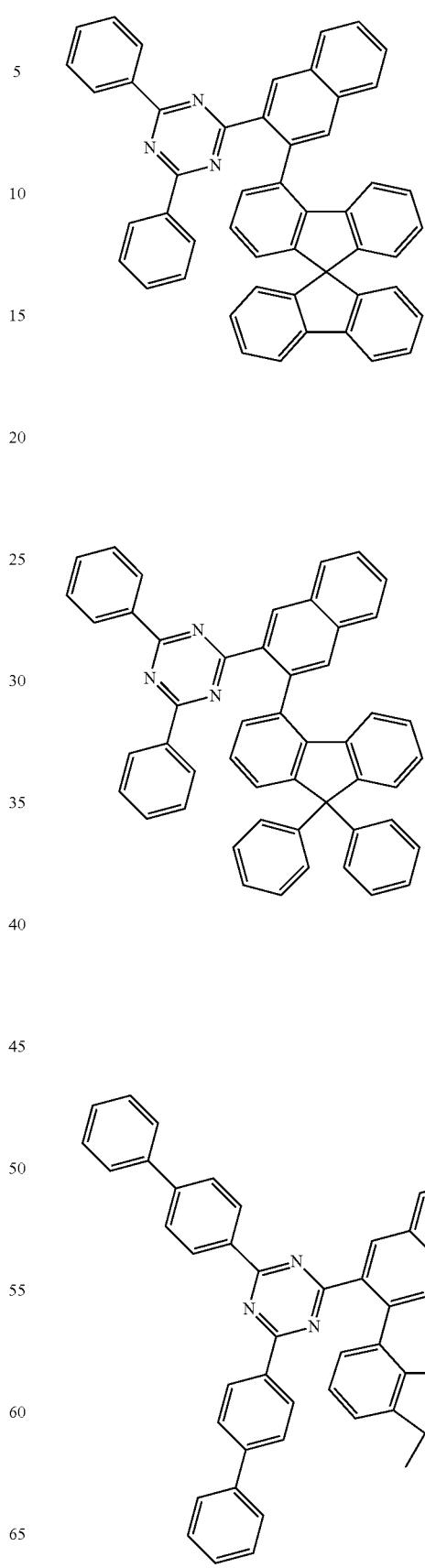

[Compound 303]
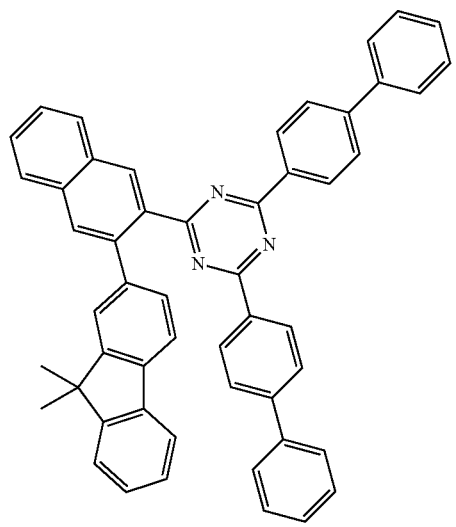
[Compound 305]
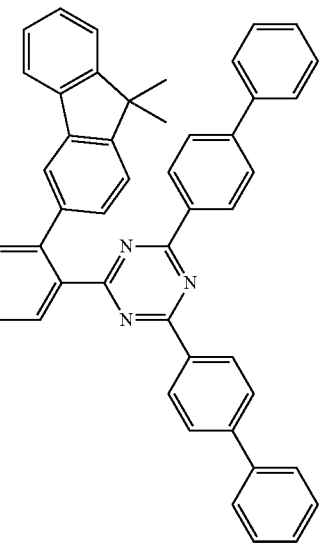
[Compound 306]
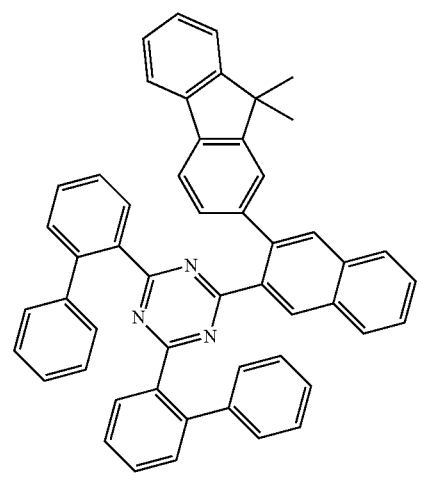
[Compound 304]
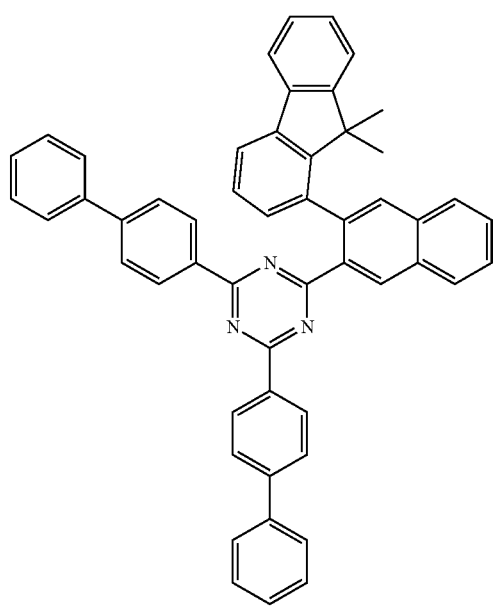
[Compound 307]
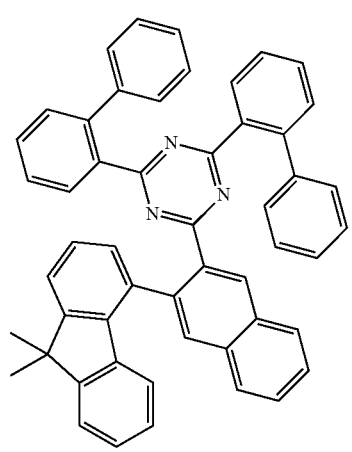

[Compound 308]
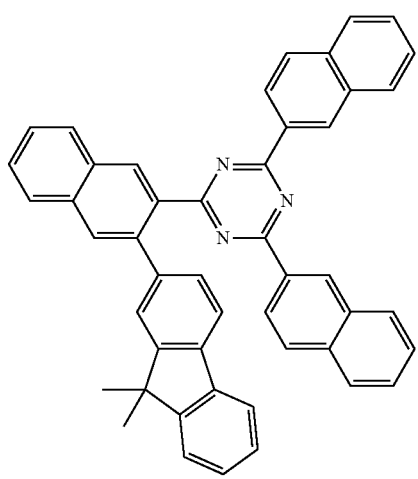
[Compound 309]
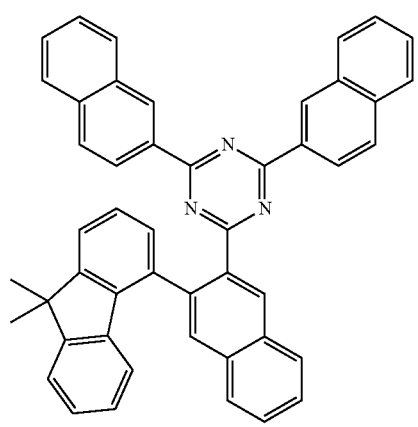
[Compound 310]
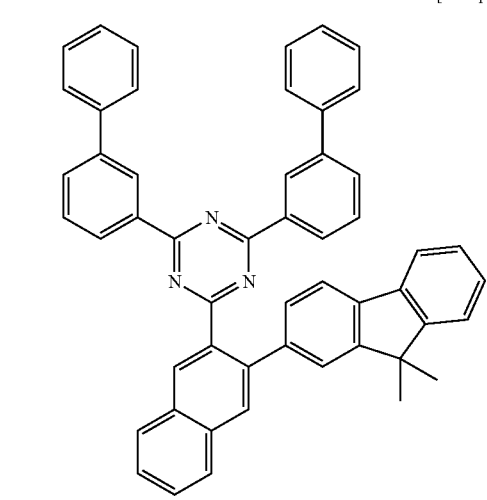
[Compound 311]
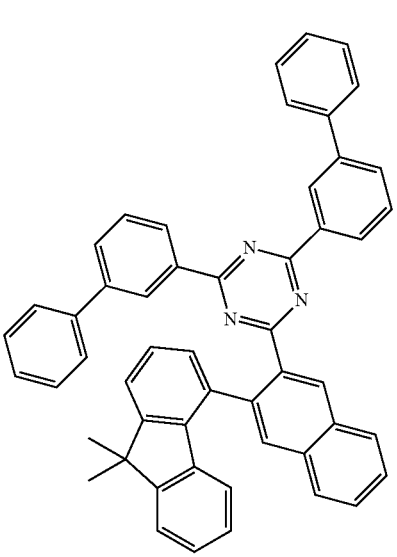
[Compound 312]
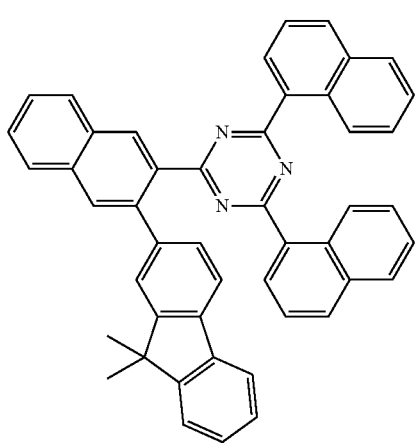
[Compound 313]
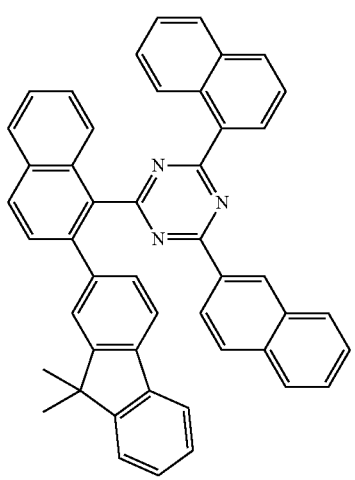

[Compound 314]

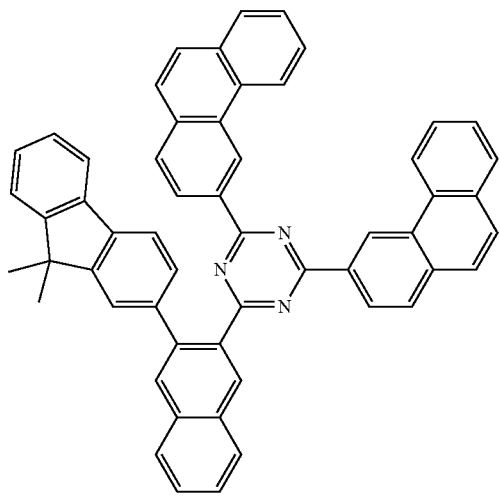

[Compound 316]

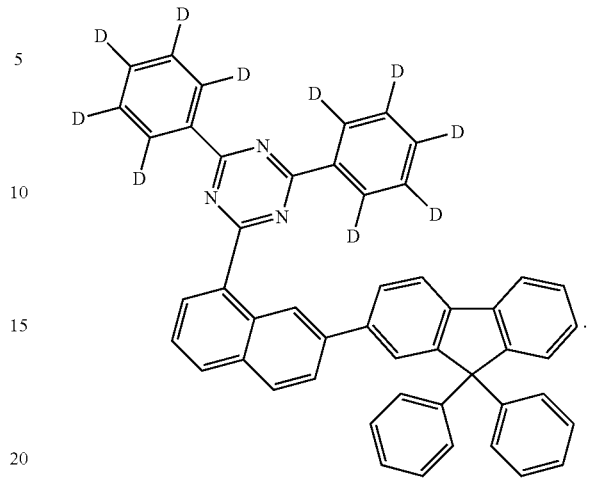

[Compound 315]

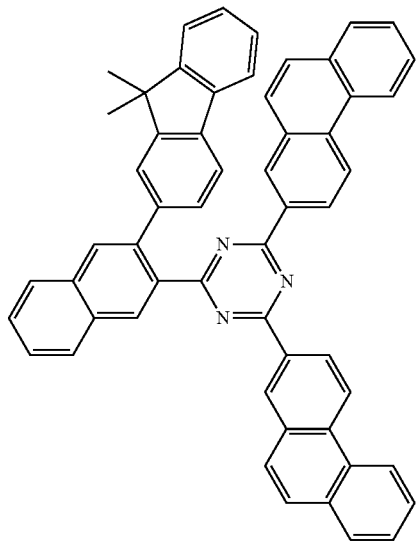

11. An organic light emitting device, comprising:
a first electrode;
a second electrode provided to face the first electrode; and
one or more organic material layers provided between the first electrode and the second electrode,
wherein one or more layers of the organic material layers comprise the compound of claim 1.

12. The organic light emitting device of claim 11, wherein the organic material layer comprising the compound is a hole injection layer, a hole transporting layer, or a layer which simultaneously injects and transports holes.

13. The organic light emitting device of claim 11, wherein the organic material layer comprising the compound is an electron injection layer, an electron transporting layer, or a layer which simultaneously injects and transports electrons.

14. The organic light emitting device of claim 11, wherein the organic material layer comprising the compound is a light emitting layer.

* * * * *